US011946067B2

(12) United States Patent
Lopes Ferreira et al.

(10) Patent No.: US 11,946,067 B2
(45) Date of Patent: Apr. 2, 2024

(54) **OPTIMIZED GENETIC TOOL FOR MODIFYING *CLOSTRIDIUM* BACTERIA**

(71) Applicant: IFP ENERGIES NOUVELLES, Rueil Malmaison (FR)

(72) Inventors: Nicolas Lopes Ferreira, Croisilles (FR); François Wasels, Metz (FR); Gwladys Chartier, Chatou (FR)

(73) Assignee: IFP ENERGIES NOUVELLES, Rueil Malmaison (FR)

( * ) Notice: Subject to any disclaimer, the term of this patent is extended or adjusted under 35 U.S.C. 154(b) by 801 days.

(21) Appl. No.: 16/421,572

(22) Filed: May 24, 2019

(65) Prior Publication Data

US 2019/0367947 A1    Dec. 5, 2019

(30) Foreign Application Priority Data

Jun. 4, 2018   (FR) ..................... 18 54835

(51) Int. Cl.
| | | |
|---|---|---|
| *C12N 15/90* | (2006.01) | |
| *C12N 1/20* | (2006.01) | |
| *C12N 15/10* | (2006.01) | |
| *C12N 15/74* | (2006.01) | |
| *C12R 1/145* | (2006.01) | |

(52) U.S. Cl.
CPC ............ *C12N 15/902* (2013.01); *C12N 1/20* (2013.01); *C12N 1/205* (2021.05); *C12N 15/102* (2013.01); *C12N 15/74* (2013.01); *C12N 2310/20* (2017.05); *C12N 2830/00* (2013.01); *C12R 2001/145* (2021.05)

(58) Field of Classification Search
None
See application file for complete search history.

(56) References Cited

U.S. PATENT DOCUMENTS

2018/0305680 A1   10/2018   Wasels et al.
2020/0087354 A1*   3/2020   Bondy-Denomy ..... A61P 43/00

FOREIGN PATENT DOCUMENTS

WO   WO 2017/064439   4/2017

OTHER PUBLICATIONS

Wasels et al. A CRISPR/Anti-CRISPR Genome Editing Approach Underlines the Synergy of Butanol Dehydrogenases in Clostridium acetobutylicum DSM 792. Accepted manuscript posted online May 8, 2020, Published Jun. 17, 2020. Applied and Environmental Microbiology. vol. 86, Iss. 13, e00408-20, p. 1-13. (Year: 2020).*
Basgall et al., Gene drive inhibition by the anti-CRISPR proteins AcrIIA2 and AcrIIA4 in *Saccharomyces cerevisiae*. Microbiology 2018;164:464-474 (Year: 2018).*
Wasels, F. et al. "A two-plasmid inducible CRISPR/Cas9 genome editing tool for *Clostridium acetobutylicum*" *Journal of Microbiological Methods*, 2017, pp. 5-11, vol. 140.
Rauch, B. J. et al. "Inhibition of CRISPR-Cas9 with Bacteriophage Proteins" *Cell*, Jan. 12, 2017, pp. 150-158, vol. 168, Supplemental pp. e1-e4, Supplemental Figures pp. 1-6.
Pawluk, A. et al. "Anti-CRISPR: discovery, mechanism and function" *Nature Reviews*, Jan. 2018, pp. 12-17, vol. 16.
Pawluk, A. et al. "Naturally Occurring Off-Switches for CRISPR-Cas9" *Cell*, Dec. 15, 2016, pp. 1829-1838, vol. 167, Supplemental pp. e1-e5, Supplemental Figures pp. 1-4.
Negahdaripour, M. et al. "Investigating CRISPR-Cas systems in *Clostridium botulinum* via bioinformatics tools" *Infection, Genetics and Evolution*, 2017, pp. 355-373, vol. 54.
French Preliminary Search Report and Written Opinion for FR 1854835 dated Nov. 27, 2018, pp. 1-9.
Collas, F. et al. "Simultaneous production of isopropanol, butanol, ethanol and 2,3-butanediol by Clostridium acetobutylicum ATCC 824 engineered strains" AMB Express, Jan. 1, 2012, pp. 1-10, vol. 2, No. 45.
Cornillot, E. et al. "The Genes for Butanol and Acetone Formation in Clostridium acetobutylicum ATCC 824 Reside on a Large Plasmid Whose Loss Leads to Degeneration of the Strain" Journal of Bacteriology, Sep. 1997, pp. 5442-5447, vol. 179, No. 17.
Wang, Y. et al. "Markerless chromosomal gene deletion in *Clostridium beijerinckii* using CRISPR/Cas9 system" *Journal of Biotechnology*, Apr. 20, 2015, pp. 1-5, vol. 200.
Xu, T. et al. "Efficient Genome Editing in *Clostridium cellulolyticum* via CRISPR-Cas9 Nickase" *Applied and Environmental Microbiology*, Jul. 2015 (posted online Apr. 24, 2015), pp. 4423-4431, vol. 81, No. 13.
Xu, T. et al. "Supplementary Data for Efficient Genome Editing in *Clostridium cellulolyticum* via CRISPR-Cas9 Nickase" *Applied and Environmental Microbiology*, Apr. 24, 2015, pp. 1-13.
Written Opinion in International Application No. PCT/FR2016/052663, dated Jan. 27, 2017, pp. 1-5.

* cited by examiner

Primary Examiner — Samuel C Woolwine
Assistant Examiner — Catherine Konopka
(74) Attorney, Agent, or Firm — SALIWANCHIK, LLOYD & EISENSCHENK

(57) ABSTRACT

The present invention concerns a genetic tool comprising at least two distinct nucleic acids optimized to facilitate the transformation and modification by homologous recombination of a bacterium of the genus *Clostridium*, typically a solventogenic bacterium.

12 Claims, 34 Drawing Sheets

Specification includes a Sequence Listing.

A

B

SEQUENCE LISTING

```
<160> NUMBER OF SEQ ID NOS: 134

<210> SEQ ID NO 1
<211> LENGTH: 50
<212> TYPE: DNA
<213> ORGANISM: Artificial Sequence
<220> FEATURE:
<223> OTHER INFORMATION: Primer deltacatB-fwd

<400> SEQUENCE: 1
tgttatggat tataagcggc tcgaggacgt caaaccatgt taatcattgc         50

<210> SEQ ID NO 2
<211> LENGTH: 50
<212> TYPE: DNA
<213> ORGANISM: Artificial Sequence
<220> FEATURE:
<223> OTHER INFORMATION: Primer deltacatB-rev

<400> SEQUENCE: 2
aatctatcac tgatagggac tcgagcaatt tcaccaaaga attcgctagc         50

<210> SEQ ID NO 3
<211> LENGTH: 28
```

```
<212> TYPE: DNA
<213> ORGANISM: Artificial Sequence
<220> FEATURE:
<223> OTHER INFORMATION: Primer RH076

<400> SEQUENCE: 3
catataataa aaggaaacct cttgatcg                                        28

<210> SEQ ID NO 4
<211> LENGTH: 20
<212> TYPE: DNA
<213> ORGANISM: Artificial Sequence
<220> FEATURE:
<223> OTHER INFORMATION: Primer RH077

<400> SEQUENCE: 4
attgccagcc taacacttgg                                                 20

<210> SEQ ID NO 5
<211> LENGTH: 50
<212> TYPE: DNA
<213> ORGANISM: Artificial Sequence
<220> FEATURE:
<223> OTHER INFORMATION: Primer RH001

<400> SEQUENCE: 5
atctccatgg acgcgtgacg tcgacataag gtaccaggaa ttagagcagc                50

<210> SEQ ID NO 6
<211> LENGTH: 43
<212> TYPE: DNA
<213> ORGANISM: Artificial Sequence
<220> FEATURE:
<223> OTHER INFORMATION: Primer RH002

<400> SEQUENCE: 6
tctatctcca gctctagacc attattattc ctccaagttt gct                       43

<210> SEQ ID NO 7
<211> LENGTH: 40
<212> TYPE: DNA
<213> ORGANISM: Artificial Sequence
<220> FEATURE:
<223> OTHER INFORMATION: Primer RH003

<400> SEQUENCE: 7
ataatggtct agagctggag atagattatt tggtactaag                           40

<210> SEQ ID NO 8
<211> LENGTH: 50
<212> TYPE: DNA
<213> ORGANISM: Artificial Sequence
<220> FEATURE:
<223> OTHER INFORMATION: Primer RH004

<400> SEQUENCE: 8
tatgaccatg attacgaatt cgagctcgaa gcgcttatta ttgcattagc                50

<210> SEQ ID NO 9
<211> LENGTH: 22
<212> TYPE: DNA
<213> ORGANISM: Artificial Sequence
<220> FEATURE:
<223> OTHER INFORMATION: Primer pEX-fwd

<400> SEQUENCE: 9
```

```
cagattgtac tgagagtgca cc                                              22

<210> SEQ ID NO 10
<211> LENGTH: 23
<212> TYPE: DNA
<213> ORGANISM: Artificial Sequence
<220> FEATURE:
<223> OTHER INFORMATION: Primer pEX-rev

<400> SEQUENCE: 10
gtgagcggat aacaatttca cac                                             23

<210> SEQ ID NO 11
<211> LENGTH: 32
<212> TYPE: DNA
<213> ORGANISM: Artificial Sequence
<220> FEATURE:
<223> OTHER INFORMATION: Primer pEC750C-fwd

<400> SEQUENCE: 11
caatattcca caatattata ttataagcta gc                                   32

<210> SEQ ID NO 12
<211> LENGTH: 17
<212> TYPE: DNA
<213> ORGANISM: Artificial Sequence
<220> FEATURE:
<223> OTHER INFORMATION: Primer M13-rev

<400> SEQUENCE: 12
caggaaacag ctatgac                                                    17

<210> SEQ ID NO 13
<211> LENGTH: 22
<212> TYPE: DNA
<213> ORGANISM: Artificial Sequence
<220> FEATURE:
<223> OTHER INFORMATION: Primer RH010

<400> SEQUENCE: 13
cggatattgc attaccagta gc                                              22

<210> SEQ ID NO 14
<211> LENGTH: 24
<212> TYPE: DNA
<213> ORGANISM: Artificial Sequence
<220> FEATURE:
<223> OTHER INFORMATION: Primer RH011

<400> SEQUENCE: 14
ttatcaatct cttacacatg gagc                                            24

<210> SEQ ID NO 15
<211> LENGTH: 24
<212> TYPE: DNA
<213> ORGANISM: Artificial Sequence
<220> FEATURE:
<223> OTHER INFORMATION: Primer RH025

<400> SEQUENCE: 15
tagtatgccg ccattattac gaca                                            24

<210> SEQ ID NO 16
<211> LENGTH: 20
<212> TYPE: DNA
<213> ORGANISM: Artificial Sequence
```

```
<220> FEATURE:
<223> OTHER INFORMATION: Primer RH134

<400> SEQUENCE: 16
gtcgacgtgg aattgtgagc                                                 20

<210> SEQ ID NO 17
<211> LENGTH: 3658
<212> TYPE: DNA
<213> ORGANISM: Artificial Sequence
<220> FEATURE:
<223> OTHER INFORMATION: pEX-A258-deltacatB

<400> SEQUENCE: 17
ctcgagctgc agcaaaaaaa gcaccgactc ggtgccactt tttcaagttg ataacggact     60
agccttattt taacttgcta tttctagctc taaaactgtg gtctctcttt tcgttgatgg    120
tggaatgata agggtttgca ccttaatttc tcctattgag aaaatcgtct cttctcagac    180
gtcaaaccat gttaatcatt gcttttatca aaaataggat ccactctatc attgatagag    240
tttgaaactc tatcattgat agagtataat atctttgttc atgtacatca tgctatctgt    300
gagttttaga gctagaaata gcaagttaaa ataaggctag tccgttatca acttgaaaaa    360
gtggcaccga gtcggtgctt tttttgaagc ttgtctttac acttttgccc attaattttt    420
gagttcctta tttttaggga gcttttatta tttttatcat gaaaatttca taaaatactc    480
ataaactaag gatgtcttca taatcagatt agtactccat tttcaatcca tttaatctgg    540
gaatatgata ttttaattac gtattattta agatatatta acgtgtaata taataccccg    600
caaatattaa ttatcacata catatccccc ctttattggg gcatttttg taccattat     660
tttagtattg tgcagtactt aaataaaaaa atgccgcaaa ttcatttta ttgaataatg     720
cggtatttct tctattcttt attttttatta ctctataaat aatgtaatca agacatgact    780
atctaaatat atgatatctt aattcataat tcgggcctcc taaaaatttt cgtaattcta    840
ttttagaagg cttttttccg tgacctagcc atttcaatct ccttttttaca atgatattta    900
cgctttagtt tattatagca cattctgtaa taccgaacta ttcaattttc agagaccatt    960
ttttattgat tcataactta agaatactac gaattactct aatattttac tttttcttat   1020
ctcttgttat tttaacatcg gaattactac taatattaat ttttattttt ccatccgcat   1080
ttgctccaac atttttttaa ctatactttc cttttgttaa taaattatgt tattgttgaa   1140
caatataaga aaagtgcgta acatttttta ttaaaaataa ttaggtattt ctatctgtgg   1200
ggtaccctcg aggtggcagc tctagagcta gcgaattctt tggtgaaatt gttatccgct   1260
cacaattcca cacaacatac gagccggaag cataaagtgt aaagcctggg gtgcctaatg   1320
agtgagctaa ctcacattaa ttgcgttgcg ctcactgccc gctttccagt cgggaaacct   1380
gtcgtgccag ctgcattaat gaatcggcca acgcgcgggg agaggcggtt tgcgtattgg   1440
gcgctcttcc gcttcctcgc tcactgactc gctgcgctcg tcgttcggc tgcggcgagc    1500
ggtatcagct cactcaaagg cggtaatacg gttatccaca gaatcagggg ataacgcagg   1560
aaagaacatg tgagcaaaag gccagcaaaa ggccaggaac cgtaaaaagg ccgcgttgct   1620
ggcgtttttc cataggctcc gccccctga cgagcatcac aaaaatcgac gctcaagtca    1680
gaggtggcga aacccgacag gactataaag ataccaggcg tttccccctg gaagctccct   1740
cgtgcgctct cctgttccga ccctgccgct accggatac ctgtccgcct ttctcccttc    1800
gggaagcgtg gcgctttctc atagctcacg ctgtaggtat ctcagttcgg tgtaggtcgt   1860
```

-continued

```
tcgctccaag ctgggctgtg tgcacgaacc ccccgttcag cccgaccgct gcgccttatc   1920
cggtaactat cgtcttgagt ccaacccggt aagacacgac ttatcgccac tggcagcagc   1980
cactggtaac aggattagca gagcgaggta tgtaggcggt gctacagagt tcttgaagtg   2040
gtggcctaac tacggctaca ctagaagaac agtatttggt atctgcgctc tgctgaagcc   2100
agttaccttc ggaaaaagag ttggtagctc ttgatccggc aaacaaacca ccgctggtag   2160
cggtggtttt tttgtttgca agcagcagat tacgcgcaga aaaaaaggat ctcaagaaga   2220
tcctttgatc ttttctacgg ggtctgacgc tcagtggaac gaaaactcac gttaagggat   2280
tttggtcatg agattatcaa aaaggatctt cacctagatc cttttaaatt aaaaatgaag   2340
ttttaaatca atctaaagta tatatgagta aacttggtct gacagttacc aatgcttaat   2400
cagtgaggca cctatctcag cgatctgtct atttcgttca tccatagttg cctgactccc   2460
cgtcgtgtag ataactacga tacgggaggg cttaccatct ggccccagtg ctgcaatgat   2520
accgcgcgaa ccacgctcac cggctccaga tttatcagca ataaaccagc cagccggaag   2580
ggccgagcgc agaagtggtc ctgcaacttt atccgcctcc atccagtcta ttaattgttg   2640
ccgggaagct agagtaagta gttcgccagt taatagtttg cgcaacgttg ttgccattgc   2700
tacaggcatc gtggtgtcac gctcgtcgtt tggtatggct tcattcagct ccggttccca   2760
acgatcaagg cgagttacat gatcccccat gttgtgcaaa aaagcggtta gctccttcgg   2820
tcctccgatc gttgtcagaa gtaagttggc cgcagtgtta tcactcatgg ttatggcagc   2880
actgcataat tctcttactg tcatgccatc cgtaagatgc ttttctgtga ctggtgagta   2940
ctcaaccaag tcattctgag aatagtgtat gcggcgaccg agttgctctt gcccggcgtc   3000
aatacgggat aataccgcgc cacatagcag aactttaaaa gtgctcatca ttggaaaacg   3060
ttcttcgggg cgaaaactct caaggatctt accgctgttg agatccagtt cgatgtaacc   3120
cactcgtgca cccaactgat cttcagcatc ttttactttc accagcgttt ctgggtgagc   3180
aaaaacagga aggcaaaatg ccgcaaaaaa gggaataagg gcgacacgga aatgttgaat   3240
actcatactc ttcctttttc aatattattg aagcatttat cagggttatt gtctcatgag   3300
cggatacata tttgaatgta tttagaaaaa taaacaaata ggggttccgc gcacatttcc   3360
ccgaaaagtg ccacctgacg tctaagaaac cattattatc atgacattaa cctataaaaa   3420
taggcgtatc acgaggccct ttcgtctcgc gcgtttcggt gatgacggtg aaaacctctg   3480
acacatgcag ctcccggaga cggtcacagc ttgtctgtaa gcggatgccg ggagcagaca   3540
agcccgtcag ggcgcgtcag cgggtgttgg cgggtgtcgg ggctggctta actatgcggc   3600
atcagagcag attgtactga gagtttggca attggtcgac ctcgagggcg cgcccgta     3658
```

<210> SEQ ID NO 18
<211> LENGTH: 660
<212> TYPE: DNA
<213> ORGANISM: Clostridium beijerinckii

<400> SEQUENCE: 18

```
atgaatttta atttgataga tattaatcat tggagtagaa agccatactt tgaacattat     60
ttaaacaatg tgaaatgtac ttatagtatg actgccaata tagaaataac tgatttattg    120
tatgaaatta aacttaaaaa tattaaattt tatcctaccc ttatttatat gattgcaact    180
gtggttaata agcataaaga attccgtatt tgttttgatc atgaaggtag tttaggatat    240
tgggatagca tgaatccaag ctatactatt tttcataaag aaaacgaaac attttcaagt    300
atttggacgg aatataacaa aagtttttta cgtttttata gtgattatct tgacgatata    360

```
aaaaactatg gaaatatcat gaagtttact ccgaaatcaa atgaacctga caatacattt      420
tctgtatcaa gcattccttg ggtgagtttt acaggattta acttgaatgt gtataatgaa      480
ggaacatatt taattcctat ttttactgca ggaaagtatt tcaaacaaga aaataaaata      540
tttattccta tatcaataca agtacatcat gctatctgtg acggttatca tgctagtaga      600
tttattaatg aaatgcaaga attagcattt agttttcaag aatggttaga aaataaataa      660

<210> SEQ ID NO 19
<211> LENGTH: 160
<212> TYPE: DNA
<213> ORGANISM: Artificial Sequence
<220> FEATURE:
<223> OTHER INFORMATION: Cassette d'expression ARNg

<400> SEQUENCE: 19
actctatcat tgatagagtt tgaaactcta tcattgatag agtataatat ctttgttcat       60
gtacatcatg ctatctgtga gttttagagc tagaaatagc aagttaaaat aaggctagtc      120
cgttatcaac ttgaaaaagt ggcaccgagt cggtgctttt                            160

<210> SEQ ID NO 20
<211> LENGTH: 808
<212> TYPE: DNA
<213> ORGANISM: Artificial Sequence
<220> FEATURE:
<223> OTHER INFORMATION: Editing template

<400> SEQUENCE: 20
gtctttacac ttttgcccat taattttttga gttccttatt tttagggagc ttttattatt      60
tttatcatga aaatttcata aaatactcat aaactaagga tgtcttcata atcagattag      120
tactccattt tcaatccatt taatctggga atatgatatt ttaattacgt attatttaag      180
atatattaac gtgtaatata ataccccgca aatattaatt atcacataca tatccccccct     240 ttattggggc attttttgta cccattattt tagtattgtg cagtacttaa ataaaaaaat      300
gccgcaaatt catttttatt gaataatgcg gtatttcttc tattctttat ttttattact      360
ctataaataa tgtaatcaag acatgactat ctaaatatat gatatcttaa ttcataattc      420
gggcctccta aaattttcg taattctatt ttagaaggct tttttccgtg acctagccat       480
ttcaatctcc tttttacaat gatatttacg ctttagttta ttatagcaca ttctgtaata     540
ccgaactatt caattttcag agaccatttt ttattgattc ataacttaag aatactacga     600
attactctaa tattttacttt tttcttatct cttgttattt taacatcgga attactacta    660
atattaattt ttattttttcc atccgcattt gctccaacat ttttttaact atactttcct    720
tttgttaata aattatgtta ttgttgaaca atataagaaa agtgcgtaac attttttatt     780
aaaaataatt aggtatttct atctgtgg                                         808

<210> SEQ ID NO 21
<211> LENGTH: 9954
<212> TYPE: DNA
<213> ORGANISM: Artificial Sequence
<220> FEATURE:
<223> OTHER INFORMATION: pCas9ind-deltacatB

<400> SEQUENCE: 21
catggataaa aagtacagta ttggtctaga cataggaact aactctgttg ggtgggctgt       60
tataacagat gaatataaag ttccatcaaa aaaatttaaa gtattaggaa acactgatag      120
```

-continued

```
acattcaata aaaaaaaact tgataggtgc tttattattc gattcaggag agactgctga    180
agctacacgt ttaaaaagaa cagctagacg tagatataca agaagaaaaa ataggatatg    240
ttatcttcaa gaaattttta gtaatgaaat ggcaaaagtt gatgattcat tctttcacag    300
actagaagaa agtttcttag ttgaagaaga taagaagcat gaaagacacc ctattttttgg   360 taatatcgta gatgaagtag catatcatga gaagtatcca actatctatc atttaagaaa    420
gaaattagtt gattctacag ataaagctga tctgagatta atatatttag ctttagctca    480
tatgattaaa tttagaggac atttttttaat agaaggtgat ttaaacccag acaacagcga    540
tgtagataaa ttatttatcc aattagttca aacttataat caattattcg aagagaatcc    600
aattaatgca agtggtgtag acgctaaggc tatattatca gctagattat caaaatctag    660
aagattagaa aatctaatag ctcaacttcc tggagaaaag aaaaatggac ttttttgggaa    720 cctaatagct ctctcactcg gactaacacc aaatttttaaa agcaattttg atcttgctga    780
agacgcaaag ttacaactat caaaggatac atacgatgat gatttagata atttgttagc    840
tcaaataggt gatcaatatg ctgatttgtt tcttgcagca aaaaacttaa gtgatgcaat    900
tttactatca gatatactta gagtaaaatac agaaataaca aaggctcctt tatcagcaag    960
tatgattaaa cgatatgatg agcatcatca agatttaaca ttattaaagg cacttgtaag   1020
acaacaatta ccagaaaaat ataaagaaat tttctttgat caatctaaaa atggatatgc   1080
tggatatata gacggtggag caagtcaaga agagttttat aaatttataa agcctatttt   1140
agaaaaaatg gatggaactg aagaattact tgttaaactt aacagagaag atttacttag   1200
aaaacaaaga acttttgata atggttcaat tcctcaccaa attcatttag gagaattaca   1260
tgctatacta agaagacaag aagattttta tccatttctt aaagataata gagaaaaaat   1320
tgaaaaaatt ttaacttttta gaataccata ttatgtagga ccacttgcaa ggggaaattc   1380
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaaagaag attcttcaa aaaaattgaa tgctttgata gtgttgaaat   1740
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acactttttg aagatagaga aatgatagaa gaaagattaa aaacatatgc   1920 acatctttttt gatgataagg ttatgaagca acttaaaaga agaagatata caggttgggg   1980
acgtttgtca agaaagctaa ttaatggtat tagagataaa caatcaggaa agactattct   2040 cgatttttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa tttttacaaac   2220 agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag aataaaaaga gctaggatca caaatattaa aagaacatcc   2400
agttgaaaat actcaattgc aaaatgaaaa gttatatttg tattacttac aaaatggaag   2460
agatatgtat gttgatcaag aactcgatat taatagatta agtgactatg atgttgatca   2520
```

```
tattgttcct caatcatttt taaaagatga ttcaatcgat aacaaagtat taactagatc    2580
agataaaaat agaggaaagt cagataatgt accatctgaa gaagttgtta aaaaaatgaa    2640
gaactattgg agacaacttt taaatgcaaa gctaattaca caaagaaaat ttgacaattt    2700
aacaaaagca gaaagaggag gattaagcga attagacaaa gctggattta taaaaagaca    2760
acttgttgag acaagacaaa taactaagca tgttgctcaa atacttgatt caagaatgaa    2820
tacaaaatat gatgaaaatg ataaattaat cagagaagta aaagtaataa cattaaagtc    2880
aaaattagta tcagatttca gaaaggattt tcaattttac aaagttcgtg aaataaataa    2940
ctatcatcat gctcatgatg catacttaaa tgctgttgta ggaactgctc ttattaagaa    3000
atatcctaaa ctagaaagcg aatttgttta tggagattat aaagtttatg atgtgcgcaa    3060
aatgatcgcg aaatccgaac aagaaatcgg taaggctaca gcaaaatatt tcttttatag    3120
taatataatg aattttttta agacagaaat aactttggct aatggtgaaa tcagaaaaag    3180
accacttatc gaaacaaatg gagagacagg agaaatagta tgggataaag gaagagattt    3240
tgctactgtt agaaaagtac taagtatgcc acaagtaaat atcgtaaaga aaactgaagt    3300
tcaaactgga ggtttctcta aggaatcaat tttacctaag agaaattcag ataagttaat    3360
tgcaaggaaa aaagattggg acccaaaaaa atacggtggt tttgatagtc caacagttgc    3420
ctatagtgtt cttgtagtag cgaaagttga gaaaggtaag tcaaaaagt tgaaaagcgt    3480 aaaagaactt cttggtatca caattatgga aagatcttca tttgaaaaaa atccaattga    3540 cttttttagaa gctaagggtt ataaagaagt taaaaaggat ttaatcataa aactaccaaa    3600
gtatagtcta tttgaactcg aaaacggaag aaaacgaatg ctcgctagcg caggagaact    3660
tcaaaaagga aatgaacttg cgctgccatc aaagtatgta aatttcttat atttagcttc    3720
tcattatgag aaattaaaag gatcaccaga ggataatgaa caaaagcaac tatttgtaga    3780
acaacacaaa cattatttag atgaaataat agaacaaata tctgaattttt ctaaagagt    3840 tatacttgcc gacgcaaatc tagataaggt gctttcagcg tataataaac acagagataa    3900
accaataaga gaacaagcag aaaacattat ccatcttttt acattaacta atcttggtgc    3960
accagctgca tttaagtact ttgatacaac aatagataga aaagataca catctactaa    4020 agaagtatta gacgcaactt taatacatca atctattaca gggctttatg aaacaagaat    4080
tgatttaagt caactaggcg gagattaagt cgacaaagta ttgttaaaaa taactctgta    4140
gaattataaa ttagttctac agagttattt tttgacccgg gtatattgat aaaaataata    4200
atagtgggta taattaagtt gttaggaggt tagttagaat gatgtcaaga ttagataaaa    4260
gtaaagtgat taacagcgca ttagagctgc ttaatgaggt cggaatcgaa ggtttaacaa    4320
cccgtaaact cgcccagaag ctaggtgtag agcagcctac attgtattgg catgtaaaaa    4380
ataagcgggc tttgctcgac gccttagcca ttgagatgtt agataggcac catactcact    4440
tttgcccttt agaaggggaa agctggcaag atttttttacg taataacgct aaaagtttta    4500 gatgtgctt actaagtcat cgcgatggag caaaagtaca tttaggtaca cggcctacag    4560
aaaaacagta tgaaactctc gaaaatcaat tagcctttt atgccaacaa ggttttcac    4620 tagagaatgc attatatgca ctcagcgctg tggggcattt tactttaggt tgcgtattgg    4680
aagatcaaga gcatcaagtc gctaaagaag aaagggaaac acctactact gatagtatgc    4740
cgccattatt acgacaagct atcgaattat ttgatcacca aggtgcagag ccagccttct    4800
tattcggcct tgaattgatc atatgcggat tagaaaaaca acttaaatgt gaaagtgggt    4860
```

```
cttaaaagca gcataacctt tttccgtgat ggtaacttca cggtaaccaa gatgtcgagt    4920
tgagctcgaa ttcgtaatca tggtcatagc tgtttcctgt gtgaaattgt tatccgctca    4980
caattccaca caacatacga gccggaagca taaagtgtaa agcctggggt gcctaatgag    5040
tgagctaact cacattaatt gcgttgcgct cactgcccgc tttccagtcg ggaaacctgt    5100
cgtgccagct gcattaatga atcggccaac gcgcgggag aggcggtttg cgtattgggc     5160
gctcttccgc ttcctcgctc actgactcgc tgcgctcggt cgttcggctg cggcgagcgg    5220
tatcagctca ctcaaaggcg gtaatacggt tatccacaga atcaggggat aacgcaggaa    5280
agaacatgtg agcaaaaggc cagcaaaagg ccaggaaccg taaaaaggcc gcgttgctgg    5340 cgttttttcca taggctccgc ccccctgacg agcatcacaa aaatcgacgc tcaagtcaga    5400
ggtggcgaaa cccgacagga ctataaagat accaggcgtt tccccctgga agctccctcg    5460
tgcgctctcc tgttccgacc ctgccgctta ccggatacct gtccgccttt ctcccttcgg    5520
gaagcgtggc gctttctcat agctcacgct gtaggtatct cagttcggtg taggtcgttc    5580
gctccaagct gggctgtgtg cacgaacccc cgttcagcc cgaccgctgc gccttatccg     5640
gtaactatcg tcttgagtcc aacccggtaa gacacgactt atcgccactg gcagcagcca    5700
ctggtaacag gattagcaga gcgaggtatg taggcggtgc tacagagttc ttgaagtggt    5760
ggcctaacta cggctacact agaaggacag tatttggtat ctgcgctctg ctgaagccag    5820
ttaccttcgg aaaagagtt ggtagctctt gatccggcaa acaaaccacc gctggtagcg     5880
gtggtttttt tgtttgcaag cagcagatta cgcgcagaaa aaaggatctc aagaagatc     5940 ctttgatctt ttctacgggg tctgacgctc agtggaacga aaactcacgt taagggattt    6000
tggtcatgag attatcaaaa aggatcttca cctagatcct tttaaattaa aaatgaagtt    6060
ttaaatcaat ctaaagtata tatgagtaaa cttggtctga cagttaccag gtccactgcc    6120
gggcctcttg cgggatcaaa agaaaacga atgatacac caatcagtgc aaaaaaagat     6180
ataatgggag ataagacggt tcgtgttcgt gctgacttgc accatatcat aaaaatcgaa    6240
acagcaaaga atggcggaaa cgtaaaagaa gttatggaaa taagacttag aagcaaactt    6300
aagagtgtgt tgatagtgca gtatcttaaa attttgtata ataggaattg aagttaaatt    6360
agatgctaaa aatttgtaat taagaaggag tgattacatg aacaaaaata taaaatattc    6420
tcaaaacttt ttaacgagtg aaaaagtact caaccaaata ataaaacaat tgaatttaaa    6480
agaaaccgat accgtttacg aaattggaac aggtaaaggg catttaacga cgaaactggc    6540
taaaataagt aaacaggtaa cgtctattga attagacagt catctattca acttatcgtc    6600
agaaaaatta aaactgaata ctcgtgtcac tttaattcac caagatattc tacagtttca    6660
attccctaac aaacagaggt ataaaattgt tgggagtatt ccttaccatt taagcacaca    6720
aattattaaa aagtggttt tgaaagcca tgcgtctgac atctatctga ttgttgaaga     6780
aggattctac aagcgtacct tggatattca ccgaacacta gggttgctct tgcacactca    6840
agtctcgatt cagcaattgc ttaagctgcc agcggaatgc tttcatccta aaccaaaagt    6900
aaacagtgtc ttaataaaac ttacccgcca taccacagat gttccagata atattggaa     6960 gctatatacg tactttgttt caaaatgggt caatcgagaa tatcgtcaac tgttactaa     7020 aaatcagttt catcaagcaa tgaaacacgc caaagtaaac aatttaagta ccgttactta    7080
tgagcaagta ttgtctattt ttaatagtta tctattattt aacgggagga ataattcta    7140 tgagtcccta ggcaggcctc cgccattatt tttttgaaca attgacaatt catttcttat    7200 ttttttattaa gtgatagtca aaaggcataa cagtgctgaa tagaaagaaa tttacagaaa    7260
```

```
agaaaattat agaatttagt atgattaatt atactcattt atgaatgttt aattgaatac    7320
aaaaaaaaat acttgttatg tattcaatta cgggttaaaa tatagacaag ttgaaaaatt    7380
taataaaaaa ataagtcctc agctcttata tattaagcta ccaacttagt atataagcca    7440
aaacttaaat gtgctaccaa cacatcaagc cgttagagaa ctctatctat agcaatattt    7500
caaatgtacc gacatacaag agaaacatta actatatata ttcaatttat gagattatct    7560
taacagatat aaatgtaaat tgcaataagt aagatttaga agtttatagc ctttgtgtat    7620
tggaagcagt acgcaaaggc ttttttattt gataaaaatt agaagtatat ttattttttc    7680
ataattaatt tatgaaaatg aaaggggtg agcaaagtga cagaggaaag cagtatctta    7740
tcaaataaca aggtattagc aatatcatta ttgactttag cagtaaacat tatgactttt    7800
atagtgcttg tagctaagta gtacgaaagg gggagcttta aaaagctcct tggaatacat    7860
agaattcata aattaattta tgaaagaag ggcgtatatg aaaacttgta aaaattgcaa     7920
agagtttatt aaagatactg aaatatgcaa aatacattcg ttgatgattc atgataaaac    7980
agtagcaacc tattgcagta aatacaatga gtcaagatgt ttacataaag ggaaagtcca    8040
atgtattaat tgttcaaaga tgaaccgata tggatggtgt gccataaaaa tgagatgttt    8100
tacagaggaa gaacagaaaa aagaacgtac atgcattaaa tattatgcaa ggagctttaa    8160
aaaagctcat gtaaagaaga gtaaaaagaa aaataatttt atttattaat ttaatattga    8220
gagtgccgac acagtatgca ctaaaaaata tatctgtggt gtagtgagcc gatacaaaag    8280
gatagtcact cgcattttca taatacatct tatgttatga ttatgtgtcg gtgggacttc    8340
acgacgaaaa cccacaataa aaaagagtt cggggtaggg ttaagcatag ttgaggcaac     8400
taaacaatca agctaggata tgcagtagca gaccgtaagg tcgttgttta ggtgtgttgt    8460
aatacatacg ctattaagat gtaaaaatac ggataccaat gaagggaaaa gtataatttt    8520
tggatgtagt ttgtttgttc atctatgggc aaactacgtc caaagccgtt tccaaatctg    8580
ctaaaaagta tatcctttct aaaatcaaag tcaagtatga aatcataaat aaagtttaat    8640
tttgaagtta ttatgatatt atgttttttct attaaaataa attaagtata tagaatagtt    8700
taataatagt atatacttaa tgtgataagt gtctgacagt gtcacagaaa ggatgattgt    8760
tatggattat aagcggctcg aggacgtcaa accatgttaa tcattgcttt tatcaaaaat    8820
aggatccact ctatcattga tagagtttga aactctatca ttgatagagt ataatatctt    8880
tgttcatgta catcatgcta tctgtgagtt ttagagctag aaatagcaag ttaaataag    8940 gctagtccgt tatcaacttg aaaaagtggc accgagtcgg tgcttttttt gaagcttgtc    9000
tttacacttt tgcccattaa ttttgagtt ccttattttt agggagcttt tattatttt     9060 atcatgaaaa tttcataaaa tactcataaa ctaaggatgc cttcataatc agattagtac    9120
tccattttca atccatttaa tctgggaata tgatatttta attacgtatt atttaagata    9180
tattaacgtg taatataata ccccgcaaat attaattatc acatacatat cccccctta     9240 ttggggcatt ttttgtaccc attattttag tattgtgcag tacttaaata aaaaaatgcc    9300
gcaaattcat ttttattgaa taatgcggta tttcttctat tctttatttt tattactcta    9360
taaataatgt aatcaagaca tgactatcta aatatatgat atcttaattc ataattcggg    9420
cctcctaaaa attttcgtaa ttctatttta gaaggctttt ttccgtgacc tagccatttc    9480
aatctccttt ttacaatgat atttacgctt tagtttatta tagcacattc tgtaataccg    9540
aactattcaa ttttcagaga ccatttttta ttgattcata acttaagaat actacgaatt    9600
```

| | |
|---|---:|
| actctaatat tttactttt cttatctctt gttatttaa catcggaatt actactaata | 9660 |
| ttaatttta ttttccatc cgcatttgct ccaacatttt tttaactata ctttccttt | 9720 |
| gttaataaat tatgttattg ttgaacaata aagaaaagt gcgtaacatt ttttattaaa | 9780 |
| aataattagg tatttctatc tgtggggtac cctcgaggtg gcagctctag agctagcgaa | 9840 |
| ttctttggtg aaattgctcg agtccctatc agtgatagat tgaaactcta tcattgatag | 9900 |
| agtataatat ctttgttcat tagagcgata aacttgaatt tgagagggaa cttc | 9954 |

<210> SEQ ID NO 22
<211> LENGTH: 8874
<212> TYPE: DNA
<213> ORGANISM: Artificial Sequence
<220> FEATURE:
<223> OTHER INFORMATION: pCas9ind

<400> SEQUENCE: 22

| | |
|---|---:|
| catggataaa aagtacagta ttggtctaga cataggaact aactctgttg ggtgggctgt | 60 |
| tataacagat gaatataaag ttccatcaaa aaaatttaaa gtattaggaa acactgatag | 120 |
| acattcaata aaaaaaaact tgataggtgc tttattattc gattcaggag agactgctga | 180 |
| agctacacgt ttaaaagaa cagctagacg tagatataca agaagaaaaa ataggatatg | 240 |
| ttatcttcaa gaaatttta gtaatgaaat ggcaaaagtt gatgattcat tctttcacag | 300 |
| actagaagaa agtttcttag ttgaagaaga taagaagcat gaaagacacc ctattttgg | 360 |
| taatatcgta gatgaagtag catatcatga gaagtatcca actatctatc atttaagaaa | 420 |
| gaaattagtt gattctacag ataaagctga tctgagatta atatatttag ctttagctca | 480 |
| tatgattaaa tttagaggac attttttaat agaaggtgat ttaaacccag acaacagcga | 540 |
| tgtagataaa ttatttatcc aattagttca aacttataat caattattcg aagagaatcc | 600 |
| aattaatgca agtggtgtag acgctaaggc tatattatca gctagattat caaaatctag | 660 |
| aagattagaa aatctaatag ctcaacttcc tggagaaaag aaaaatggac tttttgggaa | 720 |
| cctaatagct ctctcactcg gactaacacc aaattttaaa agcaattttg atcttgctga | 780 |
| agacgcaaag ttacaactat caaaggatac atacgatgat gatttagata atttgttagc | 840 |
| tcaaataggt gatcaatatg ctgatttgtt tcttgcagca aaaaacttaa gtgatgcaat | 900 |
| tttactatca gatatactta gagtaaatac agaaataaca aaggctccctt tatcagcaag | 960 |
| tatgattaaa cgatatgatg agcatcatca agatttaaca ttattaaagg cacttgtaag | 1020 |
| acaacaatta ccagaaaaat ataaagaaat tttctttgat caatctaaaa atggatatgc | 1080 |
| tggatatata gacggtggag caagtcaaga agagtttat aaatttataa agcctatttt | 1140 |
| agaaaaaatg gatggaactg aagaattact tgttaaactt aacagagaag atttacttag | 1200 |
| aaaacaaaga acttttgata atggttcaat tcctcaccaa attcatttag agaattaca | 1260 |
| tgctatacta agaagacaag aagatttta tccatttctt aaagataata gagaaaaaat | 1320 |
| tgaaaaaatt ttaacttta gaataccata ttatgtagga ccacttgcaa ggggaaattc | 1380 |
| aagatttgca tggatgacta gaaaatcaga agaaactata ccccgtggaa ttttgaaga | 1440 |
| agtagtagat aaaggagcta gtgctcaatc atttatagaa agaatgacaa attttgataa | 1500 |
| gaatcttcct aacgaaaagg ttttgccaaa gcatagcctt ctttatgagt atttacagt | 1560 |
| ttataatgag cttactaaag taaaatacgt tacagaagga atgagaaaac cagcatttt | 1620 |
| gtctggtgaa caaagaaag caatagtaga cctattattt aaaacaaata ggaaggttac | 1680 |
| cgtaaagcaa cttaagaag attacttcaa aaaaattgaa tgctttgata gtgttgaaat | 1740 |

```
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acactttttg aagatagaga aatgatagaa gaaagattaa aaacatatgc   1920
acatcttttt gatgataagg ttatgaagca acttaaaaga agaagatata caggttgggg   1980
acgtttgtca agaaagctaa ttaatggtat tagagataaa caatcaggaa agactattct   2040
cgattttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa agaacatcc    2400 agttgaaaat actcaattgc aaaatgaaaa gttatatttg tattacttac aaaatggaag   2460
agatatgtat gttgatcaag aactcgatat taatagatta agtgactatg atgttgatca   2520
tattgttcct caatcatttt taaaagatga ttcaatcgat aacaaagtat aactagatc    2580 agataaaaat agaggaaagt cagataatgt accatctgaa gaagttgtta aaaaaatgaa   2640
gaactattgg agacaacttt taaatgcaaa gctaattaca caaagaaaat ttgacaattt   2700
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaggatttt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaatatt tcttttatag    3120 taatataatg aattttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
aaaagaactt cttggtatca caattatgga aagatcttca tttgaaaaaa atccaattga   3540 cttttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
```

```
tgatttaagt caactaggcg agagattaagt cgacaaagta ttgttaaaaa taactctgta    4140
gaattataaa ttagttctac agagttattt tttgacccgg gtatattgat aaaaataata    4200
atagtgggta taattaagtt gttaggaggt tagttagaat gatgtcaaga ttagataaaa    4260
gtaaagtgat taacagcgca ttagagctgc ttaatgaggt cggaatcgaa ggtttaacaa    4320
cccgtaaact cgcccagaag ctaggtgtag agcagcctac attgtattgg catgtaaaaa    4380
ataagcgggc tttgctcgac gccttagcca ttgagatgtt agataggcac catactcact    4440
tttgcccttt agaaggggaa agctggcaag attttttacg taataacgct aaaagttttta    4500 gatgtgcttt actaagtcat cgcgatggag caaaagtaca tttaggtaca cggcctacag    4560
aaaaacagta tgaaactctc gaaaatcaat tagccttttt atgccaacaa ggttttttcac    4620 tagagaatgc attatatgca ctcagcgctg tggggcattt tactttaggt tgcgtattgg    4680
aagatcaaga gcatcaagtc gctaaagaag aaagggaaac acctactact gatagtatgc    4740
cgccattatt acgacaagct atcgaattat ttgatcacca aggtgcagag ccagccttct    4800
tattcggcct tgaattgatc atatgcggat tagaaaaaca acttaaatgt gaaagtgggt    4860
cttaaaagca gcataacctt tttccgtgat ggtaacttca cggtaaccaa gatgtcgagt    4920
tgagctcgaa ttcgtaatca tggtcatagc tgtttcctgt gtgaaattgt tatccgctca    4980
caattccaca aacatacga gccggaagca taaagtgtaa agcctggggt gcctaatgag    5040
tgagctaact cacattaatt gcgttgcgct cactgcccgc tttccagtcg ggaaacctgt    5100
cgtgccagct gcattaatga atcggccaac gcgcggggag aggcggtttg cgtattgggc    5160
gctcttccgc ttcctcgctc actgactcgc tgcgctcggt cgttcggctg cggcgagcgg    5220
tatcagctca ctcaaaggcg gtaatacggt tatccacaga atcaggggat aacgcaggaa    5280
agaacatgtg agcaaaaggc cagcaaaagg ccaggaaccg taaaaaggcc gcgttgctgg    5340 cgttttttcca taggctccgc cccctgacg agcatcacaa aaatcgacgc tcaagtcaga    5400
ggtggcgaaa cccgacagga ctataaagat accaggcgtt tccccctgga agctccctcg    5460
tgcgctctcc tgttccgacc ctgccgctta ccggatacct gtccgccttt ctcccttcgg    5520
gaagcgtggc gctttctcat agctcacgct gtaggtatct cagttcggtg taggtcgttc    5580
gctccaagct gggctgtgtg cacgaacccc ccgttcagcc cgaccgctgc gccttatccg    5640
gtaactatcg tcttgagtcc aacccggtaa gacacgactt atcgccactg gcagcagcca    5700
ctggtaacag gattagcaga gcgaggtatg taggcggtgc tacagagttc ttgaagtggt    5760
ggcctaacta cggctacact agaaggacag tatttggtat ctgcgctctg ctgaagccag    5820
ttaccttcgg aaaaagagtt ggtagctctt gatccggcaa acaaaccacc gctggtagcg    5880
gtggtttttt tgtttgcaag cagcagatta cgcgcagaaa aaaaggatct caagaagatc    5940
ctttgatctt ttctacgggg tctgacgctc agtggaacga aaactcacgt taagggattt    6000
tggtcatgag attatcaaaa aggatcttca cctagatcct ttttaaattaa aaatgaagtt    6060 ttaaatcaat ctaaagtata tatgagtaaa cttggtctga cagttaccag gtccactgcc    6120
gggcctcttg cgggatcaaa agaaaaacga atgatacac caatcagtgc aaaaaaagat    6180
ataatgggag ataagacggt tcgtgttcgt gctgacttgc accatatcat aaaaatcgaa    6240
acagcaaaga atggcggaaa cgtaaaagaa gttatggaaa taagacttag aagcaaactt    6300
aagagtgtgt tgatagtgca gtatcttaaa attttgtata ataggaattg aagttaaatt    6360
agatgctaaa aatttgtaat taagaaggag tgattacatg aacaaaaata taaaatattc    6420
tcaaaacttt ttaacgagtg aaaaagtact caaccaaata ataaaacaat tgaatttaaa    6480
```

```
agaaaccgat accgtttacg aaattggaac aggtaaaggg catttaacga cgaaactggc    6540
taaaataagt aaacaggtaa cgtctattga attagacagt catctattca acttatcgtc    6600
agaaaaatta aaactgaata ctcgtgtcac tttaattcac caagatattc tacagtttca    6660
attccctaac aaacagaggt ataaaattgt tgggagtatt ccttaccatt taagcacaca    6720
aattattaaa aaagtggttt ttgaaagcca tgcgtctgac atctatctga ttgttgaaga    6780
aggattctac aagcgtacct tggatattca ccgaacacta gggttgctct tgcacactca    6840
agtctcgatt cagcaattgc ttaagctgcc agcggaatgc tttcatccta aaccaaaagt    6900
aaacagtgtc ttaataaaac ttacccgcca taccacagat gttccagata aatattggaa    6960
gctatatacg tactttgttt caaaatgggt caatcgagaa tatcgtcaac tgtttactaa    7020
aaatcagttt catcaagcaa tgaaacacgc caaagtaaac aatttaagta ccgttactta    7080
tgagcaagta ttgtctattt ttaatagtta tctattattt aacgggagga ataattcta    7140 tgagtcccta ggcaggcctc cgccattatt ttttgaaca attgacaatt catttcttat    7200
tttttattaa gtgatagtca aaaggcataa cagtgctgaa tagaaagaaa tttacagaaa    7260
agaaaattat agaatttagt atgattaatt atactcattt atgaatgttt aattgaatac    7320
aaaaaaaaat acttgttatg tattcaatta cgggttaaaa tatagacaag ttgaaaaatt    7380
taataaaaaa ataagtcctc agctcttata tattaagcta ccaacttagt atataagcca    7440
aaacttaaat gtgctaccaa cacatcaagc cgttagagaa ctctatctat agcaatattt    7500
caaatgtacc gacatacaag agaaacatta actatatata ttcaatttat gagattatct    7560
taacagatat aaatgtaaat tgcaataagt aagatttaga agtttatagc ctttgtgtat    7620
tggaagcagt acgcaaaggc ttttttattt gataaaaatt agaagtatat ttatttttc    7680 ataattaatt tatgaaaatg aaaggggggtg agcaaagtga cagaggaaag cagtatctta    7740
tcaaataaca aggtattagc aatatcatta ttgactttag cagtaaacat tatgactttt    7800
atagtgcttg tagctaagta gtacgaaagg gggagcttta aaaagctcct tggaatacat    7860
agaattcata aattaattta tgaaaagaag ggcgtatatg aaaacttgta aaaattgcaa    7920
agagtttatt aaagatactg aaatatgcaa aatacattcg ttgatgattc atgataaaac    7980
agtagcaacc tattgcagta aatacaatga gtcaagatgt ttacataaag ggaaagtcca    8040
atgtattaat tgttcaaaga tgaaccgata tggatggtgt gccataaaaa tgagatgttt    8100
tacagaggaa gaacagaaaa aagaacgtac atgcattaaa tattatgcaa ggagctttaa    8160
aaaagctcat gtaaagaaga gtaaaagaa aaataatttt atttattaat ttaatattga    8220
gagtgccgac acagtatgca ctaaaaaata tatctgtggt gtagtgagcc gatacaaaag    8280
gatagtcact cgcattttca taatacatct tatgttatga ttatgtgtcg gtgggacttc    8340
acgacgaaaa cccacaataa aaaagagtt cggggtaggg ttaagcatag ttgaggcaac    8400
taaacaatca agctaggata tgcagtagca gaccgtaagg tcgttgttta ggtgtgttgt    8460
aatacatacg ctattaagat gtaaaaatac ggataccaat gaagggaaaa gtataatttt    8520
tggatgtagt ttgtttgttc atctatgggc aaactacgtc caaagccgtt tccaaatctg    8580
ctaaaaagta tatcctttct aaaatcaaag tcaagtatga aatcataaat aaagtttaat    8640
tttgaagtta ttatgatatt atgttttct attaaaataa attaagtata tagaatagtt    8700
taataatagt atatacttaa tgtgataagt gtctgacagt gtcacagaaa ggatgattgt    8760
tatggattat aagcggctcg agtccctatc agtgatagat tgaaactcta tcattgatag    8820
```

```
agtataatat ctttgttcat tagagcgata aacttgaatt tgagagggaa cttc           8874

<210> SEQ ID NO 23
<211> LENGTH: 10534
<212> TYPE: DNA
<213> ORGANISM: Artificial Sequence
<220> FEATURE:
<223> OTHER INFORMATION: pCas9acr

<400> SEQUENCE: 23
cgaattcgta atcatggtca tagctgtttc ctgtgtgaaa ttgttatccg ctcacaattc       60
cacacaacat acgagccgga agcataaagt gtaaagcctg gggtgcctaa tgagtgagct      120
aactcacatt aattgcgttg cgctcactgc ccgctttcca gtcgggaaac ctgtcgtgcc      180
agctgcatta atgaatcggc caacgcgcgg ggagaggcgg tttgcgtatt gggcgctctt      240
ccgcttcctc gctcactgac tcgctgcgct cggtcgttcg gctgcggcga gcggtatcag      300
ctcactcaaa ggcggtaata cggttatcca cagaatcagg ggataacgca ggaaagaaca      360
tgtgagcaaa aggccagcaa aaggccagga accgtaaaaa ggccgcgttg ctggcgtttt      420
tccataggct ccgcccccct gacgagcatc acaaaaatcg acgctcaagt cagaggtggc      480
gaaacccgac aggactataa agataccagg cgtttccccc tggaagctcc ctcgtgcgct      540
ctcctgttcc gaccctgccg cttaccggat acctgtccgc ctttctccct tcgggaagcg      600
tggcgctttc tcatagctca cgctgtaggt atctcagttc ggtgtaggtc gttcgctcca      660
agctgggctg tgtgcacgaa ccccccgttc agcccgaccg ctgcgcctta tccggtaact      720
atcgtcttga gtccaacccg gtaagacacg acttatcgcc actggcagca gccactggta      780
acaggattag cagagcgagg tatgtaggcg gtgctacaga gttcttgaag tggtggccta      840
actacggcta cactagaagg acagtatttg gtatctgcgc tctgctgaag ccagttacct      900
tcggaaaaag agttggtagc tcttgatccg gcaaacaaac caccgctggt agcggtggtt      960
ttttttgttg caagcagcag attacgcgca gaaaaaaagg atctcaagaa gatcctttga     1020
tcttttctac ggggtctgac gctcagtgga acgaaaactc acgttaaggg attttggtca     1080
tgagattatc aaaaaggatc ttcacctaga tccttttaaa ttaaaaatga agttttaaat     1140
caatctaaag tatatatgag taaacttggt ctgacagtta ccaggtccac tgccgggcct     1200
cttgcgggat caaagaaaaa acgaaatgat acaccaatca gtgcaaaaaa agatataatg     1260
ggagataaga cggttcgtgt tcgtgctgac ttgcaccata tcataaaaat cgaaacagca     1320
aagaatggcg gaaacgtaaa agaagttatg gaaataagac ttagaagcaa acttaagagt     1380
gtgttgatag tgcagtatct taaaattttg tataatagga attgaagtta aattagatgc     1440
taaaaatttg taattaagaa ggagtgatta catgaacaaa aatataaaat attctcaaaa     1500 cttttttaacg agtgaaaaag tactcaacca aataataaaa caattgaatt taaaagaaac     1560
cgataccgtt tacgaaattg gaacaggtaa agggcattta acgacgaaac tggctaaaat     1620
aagtaaacag gtaacgtcta ttgaattaga cagtcatcta ttcaacttat cgtcagaaaa     1680
attaaaactg aatactcgtg tcactttaat tcaccaagat attctacagt ttcaattccc     1740
taacaaacag aggtataaaa ttgttgggag tattccttac catttaagca cacaaattat     1800
taaaaaagtg gtttttgaaa gccatgcgtc tgacatctat ctgattgttg aagaaggatt     1860
ctacaagcgt accttggata ttcaccgaac actagggttg ctcttgcaca ctcaagtctc     1920
gattcagcaa ttgcttaagc tgccagcgga atgcttcat cctaaaccaa agtaaacag      1980 tgtcttaata aaacttaccc gccataccac agatgttcca gataaatatt ggaagctata     2040
```

```
tacgtacttt gtttcaaaat gggtcaatcg agaatatcgt caactgttta ctaaaaatca   2100
gtttcatcaa gcaatgaaac acgccaaagt aaacaattta agtaccgtta cttatgagca   2160
agtattgtct atttttaata gttatctatt atttaacggg aggaaataat tctatgagtc   2220
cctaggcagg cctccgccat tattttttg aacaattgac aattcatttc ttattttta    2280 ttaagtgata gtcaaaaggc ataacagtgc tgaatagaaa gaaatttaca gaaaagaaaa   2340
ttatagaatt tagtatgatt aattatactc atttatgaat gtttaattga atacaaaaaa   2400
aaatacttgt tatgtattca attacgggtt aaaatataga caagttgaaa aatttaataa   2460
aaaaataagt cctcagctct tatatattaa gctaccaact tagtatataa gccaaaactt   2520
aaatgtgcta ccaacacatc aagccgttag agaactctat ctatagcaat atttcaaatg   2580
taccgacata caagagaaac attaactata tatattcaat ttatgagatt atcttaacag   2640
atataaatgt aaattgcaat aagtaagatt tagaagttta tagcctttgt gtattggaag   2700
cagtacgcaa aggcttttt atttgataaa aattagaagt atatttattt tttcataatt   2760
aatttatgaa aatgaaaggg ggtgagcaaa gtgacagagg aaagcagtat cttatcaaat   2820
aacaaggtat tagcaatatc attattgact ttagcagtaa acattatgac ttttatagtg   2880
cttgtagcta agtagtacga aaggggggagc tttaaaaagc tccttggaat acatagaatt   2940
cataaattaa tttatgaaaa gaagggcgta tatgaaaact tgtaaaaatt gcaagagtt    3000 tattaaagat actgaaatat gcaaaataca ttcgttgatg attcatgata aaacagtagc   3060
aacctattgc agtaaataca atgagtcaag atgtttacat aaagggaaag tccaatgtat   3120
taattgttca aagatgaacc gatatggatg gtgtgccata aaaatgagat gttttacaga   3180
ggaagaacag aaaaaagaac gtacatgcat taaatattat gcaaggagct ttaaaaaagc   3240
tcatgtaaag aagagtaaaa agaaaaaata atttatttat taatttaata ttgagagtgc   3300
cgacacagta tgcactaaaa aatatatctg tggtgtagtg agccgataca aaaggatagt   3360
cactcgcatt ttcataatac atcttatgtt atgattatgt gtcggtggga cttcacgacg   3420
aaaacccaca ataaaaaaag agttcggggt agggttaagc atagttgagg caactaaaca   3480
atcaagctag gatatgcagt agcagaccgt aaggtcgttg tttaggtgtg ttgtaataca   3540
tacgctatta agatgtaaaa atacggatac caatgaaggg aaaagtataa ttttggatg    3600 tagtttgttt gttcatctat gggcaaacta cgtccaaagc cgtttccaaa tctgctaaaa   3660
agtatatcct ttctaaaatc aaagtcaagt atgaaatcat aaataaagtt taattttgaa   3720
gttattatga tattatgttt ttctattaaa ataaattaag tatatagaat agtttaataa   3780
tagtatatac ttaatgtgat aagtgtctga cagtgtcaca gaaaggatga ttgttatgga   3840
ttataagcgc ctcgagtccc tatcagtgat agattgaaac tctatcattg atagagtata   3900
atatctttgt tcattagagc gataaacttg aatttgagag ggaacttcca tggataaaaa   3960
gtacagtatt ggtctagaca taggaactaa ctctgttggg tgggctgtta taacagatga   4020
atataaagtt ccatcaaaaa aatttaaagt attaggaaac actgatagac attcaataaa   4080
aaaaaacttg ataggtgctt tattattcga ttcaggagag actgctgaag ctacacgttt   4140
aaaaagaaca gctagacgta gatatacaag aagaaaaaat aggatatgtt atcttcaaga   4200 aattttagt aatgaaatgg caaaagttga tgattcattc tttcacagac tagaagaaag    4260
tttcttagtt gaagaagata agaagcatga aagcacccct atttttggta atatcgtaga   4320
tgaagtagca tatcatgaga agtatccaac tatctatcat ttaagaaaga aattagttga   4380
```

```
ttctacagat aaagctgatc tgagattaat atatttagct ttagctcata tgattaaatt    4440
tagaggacat tttttaatag aaggtgattt aaacccagac aacagcgatg tagataaatt    4500
atttatccaa ttagttcaaa cttataatca attattcgaa gagaatccaa ttaatgcaag    4560
tggtgtagac gctaaggcta tattatcagc tagattatca aaatctagaa gattagaaaa    4620
tctaatagct caacttcctg gagaaaagaa aaatggactt tttgggaacc taatagctct    4680
ctcactcgga ctaacaccaa attttaaaag caattttgat cttgctgaag acgcaaagtt    4740
acaactatca aaggatacat acgatgatga tttagataat ttgttagctc aaataggtga    4800
tcaatatgct gatttgtttc ttgcagcaaa aaacttaagt gatgcaattt tactatcaga    4860
tatacttaga gtaaatacag aaataacaaa ggctccttta tcagcaagta tgattaaacg    4920
atatgatgag catcatcaag atttaacatt attaaaggca cttgtaagac aacaattacc    4980
agaaaaatat aaagaaattt tctttgatca atctaaaaat ggatatgctg atatatagaa    5040
cggtggagca agtcaagaag agtttttaaa atttataaag cctatcttag aaaaaatgga    5100
tggaactgaa gaattacttg ttaaacttaa cagagaagat ttacttagaa aacaaagaac    5160
ttttgataat ggttcaattc ctcaccaaat tcatttagga gaattacatg ctatactaag    5220
aagacaagaa gattttatc catttcttaa agataataga gaaaaaattg aaaaaatttt    5280
aactttagaa ataccatatt atgtaggacc acttgcaagg ggaaattcaa gatttgcatg    5340
gatgactaga aaatcagaag aaactataac cccgtggaat tttgaagaag tagtagataa    5400
aggagctagt gctcaatcat ttatagaaag aatgacaaat tttgataaga atcttcctaa    5460
cgaaaaggtt ttgccaaagc atagccttct ttatgagtat tttacagttt ataatgagct    5520
tactaaagta aaatacgtta cagaaggaat gagaaaacca gcattttgt ctggtgaaca    5580
aaagaaagca atagtagacc tattatttaa aacaaatagg aaggttaccg taaagcaact    5640
taaagaagat tacttcaaaa aaattgaatg ctttgatagt gttgaaatat caggagttga    5700
agatagattt aatgcttcac ttggtacata tcacgatctc ttaaaaatta taaaagataa    5760
ggatttttta gataatgaag aaaatgaaga tattcttgaa gatatagtat taacattgac    5820
acttttgaa gatagagaaa tgatagaaga aagattaaaa acatatgcac atcttttga    5880
tgataaggtt atgaagcaac ttaaaagaag aagatataca ggttggggac gtttgtcaag    5940
aaagctaatt aatggtatta gagataaaca atcaggaaag actattctcg attttcttaa    6000
atcagatgga tttgctaata gaaactttat gcaattaatt catgatgatt ctcttacttt    6060
caaagaggat attcaaaagg ctcaagtttc tggacaaggc gatagcttac acgaacacat    6120
tgctaacctt gcagggagcc ccgctatcaa aaaaggaatt ttacaaacag ttaaagttgt    6180
agatgaactt gttaaagtta tgggaagaca caaacctgag aatatagtta tagaaatggc    6240
cagagaaaat caaacaacac aaaaaggaca aaaaaattct agagagagaa tgaagagaat    6300
tgaagaagga ataaaagagc taggatcaca aatattaaaa gaacatccag ttgaaaatac    6360
tcaattgcaa aatgaaaagt tatatttgta ttacttacaa aatggaagag atatgtatgt    6420
tgatcaagaa ctcgatatta atagattaag tgactatgat gttgatcata ttgttcctca    6480
atcatttta aaagatgatt caatcgataa caaagtatta actagatcag ataaaaatag    6540
aggaaagtca gataatgtac catctgaaga agttgttaaa aaaatgaaga actattggag    6600
acaactttta aatgcaaagc taattacaca aagaaatttt gacaatttaa caaaagcaga    6660
aagaggagga ttaagcgaat tagacaaagc tggatttata aaaagacaac ttgttgagac    6720
aagacaaata actaagcatg ttgctcaaat acttgattca agaatgaata caaaatatga    6780
```

-continued

```
tgaaaatgat aaattaatca gagaagtaaa agtaataaca ttaaagtcaa aattagtatc    6840
agatttcaga aaggattttc aattttacaa agttcgtgaa ataaataact atcatcatgc    6900
tcatgatgca tacttaaatg ctgttgtagg aactgctctt attaagaaat atcctaaact    6960
agaaagcgaa tttgtttatg gagattataa agtttatgat gtgcgcaaaa tgatcgcgaa    7020
atccgaacaa gaaatcggta aggctacagc aaaatatttc ttttatagta atataatgaa    7080 ttttttttaag acagaaataa ctttggctaa tggtgaaatc agaaaaagac cacttatcga    7140
aacaaatgga gagacaggag aaatagtatg ggataaagga agagattttg ctactgttag    7200
aaaagtacta agtatgccac aagtaaatat cgtaaagaaa actgaagttc aaactggagg    7260
tttctctaag gaatcaattt tacctaagag aaattcagat aagttaattg caaggaaaaa    7320
agattgggac ccaaaaaaat acggtggttt tgatagtcca acagttgcct atagtgttct    7380
tgtagtagcg aaagttgaga aggtaagtc aaaaaagttg aaaagcgtaa aagaacttct    7440
tggtatcaca attatggaaa gatcttcatt tgaaaaaaat ccaattgact ttttagaagc    7500
taagggttat aaagaagtta aaaaggattt aatcataaaa ctaccaaagt atagtctatt    7560
tgaactcgaa aacggaagaa aacgaatgct cgctagcgca ggagaacttc aaaaaggaaa    7620
tgaacttgcg ctgccatcaa agtatgtaaa tttcttatat ttagcttctc attatgagaa    7680
attaaaagga tcaccagagg ataatgaaca aaagcaacta tttgtagaac aacacaaaca    7740
ttatttagat gaaataatag aacaaatatc tgaattttct aaaagagtta tacttgccga    7800
cgcaaatcta gataaggtgc tttcagcgta taataaacac agagataaac caataagaga    7860
acaagcagaa aacattatcc atcttttttac attaactaat cttggtgcac cagctgcatt    7920
taagtacttt gatacaacaa tagatagaaa aagatacaca tctactaaag aagtattaga    7980
cgcaacttta atacatcaat ctattacagg gctttatgaa acaagaattg atttaagtca    8040
actaggcgga gattaagtcg acaaagtatt gttaaaaata actctgtaga attataaatt    8100
agttctacag agttattttt tgacccgggt atattgataa aaataataat agtgggtata    8160
attaagttgt taggaggtta gttagaatga tgtcaagatt agataaaagt aaagtgatta    8220
acagcgcatt agagctgctt aatgaggtcg gaatcgaagg tttaacaacc cgtaaactcg    8280
cccagaagct aggtgtagag cagcctacat gtattggca tgtaaaaaat aagcgggctt    8340
tgctcgacgc cttagccatt gagatgttag ataggcacca tactcacttt tgcccctttag    8400 aaggggaaag ctggcaagat ttttacgta ataacgctaa agttttaga tgtgctttac    8460 taagtcatcg cgatggagca aaagtacatt taggtacacg gcctacagaa aaacagtatg    8520
aaactctcga aaatcaatta gccttttat gccaacaagg ttttcacta gagaatgcat    8580 tatatgcact cagcgctgtg gggcatttta ctttaggttg cgtattggaa gatcaagagc    8640
atcaagtcgc taaagaagaa agggaaacac ctactactga tagtatgccg ccattattac    8700
gacaagctat cgaattattt gatcaccaag gtgcagagcc agccttctta ttcggccttg    8760
aattgatcat atgcggatta gaaaaacaac ttaaatgtga agtgggtct taaaagcagc    8820 ataacctttt tccgtgatgg taacttcacg gtaaccaaga tgtcgagttg agctcttagt    8880
tcaactcact ttttaaggtg attgtttgca tgtcattata aaattcttct tcatcctcgt    8940
attcttgatt ccaaccgttt ttaaatgcag atatgaattt ttcaactatt gattcatttt    9000
cactttcaga aattacatac tcgtttccat cattattaac tctaataatt agctgtgtta    9060
tactattgct atccgtacca ctcaatttca ctgtgtaatc tttgtttttt atttctctaa    9120
```

| | |
|---|---:|
| ttaagtcatt aatattcatt tcagccctcc tgtgaaattg ttatccgctc acaattccac | 9180 |
| gtcgactacc gcggattcta gattctgcag tatcttcatg gtattcattt tttaatatca | 9240 |
| ttttaccctc ccaatacatt taaaataatt atgtattcat gaaacatgat tgtatattta | 9300 |
| agaaacataa ttccatataa atcatttttc aaaatagttt ttacccataa ttaaatgtta | 9360 |
| atatgtaaat taatctttta gaatagttaa aaagttctaa aatatgttat aatgtttctt | 9420 |
| ataatcttat aaattttaat aactaatata taaagatatt tctttaaaat attcttatat | 9480 |
| ttagaagaat ttattttaaa ataaaaagct tttatgttga taaactgctt tgcaaagctc | 9540 |
| tcatgtaaat gtttaatata agactactat aaaattggct aattttatag gttaggaggt | 9600 |
| agaaatgcaa atattgtgga aaaagtatgt taaagaaaac tttgaaatga atgtagatga | 9660 |
| atgtggtata gaacaaggta taccaggatt aggatataac tatgaagtat tgaaaaatgc | 9720 |
| tgttattcat tacgtaacta agggatatgg aacttttaaa tttaatggta aggtatataa | 9780 |
| cttaaaacaa ggtgatattt ttatactact aaaaggtatg caagttgagt atgtggcttc | 9840 |
| tattgatgat ccttgggaat actactggat aggatttagt ggttcaaatg ctaatgagta | 9900 |
| tttaaataga acttctatta ctaactcctg tgttgctaat tgtgaagaaa actcaaaaat | 9960 |
| tccacagata atattaaata tgtgcgaaat atcaaaaact tataatcctt caagatctga | 10020 |
| tgacatacta ttactaaaag aactttactc attattgtac gcacttatag aagaattccc | 10080 |
| aaaaccttt gaatacaaag ataaggaatt acacacatat attcaagatg ctcttaattt | 10140 |
| cattaattct aattacatgc atagcataac tgttcaagaa attgctgatt atgtgaactt | 10200 |
| aagtagaagt tatttatata aaatgttcat aaaaaacctt ggaatttctc ctcaaagata | 10260 |
| tttaataaac cttagaatgt acaaagccac cctttttatta aaaagcacta aacttcctat | 10320 |
| aggagaagtc gcaagtagtg taggttatag tgactccctg ttatttttcaa aaactttttc | 10380 |
| aaaacatttt tcaatgtctc cactaaatta cagaaataat caagtaaata aaccaagtat | 10440 |
| ataaatttaa aatacagctt taaaacaaaa aaatttcaaa aataaaaagt ataacagagg | 10500 |
| cgtaaaattaa aacctctgtt atacttttg agct | 10534 |

<210> SEQ ID NO 24
<211> LENGTH: 5754
<212> TYPE: DNA
<213> ORGANISM: Artificial Sequence
<220> FEATURE:
<223> OTHER INFORMATION: pEC750S-uppHR

<400> SEQUENCE: 24

| | |
|---|---:|
| ataaggtacc aggaattaga gcagcgctat gttcagatac atttagtgct catgcaacaa | 60 |
| gagaacataa taatgctaat atattaacta tgggtcaaag ggttgttgga gcaggtcttg | 120 |
| ctttagatat agtaaaaaca tttatatcag ctaaatttga aggagatagg caccaaaaaa | 180 |
| gaatagataa gatttcagat attgaaaaaa agtatacaca ttagaaaaaa gcagctatgc | 240 |
| tgcaaataag atcaatttat attagaaaaa agcagctatg ctgcaaataa gatcaattta | 300 |
| tattagaaaa aagcagctat gctgcaaata agatcaattt atattagaaa aagcagctat | 360 |
| tgctacaaat aagatcaatt tatattagaa aaaagtagct atgctgcaac aatattaatt | 420 |
| tatattacta gaaagctaaa tggggtatat aaatataaag ggctataaat actaaaagca | 480 |
| aacttggagg aataataatg gtctagagct ggagatagat tatttggtac taagtaatta | 540 |
| gtaatctatt agaattaaaa gctatctaca taagttctg aatgacccaa gataatttta | 600 |
| ctgggggggaa tatagaaaat ggagagacga gataagaaaa attattactt ggatatggct | 660 |

```
gaaacagttt tagagagagg aacctgtcta aggagaaact atggttctat aattgttaaa    720
aatgatgaaa taatttctac tggatacaca ggagcaccta gaggtagaaa aaattgcatg    780
gatttgaata gttgcataag agaaaagttg aaagttccaa gaggtactca ttatgagttg    840
tgtaggagtg tacatagtga agctaatgca ataataagcg cttcgagctc gaattcgtaa    900
tcatggtcat agctgtttcc tgtgtgaaat tgttatccgc tcacaattcc acacaacata    960
cgagccggaa gcataaagtg taaagcctgg ggtgcctaat gagtgagcta actcacatta   1020
attgcgttgc gctcactgcc cgctttccag tcgggaaacc tgtcgtgcca gctgcattaa   1080
tgaatcggcc aacgcgcggg gagaggcggt ttgcgtattg ggcgctcttc cgcttcctcg   1140
ctcactgact cgctgcgctc ggtcgttcgg ctgcggcgag cggtatcagc tcactcaaag   1200
gcggtaatac ggttatccac agaatcaggg gataacgcag gaaagaacat gtgagcaaaa   1260
ggccagcaaa aggccaggaa ccgtaaaaag gccgcgttgc tggcgttttt ccataggctc   1320
cgcccccctg acgagcatca caaaaatcga cgctcaagtc agaggtggcg aaacccgaca   1380
ggactataaa gataccaggc gtttccccct ggaagctccc tcgtgcgctc tcctgttccg   1440
accctgccgc ttaccggata cctgtccgcc tttctccctt cgggaagcgt ggcgctttct   1500
catagctcac gctgtaggta tctcagttcg gtgtaggtcg ttcgctccaa gctgggctgt   1560
gtgcacgaac cccccgttca gcccgaccgc tgcgccttat ccggtaacta tcgtcttgag   1620
tccaacccgg taagacacga cttatcgcca ctggcagcag ccactggtaa caggattagc   1680
agagcgaggt atgtaggcgg tgctacagag ttcttgaagt ggtggcctaa ctacggctac   1740
actagaagaa cagtatttgg tatctgcgct ctgctgaagc cagttacctt cggaaaaaga   1800
gttggtagct cttgatccgg caaacaaacc accgctggta gcggtggttt ttttgtttgc   1860
aagcagcaga ttacgcgcag aaaaaaagga tctcaagaag atcctttgat cttttctacg   1920
gggtctgacg ctcagtggaa cgaaaactca cgttaaggga ttttggtcat gagattatca   1980
aaaaggatct tcacctagat ccttttaaat taaaaatgaa gttttaaatc aatctaaagt   2040
atatatgagt aaacttggtc tgacagttac caaagctagc ttaatactag tatatactta   2100
atgtgataag tgtctgacag ctgaccggtc taaagaggtc cgccaatgaa atctataaat   2160
aaactaaatt aagtttattt aattaacaac tatggatata aaataggtac taatcaaaat   2220
agtgaggagg atatatttga atacatacga acaaattaat aaagtgaaaa aaatacttcg   2280
gaaacattta aaaataacc ttattggtac ttacatgttt ggatcaggag ttgagagtgg   2340
actaaaacca aatagtgatc ttgacttttt agtcgtcgta tctgaaccat tgacagatca   2400
aagtaaagaa atacttatac aaaaaattag acctatttca agaaaatag gagataaaag   2460 caacttacga tatattgaat taacaattat tattcagcaa gaaatggtac cgtggaatca   2520
tcctcccaaa caagaattta tttatggaga atggttacaa gagctttatg aacaaggata   2580
cattcctcag aaggaattaa attcagattt aaccataatg ctttaccaag caaaacgaaa   2640
aaataaaaga atatacggaa attatgactt agaggaatta ctacctgata ttccatttc   2700 tgatgtgaga agagccatta tggattcgtc agaggaatta atagataatt atcaggatga   2760
tgaaaccaac tctatattaa ctttatgccg tatgatttta actatggaca cgggtaaaat   2820
cataccaaaa gatattgcgg gaaatgcagt ggctgaatct tctccattag aacatagga   2880 gagaattttg ttagcagttc gtagttatct tggagagaat attgaatgga ctaatgaaaa   2940
tgtaaattta actataaact atttaaataa cagattaaaa aaattataaa aaaattgaaa   3000
```

-continued

```
aaatggtgga aacacttttt tcaattttt  tgttttatta tttaatattt gggaaatatt  3060
cattctaatt ggtaatcaga ttttagaagt tgttaacttc aggtttgtct gtaactaaaa  3120
actagtattt aacctaggat caaaaaaatt tccaataatc ccactctaag ccacaaacac  3180
gccctataaa atcccgcttt aatcccactt tgagacacat gtaatattac tttacgccct  3240
agtatagtga taattttta  cattcaatgc cacgcaaaaa aataaagggg cactataata  3300
aaagttcctt cggaactaac taaagtaaaa aattatcttt acaacctccc caaaaaaaag  3360
aacaggtaca aagtacccta atacaagc  gtaaaaaaa  tgagggtaaa aataaaaaaa  3420
taaaaaaata aaaaataaaa aaataaaaaa aataaaaaaa taaaaaaata taaaaataaa  3480
aaaatataaa aataaaaaaa tataaaaata aaaaaataaa aaaatataaa aataaaaaaa  3540
taaaaaaata taaaaatatt ttttatttaa agtttgaaaa aattttttt  atattatata  3600
atctttgaag aaaagaatat aaaaaatgag cctttataaa agcccatttt ttttcatata  3660
cgtaatatga cgttctaatg tttttattgg tacttctaac attagagtaa tttctttatt  3720
tttaaagcct ttttctttaa gggctttat  ttttttct   aatacattta attcctcttt  3780
ttttgttgct tttcctttag cttttaattg ctcttgataa ttttttttac ctctaatatt  3840
ttctcttctc ttatattcct ttttagaaat tattattgtc atatatttt  gttcttcttc  3900
tgtaatttct aataactcta taagagtttc attcttatac ttatattgct tattttatc   3960
taaataacat ctttcagcac ttctagttgc tcttataact tctctttcac ttaaatgttg  4020
tctaaacata ctattaagtt ctaaaacatc atttaatgcc ttctcaatgt cttctgtaaa  4080
gctacaaaga taatatctat ataaaaataa tataagctct ctgtgtcctt ttaaatcata  4140
ttctcttagt tcacaaagtt ttattatgtc ttgtattctt ccataatata aacttctttc  4200
tctataaata taatttattt tgcttggtct accctttttc ctttcatatg gttttaattc  4260
aggtaaaaat ccattttgta tttctcttaa gtcataaata tattcgtact catctaatat  4320
attgactact gttttgatt  tagagttat  acttcctgga actcttaata ttctcgttgc  4380
atctaaggct tgtctatctg ctccaaagta ttttaattga ttatataaat attcttgaac  4440
cgctttccat aatggtaatg ctttactagg tactgcattt attatccata ttaaatacat  4500
tcctcttcca ctatctatta catagtttgg tataggaata ctttgattaa aataattctt  4560
ttctaagtcc attaatacct ggtctttagt tttgccagtt ttataataat ccaagtctat  4620
aaacagtgta tttaactctt ttatattttc taatcgccta cacggcttat aaaaggtatt  4680
tagagttata tagatatttt catcactcat atctaaatct tttaattcag cgtatttata  4740
gtgccattgg ctatatcctt ttttatctat aacgctcctg gttatccacc ctttacttct  4800
actatgaata ttatctatat agttcttttt attcagcttt aatgcgtttc tcacttattc  4860
acctccccctt ctgtaaaact aagaaaatta tatcatattt tcaataatta ttaactattc  4920
ttaaactctt aataaaaaat agagtaagtc cccaattgaa acttaatcta ttttttatgt  4980
tttaatttat tattttatt  aaaatatttt aaactaaatt aaatgattct ttttaattt   5040
ttactatttc attccataat atattactat aattatttac aaataatatt tcttcatttg  5100
taatatttag atgatttact aattttagtt tttatatatt aaataattaa tgtataattt  5160
atataaaaaa tcaaaggagc ttataaatta tgattatttc caagatact  aaagatttaa  5220
tttttttcaa ttttaacaat acttttgta  atattatgtt taaatttaat tgtatttttt  5280
tcatataata aagccgttga agtaaaccaa tccattttcc ttatgatgtt attattaaat  5340
ttaagtttta taataatatc tttattatat ttattgtttt taaaaaaact agtgaaattt  5400
```

```
ctagtgaaat ttccggcttt attaaactta tttttaggaa ttttattttc attttcatct    5460
ttacaggatt tgattatatc tttaaatatg ttttatcaaa tattatcttt ttctaaattt    5520
atatatattt ttattatatt tattattata tatattttat ttttaagttt ctttctaaca    5580
gctattaaaa agaaacttaa aaataaaaac acgtactcta aaccaataaa taaaactatt    5640
tttattattg ctgccttgat tggaatagtt tttagtaaaa ttaatttcaa tattccacaa    5700
tattatatta taagctagca ggcctcgaga tctccatgga cgcgtgacgt cgac          5754
```

<210> SEQ ID NO 25
<211> LENGTH: 884
<212> TYPE: DNA
<213> ORGANISM: Artificial Sequence
<220> FEATURE:
<223> OTHER INFORMATION: Repair template

<400> SEQUENCE: 25

```
ataaggtacc aggaattaga gcagcgctat gttcagatac atttagtgct catgcaacaa      60
gagaacataa taatgctaat atattaacta tgggtcaaag ggttgttgga gcaggtcttg     120
ctttagatat agtaaaaaca tttatatcag ctaaatttga aggagatagg caccaaaaaa     180
gaatagataa gatttcagat attgaaaaaa agtatacaca ttagaaaaaa gcagctatgc     240
tgcaaataag atcaatttat attagaaaaa agcagctatg ctgcaaataa gatcaattta     300
tattagaaaa aagcagctat gctgcaaata agatcaattt atattagaaa aaagcagcta     360
tgctacaaat aagatcaatt tatattagaa aaaagtagct atgctgcaac aatattaatt     420
tatattacta gaaagctaaa tggggtatat aaatataaag ggctataaat actaaaagca     480
aacttggagg aataataatg gtctagagct ggagatagat tatttggtac taagtaatta     540
gtaatctatt agaattaaaa gctatctaca taagtttctg aatgacccaa gataaatttta    600 ctgggggaa tatagaaaat ggagagacga gataagaaaa attattactt ggatattgct     660
gaaacagttt tagagagagg aacctgtcta aggagaaact atggttctat aattgttaaa     720
aatgatgaaa taatttctac tggatacaca ggagcaccta gaggtagaaa aaattgcatg     780
gatttgaata gttgcataag agaaaagttg aaagttccaa gaggtactca ttatgagttg     840
tgtaggagtg tacatagtga agctaatgca ataataagcg cttc                     884
```

<210> SEQ ID NO 26
<211> LENGTH: 500
<212> TYPE: DNA
<213> ORGANISM: Artificial Sequence
<220> FEATURE:
<223> OTHER INFORMATION: upp gene upstream fragment

<400> SEQUENCE: 26

```
ataaggtacc aggaattaga gcagcgctat gttcagatac atttagtgct catgcaacaa      60
gagaacataa taatgctaat atattaacta tgggtcaaag ggttgttgga gcaggtcttg     120
ctttagatat agtaaaaaca tttatatcag ctaaatttga aggagatagg caccaaaaaa     180
gaatagataa gatttcagat attgaaaaaa agtatacaca ttagaaaaaa gcagctatgc     240
tgcaaataag atcaatttat attagaaaaa agcagctatg ctgcaaataa gatcaattta     300
tattagaaaa aagcagctat gctgcaaata agatcaattt atattagaaa aaagcagcta     360
tgctacaaat aagatcaatt tatattagaa aaaagtagct atgctgcaac aatattaatt     420
tatattacta gaaagctaaa tggggtatat aaatataaag ggctataaat actaaaagca     480
```
aacttggagg aataataatg                                                500

<210> SEQ ID NO 27
<211> LENGTH: 377
<212> TYPE: DNA
<213> ORGANISM: Artificial Sequence
<220> FEATURE:
<223> OTHER INFORMATION: upp gene downstrean fragment

<400> SEQUENCE: 27
gctggagata gattatttgg tactaagtaa ttagtaatct attagaatta aaagctatct    60
acataagttt ctgaatgacc caagataatt ttactggggg gaatatagaa aatggagaga   120
cgagataaga aaaattatta cttggatatt gctgaaacag ttttagagag aggaacctgt   180
ctaaggagaa actatggttc tataattgtt aaaaatgatg aaataatttc tactggatac   240
acaggagcac ctagaggtag aaaaaattgc atggatttga atagttgcat aagagaaaag   300
ttgaaagttc caagaggtac tcattatgag ttgtgtagga gtgtacatag tgaagctaat   360
gcaataataa gcgcttc                                                  377

<210> SEQ ID NO 28
<211> LENGTH: 2666
<212> TYPE: DNA
<213> ORGANISM: Artificial Sequence
<220> FEATURE:
<223> OTHER INFORMATION: pEX-A2-gRNA-upp

<400> SEQUENCE: 28
ctcgagtatt tttgataaaa gcaatgatta acatggtttg acgtctgaga agagacgatt    60
ttctcaatag gagaaattaa ggtgcaaacc cttatcattc caccatgatc cacctgtagc   120
aagcatgttt tagagctaga aatagcaagt taaaataagg ctagtccgtt atcaacttga   180
aaaagtggca ccgagtcggt gcttttttg ccatggacct gcttttgctc gcttggatcc   240
gaattcctgt gtgaaattgt tatccgctca caattccaca caacatacga gccggaagca   300
taaagtgtaa agcctggggt gcctaatgag tgagctaact cacattaatt gcgttgcgct   360
cactgcccgc tttccagtcg ggaaacctgt cgtgccagct gcattaatga atcggccaac   420
gcgcggggag aggcggtttg cgtattgggc gctcttccgc ttcctcgctc actgactcgc   480
tgcgctcggt cgttcggctg cggcgagcgg tatcagctca ctcaaaggcg gtaatacggt   540
tatccacaga atcaggggat aacgcaggaa agaacatgtg agcaaaaggc cagcaaaagg   600
ccaggaaccg taaaaaggcc gcgttgctgg cgttttttcca taggctccgc cccccctgacg   660
agcatcacaa aaatcgacgc tcaagtcaga ggtggcgaaa cccgacagga ctataaagat   720
accaggcgtt tcccctggaa gctccctcg tgcgctctcc tgttccgacc ctgccgctta   780
ccggatacct gtccgccttt ctcccttcgg gaagcgtggc gctttctcat agctcacgct   840
gtaggtatct cagttcggtg taggtcgttc gctccaagct gggctgtgtg cacgaacccc   900
ccgttcagcc cgaccgctgc gccttatccg gtaactatcg tcttgagtcc aacccggtaa   960
gacacgactt atcgccactg gcagcagcca ctggtaacag gattagcaga gcgaggtatg  1020
taggcggtgc tacagagttc ttgaagtggt ggcctaacta cggctacact agaagaacag  1080
tatttggtat ctgcgctctg ctgaagccag ttaccttcgg aaaagagtt ggtagctctt  1140
gatccggcaa acaaaccacc gctggtagcg gtggtttttt tgtttgcaag cagcagatta  1200
cgcgcagaaa aaaaggatct caagaagatc ctttgatctt ttctacgggg tctgacgctc  1260
agtggaacga aaactcacgt taagggattt tggtcatgag attatcaaaa aggatcttca  1320

```
cctagatcct tttaaattaa aaatgaagtt ttaaatcaat ctaaagtata tatgagtaaa    1380
cttggtctga cagttaccaa tgcttaatca gtgaggcacc tatctcagcg atctgtctat    1440
ttcgttcatc catagttgcc tgactccccg tcgtgtagat aactacgata cgggagggct    1500
taccatctgg ccccagtgct gcaatgatac cgcgactccc acgctcaccg gctccagatt    1560
tatcagcaat aaaccagcca gccggaaggg ccgagcgcag aagtggtcct gcaactttat    1620
ccgcctccat ccagtctatt aattgttgcc gggaagctag agtaagtagt tcgccagtta    1680
atagtttgcg caacgttgtt gccattgcta caggcatcgt ggtgtcacgc tcgtcgtttg    1740
gtatggcttc attcagctcc ggttcccaac gatcaaggcg agttacatga tcccccatgt    1800
tgtgcaaaaa agcggttagc tccttcggtc ctccgatcgt tgtcagaagt aagttggccg    1860
cagtgttatc actcatggtt atggcagcac tgcataattc tcttactgtc atgccatccg    1920
taagatgctt ttctgtgact ggtgagtact caaccaagtc attctgagaa tagtgtatgc    1980
ggcgaccgag ttgctcttgc ccggcgtcaa tacgggataa taccgcgcca catagcagaa    2040
ctttaaaagt gctcatcatt ggaaaacgtt cttcggggcg aaaactctca aggatcttac    2100
cgctgttgag atccagttcg atgtaaccca ctcgtgcacc caactgatct tcagcatctt    2160
ttactttcac cagcgtttct gggtgagcaa aaacaggaag gcaaaatgcc gcaaaaaagg    2220
gaataagggc gacacggaaa tgttgaatac tcatactctt cctttttcaa tattattgaa    2280
gcatttatca gggttattgt ctcatgagcg gatacatatt tgaatgtatt tagaaaaata    2340
aacaaatagg ggttccgcgc acatttcccc gaaaagtgcc acctgacgtc taagaaacca    2400
ttattatcat gacattaacc tataaaaata ggcgtatcac gaggccctttt cgtctcgcgc    2460 gtttcggtga tgacggtgaa aacctctgac acatgcagct cccggagacg gtcacagctt    2520
gtctgtaagc ggatgccggg agcagacaag cccgtcaggg cgcgtcagcg ggtgttggcg    2580
ggtgtcgggg ctggcttaac tatgcggcat cagagcagat tgtactgaga gtgcaccaat    2640
tgggtaccga gctcgcggcc gcaagc                                         2666
```

<210> SEQ ID NO 29
<211> LENGTH: 203
<212> TYPE: DNA
<213> ORGANISM: Artificial Sequence
<220> FEATURE:
<223> OTHER INFORMATION: gRNA expression cassette

<400> SEQUENCE: 29

```
tattttttgat aaaagcaatg attaacatgg tttgacgtct gagaagagac gatttctca     60 ataggagaaa ttaaggtgca aacccttatc attccaccat gatccacctg tagcaagcat    120
gttttagagc tagaaatagc aagttaaaat aaggctagtc cgttatcaac ttgaaaaagt    180
ggcaccgagt cggtgctttt ttt                                            203
```

<210> SEQ ID NO 30
<211> LENGTH: 100
<212> TYPE: DNA
<213> ORGANISM: Artificial Sequence
<220> FEATURE:
<223> OTHER INFORMATION: Constitutive promoter

<400> SEQUENCE: 30

```
tattttttgat aaaagcaatg attaacatgg tttgacgtct gagaagagac gatttctca     60 ataggagaaa ttaaggtgca aacccttatc attccaccat                          100
```

<210> SEQ ID NO 31
<211> LENGTH: 20
<212> TYPE: DNA
<213> ORGANISM: Artificial Sequence
<220> FEATURE:
<223> OTHER INFORMATION: Protospacer targeting upp

<400> SEQUENCE: 31
gatccacctg tagcaagcat                                                  20

<210> SEQ ID NO 32
<211> LENGTH: 5954
<212> TYPE: DNA
<213> ORGANISM: Artificial Sequence
<220> FEATURE:
<223> OTHER INFORMATION: pEC750S-deltaupp

<400> SEQUENCE: 32

| | |
|---|---|
| ataaggtacc aggaattaga gcagcgctat gttcagatac atttagtgct catgcaacaa | 60 |
| gagaacataa taatgctaat atattaacta tgggtcaaag ggttgttgga gcaggtcttg | 120 |
| ctttagatat agtaaaaaca tttatatcag ctaaatttga aggagatagg caccaaaaaa | 180 |
| gaatagataa gatttcagat attgaaaaaa agtatacaca ttagaaaaaa gcagctatgc | 240 |
| tgcaaataag atcaatttat attagaaaaa agcagctatg ctgcaaataa gatcaattta | 300 |
| tattagaaaa aagcagctat gctgcaaata agatcaattt atattagaaa aaagcagcta | 360 |
| tgctacaaat aagatcaatt tatattagaa aaagtagct atgctgcaac aatattaatt | 420 |
| tatattacta gaaagctaaa tggggtatat aaatataaag ggctataaat actaaaagca | 480 |
| aacttggagg aataataatg gtctagagct ggagatagat tatttggtac taagtaatta | 540 |
| gtaatctatt agaattaaaa gctatctaca taagtttctg aatgacccaa gataatttta | 600 |
| ctgggggaa tatagaaaat ggagagacga gataagaaaa attattactt ggatattgct | 660 |
| gaaacagttt tagagagagg aacctgtcta aggagaaact atggttctat aattgttaaa | 720 |
| aatgatgaaa taatttctac tggatacaca ggagcaccta gaggtagaaa aaattgcatg | 780 |
| gatttgaata gttgcataag agaaaagttg aaagttccaa gaggtactca ttatgagttg | 840 |
| tgtaggagtg tacatagtga agctaatgca ataataagcg cttcgagctc gaattcgtaa | 900 |
| tcatggtcat agctgtttcc tgtgtgaaat tgttatccgc tcacaattcc acacaacata | 960 |
| cgagccggaa gcataaagtg taaagcctgg ggtgcctaat gagtgagcta actcacatta | 1020 |
| attgcgttgc gctcactgcc cgctttccag tcgggaaacc tgtcgtgcca gctgcattaa | 1080 |
| tgaatcggcc aacgcgcggg gagaggcggt ttgcgtattg ggcgctcttc cgcttcctcg | 1140 |
| ctcactgact cgctgcgctc ggtcgttcgg ctgcggcgag cggtatcagc tcactcaaag | 1200 |
| gcggtaatac ggttatccac agaatcaggg gataacgcag gaaagaacat gtgagcaaaa | 1260 |
| ggccagcaaa aggccaggaa ccgtaaaaag gccgcgttgc tggcgttttt ccataggctc | 1320 |
| cgcccccctg acgagcatca caaaaatcga cgctcaagtc agaggtggcg aaacccgaca | 1380 |
| ggactataaa gataccaggc gtttccccct ggaagctccc tcgtgcgctc tcctgttccg | 1440 |
| accctgccgc ttaccggata cctgtccgcc tttctccctt cgggaagcgt ggcgctttct | 1500 |
| catagctcac gctgtaggta tctcagttcg gtgtaggtcg ttcgctccaa gctgggctgt | 1560 |
| gtgcacgaac cccccgttca gcccgaccgc tgcgccttat ccggtaacta tcgtcttgag | 1620 |
| tccaacccgg taagacacga cttatcgcca ctggcagcag ccactggtaa caggattagc | 1680 |
| agagcgaggt atgtaggcgg tgctacagag ttcttgaagt ggtggcctaa ctacggctac | 1740 |

```
actagaagaa cagtatttgg tatctgcgct ctgctgaagc cagttacctt cggaaaaaga    1800
gttggtagct cttgatccgg caaacaaacc accgctggta gcggtggttt ttttgtttgc    1860
aagcagcaga ttacgcgcag aaaaaaagga tctcaagaag atcctttgat cttttctacg    1920
gggtctgacg ctcagtggaa cgaaaactca cgttaaggga ttttggtcat gagattatca    1980
aaaaggatct tcacctagat ccttttaaat taaaaatgaa gttttaaatc aatctaaagt    2040
atatatgagt aaacttggtc tgacagttac caaagctagc ttaatactag tatatactta    2100
atgtgataag tgtctgacag ctgaccggtc taaagaggtc cgccaatgaa atctataaat    2160
aaactaaatt aagtttattt aattaacaac tatggatata aaataggtac taatcaaaat    2220
agtgaggagg atatatttga atacatacga acaaattaat aaagtgaaaa aaatacttcg    2280
gaaacattta aaaaataacc ttattggtac ttacatgttt ggatcaggag ttgagagtgg    2340
actaaaacca aatagtgatc ttgactttt agtcgtcgta tctgaaccat tgacagatca    2400
aagtaaagaa atacttatac aaaaaattag acctatttca aagaaaatag gagataaaag    2460
caacttacga tatattgaat aacaattat tattcagcaa gaaatggtac cgtggaatca    2520
tcctcccaaa caagaattta tttatggaga atggttacaa gagctttatg aacaaggata    2580
cattcctcag aaggaattaa attcagattt aaccataatg ctttaccaag caaaacgaaa    2640
aaataaaaga atatacggaa attatgactt agaggaatta ctacctgata ttccattttc    2700
tgatgtgaga agagccatta tggattcgtc agaggaatta atagataatt atcaggatga    2760
tgaaaccaac tctatattaa ctttatgccg tatgatttta actatggaca cgggtaaaat    2820
cataccaaaa gatattgcgg gaaatgcagt ggctgaatct tctccattag aacatagggaa    2880 gagaattttg ttagcagttc gtagttatct tggagagaat attgaatgga ctaatgaaaa    2940
tgtaaattta actataaact atttaaataa cagattaaaa aattataaa aaaattgaaa    3000 aaatggtgga aacactttt tcaattttt tgttttatta tttaatattt gggaaatatt    3060
cattctaatt ggtaatcaga ttttagaagt tgttaacttc aggtttgtct gtaactaaaa    3120
actagtattt aacctaggat caaaaaaatt tccaataatc ccactctaag ccacaaacac    3180
gccctataaa atcccgcttt aatcccactt tgagacacat gtaatattac tttacgccct    3240
agtatagtga taatttttta cattcaatgc cacgcaaaaa aataaagggg cactataata    3300
aaagttcctt cggaactaac taaagtaaaa aattatcttt acaacctccc caaaaaaaag    3360
aacaggtaca aagtacccta aatacaagc gtaaaaaaaa tgagggtaaa aataaaaaaa    3420
taaaaaaata aaaaaataaa aaaataaaaa aataaaaaaa taaaaaaata taaaaataaa    3480
aaaatataaa aataaaaaaa tataaaaata aaaaaataaa aaaatataaa aataaaaaaa    3540
taaaaaaata taaaaatatt ttttatttaa agtttgaaaa aaattttttt atattatata    3600
atctttgaag aaaagaatat aaaaaatgag cctttataaa agcccatttt ttttcatata    3660
cgtaatatga cgttctaatg ttttattgg tacttctaac attagagtaa tttctttatt    3720
tttaaagcct ttttctttaa gggctttat ttttttttctt aatacattta attcctcttt    3780
ttttgttgct tttcctttag cttttaattg ctcttgataa ttttttttac ctctaatatt    3840
ttctcttctc ttatattcct ttttagaaat tattattgtc atatatttt gttcttcttc    3900 tgtaatttct aataactcta taagagtttc attcttatac ttatattgct tattttatc    3960 taaataacat ctttcagcac ttctagttgc tcttataact tctctttcac ttaaatgttg    4020
tctaaacata ctattaagtt ctaaaacatc atttaatgcc ttctcaatgt cttctgtaaa    4080
```

```
gctacaaaga taatatctat ataaaaataa tataagctct ctgtgtcctt ttaaatcata   4140
ttctcttagt tcacaaagtt ttattatgtc ttgtattctt ccataatata aacttctttc   4200
tctataaata taatttattt tgcttggtct acccttttc ctttcatatg gttttaattc   4260
aggtaaaaat ccattttgta tttctcttaa gtcataaata tattcgtact catctaatat   4320
attgactact gtttttgatt tagagtttat acttcctgga actcttaata ttctcgttgc   4380
atctaaggct tgtctatctg ctccaaagta ttttaattga ttatataaat attcttgaac   4440
cgctttccat aatggtaatg ctttactagg tactgcattt attatccata ttaaatacat   4500
tcctcttcca ctatctatta catagtttgg tataggaata ctttgattaa aataattctt   4560
ttctaagtcc attaatacct ggtctttagt tttgccagtt ttataataat ccaagtctat   4620
aaacagtgta tttaactctt ttatattttc taatcgccta cacggcttat aaaaggtatt   4680
tagagttata tagatatttt catcactcat atctaaatct tttaattcag cgtatttata   4740
gtgccattgg ctatatcctt ttttatctat aacgctcctg gttatccacc ctttacttct   4800
actatgaata ttatctatat agttcttttt attcagcttt aatgcgtttc tcacttattc   4860
acctcccctt ctgtaaaact aagaaaatta tatcatattt tcaataatta ttaactattc   4920
ttaaactctt aataaaaaat agagtaagtc cccaattgaa acttaatcta ttttttatgt   4980
tttaatttat tatttttatt aaaatatttt aaactaaatt aaatgattct ttttaatttt   5040
ttactatttc attccataat atattactat aattatttac aaataatatt tcttcatttg   5100
taatatttag atgatttact aatttttagtt tttatatatt aaataattaa tgtataattt   5160
atataaaaaa tcaaaggagc ttataaatta tgattatttc caaagatact aaagatttaa   5220
ttttttttcaa ttttaacaat acttttttgta atattatgtt taaatttaat tgtatttttt   5280
tcatataata aagccgttga agtaaaccaa tccattttcc ttatgatgtt attattaaat   5340
ttaagtttta taataatatc tttattatat ttattgtttt taaaaaaact agtgaaattt   5400
ctagtgaaat ttccggcttt attaaactta tttttaggaa ttttattttc attttcatct   5460
ttacaggatt tgattatatc tttaaatatg ttttatcaaa tattatcttt tctaaattt   5520
atatatattt ttattatatt tattattata tatattttat ttttaagttt ctttctaaca   5580
gctattaaaa agaaacttaa aaataaaaac acgtactcta aaccaataaa taaaactatt   5640
tttattattg ctgccttgat tggaatagtt tttagtaaaa ttaatttcaa tattccacaa   5700
tattatatta taagctagca cgcctcgagt attttgata aaagcaatga ttaacatggt   5760
ttgacgtctg agaagagacg attttctcaa taggagaaat taaggtgcaa acccttatca   5820
ttccaccatg atccacctgt agcaagcatg ttttagagct agaaatagca agttaaaata   5880
aggctagtcc gttatcaact tgaaaaagtg gcaccgagtc ggtgcttttt ttgccatgga   5940
cgcgtgacgt cgac                                                    5954
```

<210> SEQ ID NO 33
<211> LENGTH: 5853
<212> TYPE: DNA
<213> ORGANISM: Artificial Sequence
<220> FEATURE:
<223> OTHER INFORMATION: pEC750C-deltaupp

<400> SEQUENCE: 33

```
atcaaaaaaa tttccaataa tcccactcta agccacaaac acgccctata aaatcccgct     60
ttaatcccac tttgagacac atgtaatatt actttacgcc ctagtatagt gataattttt    120
tacattcaat gccacgcaaa aaaataaagg ggcactataa taaaagttcc ttcggaacta    180
```

```
actaaagtaa aaaattatct ttacaacctc cccaaaaaaa agaacaggta caaagtaccc    240
tataatacaa gcgtaaaaaa aatgagggta aaaataaaaa aataaaaaaa taaaaaaata    300
aaaaaataaa aaaataaaaa aataaaaaaa tataaaaata aaaaaatata aaaataaaaa    360
aatataaaaa taaaaaaata aaaaaatata aaaataaaaa aataaaaaaa tataaaaata    420
ttttttattt aaagtttgaa aaaaattttt ttatattata taatctttga agaaaagaat    480
ataaaaaatg agcctttata aaagcccatt ttttttcata tacgtaatat gacgttctaa    540 tgttttatt ggtacttcta acattagagt aatttcttta ttttttaaagc ttttttctttt   600 aagggctttt attttttttc ttaatacatt taattcctct tttttgttg cttttccttt     660 agcttttaat tgctcttgat aatttttttt acctctaata ttttctcttc tcttatattc    720 cttttagaa attattattg tcatatattt ttgttcttct tctgtaattt ctaataactc     780
tataagagtt tcattcttat acttatattg cttattttta tctaaataac atctttcagc    840
acttctagtt gctcttataa cttctctttc acttaaatgt tgtctaaaca tactattaag    900
ttctaaaaca tcatttaatg ccttctcaat gtcttctgta aagctacaaa gataatatct    960
atataaaaat aatataagct ctctgtgtcc ttttaaatca tattctctta gttcacaaag   1020
ttttattatg tcttgtattc ttccataata taaacttctt tctctataaa tataatttat   1080
tttgcttggt ctacccttt tcctttcata tggttttaat tcaggtaaaa atccattttg    1140
tatttctctt aagtcataaa tatattcgta ctcatctaat atattgacta ctgtttttga   1200
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa tactttgatt aaaataattc ttttctaagt ccattaatac   1440
ctggtcttta gttttgccag ttttataata atccaagtct ataaacagtg tatttaactc   1500
ttttatattt tctaatcgcc tacacggctt ataaaaggta tttagagtta tatagatatt   1560
ttcatcactc atatctaaat cttttaattc agcgtattta tagtgccatt ggctatatcc   1620 tttttatct ataacgctcc tggttatcca ccctttactt ctactatgaa tattatctat    1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tattttttat gttttaattt attattttta   1860 ttaaatatt ttaaactaaa ttaaatgatt ctttttaatt tttactatt tcattccata     1920 atatattact ataattattt acaaataata tttcttcatt tgtaatattt agatgattta   1980
ctaattttag tttttatata ttaaataatt aatgtataat ttatataaaa aatcaaagga   2040
gcttataaat tatgattatt tccaaagata ctaaagattt aattttttc aattttaaca    2100 atacttttg taatattatg tttaaattta attgtatttt tttcatataa taagccgtt     2160 gaagtaaacc aatccatttt ccttatgatg ttattattaa atttaagtttt tataataata  2220 tctttattat atttattgtt tttaaaaaaa ctagtgaaat ttctagtgaa atttccggct   2280
ttattaaact tattttagg aatttttattt tcattttcat cttacagga tttgattata    2340 tcttttaaata tgttttatca aatattatct ttttctaaat ttatatatat ttttattata  2400
tttattatta tatatatttt attttttaagt ttctttctaa cagctattaa aaagaaactt  2460
aaaaataaaa acacgtactc taaaccaata aataaaacta ttttttattat tgctgccttg  2520
```

```
attggaatag ttttttagtaa aattaatttc aatattccac aatattatat tataagctag    2580
cacgcctcga gtatttttga taaaagcaat gattaacatg gtttgacgtc tgagaagaga    2640
cgattttctc aataggagaa attaaggtgc aaacccttat cattccacca tgatccacct    2700
gtagcaagca tgttttagag ctagaaatag caagttaaaa taaggctagt ccgttatcaa    2760
cttgaaaaag tggcaccgag tcggtgcttt ttttgccatg gacgcgtgac gtcgacataa    2820
ggtaccagga attagagcag cgctatgttc agatacattt agtgctcatg caacaagaga    2880
acataataat gctaatatat taactatggg tcaaagggtt gttggagcag gtcttgcttt    2940
agatatagta aaaacattta tatcagctaa atttgaagga gataggcacc aaaaaagaat    3000
agataagatt tcagatattg aaaaaagta tacacattag aaaaaagcag ctatgctgca    3060
aataagatca atttatatta gaaaaaagca gctatgctgc aaataagatc aatttatatt    3120
agaaaaagc agctatgctg caaataagat caatttatat tagaaaaaag cagctatgct    3180
acaaataaga tcaatttata ttagaaaaaa gtagctatgc tgcaacaata ttaatttata    3240
ttactagaaa gctaaatggg gtatataaat ataagggct ataaatacta aaagcaaact    3300
tggaggaata ataatggtct agagctggag atagattatt tggtactaag taattagtaa    3360
tctattagaa ttaaaagcta tctacataag tttctgaatg acccaagata attttactgg    3420
ggggaatata gaaaatggag agacgagata agaaaaatta ttacttggat attgctgaaa    3480
cagttttaga gagaggaacc tgtctaagga gaaactatgg ttctataatt gttaaaaatg    3540
atgaaataat ttctactgga tacacaggag cacctagagg tagaaaaaat tgcatggatt    3600
tgaatagttg cataagagaa aagttgaaag ttccaagagg tactcattat gagttgtgta    3660
ggagtgtaca tagtgaagct aatgcaataa taagcgcttc gagctcgaat tcgtaatcat    3720
ggtcatagct gtttcctgtg tgaaattgtt atccgctcac aattccacac aacatacgag    3780
ccggaagcat aaagtgtaaa gcctggggtg cctaatgagt gagctaactc acattaattg    3840
cgttgcgctc actgcccgct ttccagtcgg gaaacctgtc gtgccagctg cattaatgaa    3900
tcggccaacg cgcggggaga ggcggtttgc gtattgggcg ctcttccgct tcctcgctca    3960
ctgactcgct gcgctcggtc gttcggctgc ggcgagcgg atcagctcac tcaaaggcgg    4020
taatacggtt atccacagaa tcaggggata acgcaggaaa gaacatgtga gcaaaaggcc    4080
agcaaaaggc caggaaccgt aaaaaggccg cgttgctggc gtttttccat aggctccgcc    4140
cccctgacga gcatcacaaa aatcgacgct caagtcagag gtggcgaaac ccgacaggac    4200
tataaagata ccaggcgttt ccccctggaa gctccctcgt gcgctctcct gttccgaccc    4260
tgccgcttac cggatacctg tccgcctttc tcccttcggg aagcgtggcg ctttctcata    4320
gctcacgctg taggtatctc agttcggtgt aggtcgttcg ctccaagctg ggctgtgtgc    4380
acgaaccccc cgttcagccc gaccgctgcg ccttatccgg taactatcgt cttgagtcca    4440
acccggtaag acacgactta tcgccactgg cagcagccac tggtaacagg attagcagag    4500
cgaggtatgt aggcggtgct acagagttct tgaagtggtg gcctaactac ggctacacta    4560
gaagaacagt atttggtatc tgcgctctgc tgaagccagt taccttcgga aaaagagttg    4620
gtagctcttg atccggcaaa caaaccaccg ctggtagcgg tggttttttt gtttgcaagc    4680
agcagattac gcgcagaaaa aaaggatctc aagaagatcc tttgatcttt tctacggggt    4740
ctgacgctca gtggaacgaa aactcacgtt aagggatttt ggtcatgaga ttatcaaaaa    4800
ggatcttcac ctagatcctt ttaaattaaa aatgaagttt taaatcaatc taagtatat    4860
atgagtaaac ttggtctgac agttaccaaa gctagcttaa tactagtata tacttaatgt    4920
```

-continued

| | |
|---|---|
| gataagtgtc tgacagctga ccggtctaaa gaggtcccta gcgcctacgg ggaatttgta | 4980 |
| tcgataaggg gtacaaattc ccactaagcg ctcggccggg gatcgatccc cgggtacgta | 5040 |
| cccggcagtt tttcttttc ggcaagtgtt caagaagtta ttaagtcggg agtgcagtcg | 5100 |
| aagtgggcaa gttgaaaaat tcacaaaaat gtggtataat atctttgttc attagagcga | 5160 |
| taaacttgaa tttgagaggg aacttagatg gtatttgaaa aaattgataa aaatagttgg | 5220 |
| aacagaaaag agtattttga ccactacttt gcaagtgtac cttgtaccta cagcatgacc | 5280 |
| gttaaagtgg atatcacaca aataaaggaa aagggaatga aactatatcc tgcaatgctt | 5340 |
| tattatattg caatgattgt aaaccgccat tcagagttta ggacggcaat caatcaagat | 5400 |
| ggtgaattgg ggatatatga tgagatgata ccaagctata caatatttca caatgatact | 5460 |
| gaaacatttt ccagcctttg gactgagtgt aagtctgact ttaaatcatt tttagcagat | 5520 |
| tatgaaagtg atacgcaacg gtatggaaac aatcatagaa tggaaggaaa gccaaatgct | 5580 |
| ccggaaaaca ttttaatgt atctatgata ccgtggtcaa ccttcgatgg ctttaatctg | 5640 |
| aatttgcaga aaggatatga ttatttgatt cctattttta ctatggggaa atattataaa | 5700 |
| gaagataaca aaattatact tcctttggca attcaagttc atcacgcagt atgtgacgga | 5760 |
| tttcacattt gccgttttgt aaacgaattg caggaattga taaatagtta acttcaggtt | 5820 |
| tgtctgtaac taaaaactag tatttaacct agg | 5853 |

<210> SEQ ID NO 34
<211> LENGTH: 4966
<212> TYPE: DNA
<213> ORGANISM: Artificial Sequence
<220> FEATURE:
<223> OTHER INFORMATION: pGRNA-pNF2

<400> SEQUENCE: 34

| | |
|---|---|
| agctcggtac ccggggatcc tctagagtcg acgtcacgcg tccatggaga tctcgaggcg | 60 |
| tgctagctta taatataata ttgtggaata ttgaaattaa ttttactaaa aactattcca | 120 |
| atcaaggcag caataataaa aatagtttta tttattggtt tagagtacgt gttttattt | 180 |
| ttaagtttct tttaatagc tgttagaaag aaacttaaaa ataaaatata tataataata | 240 |
| aatataataa aaatatatat aaatttagaa aaagataata tttgataaaa catatttaaa | 300 |
| gataatcaa atcctgtaa agatgaaaat gaaaataaaa ttcctaaaaa taagtttaat | 360 |
| aaagccggaa atttcactag aaatttcact agtttttta aaaacaataa atataataaa | 420 |
| gatattatta taaaacttaa atttaataat aacatcataa ggaaaatgga ttggtttact | 480 |
| tcaacggctt tattatatga aaaaaataca attaaattta acataatat tacaaaaagt | 540 |
| attgttaaaa ttgaaaaaaa ttaaatcttt agtatctttg gaataatca taattttataa | 600 |
| gctcctttga ttttttatat aaattataca ttaattattt aatatataaa aactaaaatt | 660 |
| agtaaatcat ctaaatatta caaatgaaga aatattattt gtaaataatt atagtaatat | 720 |
| attatggaat gaaatagtaa aaaattaaaa agaatcattt aatttagttt aaaatatttt | 780 |
| aataaaata ataaattaaa acataaaaaa tagattaagt ttcaattggg gacttactct | 840 |
| atttttatt aagagtttaa gaatagttaa taattattga aaatatgata taattttctt | 900 |
| agttttacag aaggggaggt gaataagtga gaaacgcatt aaagctgaat aaaaagaact | 960 |
| atatagataa tattccatagt agaagtaaag ggtggataac caggagcgtt atagataaaa | 1020 |
| aaggatatag ccaatggcac tataaatacg ctgaattaaa agatttagat atgagtgatg | 1080 |

```
aaaatatcta tataactcta aatacctttt ataagccgtg taggcgatta gaaaatataa    1140
aagagttaaa tacactgttt atagacttgg attattataa aactggcaaa actaaagacc    1200
aggtattaat ggacttagaa aagaattatt ttaatcaaag tattcctata ccaaactatg    1260
taatagatag tggaagagga atgtatttaa tatggataat aaatgcagta cctagtaaag    1320
cattaccatt atggaaagcg gttcaagaat atttatataa tcaattaaaa tactttggag    1380
cagatagaca agccttagat gcaacgagaa tattaagagt tccaggaagt ataaactcta    1440
aatcaaaaac agtagtcaat atattagatg agtacgaata tatttatgac ttaagagaaa    1500
tacaaaatgg attttttacct gaattaaaac catatgaaag gaaaaagggt agaccaagca    1560
aaataaatta tatttataga gaagaagtt tatattatgg aagaatacaa gacataataa    1620
aactttgtga actaagagaa tatgatttaa aaggacacag agagcttata ttatttttat    1680
atagatatta tctttgtagc tttacagaag acattgagaa ggcattaaat gatgttttag    1740
aacttaatag tatgtttaga caacatttaa gtgaaagaga agttataaga gcaactagaa    1800
gtgctgaaag atgttatttta gataaaaata agcaataaa gtataagaat gaaactctta    1860
tagagttatt agaaattaca gaagaagaac aaaaatatat gacaataata atttctaaaa    1920
aggaatataa gagaagagaa aatattagag gtaaaaaaaa ttatcaagag caattaaaag    1980
ctaaaggaaa agcaacaaaa aaagaggaat taaatgtatt aagaaaaaaa ataaaagccc    2040
ttaaagaaaa aggcttttaaa aataagaaa ttactctaat gttagaagta ccaataaaaa    2100
cattagaacg tcatattacg tatatgaaaa aaaatgggct tttataaagg ctcatttttt    2160
atattctttt cttcaaagat tatataatat aaaaaaattt ttttcaaact ttaaataaaa    2220 aatatttta tattttttta tttttttatt tttatatttt tttattttt tattttttata    2280 tttttttatt tttatatttt tttattttta tattttttta ttttttttatt tttttatttt    2340 tttatttttt tattttttta ttttttttatt tttaccctca tttttttttac gcttgtatta    2400 tagggtactt tgtacctgtt ctttttttg gggaggttgt aaagataatt ttttacttta    2460
gttagttccg aaggaacttt tattatagtg ccccttttatt tttttgcgtg gcattgaatg    2520
taaaaaatta tcactatact agggcgtaaa gtaatattac atgtgtctca aagtgggatt    2580
aaagcgggat tttatagggc gtgtttgtgg cttagagtgg gattattgga aatttttttg    2640
atcctaggtt aaatactagt ttttagttac agacaaacct gaagttaact atttatcaat    2700
tcctgcaatt cgtttacaaa acggcaaatg tgaaatccgt cacatactgc gtgatgaact    2760
tgaattgcca aaggaagtat aattttgtta tcttcttttat aatatttccc catagtaaaa    2820
ataggaatca aataatcata tcctttctgc aaattcagat taaagccatc gaaggttgac    2880
cacggtatca tagatacatt aaaaatgttt tccggagcat ttggctttcc ttccattcta    2940
tgattgtttc ataccgttg cgtatcactt tcataatctg ctaaaaatga tttaaagtca    3000
gacttacact cagtccaaag gctggaaaat gtttcagtat cattgtgaaa tattgtatag    3060
cttggtatca tctcatcata tatccccaat tcaccatctt gattgattgc cgtcctaaac    3120
tctgaatggc ggtttacaat cattgcaata taataaagca ttgcaggata tagtttcatt    3180 ccctttttcct ttatttgtgt gatatccact ttaacggtca tgctgtaggt acaaggtaca    3240
cttgcaaagt agtggtcaaa atactctttt ctgttccaac tatttttatc aattttttca    3300 ataccatct aagttccctc tcaaattcaa gtttatcgct ctaatgaaca aagatattat    3360
accacatttt tgtgaattt tcaacttgcc cacttcgact gcactccga cttaataact    3420 tcttgaacac ttgccgaaaa agaaaaactg ccgggtacgt acccggggat cgatccccgg    3480
```

```
ccgagcgctt agtgggaatt tgtaccoctt atcgatacaa attccccgta ggcgctaggg    3540
acctctttag accggtcagc tgtcagacac ttatcacatt aagtatatac tagtattaag    3600
ctagctttgg taactgtcag accaagttta ctcatatata ctttagattg atttaaaact    3660 tcattttaa tttaaaagga tctaggtgaa gatcctttt gataatctca tgaccaaaat     3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840
accagcggtg gtttgtttgc cggatcaaga gctaccaact cttttccga aggtaactgg    3900 cttcagcaga gcgcagatac caaatactgt tcttctagtg tagccgtagt taggccacca    3960
cttcaagaac tctgtagcac cgcctacata cctcgctctg ctaatcctgt taccagtggc    4020
tgctgccagt ggcgataagt cgtgtcttac cgggttggac tcaagacgat agttaccgga    4080
taaggcgcag cggtcgggct gaacggggg ttcgtgcaca cagcccagct tggagcgaac     4140
gacctacacc gaactgagat acctacagcg tgagctatga gaaagcgcca cgcttcccga    4200
agggagaaag gcggacaggt atccggtaag cggcagggtc ggaacaggag agcgcacgag    4260
ggagcttcca gggggaaacg cctggtatct ttatagtcct gtcgggtttc gccacctctg    4320
acttgagcgt cgatttttgt gatgctcgtc aggggggcgg agcctatgga aaaacgccag    4380
caacgcggcc ttttacggt tcctggcctt ttgctggcct tttgctcaca tgttctttcc     4440
tgcgttatcc cctgattctg tggataaccg tattaccgcc tttgagtgag ctgataccgc    4500
tcgccgcagc cgaacgaccg agcgcagcga gtcagtgagc gaggaagcgg aagagcgccc    4560
aatacgcaaa ccgcctctcc ccgcgcgttg gccgattcat taatgcagct ggcacgacag    4620
gtttcccgac tggaaagcgg gcagtgagcg caacgcaatt aatgtgagtt agctcactca    4680
ttaggcaccc caggctttac actttatgct tccggctcgt atgttgtgtg gaattgtgag    4740
cggataacaa tttcacacag gaaacagcta tgaccatgat tacgaattcg agctcactct    4800
atcattgata gagtttgaaa ctctatcatt gatagagtat aatatctttg ttcatttaag    4860
ccatctacta aacaagtttt agagctagaa atagcaagtt aaaataaggc tagtccgtta    4920
tcaacttgaa aaagtggcac cgagtcggtg cttttttga agcttg                    4966
```

<210> SEQ ID NO 35
<211> LENGTH: 400
<212> TYPE: DNA
<213> ORGANISM: Artificial Sequence
<220> FEATURE:
<223> OTHER INFORMATION: Fragment upstream of the catB gene

<400> SEQUENCE: 35

```
gtctttacac ttttgcccat taattttga gttccttatt tttagggagc ttttattatt      60
tttatcatga aaatttcata aaatactcat aaactaagga tgtcttcata atcagattag    120
tactccattt tcaatccatt taatctggga atatgatatt ttaattacgt attatttaag    180
atatattaac gtgtaatata ataccccgca aatattaatt atcacataca tatccccoct    240 ttattggggc attttttgta cccattattt tagtattgtg cagtacttaa ataaaaaaat    300
gccgcaaatt catttttatt gaataatgcg gtatttcttc tattctttat ttttattact    360
ctataaataa tgtaatcaag acatgactat ctaaatatat                          400
```

<210> SEQ ID NO 36
<211> LENGTH: 400
<212> TYPE: DNA

<213> ORGANISM: Artificial Sequence
<220> FEATURE:
<223> OTHER INFORMATION: Fragment downstream of the catB gene

<400> SEQUENCE: 36

```
aattcataat tcgggcctcc taaaaatttt cgtaattcta ttttagaagg cttttttccg      60
tgacctagcc atttcaatct ccttttaca atgatattta cgctttagtt tattatagca     120
cattctgtaa taccgaacta ttcaattttc agagaccatt ttttattgat tcataactta    180
agaatactac gaattactct aatatttac tttttcttat ctcttgttat tttaacatcg     240
gaattactac taatattaat ttttatttt ccatccgcat ttgctccaac atttttaa       300
ctatactttc cttttgttaa taaattatgt tattgttgaa caatataaga aaagtgcgta    360
acattttta ttaaaaataa ttaggtattt ctatctgtgg                           400
```

<210> SEQ ID NO 37
<211> LENGTH: 218
<212> TYPE: PRT
<213> ORGANISM: Clostridium beijerinckii

<400> SEQUENCE: 37

```
Met Asn Phe Asn Leu Ile Asp Ile Asn His Trp Ser Arg Lys Pro Tyr
1               5                   10                  15
Phe Glu His Tyr Leu Asn Asn Val Lys Cys Thr Tyr Ser Met Thr Ala
            20                  25                  30
Asn Ile Glu Ile Thr Asp Leu Leu Tyr Glu Ile Lys Leu Lys Asn Ile
        35                  40                  45
Lys Phe Tyr Pro Thr Leu Ile Tyr Met Ile Ala Thr Val Val Asn Lys
    50                  55                  60
His Lys Glu Phe Arg Ile Cys Asp His Glu Gly Ser Leu Gly Tyr Trp
65                  70                  75                  80
Asp Ser Met Asn Pro Ser Tyr Thr Ile Phe His Lys Glu Asn Glu Thr
                85                  90                  95
Phe Ser Ser Ile Trp Thr Glu Tyr Asn Lys Ser Phe Leu Arg Phe Tyr
            100                 105                 110
Ser Asp Tyr Leu Asp Asp Ile Lys Asn Tyr Gly Asn Ile Met Lys Phe
        115                 120                 125
Thr Pro Lys Ser Asn Glu Pro Asp Asn Thr Phe Ser Val Ser Ser Ile
    130                 135                 140
Pro Trp Val Ser Phe Thr Gly Phe Asn Leu Asn Val Tyr Asn Glu Gly
145                 150                 155                 160
Thr Tyr Leu Ile Pro Ile Phe Thr Ala Gly Lys Tyr Phe Lys Gln Glu
                165                 170                 175
Asn Lys Ile Phe Ile Pro Ile Ser Ile Gln Val His His Ala Ile Cys
            180                 185                 190
Asp Gly Tyr His Ala Ser Arg Phe Ile Asn Glu Met Gln Glu Leu Ala
        195                 200                 205
Phe Ser Phe Gln Glu Trp Leu Glu Asn Lys
    210                 215
```

<210> SEQ ID NO 38
<211> LENGTH: 9113
<212> TYPE: DNA
<213> ORGANISM: Artificial Sequence
<220> FEATURE:
<223> OTHER INFORMATION: pCas9ind-gRNA_catB

<400> SEQUENCE: 38

```
catggataaa aagtacagta ttggtctaga cataggaact aactctgttg ggtgggctgt      60
tataacagat gaatataaag ttccatcaaa aaaatttaaa gtattaggaa acactgatag     120
acattcaata aaaaaaaact tgataggtgc tttattattc gattcaggag agactgctga     180
agctacacgt ttaaaaagaa cagctagacg tagatataca agaagaaaaa ataggatatg     240
ttatcttcaa gaaattttta gtaatgaaat ggcaaaagtt gatgattcat tctttcacag     300
actagaagaa agtttcttag ttgaagaaga taagaagcat gaaagacacc ctattttggg     360
taatatcgta gatgaagtag catatcatga gaagtatcca actatctatc atttaagaaa     420
gaaattagtt gattctacag ataaagctga tctgagatta atatatttag ctttagctca     480
tatgattaaa tttagaggac attttttaat agaaggtgat ttaaacccag acaacagcga     540
tgtagataaa ttatttatcc aattagttca aacttataat caattattcg aagagaatcc     600
aattaatgca agtggtgtag acgctaaggc tatattatca gctagattat caaaatctag     660
aagattagaa aatctaatag ctcaacttcc tggagaaaag aaaaatggac ttttggggaa     720
cctaatagct ctctcactcg gactaacacc aaattttaaa agcaattttg atcttgctga     780
agacgcaaag ttacaactat caaaggatac atacgatgat gatttagata atttgttagc     840
tcaaataggt gatcaatatg ctgatttgtt tcttgcagca aaaaacttaa gtgatgcaat     900
tttactatca gatatactta gagtaaatac agaaataaca aaggctcctt tatcagcaag     960
tatgattaaa cgatatgatg agcatcatca agatttaaca ttattaaagg cacttgtaag    1020
acaacaatta ccagaaaaat ataaagaaat tttctttgat caatctaaaa atggatatgc    1080
tggatatata gacggtggag caagtcaaga agagttttat aaatttataa agcctatttt    1140
agaaaaaatg gatggaactg aagaattact tgttaaactt aacagagaag atttacttag    1200
aaaacaaaga acttttgata atggttcaat tcctcaccaa attcatttag gagaattaca    1260
tgctatacta agaagacaag aagattttta tccatttctt aaagataata gagaaaaaat    1320
tgaaaaaatt ttaactttta gaataccata ttatgtagga ccacttgcaa ggggaaattc    1380
aagatttgca tggatgacta gaaaatcaga agaaactata accccgtgga atttgaagaa    1440
agtagtagat aaaggagcta gtgctcaatc atttatagaa agaatgacaa attttgataa    1500
gaatcttcct aacgaaaagg ttttgccaaa gcatagcctt ctttatgagt attttacagt    1560
ttataatgag cttactaaag taaaatacgt tacagaagga atgagaaaac cagcatttt     1620 gtctggtgaa caaagaaag caatagtaga cctattattt aaaacaaata ggaaggttac     1680
cgtaaagcaa cttaaagaag attcttcaa aaaaattgaa tgctttgata gtgttgaaat    1740
atcaggagtt gaagatagat ttaatgcttc acttggtaca tatcacgatc tcttaaaaat    1800
tataaaagat aaggattttt tagataatga agaaatgaa gatattcttg aagatatagt    1860
attaacattg acactttttg aagatagaga atgatagaa gaaagattaa aaacatatgc     1920
acatcttttt gatgataagg ttatgaagca acttaaaaga agaagatata caggttgggg    1980
acgtttgtca agaaagctaa ttaatggtat tagagataaa caatcaggaa agactattct    2040
cgattttctt aaatcagatg gatttgctaa tagaaacttt atgcaattaa ttcatgatga    2100
ttctcttact ttcaaagagg atattcaaaa ggctcaagtt tctggacaag cgatagctt     2160 acacgaacac attgctaacc ttgcagggag ccccgctatc aaaaaaggaa ttttacaaac    2220
agttaaagtt gtagatgaac ttgttaaagt tatgggaaga cacaaacctg agaatatagt    2280
tatagaaatg gccagagaaa atcaaacaac acaaaaagga caaaaaaatt ctagagagag    2340
```

```
aatgaagaga attgaagaag gaataaaaga gctaggatca caaatattaa aagaacatcc    2400
agttgaaaat actcaattgc aaaatgaaaa gttatatttg tattacttac aaaatggaag    2460
agatatgtat gttgatcaag aactcgatat taatagatta agtgactatg atgttgatca    2520
tattgttcct caatcatttt taaaagatga ttcaatcgat aacaaagtat taactagatc    2580
agataaaaat agaggaaagt cagataatgt accatctgaa gaagttgtta aaaaaatgaa    2640
gaactattgg agacaacttt taaatgcaaa gctaattaca caaagaaaat ttgacaattt    2700
aacaaaagca gaaagaggag gattaagcga attagacaaa gctggattta taaaaagaca    2760
acttgttgag acaagacaaa taactaagca tgttgctcaa atacttgatt caagaatgaa    2820
tacaaaatat gatgaaaatg ataaattaat cagagaagta aaagtaataa cattaaagtc    2880
aaaattagta tcagatttca gaaggattt tcaattttac aaagttcgtg aaataaataa    2940
ctatcatcat gctcatgatg catacttaaa tgctgttgta ggaactgctc ttattaagaa    3000
atatcctaaa ctagaaagcg aatttgttta tggagattat aaagtttatg atgtgcgcaa    3060
aatgatcgcg aaatccgaac aagaaatcgg taaggctaca gcaaaatatt tcttttatag    3120
taatataatg aatttttta agacagaaat aactttggct aatggtgaaa tcagaaaaag    3180
accacttatc gaaacaaatg gagagacagg agaaatagta tgggataaag gaagagattt    3240
tgctactgtt agaaaagtac taagtatgcc acaagtaaat atcgtaaaga aaactgaagt    3300
tcaaactgga ggtttctcta aggaatcaat tttacctaag agaaattcag ataagttaat    3360
tgcaaggaaa aaagattggg acccaaaaaa atacggtggt tttgatagtc aacagttgc    3420 ctatagtgtt cttgtagtag cgaaagttga gaaaggtaag tcaaaaaagt tgaaaagcgt    3480
aaaagaactt cttggtatca caattatgga aagatcttca tttgaaaaaa atccaattga    3540 cttttagaa gctaagggtt ataaagaagt taaaaaggat ttaatcataa aactaccaaa    3600
gtatagtcta tttgaactcg aaaacggaag aaaacgaatg ctcgctagcg caggagaact    3660
tcaaaaagga aatgaacttg cgctgccatc aaagtatgta aatttcttat atttagcttc    3720
tcattatgag aaattaaaag gatcaccaga ggataatgaa caaaagcaac tatttgtaga    3780
acaacacaaa cattatttag atgaaataat agaacaaata tctgaatttt ctaaaagagt    3840
tatacttgcc gacgcaaatc tagataaggt gctttcagcg tataataaac acagagataa    3900
accaataaga gaacaagcag aaaacattat ccatcttttt acattaacta atcttggtgc    3960
accagctgca tttaagtact ttgatacaac aatagataga aaaagataca catctactaa    4020
agaagtatta gacgcaactt taatacatca atctattaca gggctttatg aaacaagaat    4080
tgatttaagt caactaggcg gagattaagt cgacaaagta ttgttaaaaa taactctgta    4140
gaattataaa ttagttctac agagttattt tttgacccgg gtatattgat aaaaataata    4200
atagtgggta taattaagtt gttaggaggt tagttagaat gatgtcaaga ttagataaaa    4260
gtaaagtgat taacagcgca ttagagctgc ttaatgaggt cggaatcgaa ggtttaacaa    4320
cccgtaaact cgcccagaag ctaggtgtag agcagcctac attgtattgg catgtaaaaa    4380
ataagcgggc tttgctcgac gccttagcca ttgagatgtt agataggcac catactcact    4440
tttgcccttt agaagggaa agctggcaag atttttacg taataacgct aaagttttta    4500
gatgtgcttt actaagtcat cgcgatggag caaaagtaca tttaggtaca cggcctacag    4560
aaaaacagta tgaactctc gaaaatcaat tagcctttt atgccaacaa ggttttcac    4620 tagagaatgc attatatgca ctcagcgctg tggggcattt tacttaggt tgcgtattgg    4680 aagatcaaga gcatcaagtc gctaaagaag aaagggaaac acctactact gatagtatgc    4740
```

```
cgccattatt acgacaagct atcgaattat ttgatcacca aggtgcagag ccagccttct    4800
tattcggcct tgaattgatc atatgcggat tagaaaaaca acttaaatgt gaaagtgggt    4860
cttaaaagca gcataacctt tttccgtgat ggtaacttca cggtaaccaa gatgtcgagt    4920
tgagctcgaa ttcgtaatca tggtcatagc tgtttcctgt gtgaaattgt tatccgctca    4980
caattccaca acaacatacga gccggaagca taaagtgtaa agcctggggt gcctaatgag    5040
tgagctaact cacattaatt gcgttgcgct cactgcccgc tttccagtcg ggaaacctgt    5100
cgtgccagct gcattaatga atcggccaac gcgcgggag aggcggtttg cgtattgggc    5160
gctcttccgc ttcctcgctc actgactcgc tgcgctcggt cgttcggctg cggcgagcgg    5220
tatcagctca ctcaaaggcg gtaatacggt tatccacaga atcaggggat aacgcaggaa    5280
agaacatgtg agcaaaaggc cagcaaaagg ccaggaaccg taaaaaggcc gcgttgctgg    5340
cgttttccca taggctccgc cccctgacg agcatcacaa aaatcgacgc tcaagtcaga    5400
ggtggcgaaa cccgacagga ctataaagat accaggcgtt tccccctgga agctccctcg    5460
tgcgctctcc tgttccgacc ctgccgctta ccggatacct gtccgccttt ctcccttcgg    5520
gaagcgtggc gctttctcat agctcacgct gtaggtatct cagttcggtg taggtcgttc    5580
gctccaagct gggctgtgtg cacgaacccc ccgttcagcc cgaccgctgc gccttatccg    5640
gtaactatcg tcttgagtcc aacccggtaa gacacgactt atcgccactg gcagcagcca    5700
ctggtaacag gattagcaga gcgaggtatg taggcggtgc tacagagttc ttgaagtggt    5760
ggcctaacta cggctacact agaaggacag tatttggtat ctgcgctctg ctgaagccag    5820
ttaccttcgg aaaagagtt ggtagctctt gatccggcaa acaaaccacc gctggtagcg    5880 gtggttttt tgtttgcaag cagcagatta cgcgcagaaa aaaaggatct caagaagatc    5940
ctttgatctt ttctacgggg tctgacgctc agtggaacga aaactcacgt taagggattt    6000
tggtcatgag attatcaaaa aggatcttca cctagatcct tttaaattaa aaatgaagtt    6060
ttaaatcaat ctaaagtata tatgagtaaa cttggtctga cagttaccag gtccactgcc    6120
gggcctcttg cgggatcaaa agaaaaacga aatgatacac caatcagtgc aaaaaaagat    6180
ataatgggag ataagacggt tcgtgttcgt gctgacttgc accatatcat aaaaatcgaa    6240
acagcaaaga atggcggaaa cgtaaaagaa gttatggaaa taagacttag aagcaaactt    6300
aagagtgtgt tgatagtgca gtatcttaaa attttgtata ataggaattg aagttaaatt    6360
agatgctaaa aatttgtaat taagaaggag tgattacatg aacaaaaata taaatattc     6420 tcaaaacttt ttaacgagtg aaaaagtact caaccaaata ataaaacaat tgaatttaaa    6480
agaaaccgat accgtttacg aaattggaac aggtaaaggg catttaacga cgaaactggc    6540
taaaataagt aaacaggtaa cgtctattga attagacagt catctattca acttatcgtc    6600
agaaaaatta aaactgaata ctcgtgtcac tttaattcac caagatattc tacagtttca    6660
attccctaac aaacagaggt ataaaattgt tgggagtatt ccttaccatt taagcacaca    6720
aattattaaa aaagtggttt ttgaaagcca tgcgtctgac atctatctga ttgttgaaga    6780
aggattctac aagcgtacct tggatattca ccgaacacta gggttgctct tgcacactca    6840
agtctcgatt cagcaattgc ttaagctgcc agcggaatgc tttcatccta aaccaaaagt    6900
aaacagtgtc ttaataaaac ttacccgcca taccacagat gttccagata atattggaa    6960 gctatatacg tactttgttt caaatgggt caatcgagaa tatcgtcaac tgtttactaa    7020
aaatcagttt catcaagcaa tgaaacacgc caaagtaaac aatttaagta ccgttactta    7080
```

```
tgagcaagta ttgtctatttt ttaatagtta tctattattt aacgggagga aataattcta    7140
tgagtcccta ggcaggcctc cgccattatt tttttgaaca attgacaatt catttcttat    7200
tttttattaa gtgatagtca aaaggcataa cagtgctgaa tagaaagaaa tttacagaaa    7260
agaaaattat agaatttagt atgattaatt atactcattt atgaatgttt aattgaatac    7320
aaaaaaaaat acttgttatg tattcaatta cgggttaaaa tatagacaag ttgaaaaatt    7380
taataaaaaa ataagtcctc agctcttata tattaagcta ccaacttagt atataagcca    7440
aaacttaaat gtgctaccaa cacatcaagc cgttagagaa ctctatctat agcaatattt    7500
caaatgtacc gacatacaag agaaacatta actatatata ttcaatttat gagattatct    7560
taacagatat aaatgtaaat tgcaataagt aagatttaga agtttatagc ctttgtgtat    7620
tggaagcagt acgcaaaggc ttttttattt gataaaaatt agaagtatat ttattttttc    7680
ataattaatt tatgaaaatg aaaggggtg agcaaagtga cagaggaaag cagtatctta     7740
tcaaataaca aggtattagc aatatcatta ttgactttag cagtaaacat tatgactttt    7800
atagtgcttg tagctaagta gtacgaaagg gggagcttta aaaagctcct tggaatacat    7860
agaattcata aattaattta tgaaaagaag ggcgtatatg aaaacttgta aaaattgcaa    7920
agagtttatt aaagatactg aaatatgcaa aatacattcg ttgatgattc atgataaaac    7980
agtagcaacc tattgcagta aatacaatga gtcaagatgt ttacataaag ggaaagtcca    8040
atgtattaat tgttcaaaga tgaaccgata tggatggtgt gccataaaaa tgagatgttt    8100
tacagaggaa gaacagaaaa aagaacgtac atgcattaaa tattatgcaa ggagctttaa    8160
aaaagctcat gtaaagaaga gtaaaagaa aaataatttt atttattaat ttaatattga     8220
gagtgccgac acagtatgca ctaaaaaata tatctgtggt gtagtgagcc gatacaaaag    8280
gatagtcact cgcattttca taatacatct tatgttatga ttatgtgtcg gtgggacttc    8340
acgacgaaaa cccacaataa aaaagagtt cggggtaggg ttaagcatag ttgaggcaac     8400
taaacaatca agctaggata tgcagtagca gaccgtaagg tcgttgttta ggtgtgttgt    8460
aatacatacg ctattaagat gtaaaaatac ggataccaat gaagggaaaa gtataatttt    8520
tggatgtagt ttgtttgttc atctatgggc aaactacgtc caaagccgtt tccaaatctg    8580
ctaaaaagta tatcctttct aaaatcaaag tcaagtatga aatcataaat aaagtttaat    8640
tttgaagtta ttatgatatt atgttttttct attaaaataa attaagtata tagaatagtt    8700
taataatagt atatacttaa tgtgataagt gtctgacagt gtcacagaaa ggatgattgt    8760
tatggattat aagcggctcg aggacgtcaa accatgttaa tcattgcttt tatcaaaaat    8820
aggatccact ctatcattga tagagtttga aactctatca ttgatagagt ataatatctt    8880
tgttcatgta catcatgcta tctgtgagtt ttagagctag aaatagcaag ttaaaataag    8940
gctagtccgt tatcaacttg aaaaagtggc accgagtcgg tgctttttt gaagcttgtc     9000 tttcactttt tgcccctcga gtccctatca gtgatagatt gaaactctat cattgataga    9060
gtataatatc tttgttcatt agagcgataa acttgaattt gagagggaac ttc           9113
```

<210> SEQ ID NO 39
<211> LENGTH: 20
<212> TYPE: DNA
<213> ORGANISM: Artificial Sequence
<220> FEATURE:
<223> OTHER INFORMATION: Primer pNF2

<400> SEQUENCE: 39
gggcgcactt atacaccacc                                                 20

<210> SEQ ID NO 40
<211> LENGTH: 20
<212> TYPE: DNA
<213> ORGANISM: Artificial Sequence
<220> FEATURE:
<223> OTHER INFORMATION: Primer pNF2

<400> SEQUENCE: 40
tgctacgcac cccctaaagg                                              20

<210> SEQ ID NO 41
<211> LENGTH: 50
<212> TYPE: DNA
<213> ORGANISM: Artificial Sequence
<220> FEATURE:
<223> OTHER INFORMATION: DeltacatB_gRNA_rev

<400> SEQUENCE: 41
aatctatcac tgatagggac tcgaggggca aaagtgtaaa gacaagcttc              50

<210> SEQ ID NO 42
<211> LENGTH: 20
<212> TYPE: DNA
<213> ORGANISM: Artificial Sequence
<220> FEATURE:
<223> OTHER INFORMATION: Primer pCas9ind_fwd

<400> SEQUENCE: 42
agctcttgat ccggcaaaca                                              20

<210> SEQ ID NO 43
<211> LENGTH: 20
<212> TYPE: DNA
<213> ORGANISM: Artificial Sequence
<220> FEATURE:
<223> OTHER INFORMATION: Primer pCas9ind _rev

<400> SEQUENCE: 43
gcaaccctag tgttcggtga                                              20

<210> SEQ ID NO 44
<211> LENGTH: 219
<212> TYPE: PRT
<213> ORGANISM: Clostridium butyricum

<400> SEQUENCE: 44

Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Lys Ser Phe Leu Arg Phe
            100                 105                 110

Tyr Ser Asp Tyr Leu Asp Asp Ile Lys Asn Tyr Gly Asn Ile Met Lys

```
                115                 120                 125
        Phe Thr Pro Lys Ser Asn Glu Pro Asp Asn Thr Phe Ser Val Ser Ser
            130                 135                 140

Ile Pro Trp Val Ser Phe Thr Gly Phe Asn Leu Asn Val Tyr Asn Glu
        145                 150                 155                 160

Gly Thr Tyr Leu Ile Pro Ile Phe Thr Ala Gly Lys Tyr Phe Lys Gln
                        165                 170                 175

Glu Asn Lys Ile Phe Ile Pro Ile Ser Ile Gln Val His His Ala Ile
                    180                 185                 190

Cys Asp Gly Tyr His Ala Ser Arg Phe Ile Asn Glu Met Gln Glu Leu
                195                 200                 205

Ala Phe Ser Phe Gln Glu Trp Leu Glu Asn Lys
            210                 215

<210> SEQ ID NO 45
<211> LENGTH: 219
<212> TYPE: PRT
<213> ORGANISM: Clostridium beijerinckii

<400> SEQUENCE: 45

Met Asn Phe Asn Leu Ile Asp Ile Asn His Trp Ile Arg Lys Pro Tyr
1               5                   10                  15

Phe Glu His Tyr Leu Asn Asn Val Lys Cys Thr Tyr Ser Met Thr Ala
                20                  25                  30

Asn Ile Glu Ile Thr Asp Leu Leu Tyr Glu Ile Lys Leu Lys Asn Ile
            35                  40                  45

Lys Phe Tyr Pro Thr Leu Ile Tyr Met Ile Ala Thr Val Val Asn Asn
        50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Lys Ser Phe Leu Arg Phe
                100                 105                 110

Tyr Ser Asp Tyr Leu Asp Asp Ile Lys Asn Tyr Gly Asn Ile Met Lys
            115                 120                 125

Phe Thr Pro Lys Ser Asn Glu Pro Asp Asn Thr Phe Ser Val Ser Ser
        130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215

<210> SEQ ID NO 46
<211> LENGTH: 219
<212> TYPE: PRT
<213> ORGANISM: Clostridium beijerinckii

<400> SEQUENCE: 46

Met Asn Phe Asn Leu Ile Asp Ile Asn His Trp Ser Arg Lys Pro Tyr
```

```
  1               5                  10                  15
Phe Glu His Tyr Leu Asn Asn Val Lys Cys Thr Tyr Ser Met Thr Ala
                20                  25                  30

Asn Ile Glu Ile Thr Asp Leu Leu Tyr Glu Ile Lys Leu Lys Asn Ile
                35                  40                  45

Lys Phe Tyr Pro Thr Leu Ile Tyr Met Ile Ala Thr Val Val Asn Asn
                50                  55                  60

His Glu Glu Phe Arg Ile Cys Phe Asp His Glu Gly Ser Leu Gly Tyr
 65                 70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Lys Ser Phe Leu Arg Phe
                100                 105                 110

Tyr Ser Asp Tyr Leu Asp Asp Ile Lys Asn Tyr Gly Asn Ile Met Lys
                115                 120                 125

Phe Thr Pro Lys Ser Asn Glu Pro Asp Asn Thr Phe Ser Val Ser Ser
                130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Val Phe Ile Pro Ile Ser Ile Gln Val His His Ala Ile
                180                 185                 190

Cys Asp Gly Tyr His Ala Ser Arg Phe Ile Asn Glu Met Gln Glu Leu
                195                 200                 205

Ala Phe Ser Phe Gln Glu Trp Leu Glu Asn Lys
                210                 215

<210> SEQ ID NO 47
<211> LENGTH: 219
<212> TYPE: PRT
<213> ORGANISM: Clostridium beijerinckii

<400> SEQUENCE: 47

Met Asn Phe Asn Leu Ile Asp Ile Asn His Trp Ser Arg Lys Pro Tyr
 1               5                  10                  15

Phe Glu His Tyr Leu Asn Asn Val Lys Cys Thr Tyr Ser Met Thr Ala
                20                  25                  30

Asn Ile Glu Ile Thr Asp Leu Leu Tyr Glu Ile Lys Leu Lys Asn Ile
                35                  40                  45

Lys Phe Tyr P

```
Gly Thr Tyr Leu Ile Pro Ile Phe Thr Ala Gly Lys Tyr Phe Lys Gln
            165                 170                 175

Gly Asn Lys Ile Phe Ile Pro Ile Ser Ile Gln Val His His Ala Ile
        180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
        210                 215

<210> SEQ ID NO 48
<211> LENGTH: 219
<212> TYPE: PRT
<213> ORGANISM: Artificial Sequence
<220> FEATURE:
<223> OTHER INFORMATION: Clostridium sp.2-1

<400> SEQUENCE: 48

Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Asn Val Val Asn Asn
50                  55                  60

His Lys Glu Phe Arg Ile Cys Phe Asp His Asn Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Gly Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Gln Pro Asp Asn Thr Phe Ser Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215

<210> SEQ ID NO 49
<211> LENGTH: 219
<212> TYPE: PRT
<213> ORGANISM: Artificial Sequence
<220> FEATURE:
<223> OTHER INFORMATION: Clostridium diolis

<400> SEQUENCE: 49

Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
            20                  25                  30
```

```
Asn Ile Glu Ile Thr Asp Leu Leu Tyr Glu Ile Lys Leu Lys Asn Ile
             35                  40                  45

Lys Phe Tyr Pro Thr Leu Ile Tyr Met Ile Ala Asn Val Val Asn Asn
         50                  55                  60

His Lys Glu Phe Arg Ile Cys Phe Asp His Asn Gly Ser Leu Gly Tyr
 65                  70                  75                  80

Trp Asp Ser Met Asn Pro Ser Tyr Thr Val Phe His Lys Glu Asn Glu
                 85                  90                  95

Thr Phe Ser Ser Ile Trp Thr Glu Tyr Asn Glu Ser Phe Leu Arg Phe
                100                 105                 110

Tyr Ser Asp Tyr Leu Asp Asp Ile Lys Asn Tyr Gly Asn Ile Met Lys
            115                 120                 125

Phe Thr Pro Lys Ser Asn Glu Pro Asp Asn Thr Phe Ser Val Ser Ser
        130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215

<210> SEQ ID NO 50
<211> LENGTH: 219
<212> TYPE: PRT
<213> ORGANISM: Clostridium beijerinckii

<400> SEQUENCE: 50

Met Asn Phe Asn Leu Ile Asp Ile Asn His Trp Ile Arg Lys Pro Tyr
1               5                  10                  15

Phe Glu His Tyr Leu Asn Asn Val Lys Cys Thr Tyr Ser Met Thr Ala
                20                  25                  30

Asn Ile Glu Ile Thr Asp Leu Leu Tyr Glu Ile Lys Leu Lys Asn Ile
             35                  40                  45

Lys Phe Tyr Pro Thr Leu Ile Tyr Met Ile Ala Thr Val Val Asn Asn
         50                  55                  60

His Lys Glu Phe Arg Ile Cys Phe Asp His Lys Gly Ser Leu Gly Tyr
 65                  70                  75                  80

Trp Asp Ser Met Asn Pro Ser Tyr Thr Ile Phe His Lys Glu Asn Glu
                 85                  90                  95

Thr Phe Ser Ser Ile Trp Thr Glu Tyr Asn Lys Ser Phe Leu Arg Phe
                100                 105                 110

Tyr Ser Asp Tyr Leu Asp Asp Ile Lys Asn Tyr Gly Asn Ile Met Lys
            115                 120                 125

Phe Thr Pro Lys Ser Asn Gln Pro Asp Asn Thr Phe Ser Val Ser Ser
        130                 135                 140

Ile Pro Trp Val Ser Phe Thr Gly Phe Asn Leu Asn Val Asn Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Ile
```

-continued

```
                180                 185                 190
Cys Asp Gly Tyr His Ala Ser Arg Phe Ile Asn Glu Met Gln Glu Leu
            195                 200                 205

Ala Phe Ser Phe Lys Glu Trp Leu Glu Asn Lys
        210                 215

<210> SEQ ID NO 51
<211> LENGTH: 221
<212> TYPE: PRT
<213> ORGANISM: Clostridium beijerinckii

<400> SEQUENCE: 51

Met Asn Phe Asn Leu Ile Asp Ile Asn Asn Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Asn Val Val Asn Asn
    50                  55                  60

His Lys Glu Phe Arg Ile Cys Phe Asp His Glu Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys Tyr Ile
    210                 215                 220

<210> SEQ ID NO 52
<211> LENGTH: 219
<212> TYPE: PRT
<213> ORGANISM: Clostridium beijerinckii

<400> SEQUENCE: 52

Met Asn Phe Asn Leu Ile Asp Ile Asn Asn Trp Ser Arg Lys Pro Tyr
1               5                   10                  15

Phe Glu His Tyr Leu Asn Asn Val Lys Cys Thr Tyr Ser Met Thr Ala
            20                  25

```
65                  70                  75                  80
Trp Asp Ser Met Asn Pro Ser Tyr Thr Ile Phe His Lys Glu Asn Glu
                85                  90                  95
Thr Phe Ser Ser Ile Trp Thr Glu Tyr Asn Glu Ser Phe Leu Arg Phe
                100                 105                 110
Tyr Ser Asp Tyr Leu Asp Ile Lys Asn Tyr Gly Asn Ile Met Lys
                115                 120                 125
Phe Thr Pro Lys Ser Asn Glu Pro Asp Asn Thr Phe Pro Val Ser Ser
                130                 135                 140
Ile Pro Trp Val Ser Phe Thr Gly Phe Asn Leu Asn Val Tyr Asn Glu
145                 150                 155                 160
Gly Thr Tyr Leu Ile Pro Ile Phe Thr Ala Gly Lys Tyr Phe Lys Gln
                    165                 170                 175
Gly Asn Lys Ile Phe Ile Pro Ile Ser Ile Gln Val His His Ala Ile
                180                 185                 190
Cys Asp Gly Tyr His Ala Ser Arg Phe Ile Asn Glu Met Gln Glu Leu
                195                 200                 205
Ala Phe Ser Phe Arg Glu Trp Leu Glu Asn Lys
210                 215

<210> SEQ ID NO 53
<211> LENGTH: 219
<212> TYPE: PRT
<213> ORGANISM: Clostridium saccharoperbutylacetonicum

<400> SEQUENCE: 53

Met Asn Phe Asn Leu Ile Asp Ile Asn His Trp Ser Arg Lys Pro Tyr
1               5                   10                  15
Phe Glu His Tyr Leu Asn Thr Val Lys Cys Thr Tyr Ser Met Thr Ala
                20                  25                  30
Asn Ile Glu Ile Thr Asp Leu Leu Tyr Glu Ile Lys Leu Lys Asn Ile
            35                  40                  45
Lys Phe Tyr Pro Thr Leu Ile Tyr Met Ile Ala Thr Val Val Asn Asn
50                  55                  60
His Lys Glu Phe Arg Ile Cys Phe Asp His Lys Gly Ser Leu Gly Tyr
65                  70                  75                  80
Trp Asp Ser Met Asn Pro Ser Tyr Thr Ile Phe His Lys Glu Asn Glu
                85                  90                  95
Thr Phe Ser Ser Ile Trp Thr Glu Tyr Asn Glu Ser Phe Leu Arg Phe
                100                 105                 110
Tyr Ser Asp Tyr Ile Asp Ile Lys Asn Tyr Gly Asn Ile Met Lys
                115                 120                 125
Phe Thr Pro Lys Ser Asn Glu Pro Asp Asn Ile Phe Pro Val Ser Ser
                130                 135                 140
Ile Pro Trp Val Ser Phe Thr Gly Phe Asn Leu Asn Val Tyr Asn Glu
145                 150                 155                 160
Gly Thr Tyr Leu Ile Pro Ile Phe Thr Ala Gly Lys Tyr Phe Lys Gln
                    165                 170                 175
Glu Asn Lys Ile Phe Ile Pro Ile Ser Ile Gln Val His His Ala Val
                180                 185                 190
Cys Asp Gly Tyr His Ala Ser Arg Phe Ile Asn Glu Met Gln Glu Leu
                195                 200                 205
Ala Phe Ser Phe Gln Glu Trp Leu Glu Asn Lys
210                 215
```

<210> SEQ ID NO 54
<211> LENGTH: 219
<212> TYPE: PRT
<213> ORGANISM: Clostridium saccharoperbutylacetonicum

<400> SEQUENCE: 54

Met Asn Phe Asn Leu Ile Asp Ile Asn His Trp Ser Arg Lys Pro Tyr
1               5                   10                  15

Phe Glu His Tyr Leu Asn Thr Val Lys Cys Thr Tyr Ser Met Thr Ala
                20                  25                  30

Asn Ile Glu Ile Thr Asp Leu Leu Tyr Glu Ile Lys Leu Lys Asn Ile
            35                  40                  45

Lys Phe Tyr Pro Thr Leu Ile Tyr Met Ile Ala Thr Val Val Asn Asn
50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe Tyr Lys Glu Asn Glu
                85                  90                  95

Thr Phe Ser Ser Ile Trp Thr Glu Tyr Asn Glu Ser Phe Leu Arg Phe
                100                 105                 110

Tyr Ser Asp Tyr Ile Asp Asp Ile Lys Asn Tyr Gly Asn Ile Met Lys
            115                 120                 125

Phe Thr Pro Lys Ser Asn Glu Pro Asp Asn Ile Phe Pro Val Ser Ser
130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Val
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215

<210> SEQ ID NO 55
<211> LENGTH: 219
<212> TYPE: PRT
<213> ORGANISM: Clostridium beijerinckii

<400> SEQUENCE: 55

Met Asn Phe Asn Leu Ile Asp Ile Asn Asn Trp Ser Arg Lys Pro Tyr
1               5                   10                  15

Phe Glu His Tyr Leu Asn Asn Val Lys Cys Thr Tyr Ser Met Thr Ala
                20                  25                  30

Asn Ile Glu Ile Thr Asp Leu Leu Tyr Glu Ile Lys Leu Lys Asn Ile
            35                  40                  45

Lys Phe Tyr Pro Thr Leu Ile Tyr Met Ile Ala Thr Val Val Asn Asn
50                  55                  60

His Lys Glu Phe Arg Ile Cys Phe Asp His Asn Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Glu Ser Phe Leu Arg Phe
                100                 105                 110

-continued

Tyr Ser Asp Tyr Leu Asp Asp Ile Lys Asn Tyr Gly Asn Ile Met Lys
            115                 120                 125

Phe Thr Pro Lys Ser Asn Arg Ser Asp Asn Thr Phe Pro Val Ser Ser
        130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His Ala Ile
            180                 185                 190

Cys Asp Gly Tyr His Ala Ser Arg Phe Ile Asn Glu Met Gln Glu Leu
            195                 200                 205

Ala Phe Ser Phe Arg Glu Trp Leu Glu Asn Lys
        210                 215

<210> SEQ ID NO 56
<211> LENGTH: 221
<212> TYPE: PRT
<213> ORGANISM: Clostridium beijerinckii

<400> SEQUENCE: 56

Met Asn Phe Asn Leu Ile Asp Ile Asn His Trp Asn Arg Lys Pro Phe
1               5                   10                  15

Phe Glu His Tyr Leu Asn Asn Val Lys Cys Thr Tyr Ser Met Thr Ala
                20                  25                  30

Asn Ile Glu Ile Thr Asp Leu Leu Tyr Glu Ile Lys Leu Lys Asn Ile
            35                  40                  45

Lys Phe Tyr Pro Thr Leu Ile Tyr Met Ile Ala Thr Val Val Asn Asn
50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe His Glu Gly Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
            115                 120                 125

Phe Thr Pro Lys Ser Asn Glu Pro Asp Asn Thr Phe Pro Val Ser Ser
        130                 135                 140

Ile Pro Trp Val Ser Phe Thr Gly Phe Asn Leu Asn Val Cys Asn Glu
145                 150                 155                 160

Gly Thr Tyr Leu Thr Pro Ile Phe Thr Ala Gly Lys Tyr Phe Lys Gln
                165                 170                 175

Glu Asn Lys Ile Phe Ile Pro Ile Ser Ile Gln Val His His Ser Ile
            180                 185                 190

Cys Asp Gly Tyr His Ala Ser Arg Phe Ile Asn Glu Met Gln Glu Leu
            195                 200                 205

Ala Phe Ser Phe Gln Glu Trp Leu Glu Asn Lys Tyr Ile
        210                 215                 220

<210> SEQ ID NO 57
<211> LENGTH: 219
<212> TYPE: PRT
<213> ORGANISM: Clostridium beijerinckii

<400> SEQUENCE: 57

Met Asn Phe Asn Leu Ile Asp Ile Lys His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Arg Leu Lys Asn Ile
        35                  40                  45

Lys Leu Tyr Pro Thr Leu Ile Tyr Met Ile Ala Thr Val Val Asn Asn
    50                  55                  60

His Lys Glu Phe Arg Thr Cys Phe Asp His Ser Gly Ser Leu Gly Tyr
65                  70                  75                  80

Trp Asp Ser Met Ser Pro Ser Tyr Thr Ile Phe His Lys Glu Asn Glu
                85                  90                  95

Thr Phe Ser Ser Ile Trp Thr Glu Tyr Asn Glu Ser Phe Pro Arg Phe
            100                 105                 110

Tyr Ser Asp Tyr Phe Asp Ile Lys Asn Tyr Gly Asn Ile Met Lys
            115                 120                 125

Phe Thr Pro Lys Leu Asn Glu Pro Asp Asn Thr Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Thr Gly Lys Tyr Phe Lys Gln
                165                 170                 175

Glu Asn Lys Met Phe Ile Pro Ile Ser Ile Gln Val His His Ala Ile
            180                 185                 190

Cys Asp Gly Tyr His Ala Ser Arg Phe Ile Asn Glu Met Gln Glu Leu
            195                 200                 205

Ala Phe Ser Phe Gln Asp Trp Leu Glu Asn Lys
    210                 215

<210> SEQ ID NO 58
<211> LENGTH: 219
<212> TYPE: PRT
<213> ORGANISM: Clostridium botulinum

<400> SEQUENCE: 58

Met Lys Phe Asn Leu Ile Asp Ile Glu His Trp Asn Arg Lys Pro Tyr
1               5                   10                  15

Phe Glu Tyr Tyr Leu His Ser Val Arg Cys Thr Tyr Ser Met Thr Ala
            20                  25                  30

Asn Ile Glu Ile Thr Asn Leu Leu His Glu Ile Lys Leu Lys Lys Leu
        35                  40                  45

Lys Leu Tyr Pro Thr Leu Ile Tyr Ile Ile Ala Thr Val Val Asn Asn
    50                  55                  60

His Lys Glu Phe Arg Thr Cys Phe Asp Glu Asn Gly Asn Leu Gly Tyr
65                  70                  75                  80

Trp Asp Ser Met Ser Pro Ser Tyr Thr Ile Phe His Lys Asp Asn Glu
                85                  90                  95

Thr Phe Ser Ser Ile Trp Thr Asp Tyr Asp Glu Ser Phe Ser Cys Phe
            100                 105                 110

Tyr Asn Asp Tyr Leu Asp Ile Lys Asn Tyr Gly Ala Ile Met Lys
            115                 120                 125

Phe Thr Pro Lys Leu Asn Glu Pro Ala Asn Thr Phe Pro Val Ser Ser
    130                 135                 140

Ile Pro Trp Val Asn Phe Thr Gly Phe Asn Leu Asn Val Tyr Asn Asn
145                 150                 155                 160

```
Gly Thr Tyr Leu Val Pro Ile Phe Thr Met Gly Lys Tyr Phe Glu Gln
                165                 170                 175

Asn Asn Lys Ile Phe Ile Pro Met Ser Ile Gln Val His His Ala Val
            180                 185                 190

Cys Asp Gly Tyr His Ile Ser Arg Phe Ile Asn Glu Val Gln Glu Leu
        195                 200                 205

Ala Leu Asn Ser Gln Thr Trp Leu Lys His Lys
    210                 215

<210> SEQ ID NO 59
<211> LENGTH: 219
<212> TYPE: PRT
<213> ORGANISM: Artificial Sequence
<220> FEATURE:
<223> OTHER INFORMATION: Anaerocolumna aminovalerica

<400> SEQUENCE: 59

Met Lys Phe Asn Leu Ile Asp Ile Glu Asn Trp Asn Arg Lys Pro Tyr
1               5                   10                  15

Phe Glu His Tyr Leu Asn Ser Val Arg Cys Thr Tyr Ser Met Thr Ala
            20                  25                  30

Asn Ile Glu Ile Thr Asn Leu Leu His Glu Ile Lys Leu Lys Asp Leu
        35                  40                  45

Lys Leu Tyr Pro Thr Leu Ile Tyr Ile Leu Ala Thr Val Val Asn Asn
    50                  55                  60

His Lys Glu Phe Arg Thr Cys Phe Asp Glu Asn Gly Asn Leu Gly Tyr
65                  70                  75                  80

Trp Asp Ser Met Ser Pro Ser Tyr Thr Ile Phe His Lys Glu Asn Glu
                85                  90                  95

Thr Phe Ser Ser Ile Trp Thr Glu Tyr Asp Glu Ser Phe Ser Arg Phe
            100                 105                 110

Tyr Thr Ala Tyr Leu Asp Asp Ile Lys Asn His Gly Asn Ile Met Lys
        115                 120                 125

Phe Thr Pro Lys Leu Asn Glu Pro Ala Asn Thr Phe Pro Ile Ser Ser
    130                 135                 140

Ile Pro Trp Val Ser Phe Thr Gly Phe Asn Leu Asn Val Tyr Asn Asp
145                 150                 155                 160

Gly Lys Tyr Leu Leu Pro Ile Phe Thr Thr Gly Lys Tyr Phe Glu Gln
                165                 170                 175

Asn Ser Lys Ile Phe Ile Pro Met Ser Val Gln Val His His Ala Val
            180                 185                 190

Cys Asp Gly Tyr His Ile Ser Arg Phe Ile Asn Glu Val Gln Glu Val
        195                 200                 205

Ile Leu Asn Tyr Gln Thr Trp Leu Gly Asp Lys
    210                 215

<210> SEQ ID NO 60
<211> LENGTH: 219
<212> TYPE: PRT
<213> ORGANISM: Artificial Sequence
<220> FEATURE:
<223> OTHER INFORMATION: Desnuesiella massiliensis

<400> SEQUENCE: 60

Met Lys Phe Asn Leu Ile Asp Ile Glu His Trp Asn Arg Lys Pro Tyr
1               5                   10                  15

Phe Glu His Tyr Leu Asn Ser Val Arg Cys Thr Tyr Ser Met Thr Ala
```

```
                    20                  25                  30
Asn Ile Glu Ile Thr Asn Leu Leu His Asp Ile Lys Leu Lys Lys Leu
            35                  40                  45

Lys Leu Tyr Pro Thr Leu Ile Tyr Ile Ile Ala Thr Val Val Asn Asn
        50                  55                  60

His Glu Glu Phe Arg Thr Cys Phe Tyr Glu Asn Gly Asn Leu Gly Tyr
65                  70                  75                  80

Trp Asp Ser Met Ser Pro Ser Tyr Thr Ile Phe His Lys Asp Asn Glu
                85                  90                  95

Thr Phe Ser Glu Ile Trp Ser Glu Tyr Asp Glu Ser Phe Ser Cys Phe
            100                 105                 110

Tyr Ser Lys Tyr Leu Asp Asp Ile Lys Asn Tyr Gly Asp Ile Met Arg
        115                 120                 125

Phe Thr Pro Lys Leu Asn Glu Pro Ala Asn Thr Phe Pro Ile Ser Cys
    130                 135                 140

Ile Pro Trp Val Ser Phe Thr Gly Phe Asn Leu Asn Val Tyr Asn Asp
145                 150                 155                 160

Gly Arg Tyr Leu Val Pro Ile Phe Thr Ile Gly Lys Tyr Phe Glu Gln
                165                 170                 175

Asn Asn Lys Ile Phe Ile Pro Met Ser Ile Gln Val His His Ala Val
            180                 185                 190

Cys Asp Gly Tyr His Thr Ser Arg Phe Ile Asn Glu Val Gln Glu Leu
        195                 200                 205

Ala Leu Asn Ser Gln Thr Trp Leu Arg His Lys
    210                 215

<210> SEQ ID NO 61
<211> LENGTH: 219
<212> TYPE: PRT
<213> ORGANISM: Artificial Sequence
<220> FEATURE:
<223> OTHER INFORMATION: Clostridium sp. HMP27

<400> SEQUENCE: 61

Met Lys Phe Asn Leu Ile Asp Thr Glu His Trp Asn Arg Lys Pro Tyr
1               5                   10                  15

Phe Glu His Tyr Leu Asn Ser Val Arg Cys Thr Tyr Ser Ile Thr Ala
                20                  25                  30

Asn Ile Glu Ile Thr Asn Leu Leu His Asp Ile Lys Gln Lys Lys Leu
            35                  40                  45

Lys Leu Tyr Pro Thr Phe Ile Tyr Ile Ile Ala Thr Val Val Asn Thr
        50                  55                  60

His Lys Glu Phe Arg Thr Cys Phe Asp Glu Ser Gly Asn Leu Gly Tyr
65                  70                  75                  80

Trp Asp Ser Met Ser Pro Ser Tyr Thr Ile Phe His Lys Asp Asn Glu
                85                  90                  95

Thr Phe Ser Ser Ile Trp Thr Gly Tyr Asp Lys Ser Phe Ser Cys Phe
            100                 105                 110

Tyr Ser Lys Tyr Leu His Asp Ile Lys Asn Tyr Gly Asp Ile Met Ser
        115                 120                 125

Phe Thr Pro Lys Leu Asn Glu Pro Ala Asn Thr Phe Pro Ile Ser Cys
    130                 135                 140

Ile Pro Trp Val Ser Phe Thr Gly Phe Asn Leu Asn Ile Tyr Asn Asp
145                 150                 155                 160

Gly Thr Tyr Leu Val Pro Ile Phe Thr Ile Gly Lys Tyr Phe Lys Gln
```

```
                        165                 170                 175
Ala Asp Lys Ile Leu Ile Pro Ile Ser Ile Gln Val His His Ala Val
                180                 185                 190

Cys Asp Gly Tyr His Thr Ser Arg Phe Ile Asn Glu Val Gln Glu Leu
            195                 200                 205

Ile Leu Asn Tyr Gln Thr Trp Leu Lys His Lys
        210                 215

<210> SEQ ID NO 62
<211> LENGTH: 219
<212> TYPE: PRT
<213> ORGANISM: Artificial Sequence
<220> FEATURE:
<223> OTHER INFORMATION: Clostridium drakei

<400> SEQUENCE: 62

Met Lys Phe Asn Leu Ile Asp Ile Glu Asn Trp Asn Arg Lys Pro Tyr
1               5                   10                  15

Phe Glu His Tyr Leu Asn Ala Val Arg Cys Thr Tyr Ser Met Thr Ala
            20                  25                  30

Asn Ile Glu Ile Thr Gly Leu Leu Arg Glu Ile Lys Leu Lys Gly Leu
        35                  40                  45

Lys Leu Tyr Pro Thr Leu Ile Tyr Ile Thr Ala Val Ile Asn Arg
    50                  55                  60

His Lys Glu Phe Arg Thr Cys Phe Asp Glu Asn Arg Lys Leu Gly Tyr
65                  70                  75                  80

Trp Asp Ser Met Ser Pro Ser Tyr Thr Val Phe His Lys Glu Asp Glu
                85                  90                  95

Thr Phe Ser Ser Ile Trp Thr Glu Tyr Asp Glu Ser Phe Pro Arg Phe
            100                 105                 110

Tyr Asp Asn Tyr Leu Asp Asp Ile Lys Ser Tyr Gly Asp Val Leu Lys
        115                 120                 125

Phe Met Pro Lys Pro Asp Glu Pro Gly Asn Thr Phe Asn Val Ser Ser
    130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Met Gly Lys Phe Phe His Gln
                165                 170                 175

Asp Asn Lys Ile Phe Ile Pro Met Ser Ile Gln Val His His Ala Val
            180                 185                 190

Cys Asp Gly Tyr His Thr Ser Arg Phe Phe Asn Glu Val Gln Glu Leu
        195                 200                 205

Ser Ser Asn Phe Glu Thr Trp Leu Asp Glu Lys
    210                 215

<210> SEQ ID NO 63
<211> LENGTH: 219
<212> TYPE: PRT
<213> ORGANISM: Clostridium scatologenes

<400> SEQUENCE: 63

Met Lys Phe Asn Leu Ile Asp Ile Glu Asp Trp Asn Arg Lys Pro Tyr
1               5                   10                  15

Phe Glu His Tyr Leu Asn Ala Val Arg Cys Thr Tyr Ser Met Thr Ala
            20                  25                  30

Asn Ile Glu Ile Thr Gly Leu Leu Arg Glu Ile Lys Leu Lys Gly Leu
        35                  40                  45
```

```
Lys Leu Tyr Pro Thr Leu Ile Tyr Ile Ile Thr Ala Val Ile Asn Arg
 50                  55                  60

His Lys Glu Phe Arg Thr Cys Phe Asp Glu Asn Arg Lys Leu Gly Tyr
 65                  70                  75                  80

Trp Asp Ser Met Ser Pro Ser Tyr Thr Val Phe His Lys Glu Asp Glu
                 85                  90                  95

Thr Phe Ser Ser Ile Trp Thr Glu Tyr Asp Glu Ser Phe Pro Arg Phe
                100                 105                 110

Tyr Asp Asn Tyr Leu Asp Asp Ile Lys Ser Tyr Gly Asp Val Leu Lys
            115                 120                 125

Phe Met Pro Lys Pro Asp Glu Pro Gly Asn Thr Phe Asn Val Ser Ser
130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Met Gly Lys Phe Phe His Gln
            165                 170                 175

Asp Asn Lys Ile Phe Ile Pro Met Ser Ile Gln Val His His Ala Val
            180                 185                 190

Cys Asp Gly Tyr His Thr Ser Arg Phe Phe Asn Glu Val Gln Glu Leu
            195                 200                 205

Ser Ser Asn Phe Glu Thr Trp Leu Gly Glu Lys
            210                 215

<210> SEQ ID NO 64
<211> LENGTH: 219
<212> TYPE: PRT
<213> ORGANISM: Artificial Sequence
<220> FEATURE:
<223> OTHER INFORMATION: Clostridium tunisiense

<400> SEQUENCE: 64

Met Lys Phe Asn Leu Ile Asp Thr Glu His Trp Asp Arg Lys Pro Tyr
  1               5                  10                  15

Phe Glu His Tyr Phe Asn Ser Val Lys Cys Thr Tyr Ser Met Thr Ala
                 20                  25                  30

Asn Ile Glu Ile Thr Asn Leu Leu Asn His Ile Arg Leu Lys Lys Leu
             35                  40                  45

Lys Leu Tyr Pro Thr Leu Ile Tyr Ile Ile Ala Thr Val Val Asn Asn
 50                  55                  60

His Glu Glu Phe Arg Ile Cys Phe Asp Glu Asn Asn Asn Leu Gly Tyr
 65                  70                  75                  80

Trp Asp Ser Met Ser Pro Asn Tyr Thr Ile Phe His Glu Asp Asn Lys
                 85                  90                  95

Thr Phe Ser Ser Ile Trp Thr Glu Tyr Glu Glu Ser Phe Ser Gly Phe
                100                 105                 110

Tyr Asn Lys Tyr Leu Glu Asp Ile Lys Thr Tyr Gly His Ile Met Ser
            115                 120                 125

Phe Glu Pro Lys Leu Asn Glu Ser Thr Asn Thr Phe Pro Ile Ser Cys
130                 135                 140

Ile Pro Trp Val Ser Phe Thr Gly Phe Asn Leu Asn Ile Gln Asp Asp
145                 150                 155                 160

Gly Thr Tyr Leu Thr Pro Ile Phe Thr Leu Gly Lys Tyr Phe Glu Gln
            165                 170                 175

Asn Asn Lys Thr Phe Ile Pro Ile Ser Ile Gln Val His His Ala Val
            180                 185                 190
```

```
Cys Asp Gly Tyr His Thr Ser Arg Phe Ile Asn Glu Val Gln Glu Leu
        195                 200                 205

Ala Ser Asp Phe Gln Ile Trp Leu Thr Tyr Lys
    210                 215

<210> SEQ ID NO 65
<211> LENGTH: 219
<212> TYPE: PRT
<213> ORGANISM: Artificial Sequence
<220> FEATURE:
<223> OTHER INFORMATION: Lachnospiraceae

<400> SEQUENCE: 65

Met Lys Phe Asn Leu Ile Asp Ile Glu Asp Trp Asn Arg Lys Pro Tyr
1               5                   10                  15

Phe Glu His Tyr Leu Asn Ala Val Arg Cys Thr Tyr Ser Met Thr Ala
            20                  25                  30

Asn Ile Glu Ile Thr Gly Leu Leu Arg Glu Ile Lys Leu Lys Gly Leu
        35                  40                  45

Lys Leu Tyr Pro Thr Leu Ile Tyr Ile Ile Thr Val Val Asn Arg
    50                  55                  60

His Lys Glu Phe Arg Thr Cys Phe Asp Gln Lys Gly Lys Leu Gly Tyr
65                  70                  75                  80

Trp Asp Ser Met Asn Pro Ser Tyr Thr Val Phe His Lys Asp Asn Glu
                85                  90                  95

Thr Phe Ser Ser Ile Trp Thr Glu Tyr Asp Glu Asn Phe Pro Arg Phe
            100                 105                 110

Tyr Tyr Asn Tyr Leu Glu Asp Ile Arg Asn Tyr Ser Asp Val Leu Asn
        115                 120                 125

Phe Met Pro Lys Thr Gly Glu Pro Ala Asn Thr Ile Asn Val Ser Ser
    130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Leu Gly Lys Tyr Phe Gln Gln
                165                 170                 175

Asp Asn Lys Ile Leu Leu Pro Met Ser Val Gln Val His His Ala Val
            180                 185                 190

Cys Asp Gly Tyr His Thr Ser Arg Phe Phe Asn Glu Ala Gln Glu Leu
        195                 200                 205

Ala Ser Asn Tyr Glu Thr Trp Leu Gly Glu Lys
    210                 215

<210> SEQ ID NO 66
<211> LENGTH: 219
<212> TYPE: PRT
<213> ORGANISM: Clostridium perfringens

<400> SEQUENCE: 66

Met Lys Phe As

```
His Lys Glu Phe Arg Thr Cys Phe Asp Gln Lys Gly Lys Leu Gly Tyr
 65                  70                  75                  80

Trp Asp Ser Met Asn Pro Ser Tyr Thr Val Phe His Lys Asp Asn Glu
                 85                  90                  95

Thr Phe Ser Ser Ile Trp Thr Glu Tyr Asp Glu Asn Phe Pro Arg Phe
            100                 105                 110

Tyr Tyr Asn Tyr Leu Glu Asp Ile Arg Asn Tyr Ser Asp Val Leu Asn
            115                 120                 125

Phe Met Pro Lys Thr Gly Glu Pro Ala Asn Thr Ile Asn Val Ser Ser
130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Leu Gly Lys Tyr Phe Gln Gln
                165                 170                 175

Asp Asn Lys Ile Leu Leu Pro Met Ser Val Gln Val His His Ala Val
            180                 185                 190

Cys Asp Gly Tyr His Ile Ser Arg Phe Phe Asn Glu Ala Gln Glu Leu
            195                 200                 205

Ala Ser Asn Tyr Glu Thr Trp Leu Gly Glu Lys
210                 215
```

<210> SEQ ID NO 67
<211> LENGTH: 218
<212> TYPE: PRT
<213> ORGANISM: Artificial Sequence
<220> FEATURE:
<223> OTHER INFORMATION: Clostrdium sp. BL8

<400> SEQUENCE: 67

```
Met Lys Phe Asn Leu Ile Asp Ile Asp Gln Trp Asp Arg Lys Pro Tyr
  1               5                  10                  15

Phe Glu His Tyr Phe Asn Ser Val Lys Cys Thr Tyr Ser Ile Thr Ala
                 20                  25                  30

Asn Ile Glu Ile Thr Asn Leu Leu Lys Asp Ile Lys Ile Thr Lys Leu
             35                  40                  45

Lys Leu Tyr Pro Thr Leu Ile Tyr Ile Ile Ala Thr Val Ile Asn Asn
 50                  55                  60

His Glu Glu Phe Arg Thr Cys Phe Asp Glu Asn Asn Asn Leu Gly Tyr
 65                  70                  75                  80

Trp Asp Ser Met Ser Pro Asn Tyr Thr Ile Phe His Glu Glu Thr Lys
                 85                  90                  95

Thr Phe Ser Asn Ile Trp Thr Glu Tyr Asp Lys Ser Phe Ser Gly Phe
            100                 105                 110

Tyr Asn Lys Tyr Val Glu Asp Asn Lys Asn Tyr Gly Asn Ile Met Asn
            115                 120                 125

Phe Asp Pro Lys Leu Asn Glu Pro Ala Asn Thr Phe Pro Ile Ser Cys
130                 135                 140

Ile Pro Trp Val Ser Phe Thr Gly Phe Asn Leu Asn Ile Gln Asp His
145                 150                 155                 160

Gly Thr Tyr Leu Thr Pro Ile Phe Thr Leu Gly Lys Tyr Phe Glu Glu
                165                 170                 175

Asn Asn Lys Val Phe Ile Pro Met Ser Ile Gln Val His His Ala Val
            180                 185                 190

Cys Asp Gly Tyr His Thr Ser Arg Phe Ile Asn Glu Val Gln Glu Leu
            195                 200                 205
```

Ala Ser Asn Ser Gln Ser Trp Leu Lys His
    210                 215

<210> SEQ ID NO 68
<211> LENGTH: 660
<212> TYPE: DNA
<213> ORGANISM: Clostridium perfringens

<400> SEQUENCE: 68

| | | | | | |
|---|---|---|---|---|---|
| atgaaattta | atttgataga | tattgaggat | tggaatagaa | agccatactt | tgagcattat | 60 |
| ttaaatgcgg | ttaggtgcac | ttacagtatg | actgcaaata | tagagataac | tggtttactg | 120 |
| cgtgaaatta | aacttaaggg | cctgaaactg | taccctacgc | ttatttatat | catcacaact | 180 |
| gtggttaacc | gtcacaagga | gttccgcacc | tgttttgatc | aaaaaggtaa | gttaggatac | 240 |
| tgggatagta | tgaacccaag | ttatactgtc | tttcataagg | ataacgaaac | ttttcaagt | 300 |
| atttggacag | agtatgacga | gaacttccca | cgttttttact | ataattaccct | tgaggatatt | 360 |
| agaaactata | gcgacgtttt | gaatttcatg | cctaagacag | gtgaacctgc | taatacaatt | 420 |
| aatgtgtcca | gcattccttg | ggtgaatttt | accggattca | acctgaatat | atacaatgat | 480 |
| gcaacatatc | taatccctat | ttttactttg | ggtaagtatt | ttcagcagga | taataaaatt | 540 |
| ttattaccta | tgtctgtaca | ggtgcatcat | gcggtttgcg | acggttatca | tataagcaga | 600 |
| tttttttaatg | aggcacagga | attagcgtca | aattatgaga | catggttagg | agaaaaataa | 660 |

<210> SEQ ID NO 69
<211> LENGTH: 624
<212> TYPE: DNA
<213> ORGANISM: Clostridium difficile

<400> SEQUENCE: 69

| | | | | | |
|---|---|---|---|---|---|
| atggtatttg | aaaaaattga | taaaaatagt | tggaacagaa | aagagtattt | tgaccactac | 60 |
| tttgcaagtg | taccttgtac | atacagcatg | accgttaaag | tggatatcac | acaaataaag | 120 |
| gaaaagggaa | tgaaactata | tcctgcaatg | ctttattata | ttgcaatgat | tgtaaaccgc | 180 |
| cattcagagt | ttaggacggc | aatcaatcaa | gatggtgaat | tggggatata | tgatgagatg | 240 |
| ataccaagct | atacaatatt | tcacaatgat | actgaaacat | tttccagcct | ttggactgag | 300 |
| tgtaagtctg | actttaaatc | atttttagca | gattatgaaa | gtgatacgca | acggtatgga | 360 |
| aacaatcata | gaatggaagg | aaagccaaat | gctccggaaa | acattttttaa | tgtatctatg | 420 |
| ataccgtggt | caaccttcga | tggctttaat | ctgaatttgc | agaaaggata | tgattatttg | 480 |
| attcctatt | ttactatggg | gaaatattat | aaagaagata | caaaattat | acttcctttg | 540 |
| gcaattcaag | ttcatcacgc | agtatgtgac | ggatttcaca | tttgccgttt | tgtaaacgaa | 600 |
| ttgcaggaat | tgataaatag | ttaa | | | | 624 |

<210> SEQ ID NO 70
<211> LENGTH: 624
<212> TYPE: DNA
<213> ORGANISM: Clostridium perfringens

<400> SEQUENCE: 70

| | | | | | |
|---|---|---|---|---|---|
| atggtatttg | aaaaaattga | taaaaatagt | tggaacagaa | aagagtattt | tgaccactac | 60 |
| tttgcaagtg | taccttgtac | atacagcatg | accgttaaag | tggatatcac | acaaataaag | 120 |
| gaaaagggaa | tgaaactata | tcctgcaatg | ctttattata | ttgcaatgat | tgtaaaccgc | 180 |
| cattcagagt | ttaggacggc | aatcaatcaa | gatggtgaat | tggggatata | tgatgagatg | 240 |

```
ataccaagct atacaatatt tcacaatgat actgaaacat tttccagcct ttggactgag    300
tgtaagtctg actttaaatc attttagca gattatgaaa gtgatacgca acggtatgga    360
aacaatcata gaatggaagg aaagccaaat gctccggaaa acattttaa tgtatctatg    420 ataccgtggt caaccttcga tggctttaat ctgaatttgc agaaaggata tgattatttg    480
attcctattt ttactatggg gaaatattat aaagaagata caaaattat acttcctttg    540 gcaattcaag ttcatcacgc agtatgtgac ggatttcaca tttgccgttt tgtaaacgaa    600
ttgcaggaat tgataaatag ttaa                                          624
```

<210> SEQ ID NO 71
<211> LENGTH: 3897
<212> TYPE: DNA
<213> ORGANISM: Artificial Sequence
<220> FEATURE:
<223> OTHER INFORMATION: MAD7 optimized

<400> SEQUENCE: 71

```
ctcgagtccc tatcagtgat agattgaaac tctatcattg atagagtata atatctttgt     60
tcattagagc gataaacttg aatttgagag ggaacttaga tgaacaacgg cacaaataat    120
tttcagaact tcatagggat atcaagtttg cagaaaacgt taagaaatgc tttaataccc    180
acggaaacca cgcaacagtt catagttaag aacggaataa ttaagaaga tgagttaaga    240 ggcgagaaca gacagatttt aaaagatata atggatgact actacagagg attcatatct    300
gagactttaa gttctattga tgacatagat tggactagct tattcgaaaa aatggaaatt    360
cagttaaaaa atggtgataa taagatacc ttaattaagg aacagacaga gtatagaaaa    420
gcaatacata aaaaatttgc gaacgacgat agatttaaga acatgtttag cgccaaatta    480
attagtgaca tattacctga atttgttata cacaacaata attattcggc atcagagaaa    540
gaggaaaaaa cccaggtgat aaaattgttt tcgagatttg cgactagctt taaagattac    600
ttcaagaaca gagcaaattg ctttttcagcg gacgatattt catcaagcag ctgccataga    660
atagttaacg acaatgcaga gatattcttt tcaaatgcgt tagtttacag aagaatagta    720
aaatcgttaa gcaatgacga tataaacaaa atttcgggcg atatgaaaga ttcattaaaa    780
gaaatgagtt tagaagaaat atattcttac gagaagtatg gggaatttat tacccaggaa    840
ggcattagct ctataatga tatatgtggg aaagtgaatt ctttttatgaa cttatattgt    900 cagaaaaata agaaaaacaa aaatttatac aaacttcaga aacttcacaa acagattcta    960
tgcattgcgg acactagcta tgaggttccg tataaatttg aaagtgacga ggaagtgtac   1020
caatcagtta acggcttcct tgataacatt agcagcaaac atatagttga aagattaaga   1080
aaaataggcg ataactataa cggctacaac ttagataaaa tttatatagt gtccaaattt   1140
tacgagagcg ttagccaaaa aacctacaga gactgggaaa caattaatac cgccttagaa   1200
attcattaca ataatatatt gccgggtaac ggtaaaagta aagccgacaa agtaaaaaaa   1260
gcggttaaga atgatttaca gaaatccata accgaaataa atgaactagt gtcaaactat   1320
aagttatgca gtgacgacaa cataaaagcg gagacttata tacatgagat tagccatata   1380
ttgaataact tgaagcaca ggaattgaaa tacaatccgg aaattcacct agttgaatcc   1440
gagttaaaag cgagtgagct taaaaacgtg ttagacgtga taatgaatgc gtttcattgg   1500
tgttcggttt ttatgactga ggaacttgtt gataaagaca caattttta tgcggaatta   1560 gaggagattt acgatgaaat ttatccagta attagtttat acaacttagt tagaaactac   1620
gttacccaga aaccgtacag cacgaaaaag attaaattga acttcggaat accgacgtta   1680
```

```
gcagacggtt ggtcaaagtc caaagagtat tctaataacg ctataatatt aatgagagac    1740
aatttatatt atttaggcat atttaatgcg aagaataaac cggacaagaa gattatagag    1800
ggtaatacgt cagaaaataa gggtgactac aaaaagatga tttataattt gttaccgggt    1860
cccaacaaaa tgataccgaa agttttcttg agcagcaaga cgggggtgga aacgtataaa    1920
ccgagcgcct atatactaga ggggtataaa cagaataaac atataaagtc ttcaaaagac    1980
tttgatataa ctttctgtca tgatttaata gactacttca aaaactgtat tgcaattcat    2040
cccgagtgga aaaacttcgg ttttgatttt agcgacacca gtacttatga agacatttcc    2100
gggttttata gagaggtaga gttacaaggt tacaagattg attggacata cattagcgaa    2160
aaagacattg atttattaca ggaaaaaggt caattatatt tattccagat atataacaaa    2220
gatttttcga aaaaatcaac cgggaatgac aaccttcaca ccatgtactt aaaaaatctt    2280
ttctcagaag aaaatcttaa ggatatagtt ttaaaactta acggcgaagc ggaaatattc    2340
ttcaggaaga gcagcataaa gaacccaata attcataaaa aaggctcgat tttagttaac    2400
agaacctacg aagcagaaga aaaagaccag tttggcaaca ttcaaattgt gagaaaaaat    2460
attccggaaa acatttatca ggagttatac aaatacttca acgataaaag cgacaaagag    2520
ttatctgatg aagcagccaa attaaagaat gtagtgggac accacgaggc agcgacgaat    2580
atagttaagg actatagata cacgtatgat aaatacttcc ttcatatgcc tattacgata    2640
aatttcaaag ccaataaaac gggttttatt aatgatagga tattacagta tatagctaaa    2700
gaaaaagact tacatgtgat aggcattgat agaggcgaga gaacttaat atacgtgtcc     2760 gtgattgata cttgtggtaa tatagttgaa cagaaaagct ttaacattgt aaacggctac    2820
gactatcaga taaaattaaa acaacaggag ggcgctagac agattgcgag aaaagaatgg    2880
aaagaaattg gtaaaattaa agagataaaa gagggctact taagcttagt aatacacgag    2940
atatctaaaa tggtaataaa atacaatgca attatagcga tggaggattt gtcttatggt    3000
tttaaaaaag ggagatttaa ggttgaaaga caagtttacc agaaatttga aaccatgtta    3060
ataaataaat taactctatt agtatttaaa gatatttcga ttaccgagaa tggcggttta    3120
ttaaaaggtt atcagttaac atacattcct gataaactta aaaacgtggg tcatcagtgc    3180
ggctgcattt tttatgtgcc tgctgcatac acgagcaaaa ttgatccgac caccggcttt    3240
gtgaatatat ttaaatttaa agacttaaca gtggacgcaa aaagagaatt cattaaaaaa    3300
tttgactcaa ttagatatga cagtgaaaaa aatttattct gctttacatt tgactacaat    3360
aactttatta cgcaaaacac ggttatgagc aaatcatcgt ggagtgtgta tacatacggc    3420
gtgagaataa aagaagatt tgtgaacggc agattctcaa acgaaagtga taccattgac    3480
ataaccaaag atatggagaa aacgttggaa atgacggaca ttaactggag agatggccac    3540
gatcttagac aagacattat agattatgaa attgttcagc acatattcga aattttcaga    3600
ttaacagtgc aaatgagaaa ctccttgtct gaattagagg acagagatta cgatagatta    3660
atttcacctg tattaaacga aaataacatt ttttatgaca gcgcgaaagc gggggatgca    3720
cttcctaagg atgccgatgc aaatggtgcg tattgtattg cattaaaagg gttatatgaa    3780
attaaacaaa ttaccgaaaa ttggaaagaa gatggtaaat tttcgagaga taaattaaaa    3840
ataagcaata aagattggtt cgactttata cagaataaga gatatttata agtcgac      3897
```

<210> SEQ ID NO 72
<211> LENGTH: 1263
<212> TYPE: PRT

-continued

<213> ORGANISM: Artificial Sequence
<220> FEATURE:
<223> OTHER INFORMATION: MAD7

<400> SEQUENCE: 72

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
```

-continued

```
            385                 390                 395                 400
Asn Glu Leu Val Ser Asn Tyr Lys Leu Cys Ser Asp Asp Asn Ile Lys
                    405                 410                 415
Ala Glu Thr Tyr Ile His Glu Ile Ser His Ile Leu Asn Asn Phe Glu
                    420                 425                 430
Ala Gln Glu Leu Lys Tyr Asn Pro Glu Ile His Leu Val Glu Ser Glu
                    435                 440                 445
Leu Lys Ala Ser Glu Leu Lys Asn Val Leu Asp Val Ile Met Asn Ala
            450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                    485                 490                 495
Val Ile Ser Leu Tyr Asn Leu Val Arg Asn Tyr Val Thr Gln Lys Pro
                    500                 505                 510
Tyr Ser Thr Lys Lys Ile Lys Leu Asn Phe Gly Ile Pro Thr Leu Ala
                    515                 520                 525
Asp Gly Trp Ser Lys Ser Lys Glu Tyr Ser Asn Asn Ala Ile Ile Leu
            530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                    565                 570                 575
Tyr Lys Lys Met Ile Tyr Asn Leu Leu Pro Gly Pro Asn Lys Met Ile
                    580                 585                 590
Pro Lys Val Phe Leu Ser Ser Lys Thr Gly Val Glu Thr Tyr Lys Pro
                    595                 600                 605
Ser Ala Tyr Ile Leu Glu Gly Tyr Lys Gln Asn Lys His Ile Lys Ser
            610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                    645                 650                 655
Phe Ser Asp Thr Ser Thr Tyr Glu Asp Ile Ser Gly Phe Tyr Arg Glu
                    660                 665                 670
Val Glu Leu Gln Gly Tyr Lys Ile Asp Trp Thr Tyr Ile Ser Glu Lys
                    675                 680                 685
Asp Ile Asp Leu Leu Gln Glu Lys Gly Gln Leu Tyr Leu Phe Gln Ile
            690                 695                 700
Tyr Asn Lys Asp Phe Ser Lys Lys Ser Thr Gly Asn Asp Asn Leu His
705                 710                 715                 720
Thr Met Tyr Leu Lys Asn Leu Phe Ser Glu Asn Leu Lys Asp Ile
                    725                 730                 735
Val Leu Lys Leu Asn Gly Glu Ala Glu Ile Phe Phe Arg Lys Ser Ser
                    740                 745                 750
Ile Lys Asn Pro Ile Ile His Lys Lys Gly Ser Ile Leu Val Asn Arg
                    755                 760                 765
Thr Tyr Glu Ala Glu Glu Lys Asp Gln Phe Gly Asn Ile Gln Ile Val
            770                 775                 780
Arg Lys Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                    805                 810                 815
```

```
Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215
```

Cys Ile Ala Leu Lys Gly Leu Tyr Glu Ile Lys Gln Ile Thr Glu
        1220                1225                1230

Asn Trp Lys Glu Asp Gly Lys Phe Ser Arg Asp Lys Leu Lys Ile
        1235                1240                1245

Ser Asn Lys Asp Trp Phe Phe Ile Gln Asn Lys Arg Tyr Leu
        1250                1255                1260

<210> SEQ ID NO 73
<211> LENGTH: 363
<212> TYPE: DNA
<213> ORGANISM: Artificial Sequence
<220> FEATURE:
<223> OTHER INFORMATION: Promoter CatB

<400> SEQUENCE: 73
taaaaaatgt tacgcactttt tcttatattg ttcaacaata acataattta ttaacaaaag    60
gaaagtatag ttaaaaaaat gttggagcaa atgcggatgg aaaaataaaa attaatatta   120
gtagtaattc cgatgttaaa ataacaagag ataagaaaaa gtaaaatatt agagtaattc   180
gtagtattct taagttatga atcaataaaa aatggtctct gaaaattgaa tagttcggta   240
ttacagaatg tgctataata aactaaagcg taaatatcat tgtaaaaagg agattgaaat   300
ggctaggtca cggaaaaaag ccttctaaaa tagaattacg aaaattttta ggaggcccga   360
att                                                                 363

<210> SEQ ID NO 74
<211> LENGTH: 322
<212> TYPE: DNA
<213> ORGANISM: Artificial Sequence
<220> FEATURE:
<223> OTHER INFORMATION: Promoter CATQ

<400> SEQUENCE: 74
ctgcgtacac atccagacat cgctttagag tatggtgaat taaagatgga gcgggcttat    60
cgattctcag aggatattga aggctactgc actggtaagg atgcatttgt aaagcaacta   120
gaaaaggatg ctttgcgatg gtggcaaact gtctgttagg aggttattct caaaggattg   180
caagaagcag ttgaggataa tccgtataac taactattac acattcttaa cattgctggt   240
ttgtatcggt agaataacac gaattaacaa aggatatatt ttgtagtagc aagtgtattt   300
gttttatatt ctatgaacct at                                            322

<210> SEQ ID NO 75
<211> LENGTH: 1368
<212> TYPE: PRT
<213> ORGANISM: Streptococcus pyogenes

<400> SEQUENCE: 75

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser

-continued

```
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
            130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
            210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
```

```
Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925
```

```
Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
```

| | | | |
|---|---|---|---|
| | 1325 | 1330 | 1335 |

Thr Lys Glu Val Leu Asp Ala Thr Leu Ile His Gln Ser Ile Thr
     1340                 1345               1350

Gly Leu Tyr Glu Thr Arg Ile Asp Leu Ser Gln Leu Gly Gly Asp
     1355                 1360               1365

<210> SEQ ID NO 76
<211> LENGTH: 4107
<212> TYPE: DNA
<213> ORGANISM: Streptococcus pyogenes

<400> SEQUENCE: 76

| | |
|---|---|
| atggataaga aatactcaat aggcttagat atcggcacaa atagcgtcgg atgggcggtg | 60 |
| atcactgatg aatataaggt tccgtctaaa aagttcaagg ttctgggaaa tacagaccgc | 120 |
| cacagtatca aaaaaaatct tataggggct ctttttatttg acagtggaga gacagcggaa | 180 |
| gcgactcgtc tcaaacggac agctcgtaga aggtatacac gtcggaagaa tcgtatttgt | 240 |
| tatctacagg agatttttc aaatgagatg gcgaaagtag atgatagttt ctttcatcga | 300 |
| cttgaagagt cttttttggt ggaagaagac aagaagcatg aacgtcatcc tattttgga | 360 |
| aatatagtag atgaagttgc ttatcatgag aaatatccaa ctatctatca tctgcgaaaa | 420 |
| aaattggtag attctactga taaagcggat ttgcgcttaa tctatttggc cttagcgcat | 480 |
| atgattaagt ttcgtggtca tttttttgatt gagggagatt taaatcctga taatagtgat | 540 |
| gtggacaaac tatttatcca gttggtacaa acctacaatc aattatttga agaaaaccct | 600 |
| attaacgcaa gtggagtaga tgctaaagcg attctttctg cacgattgag taaatcaaga | 660 |
| cgattagaaa atctcattgc tcagctcccc ggtgagaaga aaatggctt atttgggaat | 720 |
| ctcattgctt tgtcattggg tttgaccccct aattttaaat caattttga tttggcagaa | 780 |
| gatgctaaat tacagctttc aaaagatact tacgatgatg atttagataa tttattggcg | 840 |
| caaattggag atcaatatgc tgatttgttt ttggcagcta agaatttatc agatgctatt | 900 |
| ttactttcag atatcctaag agtaaatact gaaataacta aggctcccct atcagcttca | 960 |
| atgattaaac gctacgatga acatcatcaa gacttgactc ttttaaaagc tttagttcga | 1020 |
| caacaacttc cagaaaagta taaagaaatc tttttttgatc aatcaaaaaa cggatatgca | 1080 |
| ggttatattg atgggggagc tagccaagaa gaattttata aatttatcaa accaatttta | 1140 |
| gaaaaaatgg atggtactga ggaattattg gtgaaactaa atcgtgaaga tttgctgcgc | 1200 |
| aagcaacgga cctttgacaa cggctctatt ccccatcaaa ttcacttggg tgagctgcat | 1260 |
| gctatttga aagacaaga agactttat ccatttttaa aagacaatcg tgagaagatt | 1320 |
| gaaaaaatct tgacttttcg aattccttat tatgttggtc cattggcgcg tggcaatagt | 1380 |
| cgttttgcat ggatgactcg gaagtctgaa gaaacaatta ccccatggaa ttttgaagaa | 1440 |
| gttgtcgata aggtgcttc agctcaatca tttattgaac gcatgacaaa ctttgataaa | 1500 |
| aatcttccaa atgaaaaagt actaccaaaa catagtttgc tttatgagta ttttacggtt | 1560 |
| tataacgaat tgacaaaggt caaatatgtt actgaaggaa tgcgaaaacc agcatttctt | 1620 |
| tcaggtgaac agaagaaagc cattgttgat ttactcttca aaacaaatcg aaaagtaacc | 1680 |
| gttaagcaat aaaagaaga ttatttcaaa aaaatagaat gttttgatag tgttgaaatt | 1740 |
| tcaggagttg aagatagatt taatgcttca ttaggtacct accatgattt gctaaaaatt | 1800 |
| attaaagata agattttttt ggataatgaa gaaaatgaag atatcttaga ggatattgtt | 1860 |
| ttaacattga cctatttga agatagggag atgattgagg aaagacttaa aacatatgct | 1920 |

```
cacctctttg atgataaggt gatgaaacag cttaaacgtc gccgttatac tggttgggga    1980
cgtttgtctc gaaaattgat taatggtatt agggataagc aatctggcaa acaatatta    2040 gatttttga aatcagatgg ttttgccaat cgcaattta tgcagctgat ccatgatgat    2100
agtttgacat ttaagaaga cattcaaaaa gcacaagtgt ctggacaagg cgatagttta    2160
catgaacata ttgcaaattt agctggtagc cctgctatta aaaaggtat tttacagact    2220 gtaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aatggaaga    2460 gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata aagtacgtga gattaacaat    2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060 atgattgcta agtctgagca agaaataggc aaagcaaccg caaaatattt ctttactct    3120 aatatcatga acttcttcaa aacagaaatt acacttgcaa atggagagat cgcaaacgc    3180 cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aagggaaat cgaagaagtt aaaatccgtt    3480
aaagagttac tagggatcac aattatgaaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660 caaaaggaa atgagctggc tctgccaagc aaatatgtga ttttttata tttagctagt    3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                        4107

<210> SEQ ID NO 77
<211> LENGTH: 1170
<212> TYPE: DNA
```

<213> ORGANISM: Artificial Sequence
<220> FEATURE:
<223> OTHER INFORMATION: bdhA

<400> SEQUENCE: 77

```
atgctaagtt ttgattattc aataccaact aaagttttt ttggaaaagg aaaaatagac    60
gtaattggag aagaaattaa gaaatatggc tcaagagtgc ttatagttta tggcggagga   120
agtataaaaa ggaacggtat atatgataga gcaacagcta tattaaaaga aaacaatata   180
gctttctatg aactttcagg agtagagcca atcctagga taacaacagt aaaaaaaggc   240
atagaaatat gtagagaaaa taatgtggat ttagtattag caataggggg aggaagtgca   300
atagactgtt ctaaggtaat tgcagctgga gtttattatg atggcgatac atgggacatg   360
gttaaagatc catctaaaat aactaaagtt cttccaattg caagtatact tactctttca   420
gcaacagggt ctgaaatgga tcaaattgca gtaatttcaa atatggagac taatgaaaag   480
cttggagtag acatgatga tatgagacct aaattttcag tgttagatcc tacatatact   540
tttacagtac ctaaaaatca aacagcagcg ggaacagctg acattatgag tcacaccttt   600
gaatcttact ttagtggtgt tgaaggtgct tatgtgcagg acggtatagc agaagcaatc   660
ttaagaacat gtataaagta tggaaaaata gcaatggaga agactgatga ttacgaggct   720
agagctaatt tgatgtgggc ttcaagttta gctataaatg gtctattatc acttggtaag   780
gatagaaaat ggagttgtca tcctatggaa cacgagttaa gtgcatatta tgatataaca   840
catggtgtag acttgcaat tttaacacct aattggatgg aatatattct aaatgacgat   900
acacttcata aatttgtttc ttatggaata aatgtttggg aatagacaa gaacaaagat   960
aactatgaaa tagcacgaga ggctattaaa aatacgagag aatactttaa ttcattgggt  1020
attccttcaa agcttagaga agttggaata ggaaaagata aactagaact aatggcaaag  1080
caagctgtta gaaattctgg aggaacaata ggaagtttaa gaccaataaa tgcagaggat  1140
gttcttgaga tatttaaaaa atcttattaa                                   1170
```

<210> SEQ ID NO 78
<211> LENGTH: 1173
<212> TYPE: DNA
<213> ORGANISM: Artificial Sequence
<220> FEATURE:
<223> OTHER INFORMATION: bdhB

<400> SEQUENCE: 78

```
gtggttgatt tcgaatattc aataccaact agaattttt tcggtaaaga taagataaat    60
gtacttggaa gagagcttaa aaaatatggt tctaaagtgc ttatagttta tggtggagga   120
agtataaaga gaaatggaat atatgataaa gctgtaagta tacttgaaaa aaacagtatt   180
aaattttatg aacttgcagg agtagagcca atccaagag taactacagt tgaaaaagga   240
gttaaaatat gtagagaaaa tggagttgaa gtagtactag ctataggtgg aggaagtgca   300
atagattgcg caaaggttat agcagcagca tgtgaatatg atggaaatcc atgggatatt   360
gtgttagatg gctcaaaaat aaaaagggtg cttcctatag ctagtatatt aaccattgct   420
gcaacaggat cagaaatgga tacgtgggca gtaataaaata atatgataaa aacgaaaaa   480
ctaattgcgg cacatccaga tatggctcct aagttttcta tattagatcc aacgtatacg   540
tataccgtac ctaccaatca aacagcagca ggaacagctg atattatgag tcatataattt   600
gaggtgtatt ttagtaatac aaaaaacagca tatttgcagg atagaatggc agaagcgtta   660
ttaagaactt gtattaaata tggaggaata gctcttgaga agccggatga ttatgaggca   720
```

```
agagccaatc taatgtgggc ttcaagtctt gcgataaatg gacttttaac atatggtaaa      780
gacactaatt ggagtgtaca cttaatggaa catgaattaa gtgcttatta cgacataaca      840
cacggcgtag ggcttgcaat tttaacacct aattggatgg agtatatttt aaataatgat      900
acagtgtaca agtttgttga atatggtgta aatgtttggg gaatagacaa agaaaaaaat      960
cactatgaca tagcacatca agcaatacaa aaacaagag attactttgt aaatgtacta      1020
ggtttaccat ctagactgag agatgttgga attgaagaag aaaaattgga cataatggca     1080
aaggaatcag taaagcttac aggaggaacc ataggaaacc taagaccagt aaacgcctcc     1140
gaagtcctac aaatattcaa aaaatctgtg taa                                  1173

<210> SEQ ID NO 79
<211> LENGTH: 6560
<212> TYPE: DNA
<213> ORGANISM: Artificial Sequence
<220> FEATURE:
<223> OTHER INFORMATION: pGRNA-deltabdhB

<400> SEQUENCE: 79
gatccccggg taccgagctc gaattcgtaa tcatggtcat agctgtttcc tgtgtgaaat       60
tgttatccgc tcacaattcc acacaacata cgagccggaa gcataaagtg taaagcctgg      120
ggtgcctaat gagtgagcta actcacatta attgcgttgc gctcactgcc cgctttccag      180
tcgggaaacc tgtcgtgcca gctgcattaa tgaatcggcc aacgcgcggg gagaggcggt      240
ttgcgtattg ggcgctcttc cgcttcctcg ctcactgact cgctgcgctc ggtcgttcgg      300
ctgcggcgag cggtatcagc tcactcaaag gcggtaatac ggttatccac agaatcaggg      360
gataacgcag gaaagaacat gtgagcaaaa ggccagcaaa aggccaggaa ccgtaaaaag      420
gccgcgttgc tggcgttttt ccataggctc cgcccccctg acgagcatca caaaaatcga      480
cgctcaagtc agaggtggcg aaacccgaca ggactataaa gataccaggc gtttccccct      540
ggaagctccc tcgtgcgctc tcctgttccg accctgccgc ttaccggata cctgtccgcc      600
tttctccctt cggaagcgt ggcgctttct catagctcac gctgtaggta tctcagttcg      660
gtgtaggtcg ttcgctccaa gctgggctgt gtgcacgaac cccccgttca gcccgaccgc      720
tgcgccttat ccggtaacta tcgtcttgag tccaacccgg taagacacga cttatcgcca      780
ctggcagcag ccactggtaa caggattagc agagcgaggt atgtaggcgg tgctacagag      840
ttcttgaagt ggtggcctaa ctacggctac actagaagaa cagtatttgg tatctgcgct      900
ctgctgaagc cagttacctt cggaaaaaga gttggtagct cttgatccgg caaacaaacc      960
accgctggta gcggtggttt ttttgtttgc aagcagcaga ttacgcgcag aaaaaaagga     1020
tctcaagaag atcctttgat cttttctacg ggtctgacg ctcagtggaa cgaaaactca     1080
cgttaaggga ttttggtcat gagattatca aaaaggatct tcacctagat ccttttaaat     1140
taaaaatgaa gttttaaatc aatctaaagt atatatgagt aaacttggtc tgacagttac     1200
caaagctagc ttaatactag tatatactta atgtgataag tgtctgacag ctgaccggtc     1260
taaagaggtc cctagcgcct acggggaatt tgtatcgata aggggtacaa attcccacta     1320
agcgctcggc cggggatcga tccccgggta cgtacccggc agttttttctt tttcggcaag     1380 tgttcaagaa gttattaagt cgggagtgca gtcgaagtgg gcaagttgaa aaattcacaa     1440
aaatgtggta taatatcttt gttcattaga gcgataaact tgaatttgag agggaactta     1500 gatggtatttt gaaaaaattg ataaaaatag ttggaacaga aagagtatt ttgaccacta     1560
```

```
ctttgcaagt gtaccttgta cctacagcat gaccgttaaa gtggatatca cacaaataaa   1620
ggaaaaggga atgaaactat atcctgcaat gctttattat attgcaatga ttgtaaaccg   1680
ccattcagag tttaggacgg caatcaatca agatggtgaa ttggggatat atgatgagat   1740
gataccaagc tatacaatat ttcacaatga tactgaaaca ttttccagcc tttggactga   1800
gtgtaagtct gactttaaat cattttttagc agattatgaa agtgatacgc aacggtatgg   1860
aaacaatcat agaatggaag gaaagccaaa tgctccggaa acattttta atgtatctat   1920 gataccgtgg tcaaccttcg atggctttaa tctgaatttg cagaaaggat atgattattt   1980
gattcctatt tttactatgg ggaaatatta taaagaagat aacaaaatta tacttccttt   2040
ggcaattcaa gttcatcacg cagtatgtga cggatttcac atttgccgtt ttgtaaacga   2100
attgcaggaa ttgataaata gttaacttca ggtttgtctg taactaaaaa ctagtattta   2160
acctaggatc aaaaaaattt ccaataatcc cactctaagc cacaaacacg ccctataaaa   2220
tcccgcttta atcccacttt gagacacatg taatattact ttacgcccta gtatagtgat   2280
aattttttac attcaatgcc acgcaaaaaa ataaggggc actataataa aagttccttc   2340
ggaactaact aaagtaaaaa attatctttta caacctcccc aaaaaaaaga acaggtacaa   2400
agtaccctat aatacaagcg taaaaaaaat gagggtaaaa ataaaaaaat aaaaaaataa   2460
aaaaataaaa aaataaaaaa ataaaaaaat aaaaaaatat aaaaataaaa aaatataaaa   2520
ataaaaaaat aaaaaaataa aaaaataaaa aaatataaaa ataaaaaaat aaaaaaatat   2580
aaaaatattt tttatttaaa gtttgaaaaa aatttttta tattatataa tctttgaaga   2640
aaagaatata aaaaatgagc ctttataaaa gcccattttt tttcatatac gtaatatgac   2700
gttctaatgt ttttattggt acttctaaca ttagagtaat ttctttattt ttaaagcctt   2760 tttcttttaag ggcttttatt ttttttctta atacatttaa ttcctcttt tttgttgctt   2820 ttcctttagc ttttaattgc tcttgataat tttttttacc tctaatattt tctcttctct   2880
tatattcctt tttagaaatt attattgtca tatattttg ttcttcttct gtaatttcta   2940
ataactctat aagagtttca ttcttatact tatattgctt attttatct aaataacatc   3000 tttcagcact tctagttgct cttataactt ctctttcact taaatgttgt ctaaacatac   3060
tattaagttc taaaacatca tttaatgcct tctcaatgtc ttctgtaaag ctacaaagat   3120
aatatctata taaaaataat ataagctctc tgtgtccttt taaatcatat tctcttagtt   3180
cacaaagttt tattatgtct tgtattcttc cataatataa acttctttct ctataaatat   3240
aatttatttt gcttggtcta ccctttttcc tttcatatgg ttttaattca ggtaaaaatc   3300
cattttgtat ttctcttaag tcataaatat attcgtactc atctaatata ttgactactg   3360 ttttttgattt agagtttata cttcctggaa ctcttaatat tctcgttgca tctaaggctt   3420
gtctatctgc tccaaagtat tttaattgat tatataaata ttcttgaacc gctttccata   3480
atggtaatgc tttactaggt actgcattta ttatccatat taaatacatt cctcttccac   3540
tatctattac atagtttggt ataggaatac tttgattaaa ataattcttt tctaagtcca   3600
ttaatacctg gtcttttagtt ttgccagttt tataataatc caagtctata aacagtgtat   3660
ttaactcttt tatattttct aatcgcctac acggcttata aaaggtattt agagttatat   3720
agatattttc atcactcata tctaaatctt ttaattcagc gtatttatag tgccattggc   3780
tatatccttt tttatctata acgctcctgg ttatccaccc tttacttcta ctatgaatat   3840
tatctatata gttcttttta ttcagcttta atgcgtttct cacttattca cctcccttc   3900 tgtaaaacta agaaaattat atcatatttt caataattat taactattct taaactctta   3960
```

```
ataaaaaata gagtaagtcc ccaattgaaa cttaatctat tttttatgtt ttaatttatt    4020 attttatta aaatatttta aactaaatta aatgattctt tttaattttt tactatttca    4080
ttccataata tattactata attatttaca aataatattt cttcatttgt aatatttaga    4140
tgatttacta attttagttt ttatatatta aataattaat gtaaattta tataaaaaat    4200 caaaggagct tataaattat gattatttcc aaagatacta aagatttaat tttttcaat    4260 tttaacaata cttttgtaa tattatgttt aaatttaatt gtatttttt catataataa    4320 agccgttgaa gtaaaccaat ccatttcct tatgatgtta ttattaaatt taagttttat    4380
aataatatct ttattatatt tattgttttt aaaaaaacta gtgaaatttc tagtgaaatt    4440
tccggcttta ttaaacttat ttttaggaat tttattttca ttttcatctt tacaggattt    4500
gattatatct ttaaatatgt tttatcaaat attatctttt tctaaattta tatatatttt    4560
tattatattt attattatat atattttatt tttaagtttc tttctaacag ctattaaaaa    4620
gaaacttaaa aataaaaaca cgtactctaa accaataaat aaaactattt ttattattgc    4680
tgccttgatt ggaatagttt ttagtaaaat taatttcaat attccacaat attatattat    4740
aagctagcac gcctcgagac tctatcattg atagagtttg aaactctatc attgatagag    4800
tataatatct ttgttcatgc ttattacgac ataacacagt tttagagcta gaaatagcaa    4860
gttaaaataa ggctagtccg ttatcaactt gaaaaagtgg caccgagtcg gtgcttttt    4920 tgaagcttct cgagatctcc atggacgcgt gacgtcgact cttaagaaca tgtataaagt    4980
atggaaaaat agcaatggag aagactgatg attacgaggc tagagctaat ttgatgtggg    5040
cttcaagttt agctataaat ggtctattat cacttggtaa ggatagaaaa tggagttgtc    5100
atcctatgga acacgagtta agtgcatatt atgatataac acatggtgta ggacttgcaa    5160
ttttaacacc taattggatg aatatattc taaatgacga tacacttcat aaatttgttt    5220
cttatggaat aaatgtttgg ggaatagaca agaacaaaga taactatgaa atagcacgag    5280
aggctattaa aaatacgaga gaatacttta attcattggg tattccttca aagcttagag    5340
aagttggaat aggaaaagat aaactagaac taatggcaaa gcaagctgtt agaaaattctg    5400 gaggaacaat aggaagttta agaccaataa atgcagagga tgttcttgag atatttaaaa    5460
aatcttatta atagaaactg tagaggtatt tttataattt aaaagatgtt aaagagtgag    5520
gagtaatttt gttctaacgc ctcactcttt tcattttatg attaaatgta tgctgattta    5580
cgctaactta aatcctaaat aataacctaa tgttaatatt ttgtaacaaa tggataaaag    5640
cgtaaaaata ttattgtaat aattttaagt aggtttaaaa tatatataat gtagaagcat    5700
tcctacatta tattatttaa ataataatct aaacaggagg ggttaaagtg gttgatttca    5760
aatctgtgta aacctaccgg ggtttgggcg tagccattat attcatgaac tccaagaaag    5820
cagtatgcta gcaaagaaat aaaactcaaa gcagagagaa aatttagaca ttcaactata    5880
aataaaaaat acccccaaaa gcattaatat cttggggagt attttttatt ttgaagtatt    5940
ctgttcagct aaatattctt ctaaggtaat acctctgttc ataatttctt gtgaggcagg    6000
aagaccgata tatcttacat gccatggctc aaaattatac tttgttatgt tttctttatc    6060
cttaggatat cttattatga aaccatattt accacaattt gttgaagcc atttataaga    6120 atttgtattc ataaatccat catctaaaga agagtattcg gttgatagta agtccattgc    6180
caatccagtt tgatgctcac ttgtaccagg ttcagctaca tatttatcag cttcggcttt    6240
tccgtctcgt gctactttt cattatataa tttttgctga tacgaataag gtctataacc    6300
```

-continued

```
tgaaacagct agaagtgtaa gaccatcctt tgatgctgca ttaaacatat tttcaagtcc    6360
tgttgcagct tcgctctcca tttgatttac attaggatca gaactactaa taaatttaac    6420
gttaggagtt ctcaaatttt gaggtatata gtttcctgat aatttacttt gcttgtttac    6480
aagtaggatg ttctgtttct ttacctcggg tttcttggct tgttttttag gtgtagaaac    6540 tttcttttg ggttcgtttg                                                 6560
```

<210> SEQ ID NO 80
<211> LENGTH: 6560
<212> TYPE: DNA
<213> ORGANISM: Artificial Sequence
<220> FEATURE:
<223> OTHER INFORMATION: pGRNA_deltabdhA_deltabdhB

<400> SEQUENCE: 80

```
gatccccggg taccgagctc gaattcgtaa tcatggtcat agctgtttcc tgtgtgaaat      60
tgttatccgc tcacaattcc acacaacata cgagccggaa gcataaagtg taaagcctgg     120
ggtgcctaat gagtgagcta actcacatta attgcgttgc gctcactgcc cgctttccag     180
tcgggaaacc tgtcgtgcca gctgcattaa tgaatcggcc aacgcgcggg gagaggcggt     240
ttgcgtattg ggcgctcttc cgcttcctcg ctcactgact cgctgcgctc ggtcgttcgg     300
ctgcggcgag cggtatcagc tcactcaaag gcggtaatac ggttatccac agaatcaggg     360
gataacgcag gaaagaacat gtgagcaaaa ggccagcaaa aggccaggaa ccgtaaaaag     420
gccgcgttgc tggcgttttt ccataggctc cgcccccctg acgagcatca caaaaatcga     480
cgctcaagtc agaggtggcg aaacccgaca ggactataaa gataccaggc gtttccccct     540
ggaagctccc tcgtgcgctc tcctgttccg accctgccgc ttaccggata cctgtccgcc     600
tttctccctt cgggaagcgt ggcgctttct catagctcac gctgtaggta tctcagttcg     660
gtgtaggtcg ttcgctccaa gctgggctgt gtgcacgaac cccccgttca gcccgaccgc     720
tgcgccttat ccggtaacta tcgtcttgag tccaacccgg taagacacga cttatcgcca     780
ctggcagcag ccactggtaa caggattagc agagcgaggt atgtaggcgg tgctacagag     840
ttcttgaagt ggtggcctaa ctacggctac actagaagaa cagtatttgg tatctgcgct     900
ctgctgaagc cagttacctt cggaaaaaga gttggtagct cttgatccgg caaacaaacc     960
accgctggta gcggtggttt ttttgtttgc aagcagcaga ttacgcgcag aaaaaaagga    1020
tctcaagaag atcctttgat cttttctacg ggtctgacg ctcagtggaa cgaaaactca    1080
cgttaaggga ttttggtcat gagattatca aaaaggatct tcacctagat ccttttaaat    1140
taaaaatgaa gttttaaatc aatctaaagt atatatgagt aaacttggtc tgacagttac    1200
caaagctagc ttaatactag tatatactta atgtgataag tgtctgacag ctgaccggtc    1260
taaagaggtc cctagcgcct acggggaatt tgtatcgata aggggtacaa attcccacta    1320
agcgctcggc cggggatcga tccccggta cgtacccggc agttttctt tttcggcaag    1380 tgttcaagaa gttattaagt cgggagtgca gtcgaagtgg gcaagttgaa aaattcacaa    1440
aaatgtggta taatatcttt gttcattaga gcgataaact tgaatttgag agggaactta    1500
gatggtattt gaaaaaattg ataaaaatag ttggaacaga aaagagtatt ttgaccacta    1560
ctttgcaagt gtaccttgta cctacagcat gaccgttaaa gtggatatca cacaaataaa    1620
ggaaaaggga atgaaactat atcctgcaat gctttattat attgcaatga ttgtaaaccg    1680
ccattcagag tttaggacgg caatcaatca agatggtgaa ttggggatat atgatgagat    1740
gataccaagc tatacaatat tcacaatga tactgaaaca ttttccagcc tttggactga    1800
```

```
gtgtaagtct gactttaaat catttttagc agattatgaa agtgatacgc aacggtatgg    1860
aaacaatcat agaatggaag gaaagccaaa tgctccggaa acatttttta atgtatctat    1920
gataccgtgg tcaaccttcg atggctttaa tctgaatttg cagaaaggat atgattattt    1980
gattcctatt tttactatgg ggaaatatta taaagaagat aacaaaatta tacttccttt    2040
ggcaattcaa gttcatcacg cagtatgtga cggatttcac atttgccgtt ttgtaaacga    2100
attgcaggaa ttgataaata gttaacttca ggtttgtctg taactaaaaa ctagtattta    2160
acctaggatc aaaaaaattt ccaataatcc cactctaagc cacaaacacg ccctataaaa    2220
tcccgcttta atcccacttt gagacacatg taatattact ttacgcccta gtatagtgat    2280 aatttttttac attcaatgcc acgcaaaaaa ataaggggc actataataa aagttccttc    2340
ggaactaact aaagtaaaaa attatcttta caacctcccc aaaaaaaaga acaggtacaa    2400
agtaccctat aatacaagcg taaaaaaaat gagggtaaaa ataaaaaaat aaaaaaataa    2460
aaaaataaaa aaataaaaaa ataaaaaaat aaaaaaatat aaaaataaaa aaatataaaa    2520
ataaaaaaat ataaaaataa aaaaataaaa aaatataaaa ataaaaaaat aaaaaaatat    2580
aaaaatattt tttatttaaa gtttgaaaaa aattttttta tattatataa tctttgaaga    2640
aaagaatata aaaaatgagc ctttataaaa gcccattttt tttcatatac gtaatatgac    2700
gttctaatgt ttttattggt acttctaaca ttagagtaat ttcttttattt ttaaagcctt    2760 tttctttaag ggcttttatt tttttctta atacatttaa ttcctctttt tttgttgctt    2820 ttccttttagc ttttaattgc tcttgataat tttttttacc tctaatattt tctcttctct    2880
tatattcctt tttagaaatt attattgtca tatattttttg ttcttcttct gtaatttcta    2940
ataactctat aagagtttca ttcttatact tatattgctt attttttatct aaataacatc    3000 tttcagcact tctagttgct cttataactt ctctttcact taaatgttgt ctaaacatac    3060
tattaagttc taaacatca tttaatgcct tctcaatgtc ttctgtaaag ctacaaagat    3120
aatatctata taaaaataat ataagctctc tgtgtccttt taaatcatat tctcttagtt    3180
cacaaagttt tattatgtct tgtattcttc cataatataa acttctttct ctataaaatat    3240 aatttatttt gcttggtcta cccttttttcc tttcatatgg ttttaattca ggtaaaaatc    3300 catttttgtat ttctcttaag tcataaaatat attcgtactc atctaatata ttgactactg    3360 tttttttgattt agagtttata cttcctggaa ctcttaaatat tctcgttgca tctaaggctt    3420
gtctatctgc tccaaagtat tttaattgat tatataaata ttcttgaacc gctttccata    3480
atggtaatgc tttactaggt actgcattta ttatccatat taaatacatt cctcttccac    3540
tatctattac atagttttggt ataggaatac tttgattaaa ataattcttt tctaagtcca    3600
ttaatacctg gtctttagtt ttgccagttt tataataatc caagtctata aacagtgtat    3660
ttaactcttt tatattttct aatcgcctac acggcttata aaaggtattt agagttatat    3720 agatatttc atcactcata tctaaatctt ttaattcagc gtatttatag tgccattggc    3780
tatatccttt tttatctata acgctcctgg ttatccaccc tttacttcta ctatgaatat    3840
tatctatata gttcttttta ttcagcttta atgcgtttct cactattca cctcccttc    3900 tgtaaaacta agaaaattat atcatatttt caataattat taactattct taaactctta    3960 ataaaaaaata gagtaagtcc ccaattgaaa cttaatctat tttttatgtt ttaatttatt    4020 attttttatta aaatatttta aactaaatta aatgattctt tttaattttt tactatttca    4080
ttccataata tattactata attatttaca aataatattt cttcatttgt aatatttaga    4140
```

```
tgatttacta attttagttt ttatatatta aataattaat gtataattta tataaaaaat    4200
caaaggagct tataaattat gattatttcc aaagatacta aagatttaat tttttttcaat   4260 tttaacaata cttttttgtaa tattatgttt aaatttaatt gtattttttt catataataa   4320
agccgttgaa gtaaaccaat ccattttcct tatgatgtta ttattaaatt taagttttat   4380
aataatatct ttattatatt tattgttttt aaaaaaacta gtgaaatttc tagtgaaatt   4440
tccggcttta ttaaacttat ttttaggaat tttattttca ttttcatctt tacaggattt   4500
gattatatct ttaaatatgt tttatcaaat attatctttt tctaaattta tatatatttt   4560
tattatattt attattatat atattttatt tttaagtttc tttctaacag ctattaaaaa   4620
gaaacttaaa aataaaaaca cgtactctaa accaataaat aaaactattt ttattattgc   4680
tgccttgatt ggaatagttt ttagtaaaat taatttcaat attccacaat attatatatt   4740
aagctagcac gcctcgagac tctatcattg atagagtttg aaactctatc attgatagag   4800
tataatatct ttgttcatgc ttattacgac ataacacagt tttagagcta gaaatagcaa   4860
gttaaaataa ggctagtccg ttatcaactt gaaaaagtgg caccgagtcg gtgcttttt   4920 tgaagcttct cgagatctcc atggacgcgt gacgtcgacc ttctaatctc ctctactatt   4980
ttagggttag ctacattagc taaataggta atagctacag ttgtctttga attctcacct   5040
aaagtaagtt cttccacttt aaaatcagtg cttctaattt ttttttcttaa aagggctaca   5100 tttgtggtta aagattcagt gaagccctct ctaggacctc ttattacagt ttcaacagtt   5160
ggttctgtta tagctctttc agggggtttt ccaatactta taataattgc tttactttca   5220
ccatctagga ataatgctat acttcctttt aaaatggaca atataacatc atccatgctt   5280
ttatatacat ttttatcatt aacagcaaaa attgattttg tatattcaaa tatgtttaaa   5340
tggggatggt tattgtaatc ttcttctata agttttttta taacagagga ttctattaca   5400
tcagattgga taagattatt tatgtagaca atcattgcag aaaaatttct attattagct   5460
atttaaaatt ctctaatcgt taaatctgag caatttgtaa ataagtttc tatagtatgt    5520 ttatttgttt taaggctagt tgaaaccgtc ttcgcgttat ttttagatgc ttcttcttta   5580
ttaaaaattt tattaaacaa cgaaaaattc acccctcaa tttatttata taatagtagt    5640
ttgcatgaaa tttcgttgtt tattcatatt agatgcttgt attaaaataa taaaatagta   5700
aaatataagt agacaaacta taaatctatt actaggaggt aagaagtatg ctaagttta    5760 aatctgtgta aacctaccgg ggtttgggcg tagccattat attcatgaac tccaagaaag   5820
cagtatgcta gcaaagaaat aaaactcaaa gcagagagaa aatttagaca ttcaactata   5880
aataaaaaat acccccaaa gcattaatat cttggggagt attttttatt ttgaagtatt    5940
ctgttcagct aaatattctt ctaaggtaat acctctgttc ataatttctt gtgaggcagg   6000
aagaccgata tatcttacat gccatggctc aaaattatac tttgttatgt tttctttatc   6060
cttaggatat cttattatga aaccatattt accacaattt tgttgaagcc atttataaga   6120
atttgtattc ataaatccat catctaaaga agagtattcg gttgatagta agtccattgc   6180
caatccagtt tgatgctcac ttgtaccagg ttcagctaca tatttatcag cttcggcttt   6240
tccgtctcgt gctactttt cattatataa ttttgctga tacgaataag gtctataacc    6300
tgaaacagct agaagtgtaa gaccatcctt tgatgctgca ttaaacatat tttcaagtcc   6360
tgttgcagct tcgctctcca tttgatttac attaggatca gaactactaa taaattaac    6420 gttaggagtt ctcaaatttt gaggtatata gtttcctgat aatttacttt gcttgtttac   6480
aagtaggatg ttctgtttct ttacctcggg tttcttggct tgttttttag gtgtagaaac   6540
```

```
tttcttttg ggttcgtttg                                              6560
```

<210> SEQ ID NO 81
<211> LENGTH: 1654
<212> TYPE: DNA
<213> ORGANISM: Artificial Sequence
<220> FEATURE:
<223> OTHER INFORMATION: bgaR acrIIA4 cassette

<400> SEQUENCE: 81

```
aaaaagtata acagaggttt taatttacgc ctctgttata cttttattt ttgaaatttt     60
tttgttttaa agctgtattt taaatttata tacttggttt atttacttga ttatttctgt    120
aatttagtgg agacattgaa aaatgttttg aaaaagtttt tgaaaataac agggagtcac    180
tataacctac actacttgcg acttctccta taggaagttt agtgcttttt aataaaaggg    240
tggctttgta cattctaagg tttattaaat atctttgagg agaaattcca aggtttttta    300
tgaacatttt atataaataa cttctactta agttcacata atcagcaatt tcttgaacag    360
ttatgctatg catgtaatta gaattaatga aattaagagc atcttgaata tatgtgtgta    420
attccttatc tttgtattca aaaggttttg ggaattcttc tataagtgcg tacaataatg    480
agtaaagttc ttttagtaat agtatgtcat cagatcttga aggattataa gttttgata     540
tttcgcacat atttaatatt atctgtggaa ttttgagtt ttcttcacaa ttagcaacac     600
aggagttagt aatagaagtt ctatttaaat actcattagc atttgaacca ctaaatccta    660
tccagtagta ttcccaagga tcatcaatag aagccacata ctcaacttgc atacctttta    720
gtagtataaa aatatcacct tgttttaagt tatataccttc accattaaat ttaaaagttc    780
catatcccct agttacgtaa tgaataacag catttttcaa tacttcatag ttatatccta    840
atcctggtat accttgttct ataccacatt catctacatt catttcaaag ttttctttaa    900
catactttt ccacaatatt tgcatttcta cctcctaacc tataaaatta gccaattta     960
tagtagtctt atattaaaca tttacatgag agctttgcaa agcagtttat caacataaaa    1020
gcttttatt ttaaaataaa ttcttctaaa tataagaata ttttaaagaa atatctttat    1080
atattagtta ttaaaattta taagattata agaaacatta taacatattt tagaactttt    1140
taactattct aaaagattaa tttacatatt aacatttaat tatgggtaaa aactattttg    1200
aaaaatgatt tatatggaat tatgtttctt aaatatacaa tcatgtttca tgaatacata    1260
attatttaa atgtattggg agggtaaaat gatattaaaa aatgaatacc atgaagatac    1320
tgcagaatct agaatccgcg gtagtcgacg tggaattgtg agcggataac aatttcacag    1380
gagggctgaa atgaatatta atgacttaat tagagaaata aaaacaaag attacacagt    1440
gaaattgagt ggtacggata gcaatagtat aacacagcta attattagag ttaataatga    1500
tggaaacgag tatgtaattt ctgaaagtga aaatgaatca atagttgaaa aattcatatc    1560
tgcatttaaa aacggttgga atcaagaata cgaggatgaa gaagaatttt ataatgacat    1620
gcaaacaatc accttaaaaa gtgagttgaa ctaa                                1654
```

<210> SEQ ID NO 82
<211> LENGTH: 4984
<212> TYPE: DNA
<213> ORGANISM: Artificial Sequence
<220> FEATURE:
<223> OTHER INFORMATION: pGRNAind

<400> SEQUENCE: 82

-continued

| | | | | | |
|---|---|---|---|---|---|
| caagcttcaa | aaaaagcacc | gactcggtgc | cacttttca | agttgataac | ggactagcct | 60 |
| tattttaact | tgctatttct | agctctaaaa | cagagaccgc | tagcgatatc | ccgggagat | 120 |
| ctggtctcaa | tgaacaaaga | tattatactc | tatcaatgat | agagtttcaa | actctatcaa | 180 |
| tgatagagtg | agctcgaatt | cgtaatcatg | gtcatagctg | tttcctgtgt | gaaattgtta | 240 |
| tccgctcaca | attccacaca | acatacgagc | cggaagcata | aagtgtaaag | cctggggtgc | 300 |
| ctaatgagtg | agctaactca | cattaattgc | gttgcgctca | ctgcccgctt | tccagtcggg | 360 |
| aaacctgtcg | tgccagctgc | attaatgaat | cggccaacgc | gcggggagag | gcggtttgcg | 420 |
| tattgggcgc | tcttccgctt | cctcgctcac | tgactcgctg | cgctcggtcg | ttcggctgcg | 480 |
| gcgagcggta | tcagctcact | caaaggcggt | aatacggtta | tccacagaat | caggggataa | 540 |
| cgcaggaaag | aacatgtgag | caaaaggcca | gcaaaaggcc | aggaaccgta | aaaaggccgc | 600 |
| gttgctggcg | tttttccata | ggctccgccc | ccctgacgag | catcacaaaa | atcgacgctc | 660 |
| aagtcagagg | tggcgaaacc | cgacaggact | ataaagatac | caggcgtttc | ccctggaag | 720 |
| ctccctcgtg | cgctctcctg | ttccgaccct | gccgcttacc | ggatacctgt | ccgcctttct | 780 |
| cccttcggga | agcgtggcgc | tttctcatag | ctcacgctgt | aggtatctca | gttcggtgta | 840 |
| ggtcgttcgc | tccaagctgg | gctgtgtgca | cgaaccccc | gttcagcccg | accgctgcgc | 900 |
| cttatccggt | aactatcgtc | ttgagtccaa | cccggtaaga | cacgacttat | cgccactggc | 960 |
| agcagccact | ggtaacagga | ttagcagagc | gaggtatgta | ggcggtgcta | cagagttctt | 1020 |
| gaagtggtgg | cctaactacg | gctacactag | aagaacagta | tttggtatct | gcgctctgct | 1080 |
| gaagccagtt | accttcggaa | aaagagttgg | tagctcttga | tccggcaaac | aaaccaccgc | 1140 |
| tggtagcggt | ggtttttttg | tttgcaagca | gcagattacg | cgcagaaaaa | aaggatctca | 1200 |
| agaagatcct | ttgatctttt | ctacggggtc | tgacgctcag | tggaacgaaa | actcacgtta | 1260 |
| agggattttg | gtcatgagat | tatcaaaaag | gatcttcacc | tagatccttt | taaattaaaa | 1320 |
| atgaagtttt | aaatcaatct | aaagtatata | tgagtaaact | tggtctgaca | gttaccaaag | 1380 |
| ctagcttaat | actagtatat | acttaatgtg | ataagtgtct | gacagctgac | cggtctaaag | 1440 |
| aggtccctag | cgcctacggg | gaatttgtat | cgataagggg | tacaaattcc | cactaagcgc | 1500 |
| tcggccgggg | atcgatcccc | gggtacgtac | ccggcagttt | ttcttttcg | gcaagtgttc | 1560 |
| aagaagttat | taagtcggga | gtgcagtcga | agtgggcaag | ttgaaaaatt | cacaaaaatg | 1620 |
| tggtataata | tctttgttca | ttagagcgat | aaacttgaat | ttgagaggga | acttagatgg | 1680 |
| tatttgaaaa | aattgataaa | atagttggaa | acagaaaaga | gtattttgac | cactactttg | 1740 |
| caagtgtacc | ttgtacctac | agcatgaccg | ttaaagtgga | tatcacacaa | ataaaggaaa | 1800 |
| agggaatgaa | actatatcct | gcaatgcttt | attatattgc | aatgattgta | aaccgccatt | 1860 |
| cagagtttag | gacggcaatc | aatcaagatg | gtgaattggg | gatatatgat | gagatgatac | 1920 |
| caagctatac | aatatttcac | aatgatactg | aaacattttc | cagcctttgg | actgagtgta | 1980 |
| agtctgactt | taaatcattt | ttagcagatt | atgaaagtga | tacgcaacgg | tatggaaaca | 2040 |
| atcatagaat | ggaaggaaag | ccaaatgctc | cggaaaacat | ttttaatgta | tctatgatac | 2100 |
| cgtggtcaac | cttcgatggc | tttaatctga | atttgcagaa | aggatatgat | tatttgattc | 2160 |
| ctatttttac | tatggggaaa | tattataaag | aagataacaa | aattatactt | cctttggcaa | 2220 |
| ttcaagttca | tcacgcagta | tgtgacggat | tcacatttg | ccgttttgta | aacgaattgc | 2280 |
| aggaattgat | aaatagttaa | cttcaggttt | gtctgtaact | aaaaactagt | atttaaccta | 2340 |
| ggatcaaaaa | aatttccaat | aatcccactc | taagccacaa | acacgcccta | taaatcccg | 2400 |

```
ctttaatccc actttgagac acatgtaata ttactttacg ccctagtata gtgataattt   2460
tttacattca atgccacgca aaaaaataaa ggggcactat aataaaagtt ccttcggaac   2520
taactaaagt aaaaaattat ctttacaacc tccccaaaaa aaagaacagg tacaaagtac   2580
cctataatac aagcgtaaaa aaaatgaggg taaaaataaa aaaataaaaa aataaaaaaa   2640
taaaaaaata aaaaaataaa aaataaaaaa aatataaaaa taaaaaaata taaaaataaa   2700
aaaatataaa aataaaaaaa taaaaaaata taaaaataaa aaaataaaaa aatataaaaa   2760 tatttttat ttaaagtttg aaaaaaattt tttatatta tataatcttt gaagaaaaga    2820
atataaaaaa tgagccttta taaaagccca ttttttttca tatacgtaat atgacgttct   2880
aatgttttta ttggtacttc taacattaga gtaatttctt tattttaaa gcctttttct    2940 ttaagggctt ttatttttt tcttaataca tttaattcct ctttttttgt tgcttttcct    3000 ttagcttta attgctcttg ataattttt ttacctctaa tattttctct tctcttatat     3060 tccttttag aaattattat tgtcatatat ttttgttctt cttctgtaat ttctaataac    3120
tctataagag tttcattctt atacttatat tgcttatttt tatctaaata acatctttca   3180
gcacttctag ttgctcttat aacttctctt tcacttaaat gttgtctaaa catactatta   3240
agttctaaaa catcatttaa tgccttctca atgtcttctg taaagctaca aagataatat   3300
ctatataaaa ataatataag ctctctgtgt cctttaaat catattctct tagttcacaa    3360
agttttatta tgtcttgtat tcttccataa tataaacttc tttctctata aatataattt   3420
attttgcttg gtctacccett tttcctttca tatggtttta attcaggtaa aaatccattt   3480
tgtatttctc ttaagtcata aatatattcg tactcatcta atatattgac tactgttttt   3540
gatttagagt ttatacttcc tggaactctt aatattctcg ttgcatctaa ggcttgtcta   3600
tctgctccaa agtattttaa ttgattatat aaatattctt gaaccgcttt ccataatggt   3660
aatgctttac taggtactgc atttattatc catattaaat acattcctct tccactatct   3720
attacatagt ttggtatagg aatactttga ttaaaataat tctttctaa gtccattaat    3780 acctggtctt tagttttgcc agttttataa taatccaagt ctataaacag tgtatttaac   3840
tcttttatat tttctaatcg cctacacggc ttataaaagg tatttagagt tatatagata   3900
ttttcatcac tcatatctaa atcttttaat tcagcgtatt tatagtgcca ttggctatat   3960
ccttttttat ctataacgct cctggttatc caccctttac ttctactatg aatattatct   4020
atatagttct ttttattcag ctttaatgcg tttctcactt attcacctcc ccttctgtaa   4080
aactaagaaa attatatcat attttcaata attattaact attcttaaac tcttaataaa   4140
aaatagagta agtccccaat tgaaacttaa tctattttt atgtttaat ttattatttt     4200 tattaaaata ttttaaacta aattaaatga ttccttttaa ttttttacta tttcattcca   4260
taatatatta ctataattat ttacaaataa tatttcttca tttgtaatat ttagatgatt   4320
tactaatttt agttttata tattaaataa ttaatgtata atttatataa aaaatcaaag    4380
gagcttataa attatgatta tttccaaaga tactaaagat ttaatttttt tcaatttaa    4440 caatactttt tgtaatatta tgtttaaatt taattgtatt tttttcatat aataaagccg   4500
ttgaagtaaa ccaatccatt ttccttatga tgttattatt aaatttaagt tttataataa   4560 tatcttatt atatttattg tttttaaaaa aactagtgaa atttctagtg aaatttccgg    4620
ctttattaaa cttatttta ggaatttat tttcatttc atcttacag gatttgatta      4680 tatctttaaa tatgttttat caaatattat ctttttctaa atttatatat atttttatta   4740
```

```
tatttattat tatatatatt ttatttttaa gtttctttct aacagctatt aaaagaaac    4800 ttaaaaataa aaacacgtac tctaaaccaa taaataaaac tatttttatt attgctgcct   4860
tgattggaat agtttttagt aaaattaatt tcaatattcc acaatattat attataagct   4920
agcacgcctc gagatctcca tggacgcgtg acgtcgactc tagaggatcc ccgggtaccg   4980
agct                                                                4984
```

```
<210> SEQ ID NO 83
<211> LENGTH: 200
<212> TYPE: DNA
<213> ORGANISM: Artificial Sequence
<220> FEATURE:
<223> OTHER INFORMATION: gRNA cassette

<400> SEQUENCE: 83
gagctcactc tatcattgat agagtttgaa actctatcat tgatagagta taatatcttt    60
gttcattgag accagatctc ccggggatat cgctagcggt ctctgtttta gagctagaaa   120
tagcaagtta aaataaggct agtccgttat caacttgaaa aagtggcacc gagtcggtgc   180 ttttttttgaa gcttgagctc                                              200
```

```
<210> SEQ ID NO 84
<211> LENGTH: 24
<212> TYPE: DNA
<213> ORGANISM: Artificial Sequence
<220> FEATURE:
<223> OTHER INFORMATION: primer

<400> SEQUENCE: 84
tcatgatttc tccatattag ctag                                           24
```

```
<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
aaacctagct aatatggaga aatc                                           24
```

```
<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
tcatgttaca cttggaacag gcgt                                           24
```

```
<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
aaacacgcct gttccaagtg taac                                           24
```

```
<210> SEQ ID NO 88
<211> LENGTH: 24
```

```
<212> TYPE: DNA
<213> ORGANISM: Artificial Sequence
<220> FEATURE:
<223> OTHER INFORMATION: Primer

<400> SEQUENCE: 88
tcatttccgg cagtaggatc ccca                                              24

<210> SEQ ID NO 89
<211> LENGTH: 24
<212> TYPE: DNA
<213> ORGANISM: Artificial Sequence
<220> FEATURE:
<223> OTHER INFORMATION: Primer

<400> SEQUENCE: 89
aaactgggga tcctactgcc ggaa                                              24

<210> SEQ ID NO 90
<211> LENGTH: 24
<212> TYPE: DNA
<213> ORGANISM: Artificial Sequence
<220> FEATURE:
<223> OTHER INFORMATION: Primer

<400> SEQUENCE: 90
tcatgcttat tacgacataa caca                                              24

<210> SEQ ID NO 91
<211> LENGTH: 24
<212> TYPE: DNA
<213> ORGANISM: Artificial Sequence
<220> FEATURE:
<223> OTHER INFORMATION: Primer

<400> SEQUENCE: 91
aaactgtgtt atgtcgtaat aagc                                              24

<210> SEQ ID NO 92
<211> LENGTH: 36
<212> TYPE: DNA
<213> ORGANISM: Artificial Sequence
<220> FEATURE:
<223> OTHER INFORMATION: Primer

<400> SEQUENCE: 92
atgcatggat ccaaacgaac ccaaaaagaa agtttc                                 36

<210> SEQ ID NO 93
<211> LENGTH: 30
<212> TYPE: DNA
<213> ORGANISM: Artificial Sequence
<220> FEATURE:
<223> OTHER INFORMATION: Primer

<400> SEQUENCE: 93
ggttgatttc aaatctgtgt aaacctaccg                                        30

<210> SEQ ID NO 94
<211> LENGTH: 30
<212> TYPE: DNA
<213> ORGANISM: Artificial Sequence
<220> FEATURE:
<223> OTHER INFORMATION: Primer

<400> SEQUENCE: 94
```
acacagattt gaaatcaacc actttaaccc         30

<210> SEQ ID NO 95
<211> LENGTH: 37
<212> TYPE: DNA
<213> ORGANISM: Artificial Sequence
<220> FEATURE:
<223> OTHER INFORMATION: Primer

<400> SEQUENCE: 95
atgcatgtcg actcttaaga acatgtataa agtatgg         37

<210> SEQ ID NO 96
<211> LENGTH: 36
<212> TYPE: DNA
<213> ORGANISM: Artificial Sequence
<220> FEATURE:
<223> OTHER INFORMATION: Primer

<400> SEQUENCE: 96
atgcatggat ccaaacgaac ccaaaaagaa agtttc         36

<210> SEQ ID NO 97
<211> LENGTH: 30
<212> TYPE: DNA
<213> ORGANISM: Artificial Sequence
<220> FEATURE:
<223> OTHER INFORMATION: Primer

<400> SEQUENCE: 97
gctaagtttt aaatctgtgt aaacctaccg         30

<210> SEQ ID NO 98
<211> LENGTH: 32
<212> TYPE: DNA
<213> ORGANISM: Artificial Sequence
<220> FEATURE:
<223> OTHER INFORMATION: Primer

<400> SEQUENCE: 98
acacagattt aaaacttagc atacttctta cc         32

<210> SEQ ID NO 99
<211> LENGTH: 37
<212> TYPE: DNA
<213> ORGANISM: Artificial Sequence
<220> FEATURE:
<223> OTHER INFORMATION: Primer

<400> SEQUENCE: 99
atgcatgtcg accttctaat ctcctctact attttag         37

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
acacattgaa gggagctttt         20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
ggcaacaaca tcaggccttt                                               20

<210> SEQ ID NO 102
<211> LENGTH: 4966
<212> TYPE: DNA
<213> ORGANISM: Artificial Sequence
<220> FEATURE:
<223> OTHER INFORMATION: pGRNA-xylB

<400> SEQUENCE: 102

| | | | | | |
|---|---|---|---|---|---|
| atcaaaaaaa | tttccaataa | tcccactcta | agccacaaac | acgccctata | aaatcccgct | 60 |
| ttaatcccac | tttgagacac | atgtaatatt | actttacgcc | ctagtatagt | gataattttt | 120 |
| tacattcaat | gccacgcaaa | aaaataaagg | ggcactataa | taaagttcc | ttcggaacta | 180 |
| actaaagtaa | aaaattatct | ttacaacctc | cccaaaaaaa | agaacaggta | caaagtaccc | 240 |
| tataatacaa | gcgtaaaaaa | aatgagggta | aaaataaaaa | aataaaaaaa | taaaaaaata | 300 |
| aaaaaataaa | aaaataaaaa | aataaaaaaa | tataaaaata | aaaaaatata | aaaataaaaa | 360 |
| aatataaaaa | taaaaaaata | aaaaatata | aaaataaaaa | aataaaaaaa | tataaaaata | 420 |
| tttttattt | aaagtttgaa | aaaaattttt | ttatattata | taatctttga | agaaaagaat | 480 |
| ataaaaaatg | agcctttata | aagcccatt | ttttttcata | tacgtaatat | gacgttctaa | 540 |
| tgttttatt | ggtacttcta | acattagagt | aatttcttta | tttttaaagc | cttttctttt | 600 |
| aagggctttt | attttttttc | ttaatacatt | taattcctct | tttttgttg | ctttccttt | 660 |
| agcttttaat | tgctcttgat | aatttttttt | acctctaata | ttttctcttc | tcttatattc | 720 |
| cttttagaa | attattattg | tcatatattt | ttgttcttct | tctgtaattt | ctaataactc | 780 |
| tataagagtt | tcattcttat | acttatattg | cttattttta | tctaaataac | atctttcagc | 840 |
| acttctagtt | gctcttataa | cttctctttc | acttaaatgt | tgtctaaaca | tactattaag | 900 |
| ttctaaaaca | tcatttaatg | ccttctcaat | gtcttctgta | aagctacaaa | gataatatct | 960 |
| atataaaaat | aatataagct | ctctgtgtcc | ttttaaatca | tattctctta | gttcacaaag | 1020 |
| ttttattatg | tcttgtattc | ttccataata | taaacttctt | tctctataaa | tataattat | 1080 |
| tttgcttggt | ctaccctttt | tccttcata | tggttttaat | tcaggtaaaa | atccattttg | 1140 |
| tatttctctt | aagtcataaa | tatattcgta | ctcatctaat | atattgacta | ctgttttga | 1200 |
| tttagagttt | atacttcctg | gaactcttaa | tattctcgtt | gcatctaagg | cttgtctatc | 1260 |
| tgctccaaag | tatttaatt | gattatataa | atattcttga | accgctttcc | ataatggtaa | 1320 |
| tgctttacta | ggtactgcat | ttattatcca | tattaaatac | attcctcttc | cactatctat | 1380 |
| tacatagtt | ggtataggaa | tactttgatt | aaaataattc | ttttctaagt | ccattaatac | 1440 |
| ctggtctta | gttttgccag | ttttataata | atccaagtct | ataacagtg | tatttaactc | 1500 |
| ttttatattt | tctaatcgcc | tacacggctt | ataaaaggta | tttagagtta | tatagatatt | 1560 |
| ttcatcactc | atatctaaat | cttttaattc | agcgtattta | tagtgccatt | ggctatatcc | 1620 |
| tttttatct | ataacgctcc | tggttatcca | cccttactt | ctactatgaa | tattatctat | 1680 |
| atagttcttt | ttattcagct | ttaatgcgtt | tctcacttat | tcacctcccc | ttctgtaaaa | 1740 |
| ctaagaaaat | tatatcatat | tttcaataat | tattaactat | tcttaaactc | ttaataaaaa | 1800 |
| atagagtaag | tccccaattg | aaacttaatc | tattttttat | gttttaattt | attatttta | 1860 |

```
ttaaaatatt ttaaactaaa ttaaatgatt cttttttaatt ttttactatt tcattccata    1920
atatattact ataattattt acaaataata tttcttcatt tgtaaatttt agatgattta    1980
ctaattttag tttttatata ttaaataatt aatgtataat ttatataaaa aatcaaagga    2040
gcttataaat tatgattatt tccaaagata ctaaagattt aattttttc aattttaaca     2100 atacttttg taatattatg tttaaattta attgtatttt tttcatataa taaagccgtt     2160
gaagtaaacc aatccatttt ccttatgatg ttattattaa atttaagttt tataataata    2220
tctttattat atttattgtt tttaaaaaaa ctagtgaaat ttctagtgaa atttccggct    2280
ttattaaact tattttttagg aattttattt tcattttcat ctttacagga tttgattata   2340
tctttaaata tgttttatca aatattatct ttttctaaat ttatatatat ttttattata   2400
tttattatta tatatatttt attttttaagt ttcttttctaa cagctattaa aaagaaactt 2460
aaaaataaaa acacgtactc taaaccaata aataaaacta tttttattat tgctgccttg   2520
attggaatag tttttagtaa aattaattttc aatattccac aatattatat tataagctag  2580
cacgcctcga gaagcttcaa aaaaagcacc gactcggtgc cacttttca agttgataac    2640 ggactagcct tattttaact tgctatttct agctctaaaa cctagctaat atggagaaat   2700
catgaacaaa gatattatac tctatcaatg atagagtttc aaactctatc aatgatagag  2760
tctcgagatc tccatggacg cgtgacgtcg actctagagg atccccgggt accgagctcg  2820
aattcgtaat catggtcata gctgtttcct gtgtgaaatt gttatccgct cacaattcca  2880
cacaacatac gagccggaag cataaagtgt aaagcctggg gtgcctaatg agtgagctaa  2940
ctcacattaa ttgcgttgcg ctcactgccc gctttccagt cgggaaacct gtcgtgccag  3000
ctgcattaat gaatcggcca acgcgcgggg agaggcggtt tgcgtattgg gcgctcttcc   3060
gcttcctcgc tcactgactc gctgcgctcg gtcgttcggc tgcggcgagc ggtatcagct   3120
cactcaaagg cggtaatacg gttatccaca gaatcagggg ataacgcagg aaagaacatg  3180
tgagcaaaag gccagcaaaa ggccaggaac cgtaaaaagg ccgcgttgct ggcgtttttc   3240
cataggctcc gcccccctga cgagcatcac aaaaatcgac gctcaagtca gaggtggcga  3300
aacccgacag gactataaag ataccaggcg tttccccctg gaagctccct cgtgcgctct  3360
cctgttccga ccctgccgct taccggatac ctgtccgcct ttctcccttc gggaagcgtg  3420
gcgctttctc atagctcacg ctgtaggtat ctcagttcgg tgtaggtcgt tcgctccaag  3480
ctgggctgtg tgcacgaacc ccccgttcag cccgaccgct gcgccttatc cggtaactat  3540
cgtcttgagt ccaacccggt aagacacgac ttatcgccac tggcagcagc cactggtaac  3600
aggattagca gagcgaggta tgtaggcggt gctacagagt tcttgaagtg gtggcctaac  3660
tacggctaca ctagaagaac agtatttggt atctgcgctc tgctgaagcc agttaccttc  3720
ggaaaaagag ttggtagctc ttgatccggc aaacaaacca ccgctggtag cggtggtttt  3780
tttgtttgca agcagcagat tacgcgcaga aaaaaaggat ctcaagaaga tcctttgatc  3840
ttttctacgg ggtctgacgc tcagtggaac gaaaactcac gttaagggat tttggtcatg  3900
agattatcaa aaaggatctt cacctagatc cttttaaatt aaaaatgaag ttttaaatca  3960
atctaaagta tatatgagta aacttggtct gacagttacc aaagctagct taatactagt  4020
atatacttaa tgtgataagt gtcctgacagc tgaccggtct aaagaggtcc ctagcgccta  4080
cggggaattt gtatcgataa ggggtacaaa ttcccactaa gcgctcggcc gggatcgat   4140 cccccgggtac gtacccggca gttttctttt ttcggcaagt gttcaagaag ttattaagtc  4200
gggagtgcag tcgaagtggg caagttgaaa aattcacaaa aatgtggtat aatatctttg  4260
```

```
ttcattagag cgataaactt gaatttgaga gggaacttag atggtatttg aaaaaattga    4320
taaaaatagt tggaacagaa aagagtattt tgaccactac tttgcaagtg taccttgtac    4380
ctacagcatg accgttaaag tggatatcac acaaataaag gaaaagggaa tgaaactata    4440
tcctgcaatg ctttattata ttgcaatgat tgtaaaccgc cattcagagt ttaggacggc    4500
aatcaatcaa gatggtgaat tggggatata tgatgagatg ataccaagct atacaatatt    4560
tcacaatgat actgaaacat tttccagcct ttggactgag tgtaagtctg actttaaatc    4620
atttttagca gattatgaaa gtgatacgca acggtatgga aacaatcata gaatggaagg    4680
aaagccaaat gctccggaaa acattttttaa tgtatctatg ataccgtggt caaccttcga    4740
tggctttaat ctgaatttgc agaaaggata tgattatttg attcctattt ttactatggg    4800
gaaatattat aaagaagata acaaaattat acttcctttg gcaattcaag ttcatcacgc    4860
agtatgtgac ggatttcaca tttgccgttt tgtaaacgaa ttgcaggaat tgataaatag    4920
ttaacttcag gtttgtctgt aactaaaaac tagtatttaa cctagg                   4966

<210> SEQ ID NO 103
<211> LENGTH: 4966
<212> TYPE: DNA
<213> ORGANISM: Artificial Sequence
<220> FEATURE:
<223> OTHER INFORMATION: pGRNA-xylR

<400> SEQUENCE: 103
atcaaaaaaa tttccaataa tcccactcta agccacaaac acgccctata aaatcccgct     60
ttaatcccac tttgagacac atgtaatatt actttacgcc ctagtatagt gataattttt    120
tacattcaat gccacgcaaa aaaataaagg ggcactataa taaagttcc ttcggaacta     180 actaaagtaa aaaattatct ttacaacctc cccaaaaaaa agaacaggta caaagtaccc    240
tataatacaa gcgtaaaaaa aatgagggta aaaataaaaa aataaaaaaa taaaaaaata    300
aaaaaataaa aaaataaaaa aataaaaaaa tataaaaata aaaaaatata aaaataaaaa    360
aatataaaaa taaaaaaata aaaaaatata aaaataaaaa aataaaaaaa tataaaaata    420 tttttttattt aaagtttgaa aaaaattttt ttatattata taatctttga agaaaagaat    480
ataaaaaatg agcctttata aaagcccatt tttttttcata tacgtaatat gacgttctaa    540
tgtttttatt ggtacttcta acattagagt aatttctttta tttttaaagc ctttttctttt    600 aagggctttt attttttttc ttaatacatt taattcctct tttttttgttg cttttccttt    660 agcttttaat tgctcttgat aattttttttt acctctaata ttttctcttc tcttatattc    720 cttttttagaa attattattg tcatatattt ttgttcttct tctgtaattt ctaataactc    780
tataagagtt tcattcttat acttatattg cttattttta tctaaataac atcttttcagc    840 acttctagtt gctcttataa cttctctttc acttaaatgt tgtctaaaca tactattaag    900
ttctaaaaca tcatttaatg ccttctcaat gtcttctgta aagctacaaa gataatatct    960
atataaaaat aatataagct ctctgtgtcc ttttaaatca tattctctta gttcacaaag   1020
ttttattatg tcttgtattc ttccataata taaacttctt tctctataaa tataatttat   1080
tttgcttggt ctacccttttt tcctttcata tggttttaat tcaggtaaaa atccatttttg   1140 tatttctctt aagtcataaa tatattcgta ctcatctaat atattgacta ctgttttttga   1200 tttagagttt atacttcctg gaactcttaa tattctcgtt gcatctaagg cttgtctatc   1260
tgctccaaag tatttttaatt gattatataa atattcttga accgctttcc ataatggtaa   1320
```

```
tgctttacta ggtactgcat ttattatcca tattaaatac attcctcttc cactatctat    1380
tacatagttt ggtataggaa tactttgatt aaaataattc ttttctaagt ccattaatac    1440
ctggtcttta gttttgccag ttttataata atccaagtct ataaacagtg tatttaactc    1500
ttttatattt tctaatcgcc tacacggctt ataaaaggta tttagagtta tatagatatt    1560
ttcatcactc atatctaaat cttttaattc agcgtattta tagtgccatt ggctatatcc    1620 tttttatct ataacgctcc tggttatcca ccctttactt ctactatgaa tattatctat    1680
atagttcttt ttattcagct ttaatgcgtt tctcacttat tcacctcccc ttctgtaaaa    1740
ctaagaaaat tatatcatat tttcaataat tattaactat tcttaaactc ttaataaaaa    1800
atagagtaag tccccaattg aaacttaatc tatttttat gttttaattt attattttta    1860
ttaaaatatt ttaaactaaa ttaaatgatt ctttttaatt ttttactatt tcattccata    1920
atatattact ataattattt acaaataata tttcttcatt tgtaatattt agatgattta    1980
ctaattttag tttttatata ttaaataatt aatgtataat ttatataaaa aatcaaagga    2040
gcttataaat tatgattatt tccaaagata ctaaagattt aatttttttc aatttaaca    2100 atacttttg taatattatg tttaaattta attgtatttt tttcatataa taaagccgtt    2160
gaagtaaacc aatccatttt ccttatgatg ttattattaa atttaagttt tataataata    2220
tctttattat atttattgtt tttaaaaaaa ctagtgaaat ttctagtgaa atttccggct    2280
ttattaaact tattttaggg aattttattt tcatttcat ctttacagga tttgattata    2340
tctttaaata tgttttatca aatattatct ttttctaaat ttatatatat tttattata    2400 tttattatta tatatatttt attttaagt ttctttctaa cagctattaa aaagaaactt    2460
aaaaataaaa acacgtactc taaaccaata aataaaacta tttttattat tgctgccttg    2520
attggaatag tttttagtaa aattaatttc aatattccac aatattatat tataagctag    2580
cacgcctcga gactctatca ttgatagagt ttgaaactct atcattgata gagtataata    2640
tctttgttca tgttacactt ggaacaggcg tgttttagag ctagaaatag caagttaaaa    2700
taaggctagt ccgttatcaa cttgaaaaag tggcaccgag tcggtgcttt ttttgaagct    2760
tctcgagatc tccatggacg cgtgacgtcg actctagagg atccccgggt accgagctcg    2820
aattcgtaat catggtcata gctgtttcct gtgtgaaatt gttatccgct cacaattcca    2880
cacaacatac gagccggaag cataaagtgt aaagcctggg gtgcctaatg agtgagctaa    2940
ctcacattaa ttgcgttgcg ctcactgccc gctttccagt cgggaaacct gtcgtgccag    3000
ctgcattaat gaatcggcca acgcgcgggg agaggcggtt tgcgtattgg gcgctcttcc    3060
gcttcctcgc tcactgactc gctgcgctcg gtcgttcggc tgcggcgagc ggtatcagct    3120
cactcaaagg cggtaatacg gttatccaca gaatcagggg ataacgcagg aaagaacatg    3180
tgagcaaaag gccagcaaaa ggccaggaac cgtaaaaagg ccgcgttgct ggcgtttttc    3240
cataggctcc gcccccctga cgagcatcac aaaaatcgac gctcaagtca gaggtggcga    3300
aacccgacag gactataaag ataccaggcg tttccccctg gaagctccct cgtgcgctct    3360
cctgttccga ccctgccgct taccggatac ctgtccgcct ttctcccttc gggaagcgtg    3420
gcgctttctc atagctcacg ctgtaggtat ctcagttcgg tgtaggtcgt tcgctccaag    3480
ctgggctgtg tgcacgaacc ccccgttcag cccgaccgct gcgccttatc cggtaactat    3540
cgtcttgagt ccaacccggt aagacacgac ttatcgccac tggcagcagc cactggtaac    3600
aggattagca gagcgaggta tgtaggcggt gctacagagt tcttgaagtg gtggcctaac    3660
tacggctaca ctagaagaac agtatttggt atctgcgctc tgctgaagcc agttaccttc    3720
```

```
ggaaaaagag ttggtagctc ttgatccggc aaacaaacca ccgctggtag cggtggtttt    3780
tttgtttgca agcagcagat tacgcgcaga aaaaaaggat ctcaagaaga tcctttgatc    3840
ttttctacgg ggtctgacgc tcagtggaac gaaaactcac gttaagggat tttggtcatg    3900
agattatcaa aaaggatctt cacctagatc cttttaaatt aaaaatgaag ttttaaatca    3960
atctaaagta tatatgagta aacttggtct gacagttacc aaagctagct taatactagt    4020
atatacttaa tgtgataagt gtctgacagc tgaccggtct aaagaggtcc ctagcgccta    4080
cggggaattt gtatcgataa ggggtacaaa ttcccactaa gcgctcggcc ggggatcgat    4140
ccccgggtac gtacccggca gttttctttt ttcggcaagt gttcaagaag ttattaagtc    4200
gggagtgcag tcgaagtggg caagttgaaa aattcacaaa aatgtggtat aatatctttg    4260
ttcattagag cgataaactt gaatttgaga gggaacttag atggtatttg aaaaaattga    4320
taaaaatagt tggaacagaa aagagtattt tgaccactac tttgcaagtg taccttgtac    4380
ctacagcatg accgttaaag tggatatcac acaaataaag gaaaagggaa tgaaactata    4440
tcctgcaatg ctttattata ttgcaatgat tgtaaaccgc cattcagagt ttaggacggc    4500
aatcaatcaa gatggtgaat tggggatata tgatgagatg ataccaagct atacaatatt    4560
tcacaatgat actgaaacat tttccagcct ttggactgag tgtaagtctg actttaaatc    4620 attttttagca gattatgaaa gtgatacgca acggtatgga aacaatcata gaatggaagg    4680
aaagccaaat gctccggaaa acatttttaa tgtatctatg ataccgtggt caaccttcga    4740
tggctttaat ctgaatttgc agaaaggata tgattatttg attcctatttt ttactatggg    4800 gaaatattat aaagaagata caaaattat acttcctttg gcaattcaag ttcatcacgc    4860
agtatgtgac ggatttcaca tttgccgttt tgtaaacgaa ttgcaggaat tgataaatag    4920
ttaacttcag gtttgtctgt aactaaaaac tagtatttaa cctagg                   4966

<210> SEQ ID NO 104
<211> LENGTH: 4966
<212> TYPE: DNA
<213> ORGANISM: Artificial Sequence
<220> FEATURE:
<223> OTHER INFORMATION: pGRNA-glcG

<400> SEQUENCE: 104
agctcggtac ccggggatcc tctagagtcg acgtcacgcg tccatggaga tctcgaggcg      60
tgctagctta taatataata ttgtggaata ttgaaattaa ttttactaaa aactattcca     120
atcaaggcag caataataaa aatagtttta tttattggtt tagagtacgt gtttttattt     180
ttaagtttct ttttaatagc tgttagaaag aaacttaaaa ataaaatata taataata       240 aatataataa aatatatat aaatttgaaa aaagataata tttgataaaa catatttaaa     300
gatataatca atcctgtaa agatgaaaat gaaataaaa ttcctaaaaa taagtttaat      360
aaagccggaa atttcactag aaatttcact agttttttta aaaacaataa atataataaa    420
gatattatta taaaacttaa atttaataat aacatcataa ggaaaatgga ttggtttact    480
tcaacggctt tattatatga aaaaaataca attaaattta aacataatat tacaaaaagt    540
attgttaaaa ttgaaaaaaa ttaaatcttt agtatctttg gaataatca taatttataa    600 gctcctttga ttttttatat aaattataca ttaattattt aatatataaa aactaaaatt    660
agtaaatcat ctaaatatta caaatgaaga aatattattt gtaaataatt atagtaatat    720
attatggaat gaaatagtaa aaaattaaaa agaatcattt aatttagttt aaaatatttt    780
```

```
aataaaaata ataaattaaa acataaaaaa tagattaagt ttcaattggg gacttactct    840
attttttatt aagagtttaa gaatagttaa taattattga aaatatgata taattttctt    900
agttttacag aaggggaggt gaataagtga gaaacgcatt aaagctgaat aaaaagaact    960
atatagataa tattcatagt agaagtaaag ggtggataac caggagcgtt atagataaaa   1020
aaggatatag ccaatggcac tataaatacg ctgaattaaa agatttagat atgagtgatg   1080
aaaatatcta tataactcta aatacctttt ataagccgtg taggcgatta gaaaatataa   1140
aagagttaaa tacactgttt atagacttgg attattataa aactggcaaa actaaagacc   1200
aggtattaat ggacttagaa aagaattatt ttaatcaaag tattcctata ccaaactatg   1260
taatagatag tggaagagga atgtatttaa tatggataat aaatgcagta cctagtaaag   1320
cattaccatt atggaaagcg gttcaagaat atttatataa tcaattaaaa tactttggag   1380
cagatagaca agccttagat gcaacgagaa tattaagagt tccaggaagt ataaactcta   1440
aatcaaaaac agtagtcaat atattagatg agtacgaata tatttatgac ttaagagaaa   1500
tacaaaatgg attttttacct gaattaaaac catatgaaag gaaaagggt agaccaagca   1560 aaataaaatta tatttataga gaaagaagtt tatattatgg aagaatacaa gacataataa   1620
aactttgtga actaagagaa tatgatttaa aaggacacag agagcttata ttattttat   1680 atagatatta tctttgtagc tttacagaag acattgagaa ggcattaaat gatgttttag   1740
aacttaatag tatgttagaa caacattttaa gtgaaagaga agttataaga gcaactagaa   1800
gtgctgaaag atgttattta gataaaaata agcaatataa gtataagaat gaaactctta   1860
tagagttatt agaaattaca gaagaagaac aaaaatatat gacaataata atttctaaaa   1920
aggaatataa gagaagagaa aatattagag gtaaaaaaaa ttatcaagag caattaaaag   1980
ctaaaggaaa agcaacaaaa aaagaggaat taaatgtatt aagaaaaaaa ataaaagccc   2040
ttaaagaaaa aggctttaaa aataagagaa ttactctaat gttagaagta ccaataaaaa   2100
cattagaacg tcatattacg tatatgaaaa aaaatgggct tttataaagg ctcatttttt   2160
atattctttt cttcaaagat tatataatat aaaaaaattt ttttcaaact ttaaataaaa   2220
aatattttta tatttttta ttttttttatt tttatatttt tttatttttt tattttttata   2280 ttttttatt ttatatttt tttattttta tattttttta ttttttatt tttttatttt   2340 tttatttttt tatttttta ttttttatt tttaccctca tttttttttac gcttgtatta   2400 tagggtactt tgtacctgtt cttttttttg gggaggttgt aaagataatt ttttacttta   2460
gttagttccg aaggaacttt tattatagtg cccctttatt tttttgcgtg gcattgaatg   2520
taaaaaatta tcactatact agggcgtaaa gtaatattac atgtgtctca aagtgggatt   2580
aaagcgggat tttatagggc gtgtttgtgg cttagagtgg gattattgga aattttttg   2640 atcctaggtt aaatactagt ttttagttac agacaaacct gaagttaact atttatcaat   2700
tcctgcaatt cgtttacaaa acggcaaatg tgaaatccgt cacatactgc gtgatgaact   2760
tgaattgcca aaggaagtat aatttttgtta tcttctttat aatatttccc catagtaaaa   2820
ataggaatca aataatcata tcctttctgc aaattcagat taaagccatc gaaggttgac   2880
cacggtatca tagatacatt aaaaatgttt tccggagcat ttggctttcc ttccattcta   2940
tgattgtttc catacgttg cgtatcactt tcataatctg ctaaaaatga tttaaagtca   3000
gacttacact cagtccaaag gctggaaaat gtttcagtat cattgtgaaa tattgtatag   3060
cttggtatca tctcatcata tatccccaat tcaccatctt gattgattgc cgtcctaaac   3120
tctgaatggc ggtttacaat cattgcaata taataaagca ttgcaggata tagtttcatt   3180
```

```
cccttttcct ttatttgtgt gatatccact ttaacggtca tgctgtaggt acaaggtaca      3240
cttgcaaagt agtggtcaaa atactctttt ctgttccaac tatttttatc aattttttca      3300
aataccatct aagttccctc tcaaattcaa gtttatcgct ctaatgaaca aagatattat      3360
accacatttt tgtgaatttt tcaacttgcc cacttcgact gcactccgga cttaataact      3420
tcttgaacac ttgccgaaaa agaaaaactg ccgggtacgt acccggggat cgatccccgg      3480
ccgagcgctt agtgggaatt tgtaccccct atcgatacaa attccccgta ggcgctaggg      3540
acctctttag accggtcagc tgtcagacac ttatcacatt aagtatatac tagtattaag      3600
ctagctttgg taactgtcag accaagttta ctcatatata ctttagattg atttaaaact      3660
tcatttttaa tttaaaagga tctaggtgaa gatcctttt gataatctca tgaccaaaat      3720
cccttaacgt gagttttcgt tccactgagc gtcagacccc gtagaaaaga tcaaggatc      3780 ttcttgagat ccttttttc tgcgcgtaat ctgctgcttg caaacaaaaa aaccaccgct      3840
accagcggtg gtttgtttgc cggatcaaga gctaccaact cttttccga aggtaactgg      3900 cttcagcaga gcgcagatac caaatactgt tcttctagtg tagccgtagt taggccacca      3960
cttcaagaac tctgtagcac cgcctacata cctcgctctg ctaatcctgt taccagtggc      4020
tgctgccagt ggcgataagt cgtgtcttac cgggttggac tcaagacgat agttaccgga      4080
taaggcgcag cggtcgggct gaacggggg ttcgtgcaca cagcccagct tggagcgaac      4140
gacctacacc gaactgagat acctacagcg tgagctatga gaaagcgcca cgcttcccga      4200
agggagaaag gcggacaggt atccggtaag cggcagggtc ggaacaggag agcgcacgag      4260
ggagcttcca gggggaaacg cctggtatct ttatagtcct gtcgggtttc gccacctctg      4320
acttgagcgt cgatttttgt gatgctcgtc aggggggcgg agcctatgga aaaacgccag      4380
caacgcggcc ttttacggt tcctggcctt ttgctggcct tttgctcaca tgttctttcc      4440
tgcgttatcc cctgattctg tggataaccg tattaccgcc tttgagtgag ctgataccgc      4500
tcgccgcagc cgaacgaccg agcgcagcga gtcagtgagc gaggaagcgg aagagcgccc      4560
aatacgcaaa ccgcctctcc ccgcgcgttg gccgattcat taatgcagct ggcacgacag      4620
gtttcccgac tggaaagcgg gcagtgagcg caacgcaatt aatgtgagtt agctcactca      4680
ttaggcaccc caggctttac actttatgct tccggctcgt atgttgtgtg gaattgtgag      4740
cggataacaa tttcacacag gaaacagcta tgaccatgat tacgaattcg agctcactct      4800
atcattgata gagtttgaaa ctctatcatt gatagagtat aatatctttg ttcatttccg      4860
gcagtaggat ccccagtttt agagctagaa atagcaagtt aaaataaggc tagtccgtta      4920
tcaacttgaa aaagtggcac cgagtcggtg cttttttga agcttg              4966
```

<210> SEQ ID NO 105
<211> LENGTH: 4938
<212> TYPE: DNA
<213> ORGANISM: Artificial Sequence
<220> FEATURE:
<223> OTHER INFORMATION: pGRNA-bdhB

<400> SEQUENCE: 105

```
atcaaaaaaa tttccaataa tcccactcta agccacaaac acgccctata aaatcccgct        60
ttaatcccac tttgagacac atgtaatatt actttacgcc ctagtatagt gataattttt       120
tacattcaat gccacgcaaa aaaataaagg ggcactataa taaagttcc ttcggaacta       180 actaaagtaa aaaattatct ttacaacctc cccaaaaaaa agaacaggta caaagtaccc       240
```

```
tataatacaa gcgtaaaaaa aatgagggta aaaataaaaa aataaaaaaa taaaaaaata      300
aaaaaataaa aaaataaaaa aataaaaaaa tataaaaata aaaaaatata aaaataaaaa      360
aatataaaaa taaaaaaata aaaaaatata aaaataaaaa aataaaaaaa tataaaaata      420
ttttttattt aaagtttgaa aaaaattttt ttatattata taatctttga agaaaagaat      480
ataaaaaatg agcctttata aaagcccatt tttttttcata tacgtaatat gacgttctaa     540 tgttttttatt ggtacttcta acattagagt aatttcttta ttttttaaagc cttttttcttt   600 aagggctttt attttttttc ttaatacatt taattcctct tttttttgttg cttttccttt     660 agctttttaat tgctcttgat aattttttttt acctctaata ttttctcttc tcttatattc    720 cttttttagaa attattattg tcatatattt ttgttcttct tctgtaatttt ctaataactc    780 tataagagtt tcattcttat acttatattg cttatttttta tctaaataac atctttcagc     840
acttctagtt gctcttataa cttctctttc acttaaatgt tgtctaaaca tactattaag     900
ttctaaaaca tcatttaatg ccttctcaat gtcttctgta aagctacaaa gataatatct     960
atataaaaat aatataagct ctctgtgtcc ttttaaatca tattctctta gttcacaaag    1020
ttttattatg tcttgtattc ttccataata taaacttctt tctctataaa tataaatttat    1080 tttgcttggt ctacccttttt tcctttcata tggttttaat tcaggtaaaa atccatttttg   1140 tatttctctt aagtcataaa tatattcgta ctcatctaat atattgacta ctgtttttga    1200
tttagagttt atacttcctg gaactcttaa tattctcgtt gcatctaagg cttgtctatc    1260
tgctccaaag tattttaatt gattatataa atattcttga accgctttcc ataatggtaa    1320
tgctttacta ggtactgcat ttattatcca tattaaatac attcctcttc cactatctat    1380
tacatagttt ggtataggaa tactttgatt aaaataattc ttttctaagt ccattaatac    1440 ctggtctttta gttttgccag ttttataata atccaagtct ataaacagtg tatttaactc    1500
ttttatattt tctaatcgcc tacacggctt ataaaggta tttagagtta tatagatatt     1560
ttcatcactc atatctaaat cttttaattc agcgtatttta tagtgccatt ggctatatcc   1620
ttttttatct ataacgctcc tggttatcca cccttttactt ctactatgaa tattatctat   1680 atagttctttt ttattcagct ttaatgcgtt tctcacttat tcacctcccc ttctgtaaaa   1740
ctaagaaaat tatatcatat tttcaataat tattaactat tcttaaactc ttaataaaaa    1800
atagagtaag tccccaattg aaacttaatc tatttttttat gttttaattt attattttta   1860
ttaaaatatt ttaaactaaa ttaaatgatt ctttttaatt ttttactatt tcattccata   1920
atatattact ataattattt acaaataata tttcttcatt tgtaatattt agatgattta   1980
ctaattttag tttttatata ttaaataatt aatgtataat ttatataaaa aatcaaagga    2040
gcttataaat tatgattatt tccaaagata ctaaagattt aatttttttc aattttaaca    2100 atacttttttg taatattatg tttaaattta attgtatttt tttcatataa taaagccgtt    2160
gaagtaaacc aatccatttt ccttatgatg ttattattaa atttaagttt tataataata    2220
tctttattat atttattgtt tttaaaaaaa ctagtgaaat ttctagtgaa atttccggct    2280
ttattaaact tattttttagg aattttattt tcattttcat ctttacagga tttgattata    2340
tctttaaata tgttttatca aatattatct ttttctaaat ttatatatat ttttattata    2400
tttattatta tatatatttt atttttaagt ttcttttctaa cagctattaa aaagaaactt    2460
aaaaataaaa acacgtactc taaaccaata aataaaacta ttttattat tgctgccttg     2520 attggaatag ttttttagtaa aattaatttc aatattccac aatattatat tataagctag    2580
cacgcctcga gtatattgat aaaaataata atagtgggta taattaagtt gttaggaggt    2640
```

```
tagttagagc ttattacgac ataacacagt tttagagcta gaaatagcaa gttaaaataa    2700
ggctagtccg ttatcaactt gaaaaagtgg caccgagtcg gtgctttttt tgaagcttgt    2760
cgactctaga ggatccccgg gtaccgagct cgaattcgta atcatggtca tagctgtttc    2820
ctgtgtgaaa ttgttatccg ctcacaattc cacacaacat acgagccgga agcataaagt    2880
gtaaagcctg gggtgcctaa tgagtgagct aactcacatt aattgcgttg cgctcactgc    2940
ccgctttcca gtcgggaaac ctgtcgtgcc agctgcatta atgaatcggc caacgcgcgg    3000
ggagaggcgg tttgcgtatt gggcgctctt ccgcttcctc gctcactgac tcgctgcgct    3060
cggtcgttcg gctgcggcga gcggtatcag ctcactcaaa ggcggtaata cggttatcca    3120
cagaatcagg ggataacgca ggaaagaaca tgtgagcaaa aggccagcaa aaggccagga    3180
accgtaaaaa ggccgcgttg ctggcgtttt tccataggct ccgcccccct gacgagcatc    3240
acaaaaatcg acgctcaagt cagaggtggc gaaacccgac aggactataa agataccagg    3300
cgtttccccc tggaagctcc ctcgtgcgct ctcctgttcc gaccctgccg cttaccggat    3360
acctgtccgc ctttctccct tcgggaagcg tggcgctttc tcatagctca cgctgtaggt    3420
atctcagttc ggtgtaggtc gttcgctcca agctgggctg tgtgcacgaa ccccccgttc    3480
agcccgaccg ctgcgcctta tccggtaact atcgtcttga gtccaacccg gtaagacacg    3540
acttatcgcc actggcagca gccactggta acaggattag cagagcgagg tatgtaggcg    3600
gtgctacaga gttcttgaag tggtggccta actacggcta cactagaaga acagtatttg    3660
gtatctgcgc tctgctgaag ccagttacct tcggaaaaag agttggtagc tcttgatccg    3720
gcaaacaaac caccgctggt agcggtggtt tttttgtttg caagcagcag attacgcgca    3780 gaaaaaagg atctcaagaa gatcctttga tcttttctac ggggtctgac gctcagtgga    3840
acgaaaactc acgttaaggg attttggtca tgagattatc aaaaaggatc ttcacctaga    3900
tccttttaaa ttaaaaatga agttttaaat caatctaaag tatatatgag taaacttggt    3960
ctgacagtta ccaaagctag cttaatacta gtatatactt aatgtgataa gtgtctgaca    4020
gctgaccggt ctaaagaggt ccctagcgcc tacggggaat ttgtatcgat aaggggtaca    4080
aattcccact aagcgctcgg ccggggatcg atccccgggt acgtacccgg cagttttct    4140 ttttcggcaa gtgttcaaga agttattaag tcgggagtgc agtcgaagtg ggcaagttga    4200
aaaattcaca aaaatgtggt ataatatctt tgttcattag agcgataaac ttgaatttga    4260
gagggaactt agatggtatt tgaaaaaatt gataaaaata gttggaacag aaaagagtat    4320
tttgaccact actttgcaag tgtaccttgt acctacagca tgaccgttaa agtggatatc    4380
acacaaataa aggaaaggg aatgaaacta tatcctgcaa tgctttatta tattgcaatg    4440
attgtaaacc gccattcaga gtttaggacg gcaatcaatc aagatggtga attgggata    4500 tatgatgaga tgataccaag ctatacaata tttcacaatg atactgaaac attttccagc    4560
ctttggactg agtgtaagtc tgactttaaa tcattttag cagattatga agtgatacg    4620 caacggtatg gaaacaatca tagaatggaa ggaaagccaa atgctccgga aaacattttt    4680
aatgtatcta tgataccgtg gtcaaccttc gatggcttta atctgaattt gcagaaagga    4740
tatgattatt tgattcctat ttttactatg gggaaatatt ataaagaaga taacaaaatt    4800
atacttcctt tggcaattca agttcatcac gcagtatgtg acggatttca catttgccgt    4860
tttgtaaacg aattgcagga attgataaat agttaacttc aggtttgtct gtaactaaaa    4920
actagtattt aacctagg                                                  4938
```

<210> SEQ ID NO 106
<211> LENGTH: 4790
<212> TYPE: DNA
<213> ORGANISM: Artificial Sequence
<220> FEATURE:
<223> OTHER INFORMATION: pEC750C

<400> SEQUENCE: 106

```
atcaaaaaaa tttccaataa tcccactcta agccacaaac acgccctata aatcccgct      60
ttaatcccac tttgagacac atgtaatatt actttacgcc ctagtatagt gataattttt    120
tacattcaat gccacgcaaa aaaataaagg ggcactataa taaagttcc ttcggaacta     180
actaaagtaa aaaattatct ttacaacctc cccaaaaaaa agaacaggta caaagtaccc    240
tataatacaa gcgtaaaaaa aatgagggta aaaataaaaa aataaaaaaa taaaaaaata    300
aaaaaataaa aaaataaaaa aataaaaaaa tataaaaata aaaaaatata aaaataaaaa    360
aatataaaaa taaaaaaata aaaaaatata aaaataaaaa aataaaaaaa tataaaaata    420
ttttttattt aaagtttgaa aaaaattttt ttatattata taatctttga agaaaagaat    480
ataaaaaatg agcctttata aaagcccatt tttttcata tacgtaatat gacgttctaa     540
tgttttatt ggtacttcta acattagagt aatttcttta ttttttaaagc ctttttcttt    600
aagggctttt attttttttc ttaatacatt taattcctct ttttttgttg cttttccttt    660
agcttttaat tgctcttgat aattttttt acctctaata ttttctcttc tcttatattc    720
cttttagaa attattattg tcatatattt ttgttcttct tctgtaattt ctaataactc    780
tataagagtt tcattcttat acttatattg cttattttta tctaaataac atctttcagc    840
acttctagtt gctcttataa cttctctttc acttaaatgt tgtctaaaca tactattaag   900
ttctaaaaca tcatttaatg ccttctcaat gtcttctgta aagctacaaa gataatatct    960
atataaaaat aatataagct ctctgtgtcc ttttaaatca tattctctta gttcacaaag   1020
ttttattatg tcttgtattc ttccataata taaacttctt tctctataaa tataatttat   1080
tttgcttggt ctacccttt tcctttcata tggttttaat tcaggtaaaa atccattttg    1140
tatttctctt aagtcataaa tatattcgta ctcatctaat atattgacta ctgttttttga   1200
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa actttgatt aaaataattc ttttctaagt ccattaatac    1440
ctggtcttta gttttgccag ttttataata atccaagtct ataaacagtg tatttaactc   1500
ttttatattt tctaatcgcc tacacggctt ataaaggta tttagagtta tatagatatt     1560
ttcatcactc atatctaaat cttttaattc agcgtattta tagtgccatt ggctatatcc   1620
tttttatct ataacgctcc tggttatcca ccctttactt ctactatgaa tattatctat    1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tatttttttat gttttaattt attatttta    1860
ttaaaatatt ttaaactaaa ttaaatgatt cttttttaatt tttactatt tcattccata    1920
atatattact ataattattt acaaataata tttcttcatt tgtaatattt agatgattta    1980
ctaatttttag ttttttatata ttaaataatt aatgtataat ttatataaaa aatcaaagga   2040
gcttataaat tatgattatt tccaaagata ctaaagattt aattttttttc aattttaaca   2100
```

```
atacttttg taatattatg tttaaattta attgtatttt ttcatataa taaagccgtt    2160
gaagtaaacc aatccatttt ccttatgatg ttattattaa atttaagttt tataataata   2220
tctttattat atttattgtt tttaaaaaaa ctagtgaaat ttctagtgaa atttccggct   2280
ttattaaact tatttttagg aatttttattt tcattttcat ctttacagga tttgattata  2340
tctttaaata tgttttatca aatattatct ttttctaaat ttatatatat ttttattata   2400
tttattatta tatatatttt attttttaagt ttctttctaa cagctattaa aaagaaactt  2460
aaaaataaaa acacgtactc taaaccaata aataaaacta ttttattat tgctgccttg    2520
attggaatag tttttagtaa aattaatttc aatattccac aatattatat tataagctag   2580
cacgcctcga gatctccatg gacgcgtgac gtcgactcta gaggatcccc gggtaccgag   2640
ctcgaattcg taatcatggt catagctgtt tcctgtgtga aattgttatc cgctcacaat   2700
tccacacaac atacgagccg aagcataaa gtgtaaagcc tggggtgcct aatgagtgag    2760
ctaactcaca ttaattgcgt tgcgctcact gcccgctttc cagtcgggaa acctgtcgtg   2820
ccagctgcat taatgaatcg gccaacgcgc ggggagaggc ggtttgcgta ttgggcgctc   2880
ttccgcttcc tcgctcactg actcgctgcg ctcggtcgtt cggctgcggc gagcggtatc   2940
agctcactca aaggcggtaa tacggttatc cacagaatca ggggataacg caggaaagaa   3000
catgtgagca aaaggccagc aaaaggccag gaaccgtaaa aaggccgcgt tgctggcgtt   3060
tttccatagg ctccgccccc ctgacgagca tcacaaaaat cgacgctcaa gtcagaggtg   3120
gcgaaacccg acaggactat aaagatacca ggcgtttccc cctggaagct ccctcgtgcg   3180
ctctcctgtt ccgaccctgc cgcttaccgg atacctgtcc gcctttctcc cttcgggaag   3240
cgtggcgctt tctcatagct cacgctgtag gtatctcagt tcggtgtagg tcgttcgctc   3300
caagctgggc tgtgtgcacg aaccccccgt tcagcccgac cgctgcgcct tatccggtaa   3360
ctatcgtctt gagtccaacc cggtaagaca cgacttatcg ccactggcag cagccactgg   3420
taacaggatt agcagagcga ggtatgtagg cggtgctaca gagttcttga agtggtggcc   3480
taactacggc tacactagaa gaacagtatt tggtatctgc gctctgctga agccagttac   3540
cttcggaaaa agagttggta gctcttgatc cggcaaacaa accaccgctg gtagcggtgg   3600
tttttttgtt tgcaagcagc agattacgcg cagaaaaaaa ggatctcaag aagatccttt   3660
gatcttttct acggggtctg acgctcagtg gaacgaaaac tcacgttaag ggattttggt   3720
catgagatta tcaaaaagga tcttcaccta gatccttta aattaaaaat gaagttttaa    3780
atcaatctaa agtatatatg agtaaacttg gtctgacagt taccaaagct agcttaatac   3840
tagtatatac ttaatgtgat aagtgtctga cagctgaccg gtctaaagag gtccctagcg   3900
cctacgggga atttgtatcg ataagggta caaattccca ctaagcgctc ggccgggat    3960
cgatccccgg gtacgtaccc ggcagttttt cttttcggc aagtgttcaa gaagttatta   4020
agtcgggagt gcagtcgaag tgggcaagtt gaaaaattca caaaaatgtg gtataatatc   4080
tttgttcatt agagcgataa acttgaattt gagagggaac ttagatggta tttgaaaaaa   4140
ttgataaaaa tagttggaac agaaaagagt attttgacca ctactttgca agtgtacctt   4200
gtacctacag catgaccgtt aaagtggata tcacacaaat aaaggaaaag gaatgaaac    4260
tatatcctgc aatgctttat tatattgcaa tgattgtaaa ccgccattca gagtttagga   4320
cggcaatcaa tcaagatggt gaattgggga tatatgatga gatgatacca agctatacaa   4380
tatttcacaa tgatactgaa acattttcca gcctttggac tgagtgtaag tctgactta   4440
```

```
aatcattttt agcagattat gaaagtgata cgcaacggta tggaaacaat catagaatgg    4500
aaggaaagcc aaatgctccg gaaaacattt ttaatgtatc tatgataccg tggtcaacct    4560
tcgatggctt taatctgaat ttgcagaaag gatatgatta tttgattcct attttttacta   4620 tggggaaata ttataaagaa gataacaaaa ttatacttcc tttggcaatt caagttcatc    4680
acgcagtatg tgacggattt cacatttgcc gttttgtaaa cgaattgcag gaattgataa    4740
atagttaact tcaggtttgt ctgtaactaa aaactagtat ttaacctagg               4790
```

<210> SEQ ID NO 107
<211> LENGTH: 35
<212> TYPE: DNA
<213> ORGANISM: Artificial Sequence
<220> FEATURE:
<223> OTHER INFORMATION: Primer

<400> SEQUENCE: 107

```
acttgggtcg accacgataa aacaaggttt taagg                              35
```

<210> SEQ ID NO 108
<211> LENGTH: 42
<212> TYPE: DNA
<213> ORGANISM: Artificial Sequence
<220> FEATURE:
<223> OTHER INFORMATION: Primer

<400> SEQUENCE: 108

```
taccagggat ccgtattaat gtaactatga tatcaattct tg                      42
```

<210> SEQ ID NO 109
<211> LENGTH: 46
<212> TYPE: DNA
<213> ORGANISM: Artificial Sequence
<220> FEATURE:
<223> OTHER INFORMATION: Primer

<400> SEQUENCE: 109

```
atgcatggtc ccaatgaata ggtttacact tactttagtt ttatgg                  46
```

<210> SEQ ID NO 110
<211> LENGTH: 39
<212> TYPE: DNA
<213> ORGANISM: Artificial Sequence
<220> FEATURE:
<223> OTHER INFORMATION: Primer

<400> SEQUENCE: 110

```
atgcgagtta acaacttcta aaatctgatt accaattag                          39
```

<210> SEQ ID NO 111
<211> LENGTH: 47
<212> TYPE: DNA
<213> ORGANISM: Artificial Sequence
<220> FEATURE:
<223> OTHER INFORMATION: Primer

<400> SEQUENCE: 111

```
atgcatggat cccaatgaat aggtttacac ttactttagt tttatgg                 47
```

<210> SEQ ID NO 112
<211> LENGTH: 39
<212> TYPE: DNA
<213> ORGANISM: Artificial Sequence
<220> FEATURE:
<223> OTHER INFORMATION: Primer

<400> SEQUENCE: 112
atgcgagagc tcaacttcta aaatctgatt accaattag            39

<210> SEQ ID NO 113
<211> LENGTH: 32
<212> TYPE: DNA
<213> ORGANISM: Artificial Sequence
<220> FEATURE:
<223> OTHER INFORMATION: Primer

<400> SEQUENCE: 113
atgcatggat ccgtctgaca gttaccaggt cc                   32

<210> SEQ ID NO 114
<211> LENGTH: 39
<212> TYPE: DNA
<213> ORGANISM: Artificial Sequence
<220> FEATURE:
<223> OTHER INFORMATION: Primer

<400> SEQUENCE: 114
atgcgagagc tccaattgtt caaaaaaata atggcggag            39

<210> SEQ ID NO 115
<211> LENGTH: 32
<212> TYPE: DNA
<213> ORGANISM: Artificial Sequence
<220> FEATURE:
<223> OTHER INFORMATION: Primer

<400> SEQUENCE: 115
atgcatggat cccggcagtt tttcttttc gg                    32

<210> SEQ ID NO 116
<211> LENGTH: 40
<212> TYPE: DNA
<213> ORGANISM: Artificial Sequence
<220> FEATURE:
<223> OTHER INFORMATION: Primer

<400> SEQUENCE: 116
atgcgagagc tcggttaaat actagttttt agttacagac           40

<210> SEQ ID NO 117
<211> LENGTH: 2686
<212> TYPE: DNA
<213> ORGANISM: Artificial Sequence
<220> FEATURE:
<223> OTHER INFORMATION: pUC19

<400> SEQUENCE: 117
gcgcccaata cgcaaaccgc ctctccccgc gcgttggccg attcattaat gcagctggca    60
cgacaggttt cccgactgga aagcgggcag tgagcgcaac gcaattaatg tgagttagct   120
cactcattag gcaccccagg ctttacactt tatgcttccg gctcgtatgt tgtgtggaat   180
tgtgagcgga taacaatttc acacaggaaa cagctatgac catgattacg ccaagcttgc   240
atgcctgcag gtcgactcta gaggatcccc gggtaccgag ctcgaattca ctggccgtcg   300
ttttacaacg tcgtgactgg gaaaaccctg gcgttaccca acttaatcgc cttgcagcac   360 atccccctt cgccagctgg cgtaatagcg aagaggcccg caccgatcgc ccttcccaac    420
agttgcgcag cctgaatggc gaatggcgcc tgatgcggta ttttctcctt acgcatctgt   480

```
gcggtatttc acaccgcata tggtgcactc tcagtacaat ctgctctgat gccgcatagt      540
taagccagcc ccgacacccg ccaacacccg ctgacgcgcc ctgacgggct tgtctgctcc      600
cggcatccgc ttacagacaa gctgtgaccg tctccgggag ctgcatgtgt cagaggtttt      660
caccgtcatc accgaaacgc gcgagacgaa agggcctcgt gatacgccta ttttatagg      720 ttaatgtcat gataataatg gtttcttaga cgtcaggtgg cacttttcgg ggaaatgtgc      780
gcggaacccc tatttgttta ttttctaaa tacattcaaa tatgtatccg ctcatgagac      840
aataaccctg ataaatgctt caataatatt gaaaaaggaa gagtatgagt attcaacatt      900
tccgtgtcgc ccttattccc ttttttgcgg cattttgcct tcctgttttt gctcacccag      960
aaacgctggt gaaagtaaaa gatgctgaag atcagttggg tgcacgagtg ggttacatcg     1020
aactggatct caacagcggt aagatccttg agagttttcg ccccgaagaa cgttttccaa     1080
tgatgagcac ttttaaagtt ctgctatgtg gcgcggtatt atcccgtatt gacgccgggc     1140
aagagcaact cggtcgccgc atacactatt ctcagaatga cttggttgag tactcaccag     1200
tcacagaaaa gcatcttacg gatggcatga cagtaagaga attatgcagt gctgccataa     1260
ccatgagtga taacactgcg gccaacttac ttctgacaac gatcggagga ccgaaggagc     1320
taaccgcttt tttgcacaac atgggggatc atgtaactcg ccttgatcgt tgggaaccgg     1380
agctgaatga agccatacca aacgacgagc gtgacaccac gatgcctgta gcaatggcaa     1440
caacgttgcg caaactatta actggcgaac tacttactct agcttcccgg caacaattaa     1500
tagactggat ggaggcggat aaagttgcag gaccacttct gcgctcggcc cttccggctg     1560
gctggtttat tgctgataaa tctggagccg gtgagcgtgg gtctcgcggt atcattgcag     1620
cactggggcc agatggtaag ccctcccgta tcgtagttat ctacacgacg gggagtcagg     1680
caactatgga tgaacgaaat agacagatcg ctgagatagg tgcctcactg attaagcatt     1740
ggtaactgtc agaccaagtt tactcatata ctttagat tgatttaaaa cttcatttttt     1800 aatttaaaag gatctaggtg aagatccttt ttgataatct catgaccaaa atcccttaac     1860
gtgagttttc gttccactga gcgtcagacc ccgtagaaaa gatcaaagga tcttcttgag     1920
atcctttttt tctgcgcgta atctgctgct tgcaaacaaa aaaaccaccg ctaccagcgg     1980
tggtttgttt gccggatcaa gagctaccaa ctctttttcc gaaggtaact ggcttcagca     2040
gagcgcagat accaaatact gttcttctag tgtagccgta gttaggccac cacttcaaga     2100
actctgtagc accgcctaca tacctcgctc tgctaatcct gttaccagtg gctgctgcca     2160
gtggcgataa gtcgtgtctt accgggttgg actcaagacg atagttaccg gataaggcgc     2220
agcggtcggg ctgaacgggg ggttcgtgca cacagcccag cttggagcga acgacctaca     2280
ccgaactgag atacctacag cgtgagctat gagaaagcgc cacgcttccc gaagggagaa     2340
aggcggacag gtatccggta agcggcaggg tcggaacagg agagcgcacg agggagcttc     2400 caggggggaaa cgcctggtat ctttatagtc ctgtcgggtt tcgccacctc tgacttgagc     2460 gtcgatttttt gtgatgctcg tcaggggggc ggagcctatg gaaaaacgcc agcaacgcgg     2520 ccttttttacg gttcctggcc ttttgctggc cttttgctca catgttcttt cctgcgttat     2580
cccctgattc tgtggataac cgtattaccg cctttgagtg agctgatacc gctcgccgca     2640
gccgaacgac cgagcgcagc gagtcagtga gcgaggaagc ggaaga                    2686
```

<210> SEQ ID NO 118
<211> LENGTH: 4282
<212> TYPE: DNA
<213> ORGANISM: Artificial Sequence
<220> FEATURE:
<223> OTHER INFORMATION: pNF2

<400> SEQUENCE: 118

```
ctggagagga ttgtccttat acttatcata agcatgaagg acttgttatt cctagataga      60
gaattaatta tgttaaagag atataataaa ctcattataa ttataatttt tagtataatt     120
attattgcaa ttttttcgta taaatatcta ataatgccaa aagagcatag aatagaaatt     180
tcaacattat caaacataga agtttttaaa tttaatagtt tttcaaagtt tagtaacgaa     240
aaaatgtata ctattaatga tagtgataag ttaataaaat tcaaaacact atttaataat     300
ttagataaat caaagatat aaaaaagatt agtattccgg aaagtgaaaa tttaaatgca      360
tttaaatttt ctgcacatat aaaacttaac tttaactatg ttaataaaga tagccaaata     420
actgaaggtg cttttcttat gtatattttg gtagacaatt tagaagggaa gtcatatatg     480
acttttttag acaagattc aagctatata ttagatagta atgaaactaa cattttaaga     540
gaaatattta tgaattcaga gattaattaa tttatgaatt cataaatatt atctaagcac     600
gataaaacaa ggttttaagg ataagaaaag tcatgagatt tatagtaaat cttgtgactt     660
tttttattga atagtagaga gagttcgaa gtataacacg ctatattctt gatattttta      720
gaatagcaag cattggattt gtcctgacac tttcccaaaa attaaggagt tattccttaa     780
accaaaaaga ttaatgtggg aacaaattta gtgtatccat ttttgaaggg cgcacttata     840
caccaccaaa atggtgtgtg cgaaatcttt aaaaaagatt tatcaaaaag cttttttaaa     900
gctgggacat ttagaaaatc aataatgttt tttgcccaat acgctagtct taaaatctgc     960
aaggttgata actatttagt cccaggtatt agaatggggc atatatatac aaagtatata    1020
tatgcgtaaa tatatgtggg actgtgggaa caaaattgcg tgctaaaatt gtattgaaaa    1080
ggtaatgaaa aggtcatgct ttggtattgc taacgtatag aaaaggtaat gaaaagctca    1140
tggttctata aaaagatgt acccacgaaa ataataggct ttgcctattt ccccatgtaa    1200
tatgggggca gttttctctt atgctctttc ttaacatatt gaataaatac aaaatgcagc    1260
tttgtgggaa taaaaatatt tttgttttta ttcttatagt tagacaaaat tttaatcttt    1320
tttgtgctat aacaagatta aaatttgtgg gaacattaag aaatattgtt gtcacaaata    1380
aaaaggagag tgggaacaat tgctataaaa aacgcagaaa ttaagattag agttacaaaa    1440
gagcaaaaag aattatttaa gaaaattgca aaagctgaaa atatgagtat gagtgaattt    1500
attattgtga ccacagaata tttagccaga aaaaagatg aaaatatgaa atcaaaagac    1560
atgatcgaga gaagagctgc gaagactgaa gaaaaaatta tgaagctaaa aaagaaacta    1620
aataaaaaca ggtaatatag attacagttt taagcttgtt ttccctatag actagagtaa    1680
atatataaat atacctgtca agggcttata agccccttta gggggtgcgt agcacccttg    1740
acaggtatat ttatatattt tagggtgcca ttaagggaaa caagctttaa aatgccttta    1800
aaggcatttt aaaataaata aaaaaagat ggttttacc atctttttta actcccgaaa     1860
gggagttctt tcttttcttg atactatacg taactatttc gatttgccct gaacctaatc    1920
aaagctagat aaattcagta ttagggcata aaaaaacttg cttttcggg tggaaatctg     1980
tataatttaa attgcttaga taaaaattac caattccata cgaaaggagc aagtttttaca   2040
taaggttaaa gccttatgtg aattctcatt taattacatg aataataata acacagaaag    2100
tgaagaatta aaagagcaaa gtcaactatt gcttgacaaa tgcacaaaaa agaaaaagaa    2160
aaatcctaaa tttagtagtt atatagaacc attagtaagc aagaaattat ctgaaagaat    2220
```

```
aaaggaatgt ggtgactttt tgcagatgtt atctgattta aaccttgaaa attcgaaact    2280
gcatagagca agttttttgtg gtaacagatt ttgtcctatg tgtagctggc gtattgcttg    2340
taaggatagt ttggaaatat ctattctcat ggagcattta cgcaaagagg aaagcaaaga    2400
atttatcttt ttgaccttaa caactccaaa tgtgaaaggt gcggaccttg ataattccat    2460
aaaagcatac aataaagcat ttaaaaagtt aatggaacgc aaagaggtca agagcatagt    2520
aaaaggctac ataagaaagc tagaagtaac ctataatttg gacaagagtt ccaaatcata    2580
taatacttat cacccacatt tccatgtggt actagcagtc aatagaagtt actttaaaaa    2640
gcaaaatcta tatataaacc atcatagatg gcttagtttg tggcaagagt caactggtga    2700
ttattcgata actcaagttg atgtaagaaa ggctaaaatt aacgattata agaggttta     2760 tgagcttgct aagtattcgg ctaaggattc cgactattta atcaatagag aagtgtttac    2820
ggtattctac aaatctttaa agggtaaaca ggtacttgta tttagtggat tatttaaaga    2880
cgctcataaa atgtataaga atggagagct agatctgtat aagaagttgg atactatcga    2940
atatgcttat atggtaagtt ataactggct taaaaagaag tatgatactt caaatattag    3000
agaattaact gaggaagaaa agcagaaatt caataaaaat ttaatcgaag atgtggatat    3060
tgagtaggtg ggattatatc tcacctttt tattgtcttt tcatgttgaa attttgacgc     3120
ttaatgcatg aagtattgac aagtttaaaa attacggttt ttaatcctta gttgattagc    3180
aggattatgg ccggaatgct ccgtccagtc ctgttaagga attaaaattc cctaaaaccc    3240
ttggctatga tttatagcga gaatcgtcaa ttaaaaattt aataggtgct atgaaagtcg    3300
attaataatt aattttaaaa tgcaatatga aacataatta caagaatttg acttttaata    3360
caagaattga tatcatagtt acattaatac atttattttg aaggggggaaa atgttttatg    3420 aaaagactac ttaaactacc tattttatca ttattaggat tatttttaat tggatcaact    3480
ccaacattag ctttaactaa agataataat caaaatttag atactatgaa agtaaactta    3540
tatactgaaa cagtagatgt gtttgataaa gatgcattta acaaacatt tactaataaa     3600 gatataaaat ttctagagga ttctttgaat gcaaaaataa attattcagg taaatctgtt    3660
acagtaacaa tgaaaaacaa aattaagcca tctactaaac aagggcttgt tttatatgta    3720
aatggaaaat cagttaatgt tgattcagat ggcagtataa aagtacctaa agatactaag    3780
aaaatttcta aattaaataa agataaatca atgatggatg gatcaatgat ggataaatca    3840
ttacatgatg agaattgtgt agtatcagat agttttata atgctgatgt taataatata     3900
aattcaaaag aagcagaagc tgtatttaaa gtaagttctg gtgaattatt agctaaaatg    3960
gatgaaaaag aagatgatta catacaaaag aactcatcta aaattctagc agctgcttat    4020
cataagggat atgggacaa gtactatgaa ggagattggg ttcattgcaa taggtttaat     4080
ggtcaactta cagatgatgt tcactataat tggagaactg gaagtgtttc agaaaaagca    4140
gctgcaatga gaattttta tggcagtgat tgtcatatag cattagttca agcaggtagt    4200
ggatgtacaa gtataggttc atgcgaatgc aatacagatc aaatagctgc gtattgttca    4260
ggtttcgtaa aagataaaaa ta                                             4282

<210> SEQ ID NO 119
<211> LENGTH: 5473
<212> TYPE: DNA
<213> ORGANISM: Artificial Sequence
<220> FEATURE:
<223> OTHER INFORMATION: pNF3

<400> SEQUENCE: 119
```

```
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagcttgc     240
atgcctgcag gtcgaccacg ataaaacaag gttttaagga taagaaaagt catgagattt     300
atagtaaatc ttgtgacttt ttttattgaa tagtagagag agttcggaag tataacacgc     360
tatattcttg atatttttag aatagcaagc attggatttg tcctgacact ttcccaaaaa     420
ttaaggagtt attccttaaa ccaaaaagat taatgtggga acaaatttag tgtatccatt     480
tttgaagggc gcacttatac accaccaaaa tggtgtgtgc gaaatcttta aaaagatttt     540
atcaaaaagc ttttttaaag ctgggacatt tagaaaatca ataatgtttt ttgcccaata     600
cgctagtctt aaaatctgca aggttgataa ctatttagtc ccaggtatta gaatggggca     660
tatatataca aagtatatat atgcgtaaat atatgtggga ctgtgggaac aaaattgcgt     720
gctaaaattg tattgaaaag gtaatgaaaa ggtcatgctt tggtattgct aacgtataga     780
aaaggtaatg aaaagctcat ggttctataa aaaagatgta cccacgaaaa taataggctt     840
tgcctatttc cccatgtaat atgggggcag ttttctctta tgctctttct taacatattg     900
aataaataca aaatgcagct ttgtgggaat aaaaatattt ttgttttttat tcttatagtt     960 agacaaaatt ttaatctttt ttgtgctata acaagattaa aatttgtggg aacattaaga    1020
aatattgttg tcacaaataa aaaggagagt gggaacaatt gctataaaaa acgcagaaat    1080
taagattaga gttacaaaag agcaaaaaga attatttaag aaaattgcaa aagctgaaaa    1140
tatgagtatg agtgaattta ttattgtgac cacagaatat ttagccagaa aaaaagatga    1200
aaatatgaaa tcaaaagaca tgatcgagag aagagctgcg aagactgaag aaaaaaattat   1260 gaagctaaaa aagaaactaa ataaaaacag gtaatataga ttacagttttt aagcttgttt   1320 tccctataga ctagagtaaa tatataaata tacctgtcaa gggcttataa gccccttttag   1380 ggggtgcgta gcacccttga caggtatatt tatatatttt agggtgccat taagggaaac    1440
aagctttaaa atgcctttaa aggcatttta aaataaataa aaaaaagatg gttttttacca    1500 tcttttttaa ctcccgaaag ggagttcttt ctttttcttga tactatacgt aactatttcg    1560
atttgccctg aacctaatca aagctagata aattcagtat tagggcataa aaaaacttgc    1620 ttttttcgggt ggaaatctgt ataatttaaa ttgcttagat aaaaattacc aattccatac    1680
gaaaggagca agttttacat aaggttaaag ccttatgtga attctcattt aattacatga    1740
ataataataa cacagaaagt gaagaattaa aagagcaaag tcaactattg cttgacaaat    1800
gcacaaaaaa gaaaagaaa aatcctaaat ttagtagtta tatagaacca ttagtaagca    1860
agaaattatc tgaaagaata aaggaatgtg gtgacttttt gcagatgtta tctgatttaa    1920
accttgaaaa ttcgaaactg catagagcaa gttttgtgg taacagattt tgtcctatgt    1980
gtagctggcg tattgcttgt aaggatagtt tggaaatatc tattctcatg gagcatttac    2040
gcaaagagga aagcaaagaa tttatctttt tgaccttaac aactccaaat gtgaaaggtg    2100
cggaccttga taattccata aaagcataca ataaagcatt taaaaagtta atggaacgca    2160
aagaggtcaa gagcatagta aaaggctaca taagaaagct agaagtaacc tataatttgg    2220
acaagagttc caaatcatat aatacttatc acccacattt ccatgtggta ctagcagtca    2280
atagaagtta cttttaaaaag caaatctat atataaacca tcatagatgg cttagtttgt    2340
```

```
ggcaagagtc aactggtgat tattcgataa ctcaagttga tgtaagaaag gctaaaatta    2400
acgattataa agaggtttat gagcttgcta agtattcggc taaggattcc gactatttaa    2460
tcaatagaga agtgtttacg gtattctaca aatctttaaa gggtaaacag gtacttgtat    2520
ttagtggatt atttaaagac gctcataaaa tgtataagaa tggagagcta gatctgtata    2580
agaagttgga tactatcgaa tatgcttata tggtaagtta aactggctt aaaaagaagt    2640 atgatacttc aaatattaga gaattaactg aggaagaaaa gcagaaattc aataaaaatt    2700
taatcgaaga tgtggatatt gagtaggtgg gattatatct cacctttttt attgtctttt    2760
catgttgaaa ttttgacgct taatgcatga agtattgaca agtttaaaaa ttacggtttt    2820
taatccttag ttgattagca ggattatggc cggaatgctc cgtccagtcc tgttaaggaa    2880
ttaaaattcc ctaaaaccct tggctatgat ttatagcgag aatcgtcaat taaaaattta    2940
ataggtgcta tgaaagtcga ttaataatta attttaaaat gcaatatgaa acataattac    3000
aagaatttga cttttaatac aagaattgat atcatagtta cattaatacg gatcccgggg    3060
taccgagctc gaattcactg gccgtcgttt tacaacgtcg tgactgggaa aaccctggcg    3120
ttacccaact taatcgcctt gcagcacatc cccctttcgc cagctggcgt aatagcgaag    3180
aggcccgcac cgatcgccct tcccaacagt tgcgcagcct gaatggcgaa tggcgcctga    3240
tgcggtattt tctccttacg catctgtgcg gtatttcaca ccgcatatgg tgcactctca    3300
gtacaatctg ctctgatgcc gcatagttaa gccagccccg acacccgcca cacccgctg    3360 acgcgccctg acgggcttgt ctgctcccgg catccgctta cagacaagct gtgaccgtct    3420
ccgggagctg catgtgtcag aggttttcac cgtcatcacc gaaacgcgcg agacgaaagg    3480
gcctcgtgat acgcctattt ttataggtta atgtcatgat aataatggtt cttagacgt    3540 caggtggcac ttttcgggga atgtgcgcg gaaccctat ttgtttattt ttctaaatac    3600
attcaaatat gtatccgctc atgagacaat aaccctgata aatgcttcaa taatattgaa    3660
aaaggaagag tatgagtatt caacatttcc gtgtcgccct tattccctt tttgcggcat    3720 tttgccttcc tgttttgct cacccagaaa cgctggtgaa agtaaaagat gctgaagatc    3780
agttgggtgc acgagtgggt tacatcgaac tggatctcaa cagcggtaag atccttgaga    3840
gttttcgccc cgaagaacgt tttccaatga tgagcacttt taaagttctg ctatgtggcg    3900
cggtattatc ccgtattgac gccgggcaag agcaactcgg tcgccgcata cactattctc    3960
agaatgactt ggttgagtac tcaccagtca cagaaaagca tcttacggat ggcatgacag    4020
taagagaatt atgcagtgct gccataacca tgagtgataa cactgcggcc aacttacttc    4080
tgacaacgat cggaggaccg aaggagctaa ccgcttttt gcacaacatg ggggatcatg    4140
taactcgcct tgatcgttgg gaaccggagc tgaatgaagc cataccaaac gacgagcgtg    4200
acaccacgat gcctgtagca atggcaacaa cgttgcgcaa actattaact ggcgaactac    4260
ttactctagc ttcccggcaa caattaatag actggatgga ggcggataaa gttgcaggac    4320
cacttctgcg ctcggccctt ccggctggct ggtttattgc tgataaatct ggagccggtg    4380
agcgtgggtc tcgcggtatc attgcagcac tggggccaga tggtaagccc tcccgtatcg    4440
tagttatcta cacgacgggg agtcaggcaa ctatggatga acgaaataga cagatcgctg    4500
agataggtgc ctcactgatt aagcattggt aactgtcaga ccaagtttac tcatatatac    4560
tttagattga tttaaaactt catttttaat ttaaaaggat ctaggtgaag atcctttttg    4620
ataatctcat gaccaaaatc ccttaacgtg agttttcgtt ccactgagcg tcagaccccg    4680
tagaaaagat caaaggatct tcttgagatc cttttttttct gcgcgtaatc tgctgcttgc    4740
```

```
aaacaaaaaa accaccgcta ccagcggtgg tttgtttgcc ggatcaagag ctaccaactc      4800 ttttccgaa ggtaactggc ttcagcagag cgcagatacc aaatactgtt cttctagtgt       4860
agccgtagtt aggccaccac ttcaagaact ctgtagcacc gcctacatac ctcgctctgc      4920
taatcctgtt accagtggct gctgccagtg gcgataagtc gtgtcttacc gggttggact      4980
caagacgata gttaccggat aaggcgcagc ggtcgggctg aacggggggt tcgtgcacac      5040
agcccagctt ggagcgaacg acctacaccg aactgagata cctacagcgt gagctatgag      5100
aaagcgccac gcttcccgaa gggagaaagg cggacaggta tccggtaagc ggcagggtcg      5160
gaacaggaga gcgcacgagg gagcttccag ggggaaacgc ctggtatctt tatagtcctg      5220
tcgggtttcg ccacctctga cttgagcgtc gatttttgtg atgctcgtca gggggcgga      5280 gcctatggaa aaacgccagc aacgcggcct ttttacggtt cctggccttt tgctggcctt      5340
ttgctcacat gttctttcct gcgttatccc ctgattctgt ggataaccgt attaccgcct      5400
ttgagtgagc tgataccgct cgccgcagcc gaacgaccga gcgcagcgag tcagtgagcg      5460
aggaagcgga aga                                                         5473
```

<210> SEQ ID NO 120
<211> LENGTH: 9128
<212> TYPE: DNA
<213> ORGANISM: Artificial Sequence
<220> FEATURE:
<223> OTHER INFORMATION: pMTL007S-E1

<400> SEQUENCE: 120

```
gatcgggccc cctgcagggt gtagtagcct gtgaaataag taaggaaaaa aagaagtaa       60 gtgttatata tgatgattat tttgtagatg tagataggat aatagaatcc atagaaaata     120
taggttatac agttatataa aaattacttt aaaaattaat aaaaacatgg taaaatataa     180
atcgtataaa gttgtgtaat ttttaagctt gagctcataa caatttcaca caggaaacag     240
ctatgaccat gattacggat tcactggccg tcgttttaca acgtcgtgac tgggaaaacc     300
ctggcgttac ccaacttaat cgccttgcag cacatcccc tttcgccagc tggcgtaata    360
gcgaagaggc ccgcaccgat cgcccttccc aacagttgcg cagcctgaat ggcgaatggc     420
gctaataaag atcttgtaca atctgtagga gaacctatgg gaacgaaacg aaagcgatgc     480
cgagaatctg aatttaccaa gacttaacac taactgggga taccctaaac aagaatgcct     540
aatagaaagg aggaaaaagg ctatagcact agagcttgaa aatcttgcaa gggtacggag     600
tactcgtagt agtctgagaa gggtaacgcc ctttacatgg caaaggggta cagttattgt     660
gtactaaaat taaaaattga ttagggagga aaacctcaaa atgaaaccaa caatggcaat     720
tttagaaaga atcagtaaaa attcacaaga aaatatagac gaagttttta caagactta     780 tcgttatctt ttacgtccag atatttatta cgtggcgacg cgtgcgactc atagaattat     840
ttcctcccgt taaataatag ataactatta aaaatagaca atacttgctc ataagtaacg     900
gtacttaaat tgtttacttt ggcgtgtttc attgcttgat gaaactgatt tttagtaaac     960
agttgacgat attctcgatt gacccatttt gaaacaaagt acgtatatag cttccaatat    1020
ttatctggaa catctgtggt atggcgggta agttttatta agacactgtt tacttttggt    1080
ttaggatgaa agcattccgc tggcagctta agcaattgct gaatcgagac ttgagtgtgc    1140
aagagcaacc ctagtgttcg gtgaaatacc aaggtacgct gtagaatcc ttcttcaaca    1200 atcagataga tgtcagacgc atggctttca aaaaccactt ttttaataat ttgtgtgctt    1260
```

```
aaatggtaag gaatactccc aacaatttta tacctctgtt tgttagggaa ttgaaactgt   1320
agaatatctt ggtgaattaa agtgacacga gtattcagtt ttaatttttc tgacgataag   1380
ttgaatagat gactgtctaa ttcaatagac gttacctgtt tacttatttt agccagtttc   1440
gtcgttaaat gcccttttacc tgttccaatt tcgtaaacgg tatcggtttc ttttaaattc   1500
aattgtttta ttatttggtt gagtactttt tcactcgtta aaagttttg agaatatttt    1560 atattttgt tcataccagc accagaagca ccagcatctc ttgggttaat tgaggcctga    1620
gtataaggtg acttatactt gtaatctatc taaacgggga acctctctag tagacaatcc   1680
cgtgctaaat tgtaggactg ccctttaata aatacttcta tatttaaaga ggtatttatg   1740
aaaagcggaa tttatcagat taaaaatact ttctctagag aaaatttcgt ctggattagt   1800
tacttatcgt gtaaaatctg ataaatggaa ttggttctac ataaatgcct aacgactatc   1860
cctttgggga gtagggtcaa gtgactcgaa acgatagaca acttgcttta acaagttgga   1920
gatatagtct gctctgcatg gtgacatgca gctggatata attccggggt aagattaacg   1980
accttatctg aacataatgc catatgaatc cctcctaatt tatacgtttt ctctaacaac   2040
ttaattatac ccactattat tattttatc aatataacgc gttgggaaat ggcaatgata    2100
gcgaaacaac gtaaaactct tgttgtatgc tttcattgtc atcgtcacgt gattcataaa   2160
cacaagtgaa tgtcgacagt gaattttac gaacgaacaa taacagagcc gtatactccg    2220
agaggggtac gtacggttcc cgaagagggt ggtgcaaacc agtcacagta atgtgaacaa   2280
ggcggtacct ccctacttca ccatatcatt ttctgcagcc ccctagaaat aatttttgttt 2340 aactttaaga aggagatata catatatggc tagatcgtcc attccgacag catcgccagt   2400
cactatggcg tgctgctagc gctatatgcg ttgatgcaat ttctatgcac tcgtagtagt   2460
ctgagaaggg taacgcccctt tacatggcaa aggggtacag ttattgtgta ctaaaattaa  2520
aaattgatta gggaggaaaa cctcaaaatg aaaccaacaa tggcaatttt agaaagaatc   2580
agtaaaaatt cacaagaaaa tatagacgaa gttttacaa gacttatcg ttatctttta     2640 cgtccagata tttattacgt ggcgtatcaa aatttatatt ccaataaagg agcttccaca   2700
aaaggaatat tagatgatac agcggatggc tttagtgaag aaaaaataaa aaagattatt   2760
caatctttaa aagacggaac ttactatcct caacctgtac gaagaatgta tattgcaaaa   2820
aagaattcta aaaagatgag acctttagga attccaactt tcacagataa attgatccaa   2880
gaagctgtga gaataattct tgaatctatc tatgaaccgg tattcgaaga tgtgtctcac   2940
ggttttagac ctcaacgaag ctgtcacaca gctttgaaaa caatcaaaag agagtttggc   3000
ggcgcaagat ggtttgtgga gggagatata aaaggctgct tcgataatat agaccacgtt   3060
acactcattg gactcatcaa tcttaaaatc aaagatatga aaatgagcca attgatttat   3120
aaatttctaa agcaggtta tctggaaaac tggcagtatc acaaaactta cagcggaaca    3180
cctcaaggtg gaattctatc tcctcttttg gccaacatct atcttcatga attggataag   3240
tttgttttac aactcaaaat gaagtttgac cgagaaagtc cagaaagaat aacacctgaa   3300
tatcgggagc tccacaatga gataaaaaga atttctcacc gtctcaagaa gttggagggt   3360
gaagaaaaag ctaaagttct tttagaatat caagaaaaac gtaaaagatt acccacactc   3420
ccctgtacct cacagacaaa taagtattg aaatacgtcc ggtatgcgga cgacttcatt    3480
atctctgtta aaggaagcaa agaggactgt caatggataa aagaacaatt aaaacttttt   3540
attcataaca agctaaaaat ggaattgagt gaagaaaaaa cactcatcac acatagcagt   3600
caacccgctc gttttctggg atatgatata cgagtaagga gatctggaac gataaaacga   3660
```

```
tctggtaaag tcaaaaagag aacactcaat gggagtgtag aactccttat tcctcttcaa    3720
gacaaaattc gtcaatttat ttttgacaag aaaatagcta tccaaaagaa agatagctca    3780
tggtttccag ttcacaggaa atatcttatt cgttcaacag acttagaaat catcacaatt    3840
tataattctg aactccgcgg gatttgtaat tactacggtc tagcaagtaa ttttaaccag    3900
ctcaattatt ttgcttatct tatggaatac agctgtctaa aaacgatagc ctccaaacat    3960
aagggaacac tttcaaaaac catttccatg tttaaagatg gaagtggttc gtggggatc    4020 ccgtatgaga taaagcaagg taagcagcgc cgttattttg caaattttag tgaatgtaaa    4080
tccccttatc aatttacgga tgagataagt caagctcctg tattgtatgg ctatgcccgg    4140
aatactcttg aaaacaggtt aaaagctaaa tgttgtgaat tatgtgggac gtctgatgaa    4200
aatacttcct atgaaattca ccatgtcaat aaggtcaaaa atcttaaagg caaagaaaaa    4260
tgggaaatgg caatgatagc gaaacaacgt aaaactcttg ttgtatgctt tcattgtcat    4320
cgtcacgtga ttcataaaca caagtgaatg tcgagcaccc gttctcggag cactgtccga    4380
ccgctttggc cgccgcccag tcctgctcgc ttcgctactt ggagccacta tcgactacgc    4440
gatcatggcg accacacccg tcctgtggat cgccaagccg ccgatggtag tgtggggtct    4500
ccccatgcga gagtagggaa ctgccaggca tcaaataaaa cgaaaggctc agtcgaaaga    4560
ctgggccttt cgttttatct gttgtttgtc ggtgaacgct ctcctgagta ggacaaatcc    4620
gccgggagcg gatttgaacg ttgcgaagca acggcccgga gggtggcggg caggacgccc    4680
gccataaact gccaggcatc aaattaagca gaaggccatc ctgacggatg cctttttgc    4740 gtttctacaa actcttcctg tcgtcatatc tacaagccat ccccccacag atacgggcgc    4800
gccgccatta tttttttgaa caattgacaa ttcatttctt attttttatt aagtgatagt    4860
caaaaggcat aacagtgctg aatagaaaga aatttacaga aaagaaaatt atagaatta    4920 gtatgattaa ttatactcat ttatgaatgt ttaattgaat acaaaaaaaa atacttgtta    4980
tgtattcaat tacgggttaa aatatagaca agttgaaaaa tttaataaaa aaataagtcc    5040
tcagctctta tatattaagc taccaactta gtatataagc caaaacttaa atgtgctacc    5100
aacacatcaa gccgttagag aactctatct atagcaatat ttcaaatgta ccgacataca    5160
agagaaacat taactatata tattcaattt atgagattat cttaacagat ataaatgtaa    5220
attgcaataa gtaagattta gaagtttata gcctttgtgt attggaagca gtacgcaaag    5280
gcttttttat ttgataaaaa ttagaagtat atttattttt tcataattaa tttatgaaaa    5340
tgaaaggggg tgagcaaagt gacagaggaa agcagtatct tatcaaataa caaggtatta    5400
gcaatatcat tattgacttt agcagtaaac attatgactt ttatagtgct tgtagctaag    5460
tagtacgaaa gggggagctt taaaaagctc cttggaatac atagaattca taaattaatt    5520
tatgaaaaga agggcgtata tgaaaacttg taaaaattgc aaagagttta ttaaagatac    5580
tgaaatatgc aaaatacatt cgttgatgat tcatgataaa acagtagcaa cctattgcag    5640
taaatacaat gagtcaagat gtttacataa agggaaagtc caatgtatta attgttcaaa    5700
gatgaaccga tatggatggt gtgccataaa aatgagatgt tttacagagg aagaacagaa    5760 aaagaacgt acatgcatta aatattatgc aaggagcttt aaaaaagctc atgtaaagaa    5820
gagtaaaaag aaaaaataat ttatttatta atttaatatt gagagtgccg acacagtatg    5880
cactaaaaaa tatatctgtg gtgtagtgag ccgatacaaa aggatagtca ctcgcatttt    5940
cataatacat cttatgttat gattatgtgt cggtgggact tcacgacgaa aacccacaat    6000
```

```
aaaaaaagag ttcggggtag ggttaagcat agttgaggca actaaacaat caagctagga    6060
tatgcagtag cagaccgtaa ggtcgttgtt taggtgtgtt gtaatacata cgctattaag    6120
atgtaaaaat acggatacca atgaagggaa aagtataatt tttggatgta gtttgtttgt    6180
tcatctatgg gcaaactacg tccaaagccg tttccaaatc tgctaaaaag tatatccttt    6240
ctaaaatcaa agtcaagtat gaaatcataa ataaagttta attttgaagt tattatgata    6300
ttatgttttt ctattaaaat aaattaagta tatagaatag tttaataata gtatatactt    6360
aatgtgataa gtgtctgaca gtgtcacaga aaggatgatt gttatggatt ataagcggcc    6420
ggcccaatga ataggtttac acttacttta gtttatgga aatgaaagat catatcatat     6480
ataatctaga ataaaattaa ctaaaataat tattatctag ataaaaaatt tagaagccaa    6540
tgaaatctat aaataaacta aattaagttt atttaattaa caactatgga tataaaatag    6600
gtactaatca aaatagtgag gaggatatat ttgaatacat acgaacaaat taataaagtg    6660
aaaaaaatac ttcggaaaca tttaaaaaat aaccttattg gtacttacat gtttggatca    6720
ggagttgaga gtggactaaa accaaatagt gatcttgact ttttagtcgt cgtatctgaa    6780
ccattgacag atcaaagtaa agaaatactt atacaaaaaa ttagacctat ttcaagaaa     6840 ataggagata aaagcaactt acgatatatt gaattaacaa ttattattca gcaagaaatg    6900
gtaccgtgga atcatcctcc caaacaagaa tttatttatg gagaatggtt acaagagctt    6960
tatgaacaag gatacattcc tcagaaggaa ttaaattcag atttaaccat aatgctttac    7020
caagcaaaac gaaaaaataa aagaatatac ggaaattatg acttagagga attactacct    7080
gatattccat tttctgatgt gagaagagcc attatggatt cgtcagagga attaatagat    7140
aattatcagg atgatgaaac caactctata ttaactttat gccgtatgat tttaactatg    7200
gacacgggta aaatcatacc aaaagatatt gcgggaaatg cagtggctga atcttctcca    7260
ttagaacata gggagagaat tttgttagca gttcgtagtt atcttggaga gaatattgaa    7320
tggactaatg aaaatgtaaa tttaactata aactatttaa ataacagatt aaaaaaaatta    7380 taaaaaaatt gaaaaaatgg tggaaacact ttttcaatt tttttgtttt attatttaat     7440
atttgggaaa tattcattct aattggtaat cagattttag aagtttaaac tccttttga     7500 taatctcatg accaaaatcc cttaacgtga gttttcgttc cactgagcgt cagacccgt     7560 agaaaagatc aaaggatctt cttgagatcc ttttttctg cgcgtaatct gctgcttgca     7620
aacaaaaaaa ccaccgctac cagcggtggt ttgtttgccg atcaagagc taccaactct      7680 ttttccgaag gtaactggct tcagcagagc gcagatacca aatactgttc ttctagtgta    7740
gccgtagtta ggccaccact tcaagaactc tgtagcaccg cctacatacc tcgctctgct    7800
aatcctgtta ccagtggctg ctgccagtgg cgataagtcg tgtcttaccg ggttggactc    7860
aagacgatag ttaccggata aggcgcagcg gtcgggctga acggggggtt cgtgcacaca    7920
gcccagcttg gagcgaacga cctacaccga actgagatac ctacagcgtg agctatgaga    7980
aagcgccacg cttcccgaag ggagaaaggc ggacaggtat ccggtaagcg gcagggtcgg    8040
aacaggagag cgcacgaggg agcttccagg gggaaacgcc tggtatcttt atagtcctgt    8100
cgggtttcgc cacctctgac ttgagcgtcg attttttgtga tgctcgtcag ggggcggag     8160 cctatggaaa aacgccagca acgcggcctt tttacggttc ctggccttt gctggccttt      8220 tgctcacatg ttcttttcctg cgttatcccc tgattctgtg gataaccgta ttaccgcctt    8280
tgagtgagct gataccgctc gccgcagccg aacgaccgag cgcagcgagt cagtgagcga    8340
ggaagcggaa gagcgcccaa tacgcagggc cccctgcttc ggggtcatta tagcgatttt    8400
```

```
ttcggtatat ccatccttt  tcgcacgata tacaggattt tgccaaaggg ttcgtgtaga    8460 cttccttgg  tgtatccaac ggcgtcagcc gggcaggata ggtgaagtag gcccacccgc    8520
gagcgggtgt tccttcttca ctgtcccta  ttcgcacctg gcggtgctca acgggaatcc    8580
tgctctgcga ggctggccgg ctaccgccgg cgtaacagat gagggcaagc ggatggctga    8640
tgaaaccaag ccaaccagga agggcagccc acctatcaag gtgtactgcc ttccagacga    8700
acgaagagcg attgaggaaa aggcggcggc ggccggcatg agcctgtcgg cctacctgct    8760
ggccgtcggc cagggctaca aaatcacggg cgtcgtggac tatgagcacg tccgcgagct    8820
ggcccgcatc aatggcgacc tgggccgcct gggcggcctg ctgaaactct ggctcaccga    8880
cgacccgcgc acggcgcggt tcggtgatgc cacgatcctc gccctgctgg cgaagatcga    8940
agagaagcag gacgagcttg gcaaggtcat gatgggcgtg gtccgcccga gggcagagcc    9000 atgactttt  tagccgctaa acggccggg  gggtgcgcgt gattgccaag cacgtcccca    9060
tgcgctccat caagaagagc gacttcgcgg agctggtgaa gtacatcacc gacgagcaag    9120
gcaagacc                                                            9128
```

<210> SEQ ID NO 121
<211> LENGTH: 5002
<212> TYPE: DNA
<213> ORGANISM: Artificial Sequence
<220> FEATURE:
<223> OTHER INFORMATION: pEC751S

<400> SEQUENCE: 121

```
atcaaaaaaa tttccaataa tcccactcta agccacaaac acgccctata aaatcccgct      60
ttaatcccac tttgagacac atgtaatatt actttacgcc ctagtatagt gataattttt     120
tacattcaat gccacgcaaa aaaataaagg ggcactataa taaagttcc  ttcggaacta     180 actaaagtaa aaaattatct ttacaacctc cccaaaaaaa agaacaggta caaagtaccc     240
tataatacaa gcgtaaaaaa aatgagggta aaaataaaaa aataaaaaaa taaaaaaata     300
aaaaaataaa aaaataaaaa aataaaaaaa tataaaaata aaaaaatata aaataaaaa      360 aatataaaaa taaaaaaata aaaaatata  aaataaaaa  aataaaaaaa tataaaaata     420
ttttttattt aaagtttgaa aaaaattttt ttatattata taatctttga agaaaagaat     480
ataaaaaatg agcctttata aagcccatt  ttttttcata tacgtaatat gacgttctaa     540 tgttttatt  ggtacttcta acattagagt aatttcttta tttttaaagc ctttttcttt     600 aagggcttt  atttttttc  ttaatacatt taattcctct ttttttgttg cttttccttt     660 agctttaat  tgctcttgat aattttttt  acctctaata ttttctcttc tcttatattc     720
ctttttagaa attatattg  tcatatattt ttgttcttct tctgtaattt ctaataactc     780
tataagagtt tcattcttat acttatattg cttatttta  tctaaataac atctttcagc     840 acttctagt  gctcttataa cttctctttc acttaaatgt tgtctaaaca tactattaag     900
ttctaaaaca tcatttaatg ccttctcaat gtcttctgta aagctacaaa gataatatct     960
atataaaaat aatataagct ctctgtgtcc ttttaaatca tattctctta gttcacaaag    1020
ttttattatg tcttgtattc ttccataata taaacttctt tctctataaa tataatttat    1080
tttgcttggt ctacccttt  tcctttcata tggttttaat tcaggtaaaa atccattttg    1140 tattctctt  aagtcataaa tatattcgta ctcatctaat atattgacta ctgttttga     1200 tttagagttt atacttcctg gaactcttaa tattctcgtt gcatctaagg cttgtctatc    1260
```

```
tgctccaaag tatttaatt gattatataa atattcttga accgctttcc ataatggtaa      1320
tgctttacta ggtactgcat ttattatcca tattaaatac attcctcttc cactatctat      1380
tacatagttt ggtataggaa tactttgatt aaaataattc ttttctaagt ccattaatac      1440
ctggtcttta gttttgccag ttttataata atccaagtct ataaacagtg tatttaactc      1500
ttttatattt tctaatcgcc tacacggctt ataaaggta tttagagtta tatagatatt      1560
ttcatcactc atatctaaat cttttaattc agcgtattta tagtgccatt ggctatatcc      1620 tttttatct ataacgctcc tggttatcca cctttactt ctactatgaa tattatctat        1680
atagttcttt ttattcagct ttaatgcgtt tctcacttat tcacctcccc ttctgtaaaa      1740
ctaagaaaat tatatcatat tttcaataat tattaactat tcttaaactc ttaataaaaa      1800
atagagtaag tccccaattg aaacttaatc tattttttat gttttaattt attattttta      1860
ttaaaatatt ttaaactaaa ttaaatgatt cttttaatt tttactatt tcattccata        1920 atatattact ataattattt acaaataata tttcttcatt tgtaatattt agatgattta      1980 ctaatttttag ttttttatata ttaaataatt aatgtataat ttatataaaa aatcaaagga   2040
gcttataaat tatgattatt tccaaagata ctaaagattt aatttttttc aatttttaaca    2100 atacttttg taatattatg tttaaattta attgtatttt tttcatataa taaagccgtt      2160
gaagtaaacc aatccatttt ccttatgatg ttattattaa atttaagttt tataataata    2220 tcttattat atttattgtt tttaaaaaaa ctagtgaaat ttctagtgaa atttccggct      2280
ttattaaact tattttttagg aatttttattt tcattttcat ctttacagga tttgattata  2340
tctttaaata tgttttatca aatattatct ttttctaaat ttatatatat ttttattata    2400
tttattatta tatatatttt attttttaagt ttctttctaa cagctattaa aaagaaactt   2460
aaaaataaaa acacgtactc taaaccaata aataaaacta ttttttattat tgctgccttg   2520 attggaatag ttttttagtaa aattaatttc aatattccac aatattatat tataagctag   2580
cacgcctcga gatctccatg gacgcgtgac gtcgactcta gaggatcccc gggtaccgag    2640
ctcgaattcg taatcatggt catagctgtt tcctgtgtga aattgttatc cgctcacaat    2700
tccacacaac atacgagccg gaagcataaa gtgtaaagcc tggggtgcct aatgagtgag    2760
ctaactcaca ttaattgcgt tgcgctcact gcccgctttc cagtcgggaa acctgtcgtg    2820
ccagctgcat taatgaatcg gccaacgcgc ggggagaggc ggtttgcgta ttgggcgctc    2880
ttccgcttcc tcgctcactg actcgctgcg ctcggtcgtt cggctgcggc gagcggtatc    2940
agctcactca aaggcggtaa tacggttatc cacagaatca ggggataacg caggaaagaa    3000
catgtgagca aaaggccagc aaaaggccag gaaccgtaaa aaggccgcgt tgctggcgtt    3060
tttccatagg ctccgccccc ctgacgagca tcacaaaaat cgacgctcaa gtcagaggtg    3120
gcgaaacccg acaggactat aaagatacca ggcgtttccc cctggaagct ccctcgtgcg    3180
ctctcctgtt ccgaccctgc cgcttaccgg atacctgtcc gcctttctcc cttcgggaag    3240
cgtggcgctt tctcatagct cacgctgtag gtatctcagt tcggtgtagg tcgttcgctc    3300
caagctgggc tgtgtgcacg aaccccccgt tcagcccgac cgctgcgcct tatccggtaa    3360
ctatcgtctt gagtccaacc cggtaagaca cgacttatcg ccactggcag cagccactgg    3420
taacaggatt agcagagcga ggtatgtagg cggtgctaca gagttcttga agtggtggcc    3480
taactacggc tacactagaa gaacagtatt tggtatctgc gctctgctga agccagttac    3540
cttcggaaaa agagttggta gctcttgatc cggcaaacaa accaccgctg gtagcggtgg    3600 ttttttttgtt tgcaagcagc agattacgcg cagaaaaaaa ggatctcaag aagatccttt    3660
```

```
gatcttttct acggggtctg acgctcagtg gaacgaaaac tcacgttaag ggattttggt    3720
catgagatta tcaaaaagga tcttcaccta gatcctttta aattaaaaat gaagttttaa    3780
atcaatctaa agtatatatg agtaaacttg gtctgacagt taccaaagct agcttaatac    3840
tagtatatac ttaatgtgat aagtgtctga cagctgaccg gtctaaagag gtcccaatga    3900
ataggtttac acttactta  gttttatgga aatgaaagat catatcatat ataatctaga    3960
ataaaattaa ctaaaataat tattatctag ataaaaaatt tagaagccaa tgaaatctat    4020
aaataaacta aattaagttt atttaattaa caactatgga tataaaatag gtactaatca    4080
aaatagtgag gaggatatat ttgaatacat acgaacaaat taataaagtg aaaaaaatac    4140
ttcggaaaca tttaaaaaat aaccttattg gtacttacat gtttggatca ggagttgaga    4200
gtggactaaa accaaatagt gatcttgact ttttagtcgt cgtatctgaa ccattgacag    4260
atcaaagtaa agaaatactt atacaaaaaa ttagacctat ttcaaagaaa ataggagata    4320
aaagcaactt acgatatatt gaattaacaa ttattattca gcaagaaatg gtaccgtgga    4380
atcatcctcc caaacaagaa tttatttatg gagaatggtt acaagagctt tatgaacaag    4440
gatacattcc tcagaaggaa ttaaattcag atttaaccat aatgctttac aagcaaaac     4500 gaaaaaataa agaatatac  ggaaattatg acttagagga attactacct gatattccat    4560
tttctgatgt gagaagagcc attatggatt cgtcagagga attaatagat aattatcagg    4620
atgatgaaac caactctata ttaactttat gccgtatgat tttaactatg gacacgggta    4680
aaatcatacc aaaagatatt gcgggaaatg cagtggctga atcttctcca ttagaacata    4740
gggagagaat tttgttagca gttcgtagtt atcttggaga gaatattgaa tggactaatg    4800
aaaatgtaaa tttaactata aactatttaa ataacagatt aaaaaaatta taaaaaaatt    4860
gaaaaaatgg tggaaacact ttttcaatt  ttttgtttt attatttaat atttgggaaa     4920
tattcattct aattggtaat cagatttttag aagttgttaa cttcaggttt gtctgtaact    4980
aaaaactagt atttaaccta gg                                             5002
```

<210> SEQ ID NO 122
<211> LENGTH: 3907
<212> TYPE: DNA
<213> ORGANISM: Artificial Sequence
<220> FEATURE:
<223> OTHER INFORMATION: pFW01

<400> SEQUENCE: 122

```
tcgagatctc catggacgcg tgacgtcgac tctagaggat ccccgggtac cgagctcgaa      60
ttcgtaatca tggtcatagc tgtttcctgt gtgaaattgt tatccgctca caattccaca     120
caacatacga gccggaagca taaagtgtaa agcctggggt gcctaatgag tgagctaact     180
cacattaatt gcgttgcgct cactgcccgc tttccagtcg ggaaacctgt cgtgccagct     240
gcattaatga atcggccaac gcgcggggag aggcggtttg cgtattgggc gctcttccgc     300
ttcctcgctc actgactcgc tgcgctcggt cgttcggctg cggcgagcgg tatcagctca     360
ctcaaaggcg gtaatacggt tatccacaga atcaggggat aacgcaggaa agaacatgtg     420
agcaaaaggc cagcaaaagg ccaggaaccg taaaaaggcc gcgttgctgg cgtttttcca     480
taggctccgc cccctgacg  agcatcacaa aaatcgacgc tcaagtcaga ggtggcgaaa      540
cccgacagga ctataaagat accaggcgtt tcccctgga  agctccctcg tgcgctctcc      600
tgttccgacc ctgccgctta ccggatacct gtccgccttt ctcccttcgg gaagcgtggc     660
```

```
gctttctcat agctcacgct gtaggtatct cagttcggtg taggtcgttc gctccaagct      720
gggctgtgtg cacgaacccc ccgttcagcc cgaccgctgc gccttatccg gtaactatcg      780
tcttgagtcc aacccggtaa gacacgactt atcgccactg gcagcagcca ctggtaacag      840
gattagcaga gcgaggtatg taggcggtgc tacagagttc ttgaagtggt ggcctaacta      900
cggctacact agaaggacag tatttggtat ctgcgctctg ctgaagccag ttaccttcgg      960
aaaaagagtt ggtagctctt gatccggcaa acaaaccacc gctggtagcg gtggtttttt     1020
tgtttgcaag cagcagatta cgcgcagaaa aaaggatct caagaagatc ctttgatctt      1080
ttctacgggg tctgacgctc agtggaacga aaactcacgt taagggatt tggtcatgag      1140 attatcaaaa aggatcttca cctagatcct tttaaattaa aaatgaagtt ttaaatcaat      1200
ctaaagtata tatgagtaaa cttggtctga cagttaccag gtccactgcc gggcctcttg      1260
cgggatcaaa agaaaaacga aatgatacac caatcagtgc aaaaaaagat ataatgggag     1320
ataagacggt tcgtgttcgt gctgacttgc accatatcat aaaaatcgaa acagcaaaga     1380
atggcggaaa cgtaaaagaa gttatggaaa taagacttag aagcaaactt aagagtgtgt     1440
tgatagtgca gtatcttaaa attttgtata ataggaattg aagttaaatt agatgctaaa     1500
aatttgtaat taagaaggag tgattacatg aacaaaaata taaatattc tcaaaacttt      1560 ttaacgagtg aaaagtact caaccaaata ataaacaat tgaatttaaa agaaaccgat       1620
accgtttacg aaattggaac aggtaaaggg catttaacga cgaaactggc taaaataagt     1680
aaacaggtaa cgtctattga attagacagt catctattca acttatcgtc agaaaaatta     1740
aaactgaata ctcgtgtcac tttaattcac caagatattc tacagtttca attccctaac     1800
aaacagaggt ataaaattgt tgggagtatt ccttaccatt taagcacaca aattattaaa     1860
aaagtggttt ttgaaagcca tgcgtctgac atctatctga ttgttgaaga aggattctac     1920
aagcgtacct tggatattca ccgaacacta gggttgctct tgcacactca agtctcgatt     1980
cagcaattgc ttaagctgcc agcggaatgc tttcatccta aaccaaaagt aaacagtgtc     2040
ttaataaaac ttacccgcca taccacagat gttccagata atattggaa gctatatacg      2100 tactttgttt caaaatgggt caatcgagaa tatcgtcaac tgtttactaa aaatcagttt     2160
catcaagcaa tgaaacacgc caaagtaaac aatttaagta ccgttactta tgagcaagta     2220
ttgtctattt ttaatagtta tctattattt aacgggagga ataattcta tgagtcccta      2280 ggcaggcctc cgccattatt ttttgaaca attgacaatt catttcttat tttttattaa      2340
gtgatagtca aaaggcataa cagtgctgaa tagaaagaaa tttacagaaa agaaaattat     2400
agaatttagt atgattaatt atactcattt atgaatgttt aattgaatac aaaaaaaaat     2460
acttgttatg tattcaatta cgggttaaaa tatagacaag ttgaaaaatt taataaaaaa     2520
ataagtcctc agctcttata tattaagcta ccaacttagt atataagcca aacttaaat      2580 gtgctaccaa cacatcaagc cgttagagaa ctctatctat agcaatattt caaatgtacc     2640
gacatacaag agaaacatta actatatata ttcaatttat gagattatct taacagatat     2700
aaatgtaaat tgcaataagt aagatttaga agtttatagc ctttgtgtat tggaagcagt     2760
acgcaaaggc ttttttattt gataaaaatt agaagtatat ttattttttc ataattaatt     2820
tatgaaaatg aaggggggtg agcaaagtga cagaggaaag cagtatctta tcaaataaca     2880
aggtattagc aatatcatta ttgactttag cagtaaacat tatgactttt atagtgcttg     2940
tagctaagta gtacgaaagg gggagcttta aaaagctcct tggaatacat agaattcata     3000
aattaattta tgaaaagaag ggcgtatatg aaaacttgta aaaattgcaa agagtttatt     3060
```

```
aaagatactg aaatatgcaa aatacattcg ttgatgattc atgataaaac agtagcaacc    3120
tattgcagta aatacaatga gtcaagatgt ttacataaag ggaaagtcca atgtattaat    3180
tgttcaaaga tgaaccgata tggatggtgt gccataaaaa tgagatgttt tacagaggaa    3240
gaacagaaaa aagaacgtac atgcattaaa tattatgcaa ggagctttaa aaaagctcat    3300
gtaaagaaga gtaaaaagaa aaaataattt atttattaat ttaatattga gagtgccgac    3360
acagtatgca ctaaaaaata tatctgtggt gtagtgagcc gatacaaaag gatagtcact    3420 cgcatttca taatacatct tatgttatga ttatgtgtcg gtgggacttc acgacgaaaa     3480
cccacaataa aaaagagtt cggggtaggg ttaagcatag ttgaggcaac taaacaatca     3540
agctaggata tgcagtagca gaccgtaagg tcgttgttta ggtgtgttgt aatacatacg    3600
ctattaagat gtaaaaatac ggataccaat gaagggaaaa gtaattttt tggatgtagt    3660 ttgtttgttc atctatgggc aaactacgtc caaagccgtt tccaaatctg ctaaaaagta   3720
tatcctttct aaaatcaaag tcaagtatga aatcataaat aaagtttaat ttgaagtta    3780 ttatgatatt atgttttct attaaaataa attaagtata tagaatagtt taataatagt    3840
atatacttaa tgtgataagt gtctgacagt gtcacagaaa ggatgattgt tatggattat   3900
aagcggc                                                               3907

<210> SEQ ID NO 123
<211> LENGTH: 6525
<212> TYPE: DNA
<213> ORGANISM: Artificial Sequence
<220> FEATURE:
<223> OTHER INFORMATION: pNF3S

<400> SEQUENCE: 123
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagcttgc    240
atgcctgcag gtcgaccacg ataaaacaag gttttaagga taagaaaagt catgagattt    300
atagtaaatc ttgtgacttt ttttattgaa tagtagagag agttcggaag tataacacgc    360
tatattcttg atattttag aatagcaagc attggatttg tcctgacact ttcccaaaaa    420
ttaaggagtt attccttaaa ccaaaaagat taatgtggga acaaatttag tgtatccatt    480
tttgaagggc gcacttatac accaccaaaa tggtgtgtgc gaaatcttta aaaaagattt    540
atcaaaaagc tttttaaag ctgggacatt tagaaaatca ataatgtttt tgcccaata     600 cgctagtctt aaaatctgca aggttgataa ctatttagtc ccaggtatta gaatggggca    660
tatatataca aagtatatat atgcgtaaat atatgtggga ctgtgggaac aaaattgcgt    720
gctaaaattg tattgaaaag gtaatgaaaa ggtcatgctt tggtattgct aacgtataga    780
aaaggtaatg aaaagctcat ggttctataa aaaagatgta cccacgaaaa taataggctt    840
tgcctatttc cccatgtaat atggggggcag ttttctctta tgctcttcct taacatattg    900
aataaataca aatgcagct tgtgggaat aaaaatattt ttgtttttat tcttatagtt     960
agacaaaatt ttaatctttt ttgtgctata acaagattaa aatttgtggg aacattaaga   1020
aatattgttg tcacaaataa aaaggagagt gggaacaatt gctataaaaa acgcagaaat   1080
taagattaga gttacaaaag agcaaaaaga attatttaag aaaattgcaa aagctgaaaa   1140
```

```
tatgagtatg agtgaattta ttattgtgac cacagaatat ttagccagaa aaaagatga      1200 aaatatgaaa tcaaaagaca tgatcgagag aagagctgcg aagactgaag aaaaaattat    1260
gaagctaaaa aagaaactaa ataaaaacag gtaatataga ttacagttttt aagcttgttt    1320 tccctataga ctagagtaaa tatataaata tacctgtcaa gggcttataa gccccttttag   1380 ggggtgcgta gcacccttga caggtatatt tatatatttt agggtgccat taagggaaac    1440
aagctttaaa atgcctttaa aggcatttta aaataaataa aaaaaagatg gttttttacca   1500 tcttttttaa ctcccgaaag ggagttcttt cttttcttga tactatacgt aactatttcg    1560
atttgccctg aacctaatca aagctagata aattcagtat tagggcataa aaaaacttgc    1620
tttttcgggt ggaaatctgt ataatttaaa ttgcttagat aaaaattacc aattccatac    1680
gaaaggagca agttttacat aaggttaaag ccttatgtga attctcattt aattacatga    1740
ataataataa cacagaaagt gaagaattaa aagagcaaag tcaactattg cttgacaaat    1800
gcacaaaaaa gaaaagaaa aatcctaaat ttagtagtta tatagaacca ttagtaagca    1860
agaaattatc tgaaagaata aaggaatgtg gtgacttttt gcagatgtta tctgatttaa   1920
accttgaaaa ttcgaaactg catagagcaa gttttttgtgg taacagattt tgtcctatgt   1980
gtagctggcg tattgcttgt aaggatagtt tggaaatatc tattctcatg gagcatttac    2040
gcaaagagga aagcaaagaa tttatctttt tgaccttaac aactccaaat gtgaaaggtg    2100
cggaccttga taattccata aaagcataca ataaagcatt taaaaagtta atggaacgca   2160
aagaggtcaa gagcatagta aaaggctaca taagaaagct agaagtaacc tataatttgg   2220
acaagagttc caaatcatat aatacttatc acccacattt ccatgtggta ctagcagtca    2280
atagaagtta ctttaaaaag caaaatctat atataaacca tcatagatgg cttagttttgt   2340 ggcaagagtc aactggtgat tattcgataa ctcaagttga tgtaagaaag gctaaaatta   2400
acgattataa agaggtttat gagcttgcta agtattcggc taaggattcc gactatttaa   2460
tcaatagaga agtgtttacg gtattctaca aatctttaaa gggtaaacag gtacttgtat    2520
ttagtggatt attttaaagac gctcataaaa tgtataagaa tggagagcta gatctgtata   2580
agaagttgga tactatcgaa tatgcttata tggtaagtta taactggctt aaaaagaagt    2640
atgatacttc aaatattaga gaattaactg aggaagaaaa gcagaaattc aataaaaatt   2700
taatcgaaga tgtggatatt gagtaggtgg gattatatct cacctttttt attgtctttt    2760
catgttgaaa ttttgacgct taatgcatga agtattgaca agtttaaaaa ttacggtttt    2820
taatccttag ttgattagca ggattatggc cggaatgctc cgtccagtcc tgttaaggaa    2880
ttaaaattcc ctaaaaccct tggctatgat ttatagcgag aatcgtcaat taaaaattta    2940
ataggtgcta tgaaagtcga ttaataatta atttttaaaat gcaatatgaa acataattac    3000
aagaatttga cttttaatac aagaattgat atcatagtta cattaatacg gatcccaatg    3060
aataggttta cacttacttt agttttatgg aaatgaaaga tcatatcata tataatctag    3120
aataaaatta actaaaataa ttattatcta gataaaaaat ttagaagcca atgaaatcta    3180
taaataaact aaattaagtt tatttaatta acaactatgg atataaaata ggtactaatc    3240
aaaatagtga ggaggatata tttgaataca tacgaacaaa ttaataaagt gaaaaaaata   3300
cttcggaaac atttaaaaaa taaccttatt ggtacttaca tgtttggatc aggagttgag    3360
agtggactaa aaccaaatag tgatcttgac ttttagtcg tcgtatctga accattgaca     3420
gatcaaagta aagaaatact tatacaaaaa attagaccta tttcaaagaa aataggagat    3480
aaaagcaact tacgatatat tgaattaaca attattattc agcaagaaat ggtaccgtgg    3540
```

```
aatcatcctc ccaaacaaga atttatttat ggagaatggt tacaagagct ttatgaacaa    3600
ggatacattc ctcagaagga attaaattca gatttaacca taatgcttta ccaagcaaaa    3660
cgaaaaaata aaagaatata cggaaattat gacttagagg aattactacc tgatattcca    3720
ttttctgatg tgagaagagc cattatggat tcgtcagagg aattaataga taattatcag    3780
gatgatgaaa ccaactctat attaacttta tgccgtatga ttttaactat ggacacgggt    3840
aaaatcatac caaagatat tgcgggaaat gcagtggctg aatcttctcc attagaacat    3900
agggagagaa ttttgttagc agttcgtagt tatcttggag agaatattga atggactaat    3960
gaaaatgtaa atttaactat aaactattta aataacagat taaaaaaatt ataaaaaaat    4020
tgaaaaaatg gtggaaacac ttttttcaat ttttttgttt tattatttaa tatttgggaa    4080
atattcattc taattggtaa tcagatttta gaagttgagc tcgaattcac tggccgtcgt    4140
tttacaacgt cgtgactggg aaaaccctgg cgttacccaa cttaatcgcc ttgcagcaca    4200
tcccccttc gccagctggc gtaatagcga agaggcccgc accgatcgcc cttcccaaca    4260
gttgcgcagc ctgaatggcg aatggcgcct gatgcggtat tttctcctta cgcatctgtg    4320
cggtatttca caccgcatat ggtgcactct cagtacaatc tgctctgatg ccgcatagtt    4380
aagccagccc cgacacccgc caacacccgc tgacgcgccc tgacgggctt gtctgctccc    4440
ggcatccgct tacagacaag ctgtgaccgt ctccgggagc tgcatgtgtc agaggttttc    4500
accgtcatca ccgaaacgcg cgagacgaaa gggcctcgtg atacgcctat ttttataggt    4560
taatgtcatg ataataatgg tttcttagac gtcaggtggc acttttcggg gaaatgtgcg    4620
cggaaccct atttgtttat ttttctaaat acattcaaat atgtatccgc tcatgagaca    4680
ataaccctga taaatgcttc aataatattg aaaaaggaag agtatgagta ttcaacattt    4740
ccgtgtcgcc cttattccct ttttgcggc attttgcctt cctgttttg ctcacccaga    4800
aacgctggtg aaagtaaaag atgctgaaga tcagttgggt gcacgagtgg gttacatcga    4860
actggatctc aacagcggta agatccttga gagttttcgc cccgaagaac gttttccaat    4920
gatgagcact tttaaagttc tgctatgtgg cgcggtatta tcccgtattg acgccgggca    4980
agagcaactc ggtcgccgca tacactattc tcagaatgac ttggttgagt actcaccagt    5040
cacagaaaag catcttacgg atggcatgac agtaagagaa ttatgcagtg ctgccataac    5100
catgagtgat aacactgcgg ccaacttact tctgacaacg atcggaggac cgaaggagct    5160
aaccgctttt ttgcacaaca tgggggatca tgtaactcgc cttgatcgtt gggaaccgga    5220
gctgaatgaa gccataccaa acgacgagcg tgacaccacg atgcctgtag caatggcaac    5280
aacgttgcgc aaactattaa ctggcgaact acttactcta gcttcccggc aacaattaat    5340
agactggatg gaggcggata aagttgcagg accacttctg cgctcggccc ttccggctgg    5400
ctggtttatt gctgataaat ctggagccgg tgagcgtggg tctcgcggta tcattgcagc    5460
actggggcca gatggtaagc cctcccgtat cgtagttatc tacacgacgg ggagtcaggc    5520
aactatggat gaacgaaata gacagatcgc tgagataggt gcctcactga ttaagcattg    5580
gtaactgtca gaccaagttt actcatatat actttagatt gatttaaaac ttcatttta    5640
atttaaaagg atctaggtga agatcctttt tgataatctc atgaccaaaa tcccttaacg    5700
tgagttttcg ttccactgag cgtcagaccc cgtagaaaag atcaaaggat cttcttgaga    5760
tcctttttt ctgcgcgtaa tctgctgctt gcaaacaaaa aaaccaccgc taccagcggt    5820
ggtttgtttg ccggatcaag agctaccaac tctttttccg aaggtaactg gcttcagcag    5880
```

```
agcgcagata ccaaatactg ttcttctagt gtagccgtag ttaggccacc acttcaagaa    5940
ctctgtagca ccgcctacat acctcgctct gctaatcctg ttaccagtgg ctgctgccag    6000
tggcgataag tcgtgtctta ccgggttgga ctcaagacga tagttaccgg ataaggcgca    6060
gcggtcgggc tgaacggggg gttcgtgcac acagcccagc ttggagcgaa cgacctacac    6120
cgaactgaga tacctacagc gtgagctatg agaaagcgcc acgcttcccg aagggagaaa    6180
ggcggacagg tatccggtaa gcggcagggt cggaacagga gagcgcacga gggagcttcc    6240 aggggggaaac gcctggtatc tttatagtcc tgtcgggttt cgccacctct gacttgagcg    6300 tcgattttg tgatgctcgt caggggggcg gagcctatgg aaaaacgcca gcaacgcggc    6360 cttttttacgg ttcctggcct tttgctggcc ttttgctcac atgttctttc ctgcgttatc    6420
ccctgattct gtggataacc gtattaccgc ctttgagtga gctgataccg ctcgccgcag    6480
ccgaacgacc gagcgcagcg agtcagtgag cgaggaagcg gaaga                    6525
```

<210> SEQ ID NO 124
<211> LENGTH: 6554
<212> TYPE: DNA
<213> ORGANISM: Artificial Sequence
<220> FEATURE:
<223> OTHER INFORMATION: pNF3E

<400> SEQUENCE: 124

```
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagcttgc     240
atgcctgcag gtcgaccacg ataaaacaag gttttaagga taagaaaagt catgagattt     300
atagtaaatc ttgtgacttt ttttattgaa tagtagagag agttcggaag tataacacgc     360
tatattcttg atattttag aatagcaagc attggatttg tcctgacact ttcccaaaaa     420
ttaaggagtt attccttaaa ccaaaaagat taatgtggga acaaatttag tgtatccatt     480
tttgaagggc gcacttatac accaccaaaa tggtgtgtgc gaaatcttta aaaaagatt     540 atcaaaaagc ttttttaaag ctgggacatt tagaaaatca ataatgttt ttgcccaata     600 cgctagtctt aaaatctgca aggttgataa ctatttagtc ccaggtatta gaatggggca     660
tatatataca aagtatatat atgcgtaaat atatgtggga ctgtgggaac aaaattgcgt     720
gctaaaattg tattgaaaag gtaatgaaaa ggtcatgctt tggtattgct aacgtataga     780
aaaggtaatg aaaagctcat ggttctataa aaaagatgta cccacgaaaa taataggctt     840
tgcctatttc cccatgtaat atgggggcag ttttctctta tgctctttct taacatattg     900
aataaataca aaatgcagct tgtgtgggaat aaaaatattt ttgtttttat tcttatagtt     960
agacaaaatt ttaatctttt ttgtgctata acaagattaa aatttgtggg aacattaaga    1020
aatattgttg tcacaaataa aaaggagagt gggaacaatt gctataaaaa acgcagaaat    1080
taagattaga gttacaaaag agcaaaaaga attatttaag aaaattgcaa agctgaaaa    1140 tatgagtatg agtgaattta ttattgtgac cacagaatat ttagccagaa aaaagatga    1200 aaatatgaaa tcaaaagaca tgatcgagag aagagctgcg aagactgaag aaaaaattat    1260
gaagctaaaa aagaaactaa ataaaaacag gtaatataga ttcagttttt aagcttgttt    1320
tccctataga ctgagtaaa tatataaata tacctgtcaa gggcttataa gcccctttag    1380
ggggtgcgta gcacccttga caggtatatt tatatatttt agggtgccat taagggaaac    1440
```

```
aagctttaaa atgcctttaa aggcatttta aaataaataa aaaaaagatg gttttttacca    1500 tcttttttaa ctcccgaaag ggagttctttt cttttcttga tactatacgt aactatttcg    1560
atttgccctg aacctaatca aagctagata aattcagtat tagggcataa aaaaacttgc    1620
tttttcgggt ggaaatctgt ataatttaaa ttgcttagat aaaaattacc aattccatac    1680
gaaaggagca agttttacat aaggttaaag ccttatgtga attctcattt aattacatga    1740
ataataataa cacagaaagt gaagaattaa aagagcaaag tcaactattg cttgacaaat    1800
gcacaaaaaa gaaaaagaaa aatcctaaat ttagtagtta tatagaacca ttagtaagca    1860
agaaattatc tgaaagaata aaggaatgtg gtgactttt gcagatgtta tctgatttaa     1920
accttgaaaa ttcgaaactg catagagcaa gttttgtgg taacagattt tgtcctatgt     1980
gtagctggcg tattgcttgt aaggatagtt tggaaatatc tattctcatg gagcatttac    2040
gcaaagagga aagcaaagaa tttatctttt tgaccttaac aactccaaat gtgaaaggtg    2100
cggaccttga taattccata aaagcataca ataaagcatt taaaaagtta atggaacgca    2160
aagaggtcaa gagcatagta aaaggctaca taagaaagct agaagtaacc tataatttgg    2220
acaagagttc caaatcatat aatacttatc acccacattt ccatgtggta ctagcagtca    2280
atagaagtta ctttaaaaag caaaatctat atataaacca tcatagatgg cttagtttgt    2340
ggcaagagtc aactggtgat tattcgataa ctcaagttga tgtaagaaag ctaaaatta     2400 acgattataa agaggtttat gagcttgcta agtattcggc taaggattcc gactatttaa    2460
tcaatagaga agtgtttacg gtattctaca aatctttaaa gggtaaacag gtacttgtat    2520
ttagtggatt atttaaagac gctcataaaa tgtataagaa tggagagcta gatctgtata    2580
agaagttgga tactatcgaa tatgcttata tggtaagtta taactggctt aaaaagaagt    2640
atgatacttc aaatattaga gaattaactg aggaagaaaa gcagaaattc aataaaaatt    2700
taatcgaaga tgtggatatt gagtaggtgg gattatatct cacctttttt attgtcttt     2760 catgttgaaa ttttgacgct taatgcatga agtattgaca agtttaaaaa ttacggtttt    2820
taatccttag ttgattagca ggattatggc cggaatgctc cgtccagtcc tgttaaggaa    2880
ttaaaattcc ctaaaaccct tggctatgat ttatagcgag aatcgtcaat taaaaattta    2940
ataggtgcta tgaaagtcga ttaataatta attttaaaat gcaatatgaa acataattac    3000
aagaatttga cttttaatac aagaattgat atcatagtta cattaatacg gatccgtctg    3060
acagttacca ggtccactgc cgggcctctt gcgggatcaa aagaaaaacg aaatgataca    3120
ccaatcagtc aaaaaaaga tataatggga gataagacgg ttcgtgttcg tgctgacttg    3180
caccatatca taaaaatcga aacagcaaag aatggcggaa acgtaaaaga agttatggaa    3240
ataagactta gaagcaaact taagagtgtg ttgatagtgc agtatcttaa aattttgtat    3300
aataggaatt gaagttaaat tagatgctaa aaatttgtaa ttaagaagga gtgattacat    3360
gaacaaaaat ataaaatatt ctcaaaactt tttaacgagt gaaaaagtac tcaaccaaat    3420
aataaaacaa ttgaatttaa aagaaaccga taccgtttac gaaattggaa caggtaaagg    3480
gcatttaacg acgaaactgg ctaaaataag taaacaggta acgtctattg aattagacag    3540
tcatctattc aacttatcgt cagaaaaatt aaaactgaat actcgtgtca ctttaattca    3600
ccaagatatt ctacagtttc aattccctaa caaacagagg tataaaattg ttgggagtat    3660
tccttaccat ttaagcacac aaattattaa aaaagtggtt tttgaaagcc atgcgtctga    3720
catctatctg attgttgaag aaggattcta caagcgtacc ttggatattc accgaacact    3780
```

```
agggttgctc ttgcacactc aagtctcgat tcagcaattg cttaagctgc cagcggaatg    3840 cttttcatcct aaaccaaaag taaacagtgt cttaataaaa cttacccgcc ataccacaga   3900
tgttccagat aaatattgga agctatatac gtactttgtt tcaaaatggg tcaatcgaga    3960
atatcgtcaa ctgttttacta aaaatcagtt tcatcaagca atgaaacacg ccaaagtaaa   4020
caatttaagt accgttactt atgagcaagt attgtctatt tttaatagtt atctattatt    4080
taacgggagg aaataattct atgagtccct aggcaggcct ccgccattat ttttttgaac    4140
aattggagct cgaattcact ggccgtcgtt ttacaacgtc gtgactggga aaaccctggc    4200
gttacccaac ttaatcgcct tgcagcacat ccccctttcg ccagctggcg taatagcgaa    4260
gaggcccgca ccgatcgccc ttcccaacag ttgcgcagcc tgaatggcga atggcgcctg    4320
atgcggtatt ttctccttac gcatctgtgc ggtatttcac accgcatatg gtgcactctc    4380
agtacaatct gctctgatgc cgcatagtta agccagcccc gacacccgcc aacacccgct    4440
gacgcgccct gacgggcttg tctgctcccg gcatccgctt acagacaagc tgtgaccgtc    4500
tccgggagct gcatgtgtca gaggttttca ccgtcatcac cgaaacgcgc gagacgaaag    4560
ggcctcgtga tacgcctatt tttataggtt aatgtcatga taataatggt ttcttagacg    4620
tcaggtggca cttttcgggg aaatgtgcgc ggaaccccta tttgtttatt tttctaaata    4680
cattcaaata tgtatccgct catgagacaa taaccctgat aaatgcttca ataatattga    4740
aaaaggaaga gtatgagtat tcaacatttc cgtgtcgccc ttattccctt ttttgcggca    4800
ttttgccttc ctgttttgc tcacccagaa acgctggtga agtaaaaga tgctgaagat     4860 cagttgggtg cacgagtggg ttacatcgaa ctggatctca acagcggtaa gatccttgag    4920
agttttcgcc ccgaagaacg ttttccaatg atgagcactt ttaaagttct gctatgtggc    4980
gcggtattat cccgtattga cgccgggcaa gagcaactcg gtcgccgcat acactattct    5040
cagaatgact tggttgagta ctcaccagtc acagaaaagc atcttacgga tggcatgaca    5100
gtaagagaat tatgcagtgc tgccataacc atgagtgata acactgcggc caacttactt    5160
ctgacaacga tcggaggacc gaaggagcta accgcttttt tgcacaacat ggggggatcat   5220 gtaactcgcc ttgatcgttg ggaaccggag ctgaatgaag ccataccaaa cgacgagcgt    5280
gacaccacga tgcctgtagc aatggcaaca acgttgcgca aactattaac tggcgaacta    5340
cttactctag cttcccggca acaattaata gactggatgg aggcggataa agttgcagga    5400
ccacttctgc gctcggccct tccggctggc tggtttattg ctgataaatc tggagccggt    5460
gagcgtgggt ctcgcggtat cattgcagca ctggggccag atggtaagcc ctcccgtatc    5520
gtagttatct acacgacggg gagtcaggca actatggatg aacgaaatag acagatcgct    5580
gagataggtg cctcactgat taagcattgg taactgtcag accaagttta ctcatatata    5640
ctttagattg atttaaaact tcatttttaa tttaaaagga tctaggtgaa gatcctttt    5700 gataatctca tgaccaaaat cccttaacgt gagttttcgt tccactgagc gtcagacccc    5760
gtagaaaaga tcaaaggatc ttcttgagat cctttttttc tgcgcgtaat ctgctgcttg    5820
caaacaaaaa aaccaccgct accagcggtg gtttgtttgc cggatcaaga gctaccaact    5880
ctttttccga aggtaactgg cttcagcaga gcgcagatac caaatactgt tcttctagtg    5940
tagccgtagt taggccacca cttcaagaac tctgtagcac cgcctacata cctcgctctg    6000
ctaatcctgt taccagtggc tgctgccagt ggcgataagt cgtgtcttac cgggttggac    6060
tcaagacgat agttaccgga taaggcgcag cggtcgggct gaacggggg ttcgtgcaca     6120 cagcccagct tggagcgaac gacctacacc gaactgagat acctacagcg tgagctatga    6180
```

-continued

```
gaaagcgcca cgcttcccga agggagaaag gcggacaggt atccggtaag cggcagggtc    6240
ggaacaggag agcgcacgag ggagcttcca gggggaaacg cctggtatct ttatagtcct    6300
gtcgggtttc gccacctctg acttgagcgt cgattttttgt gatgctcgtc agggggggcgg  6360
agcctatgga aaaacgccag caacgcggcc ttttttacggt tcctggcctt ttgctggcct   6420
tttgctcaca tgttctttcc tgcgttatcc cctgattctg tggataaccg tattaccgcc    6480
tttgagtgag ctgataccgc tcgccgcagc cgaacgaccg agcgcagcga gtcagtgagc    6540
gaggaagcgg aaga                                                     6554
```

<210> SEQ ID NO 125
<211> LENGTH: 6271
<212> TYPE: DNA
<213> ORGANISM: Artificial Sequence
<220> FEATURE:
<223> OTHER INFORMATION: pNF3C

<400> SEQUENCE: 125

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagcttgc    240
atgcctgcag gtcgaccacg ataaaacaag gttttaagga taagaaaagt catgagattt    300
atagtaaatc ttgtgacttt ttttattgaa tagtagagag agttcggaag tataacacgc    360
tatattcttg atatttttag aatagcaagc attggatttg tcctgacact ttcccaaaaa    420
ttaaggagtt attccttaaa ccaaaaagat taatgtggga acaaatttag tgtatccatt    480
tttgaagggc gcacttatac accaccaaaa tggtgtgtgc gaaatcttta aaaaagattt    540
atcaaaaagc ttttttaaag ctgggacatt tagaaaatca ataatgtttt ttgcccaata    600
cgctagtctt aaaatctgca aggttgataa ctatttagtc ccaggtatta gaatggggca    660
tatatataca agtatatatt atgcgtaaat atatgtggga ctgtgggaac aaaattgcgt    720
gctaaaattg tattgaaaag gtaatgaaaa ggtcatgctt tggtattgct aacgtataga    780
aaaggtaatg aaaagctcat ggttctataa aaaagatgta cccacgaaaa taataggctt    840
tgcctatttc cccatgtaat atgggggcag ttttctctta tgctctttct taacatattg    900
aataaataca aaatgcagct ttgtgggaat aaaaatattt tgttttttat tcttatagtt    960
agacaaaatt ttaatctttt ttgtgctata acaagattaa aatttgtggg aacattaaga   1020
aatattgttg tcacaaataa aaaggagagt gggaacaatt gctataaaaa acgcagaaat   1080
taagattaga gttacaaaag agcaaaaaga attatttaag aaaattgcaa aagctgaaaa   1140
tatgagtatg agtgaattta ttattgtgac cacagaatat ttagccagaa aaaagatga    1200
aaatatgaaa tcaaaagaca tgatcagag aagagctgcg aagactgaag aaaaaattat   1260
gaagctaaaa agaaactaa ataaaaacag gtaatataga ttacagttttt aagcttgttt   1320
tccctataga ctagagtaaa tatataaata tacctgtcaa gggcttataa gcccctttag   1380
ggggtgcgta gcacccttga caggtatatt tatatatttt agggtgccat taagggaaac   1440
aagctttaaa atgcctttaa aggcatttta aaataaataa aaaaaagatg gtttttacca   1500
tcttttttaa ctcccgaaag ggagttcttt cttttcttga tactatacgt aactatttcg   1560
atttgccctg aacctaatca aagctagata aattcagtat tagggcataa aaaaacttgc   1620
```

```
tttttcgggt ggaaatctgt ataatttaaa ttgcttagat aaaaattacc aattccatac    1680
gaaaggagca agttttacat aaggttaaag ccttatgtga attctcattt aattacatga    1740
ataataataa cacagaaagt gaagaattaa aagagcaaag tcaactattg cttgacaaat    1800
gcacaaaaaa gaaaagaaa aatcctaaat ttagtagtta tatagaacca ttagtaagca    1860
agaaattatc tgaaagaata aaggaatgtg gtgacttttt gcagatgtta tctgatttaa    1920
accttgaaaa ttcgaaactg catagagcaa gttttgtgg taacagattt tgtcctatgt    1980
gtagctggcg tattgcttgt aaggatagtt tggaaatatc tattctcatg gagcatttac    2040
gcaaagagga aagcaaagaa tttatctttt tgaccttaac aactccaaat gtgaaaggtg    2100
cggaccttga taattccata aaagcataca ataaagcatt taaaaagtta atggaacgca    2160
aagaggtcaa gagcatagta aaaggctaca taagaaagct agaagtaacc tataatttgg    2220
acaagagttc caaatcatat aatacttatc acccacattt ccatgtggta ctagcagtca    2280
atagaagtta cttaaaaag caaaatctat atataaacca tcatagatgg cttagtttgt    2340
ggcaagagtc aactggtgat tattcgataa ctcaagttga tgtaagaaag gctaaaatta    2400
acgattataa agaggtttat gagcttgcta agtattcggc taaggattcc gactatttaa    2460
tcaatagaga agtgtttacg gtattctaca aatctttaaa gggtaaacag gtacttgtat    2520
ttagtggatt attttaaagac gctcataaaa tgtataagaa tggagagcta gatctgtata    2580
agaagttgga tactatcgaa tatgcttata tggtaagtta taactggctt aaaaagaagt    2640
atgatacttc aaatattaga gaattaactg aggaagaaaa gcagaaattc aataaaaatt    2700
taatcgaaga tgtggatatt gagtaggtgg gattatatct cacctttttt attgtctttt    2760
catgttgaaa ttttgacgct taatgcatga agtattgaca agtttaaaaa ttacggtttt    2820
taatccttag ttgattagca ggattatggc cggaatgctc cgtccagtcc tgttaaggaa    2880
ttaaaattcc ctaaaaccct tggctatgat ttatagcgag aatcgtcaat taaaaattta    2940
ataggtgcta tgaaagtcga ttaataatta attttaaaat gcaatatgaa acataattac    3000
aagaatttga cttttaatac aagaattgat atcatagtta cattaatacg gatcccggca    3060 gttttttcttt tcggcaagt gttcaagaag ttattaagtc gggagtgcag tcgaagtggg    3120
caagttgaaa aattcacaaa aatgtggtat aatatctttg ttcattagag cgataaactt    3180
gaatttgaga gggaacttag atggtatttg aaaaaattga taaaaatagt tggaacagaa    3240
aagagtattt tgaccactac tttgcaagtg taccttgtac ctacagcatg accgttaaag    3300
tggatatcac acaaataaag gaaaagggaa tgaaactata tcctgcaatg ctttattata    3360
ttgcaatgat tgtaaaccgc cattcagagt ttaggacggc aatcaatcaa gatggtgaat    3420
tggggatata tgatgagatg ataccaagct atacaatatt tcacaatgat actgaaacat    3480
tttccagcct ttggactgag tgtaagtctg actttaaatc atttttagca gattatgaaa    3540
gtgatacgca acggtatgga aacaatcata gaatggaagg aaagccaaat gctccggaaa    3600
acatttttaa tgtatctatg ataccgtggt caaccttcga tggctttaat ctgaatttgc    3660
agaaaggata tgattatttg attcctattt ttactatggg gaaatattat aaagaagata    3720
acaaaattat acttcctttg gcaattcaag ttcatcacgc agtatgtgac ggatttcaca    3780
tttgccgttt tgtaaacgaa ttgcaggaat tgataaatag ttaacttcag gtttgtctgt    3840
aactaaaaac tagtatttaa ccgagctcga attcactggc cgtcgtttta caacgtcgtg    3900
actgggaaaa ccctggcgtt acccaactta atcgccttgc agcacatccc cctttcgcca    3960
gctggcgtaa tagcgaagag gcccgcaccg atcgcccttc ccaacagttg cgcagcctga    4020
```

```
atggcgaatg gcgcctgatg cggtattttc tccttacgca tctgtgcggt atttcacacc    4080
gcatatggtg cactctcagt acaatctgct ctgatgccgc atagttaagc cagccccgac    4140
acccgccaac acccgctgac gcgccctgac gggcttgtct gctcccggca tccgcttaca    4200
gacaagctgt gaccgtctcc gggagctgca tgtgtcagag gttttcaccg tcatcaccga    4260
aacgcgcgag acgaaagggc ctcgtgatac gcctattttt ataggttaat gtcatgataa    4320
taatggtttc ttagacgtca ggtggcactt tcggggaaa tgtgcgcgga accctattt    4380
gtttattttt ctaaatacat tcaaatatgt atccgctcat gagacaataa ccctgataaa    4440
tgcttcaata atattgaaaa aggaagagta tgagtattca acatttccgt gtcgcccta    4500
ttccctttt tgcggcattt tgccttcctg tttttgctca cccagaaacg ctggtgaaag    4560
taaaagatgc tgaagatcag ttgggtgcac gagtgggtta catcgaactg gatctcaaca    4620
gcggtaagat ccttgagagt tttcgccccg aagaacgttt tccaatgatg agcacttta    4680
aagttctgct atgtggcgcg gtattatccc gtattgacgc cgggcaagag caactcggtc    4740
gccgcataca ctattctcag aatgacttgg ttgagtactc accagtcaca gaaaagcatc    4800
ttacggatgg catgacagta agagaattat gcagtgctgc cataaccatg agtgataaca    4860
ctgcggccaa cttacttctg acaacgatcg gaggaccgaa ggagctaacc gcttttttgc    4920
acaacatggg ggatcatgta actcgcctg atcgttggga accggagctg aatgaagcca    4980
taccaaacga cgagcgtgac accacgatgc ctgtagcaat ggcaacaacg ttgcgcaaac    5040
tattaactgg cgaactactt actctagctt cccggcaaca attaatagac tggatggagg    5100
cggataaagt tgcaggacca cttctgcgct cggcccttcc ggctggctgg tttattgctg    5160
ataaatctgg agccggtgag cgtgggtctc gcggtatcat tgcagcactg gggccagatg    5220
gtaagccctc ccgtatcgta gttatctaca cgacggggag tcaggcaact atggatgaac    5280
gaaatagaca gatcgctgag ataggtgcct cactgattaa gcattggtaa ctgtcagacc    5340
aagtttactc atatatactt tagattgatt taaaacttca tttttaattt aaaaggatct    5400
aggtgaagat cctttttgat aatctcatga ccaaaatccc ttaacgtgag ttttcgttcc    5460
actgagcgtc agaccccgta gaaaagatca aaggatcttc ttgagatcct ttttttctgc    5520
gcgtaatctg ctgcttgcaa acaaaaaaac caccgctacc agcggtggtt tgtttgccgg    5580
atcaagagct accaactctt tttccgaagg taactggctt cagcagagcg cagataccaa    5640
atactgttct tctagtgtag ccgtagttag gccaccactt caagaactct gtagcaccgc    5700
ctacatacct cgctctgcta atcctgttac cagtggctgc tgccagtggc gataagtcgt    5760
gtcttaccgg gttggactca agacgatagt taccggataa ggcgcagcgg tcgggctgaa    5820
cggggggttc gtgcacacag cccagcttgg agcgaacgac ctacaccgaa ctgagatacc    5880
tacagcgtga gctatgagaa agcgccacgc ttcccgaagg gagaaaggcg gacaggtatc    5940
cggtaagcgg cagggtcgga acaggagagc gcacgaggga gcttccaggg ggaaacgcct    6000
ggtatcttta tagtcctgtc gggtttcgcc acctctgact tgagcgtcga ttttttgtgat    6060
gctcgtcagg ggggcggagc ctatggaaaa acgccagcaa cgcggccttt ttacggttcc    6120
tggccttttg ctggcctttt gctcacatgt tctttcctgc gttatcccct gattctgtgg    6180
ataaccgtat taccgccttt gagtgagctg ataccgctcg ccgcagccga acgaccgagc    6240
gcagcgagtc agtgagcgag gaagcggaag a                                     6271
```

<210> SEQ ID NO 126

<211> LENGTH: 2793
<212> TYPE: DNA
<213> ORGANISM: Artificial Sequence
<220> FEATURE:
<223> OTHER INFORMATION: OREP

<400> SEQUENCE: 126

| | |
|---|---|
| cacgataaaa caaggtttta aggataagaa aagtcatgag atttatagta aatcttgtga | 60 |
| cttttttat tgaatagtag agagagttcg gaagtataac acgctatatt cttgatattt | 120 |
| ttagaatagc aagcattgga tttgtcctga cactttccca aaaattaagg agttattcct | 180 |
| taaaccaaaa agattaatgt gggaacaaat ttagtgtatc cattttgaa gggcgcactt | 240 |
| atacaccacc aaaatggtgt gtgcgaaatc tttaaaaaag atttatcaaa aagcttttt | 300 |
| aaagctggga catttagaaa atcaataatg ttttttgccc aatacgctag tcttaaaatc | 360 |
| tgcaaggttg ataactattt agtcccaggt attagaatgg ggcatatata tacaaagtat | 420 |
| atatatgcgt aaatatatgt gggactgtgg gaacaaaatt gcgtgctaaa attgtattga | 480 |
| aaggtaatg aaaaggtcat gctttggtat tgctaacgta tagaaaaggt aatgaaaagc | 540 |
| tcatggttct ataaaaaga tgtacccacg aaaataatag gctttgccta tttccccatg | 600 |
| taatatgggg gcagttttct cttatgctct ttcttaacat attgaataaa tacaaaatgc | 660 |
| agctttgtgg gaataaaaat attttttgttt ttattcttat agttagacaa aattttaatc | 720 |
| tttttgtgc tataacaaga ttaaaatttg tgggaacatt aagaaatatt gttgtcacaa | 780 |
| ataaaagga gagtgggaac aattgctata aaaacgcag aaattaagat tagagttaca | 840 |
| aaagagcaaa aagaattatt taagaaaatt gcaaagctg aaaatatgag tatgagtgaa | 900 |
| tttattattg tgaccacaga atatttagcc agaaaaaaag atgaaaatat gaaatcaaaa | 960 |
| gacatgatcg agagaagagc tgcgaagact gaagaaaaaa ttatgaagct aaaaagaaa | 1020 |
| ctaaataaaa acaggtaata tagattacag ttttaagctt gttttcccta tagactagag | 1080 |
| taaatatata aatatacctg tcaagggctt ataagcccct ttaggggggtg cgtagcaccc | 1140 |
| ttgacaggta tatttatata ttttaggggtg ccattaaggg aaacaagctt taaaatgcct | 1200 |
| ttaaaggcat tttaaaataa ataaaaaaaa gatggttttt accatctttt ttaactcccg | 1260 |
| aaagggagtt ctttcttttc ttgatactat acgtaactat ttcgatttgc cctgaaccta | 1320 |
| atcaaagcta gataaattca gtattagggc ataaaaaaac ttgcttttc gggtggaaat | 1380 |
| ctgtataatt taaattgctt agataaaaat taccaattcc atacgaaagg agcaagtttt | 1440 |
| acataaggtt aaagccttat gtgaattctc atttaattac atgaataata ataacacaga | 1500 |
| aagtgaagaa ttaaaagagc aaagtcaact attgcttgac aaatgcacaa aaaagaaaaa | 1560 |
| gaaaaatcct aaatttagta gttatataga accattagta agcaagaaat tatctgaaag | 1620 |
| aataaaggaa tgtggtgact ttttgcagat gttatctgat ttaaaccttg aaaattcgaa | 1680 |
| actgcataga gcaagttttt gtggtaacag attttgtcct atgtgtagct ggcgtattgc | 1740 |
| ttgtaaggat agtttggaaa tatctattct catggagcat ttacgcaaag aggaaagcaa | 1800 |
| agaatttatc ttttgacct taacaactcc aaatgtgaaa ggtgcggacc ttgataattc | 1860 |
| cataaaagca tacaataaag catttaaaaa gttaatggaa cgcaaagagg tcaagagcat | 1920 |
| agtaaaaggc tacataagaa agctagaagt aacctataat ttggacaaga gttccaaatc | 1980 |
| atataatact tatcacccac atttccatgt ggtactagca gtcaatagaa gttactttaa | 2040 |
| aaagcaaaat ctatatataa accatcatag atggcttagt ttgtggcaag agtcaactgg | 2100 |
| tgattattcg ataactcaag ttgatgtaag aaaggctaaa attaacgatt ataaagaggt | 2160 |

```
ttatgagctt gctaagtatt cggctaagga ttccgactat ttaatcaata gagaagtgtt    2220
tacggtattc tacaaatctt taaagggtaa acaggtactt gtatttagtg gattatttaa    2280
agacgctcat aaaatgtata agaatggaga gctagatctg tataagaagt tggatactat    2340
cgaatatgct tatatggtaa gttataactg gcttaaaaag aagtatgata cttcaaatat    2400
tagagaatta actgaggaag aaaagcagaa attcaataaa aatttaatcg aagatgtgga    2460
tattgagtag gtgggattat atctcacctt ttttattgtc ttttcatgtt gaaattttga    2520
cgcttaatgc atgaagtatt gacaagttta aaaattacgg tttttaatcc ttagttgatt    2580
agcaggatta tggccggaat gctccgtcca gtcctgttaa ggaattaaaa ttccctaaaa    2640
cccttggcta tgatttatag cgagaatcgt caattaaaaa tttaataggt gctatgaaag    2700
tcgattaata attaatttta aaatgcaata tgaaacataa ttacaagaat ttgactttta    2760
atacaagaat tgatatcata gttacattaa tac                                 2793

<210> SEQ ID NO 127
<211> LENGTH: 2793
<212> TYPE: DNA
<213> ORGANISM: Clostridium beijerinckii

<400> SEQUENCE: 127
cacgataaaa caaggtttta aggataagaa aagtcatgag atttatagta aatcttgtga      60 cttttttat tgaatagtag agagagttcg gaagtataac acgctatatt cttgatattt     120
ttagaatagc aagcattgga tttgtcctga cactttccca aaaattaagg agttattcct     180
taaaccaaaa agattaatgt gggaacaaat ttagtgtatc cattttttgaa gggcgcactt     240 atacaccacc aaaatggtgt gtgcgaaatc ttttaaaaaag atttatcaaa aagctttttt     300
aaagctggga catttagaaa atcaataatg ttttttgccc aatacgctag tcttaaaatc     360
tgcaaggttg ataactattt agtcccaggt attagaatgg ggcatatata tacaaagtat     420
atatatgcgt aaatatatgt gggactgtgg gaacaaaatt gcgtgctaaa attgtattga     480
aaaggtaatg aaaaggtcat gctttggtat tgctaacgta tagaaaaggt aatgaaaagc     540
tcatggttct ataaaaaaga tgtacccacg aaaaataatag gctttgccta tttccccatg     600
taatatgggg gcagttttct cttatgctct ttcttaacat attgaataaa tacaaaatgc     660
agctttgtgg gaataaaaat attttttgttt ttattcttat agttagacaa aattttaatc     720 tttttttgtgc tataacaaga ttaaaatttg tgggaacatt aagaaatatt gttgtcacaa     780
ataaaaagga gagtgggaac aattgctata aaaaacgcag aaattaagat tagagttaca     840
aaagagcaaa aagaattatt taagaaaatt gcaaaagctg aaaatatgag tatgagtgaa     900
tttattattg tgaccacaga atatttagcc agaaaaaaag atgaaaatat gaaatcaaaa     960
gacatgatcg agagaagagc tgcgaagact gaagaaaaaa ttatgaagct aaaaaagaaa    1020
ctaaataaaa acaggtaata tagattacag ttttaagctt gttttcccta tagactagag    1080
taaatatata aatatacctg tcaagggctt ataagcccct ttagggggtg cgtagcaccc    1140
ttgacaggta tatttatata ttttagggtg ccattaaggg aaacaagctt taaaatgcct    1200
ttaaaggcat tttaaaataa ataaaaaaaa gatggttttt accatctttt ttaactcccg    1260
aaagggagtt ctttctttc ttgatactat acgtaactat ttcgatttgc cctgaaccta    1320
atcaaagcta gataaattca gtattagggc ataaaaaaac ttgcttttc gggtggaaat    1380 ctgtataatt taaattgctt agataaaaat taccaattcc atacgaaagg agcaagtttt    1440
```

```
acataaggtt aaagccttat gtgaattctc atttaattac atgaataata ataacacaga    1500
aagtgaagaa ttaaaagagc aaagtcaact attgcttgac aaatgcacaa aaaagaaaaa    1560
gaaaaatcct aaatttagta gttatataga accattagta agcaagaaat tatctgaaag    1620
aataaaggaa tgtggtgact ttttgcagat gttatctgat ttaaaccttg aaaattcgaa    1680
actgcataga gcaagttttt gtggtaacag atttttgtcct atgtgtagct ggcgtattgc    1740
ttgtaaggat agtttggaaa tatctattct catggagcat ttacgcaaag aggaaagcaa    1800
agaatttatc ttttttgacct aacaactcc aaatgtgaaa ggtgcggacc ttgataattc    1860
cataaaagca acaataaag catttaaaaa gttaatggaa cgcaaagagg tcaagagcat    1920
agtaaaaggc tacataagaa agctagaagt aacctataat ttggacaaga gttccaaatc    1980
atataatact tatcacccac atttccatgt ggtactagca gtcaatagaa gttacttttaa   2040 aaagcaaaat ctatatataa accatcatag atggcttagt ttgtggcaag agtcaactgg    2100
tgattattcg ataactcaag ttgatgtaag aaaggctaaa attaacgatt ataaagaggt    2160
ttatgagctt gctaagtatt cggctaagga ttccgactat ttaatcaata gagaagtgtt    2220
tacggtattc tacaaatctt taagggtaa acaggtactt gtatttagtg gattatttaa    2280
agacgctcat aaaatgtata agaatggaga gctagatctg tataagaagt tggatactat    2340
cgaatatgct tatatggtaa gttataactg gcttaaaaag aagtatgata cttcaaatat    2400
tagagaatta actgaggaag aaaagcagaa attcaataaa aatttaatcg aagatgtgga    2460
tattgagtag gtgggattat atctcacctt tttattgtc ttttcatgtt gaaattttga     2520
cgcttaatgc atgaagtatt gacaagttta aaaattacgg ttttaatcc ttagttgatt     2580 agcaggatta tggccggaat gctccgtcca gtcctgttaa ggaattaaaa ttccctaaaa    2640 ccctttggcta tgatttatag cgagaatcgt caattaaaaa tttaataggt gctatgaaag   2700
tcgattaata attaattta aaatgcaata tgaaacataa ttacaagaat ttgacttta      2760 atacaagaat tgatatcata gttacattaa tac                                 2793
```

<210> SEQ ID NO 128
<211> LENGTH: 329
<212> TYPE: PRT
<213> ORGANISM: Clostridium beijerinckii

<400> SEQUENCE: 128

```
Met Asn Asn Asn Thr Glu Ser Glu Glu Leu Lys Glu Gln Ser Gln
1               5                   10                  15

Leu Leu Leu Asp Lys Cys Thr Lys Lys Lys Lys Asn Pro Lys Phe
                20                  25                  30

Ser Ser Tyr Ile Glu Pro Leu Val Ser Lys Lys Leu Ser Glu Arg Ile
                35                  40                  45

Lys Glu Cys Gly Asp Phe Leu Gln Met Leu Ser Asp Leu Asn Leu Glu
        50                  55                  60

Asn Ser Lys Leu His Arg Ala Ser Phe Cys Gly Asn Arg Phe Cys Pro
65                  70                  75                  80

Met Cys Ser Trp Arg Ile Ala Cys Lys Asp Ser Leu Glu Ile Ser Ile
                85                  90                  95

Leu Met Glu His Leu Arg Lys Glu Glu Ser Lys Glu Phe Ile Phe Leu
                100                 105                 110

Thr Leu Thr Thr Pro Asn Val Lys Gly Ala Asp Leu Asp Asn Ser Ile
                115                 120                 125

Lys Ala Tyr Asn Lys Ala Phe Lys Lys Leu Met Glu Arg Lys Glu Val
```

```
                130                 135                 140
Lys Ser Ile Val Lys Gly Tyr Ile Arg Lys Leu Glu Val Thr Tyr Asn
145                 150                 155                 160

Leu Asp Lys Ser Ser Lys Ser Tyr Asn Thr Tyr His Pro His Phe His
                165                 170                 175

Val Val Leu Ala Val Asn Arg Ser Tyr Phe Lys Lys Gln Asn Leu Tyr
                180                 185                 190

Ile Asn His His Arg Trp Leu Ser Leu Trp Gln Glu Ser Thr Gly Asp
                195                 200                 205

Tyr Ser Ile Thr Gln Val Asp Val Arg Lys Ala Lys Ile Asn Asp Tyr
                210                 215                 220

Lys Glu Val Tyr Glu Leu Ala Lys Tyr Ser Ala Lys Asp Ser Asp Tyr
225                 230                 235                 240

Leu Ile Asn Arg Glu Val Phe Thr Val Phe Tyr Lys Ser Leu Lys Gly
                245                 250                 255

Lys Gln Val Leu Val Phe Ser Gly Leu Phe Lys Asp Ala His Lys Met
                260                 265                 270

Tyr Lys Asn Gly Glu Leu Asp Leu Tyr Lys Lys Leu Asp Thr Ile Glu
                275                 280                 285

Tyr Ala Tyr Met Val Ser Tyr Asn Trp Leu Lys Lys Lys Tyr Asp Thr
                290                 295                 300

Ser Asn Ile Arg Glu Leu Thr Glu Glu Lys Gln Lys Phe Asn Lys
305                 310                 315                 320

Asn Leu Ile Glu Asp Val Asp Ile Glu
                325

<210> SEQ ID NO 129
<211> LENGTH: 256
<212> TYPE: PRT
<213> ORGANISM: Artificial Sequence
<220> FEATURE:
<223> OTHER INFORMATION: Consensus COG5655

<400> SEQUENCE: 129

Met Cys Gln Lys Arg Ser Asp Tyr Ser Asp Glu Lys Ala Trp Leu Lys
1               5                   10                  15

Asp Lys Ser Lys Asp Gly Lys Val Glu Pro Trp Arg Glu Lys Lys Glu
                20                  25                  30

Ala Asn Val Lys Tyr Phe Glu Leu Leu Lys Ile Leu Met Phe Lys Lys
                35                  40                  45

Ala Glu Arg Val Tyr Arg Cys Asn Glu Leu Leu Glu Leu Gln Lys Val
50                  55                  60

Asn Glu Thr Gly Glu Asn Lys Leu Cys Pro Asn Trp Phe Cys Lys Ser
65                  70                  75                  80

Leu Leu Cys Pro Met Cys Asn Trp Arg Lys Pro Met Lys Ser Asp Leu
                85                  90                  95

Gln Asp Gly Leu Tyr Val Lys Arg Val Ile Ser Tyr Gly Pro Leu Leu
                100                 105                 110

Lys Trp Lys His Leu Lys Leu Asn Leu Lys Asn Val Glu Asp Gly Asp
                115                 120                 125

Leu Leu Asn Lys Ser Leu Asp Glu Met Ala Leu Gly Phe Lys Arg Thr
                130                 135                 140

Met Gly Phe Lys Lys Ile Ala Lys Asn Phe Val Gly Phe Met Lys Ser
145                 150                 155                 160

Thr Glu Ile Thr Tyr Asn Glu Lys Asp Asn Ser Tyr Asn Gln His Met
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| His | Val | Leu | Phe | Cys | Ser | Glu | Gln | Thr | Tyr | Phe | Lys | Asn | Phe | Ile | Asn |
|     |     |     | 180 |     |     |     |     | 185 |     |     |     |     | 190 |     |     |
| Asn | Thr | Pro | Gln | Glu | Phe | Trp | Asn | Lys | Arg | Trp | Ser | Lys | Ala | Met | Lys |
|     |     |     | 195 |     |     |     |     | 200 |     |     |     |     | 205 |     |     |
| Leu | Asp | Tyr | Asp | Pro | Gln | Val | Met | Lys | Leu | Trp | Thr | Met | Tyr | Lys | Lys |
|     |     |     | 210 |     |     |     |     | 215 |     |     |     |     | 220 |     |     |
| Glu | Ile | Lys | Asn | Tyr | Ile | Gln | Thr | Ala | Leu | Gln | Glu | Thr | Ala | Lys | Tyr |
| 225 |     |     |     |     | 230 |     |     |     |     | 235 |     |     |     |     | 240 |
| Asp | Val | Lys | Asp | Met | Asp | Ser | Ala | Thr | Ile | Asp | Asp | Glu | Lys | Ser | Leu |
|     |     |     |     | 245 |     |     |     |     | 250 |     |     |     |     | 255 |     |

<210> SEQ ID NO 130
<211> LENGTH: 768
<212> TYPE: DNA
<213> ORGANISM: Enterococcus faecalis

<400> SEQUENCE: 130

```
gtgaggagga tatatttgaa tacatacgaa caaattaata aagtgaaaaa aatacttcgg      60
aaacatttaa aaaataaccct tattggtact tacatgtttg gatcaggagt tgagagtgga    120
ctaaaaccaa atagtgatct tgacttttta gtcgtcgtat ctgaaccatt gacagatcaa    180
agtaaagaaa tacttataca aaaaattaga cctatttcaa agaaaatagg agataaaagc    240
aacttacgat atattgaatt aacaattatt attcagcaag aaatggtacc gtggaatcat    300
cctcccaaac aagaatttat ttatggagaa tggttacaag agctttatga acaaggatac    360
attcctcaga aggaattaaa ttcagattta accataatgc tttaccaagc aaaacgaaaa    420
aataaaagaa tatacggaaa ttatgactta gaggaattac tacctgatat tccattttct    480
gatgtgagaa gagccattat ggattcgtca gaggaattaa tagataatta tcaggatgat    540
gaaaccaact ctatattaac tttatgccgt atgattttaa ctatggacac gggtaaaatc    600
ataccaaaag atattgcggg aaatgcagtg gctgaatctt ctccattaga acatagggag    660
agaattttgt tagcagttcg tagttatctt ggagagaata ttgaatggac taatgaaaat    720
gtaaatttaa ctataaacta tttaaataac agattaaaaa aattataa                 768
```

<210> SEQ ID NO 131
<211> LENGTH: 738
<212> TYPE: DNA
<213> ORGANISM: Clostridium difficile

<400> SEQUENCE: 131

```
atgaacaaaa atataaaata ttctcaaaac tttttaacga gtgaaaaagt actcaaccaa     60
ataataaaac aattgaattt aaaagaaacc gataccgttt acgaaattgg aacaggtaaa   120
gggcatttaa cgacgaaact ggctaaaata agtaaacagg taacgtctat tgaattagac   180
agtcatctat tcaacttatc gtcagaaaaa ttaaaactga atactcgtgt cactttaatt   240
caccaagata ttctacagtt tcaattccct aacaaacaga ggtataaaat tgttgggagt   300
attccttacc atttaagcac acaaattatt aaaaaagtgg tttttgaaag ccatgcgtct   360
gacatctatc tgattgttga agaaggattc tacagcgta ccttggatat tcaccgaaca   420
ctagggttgc tcttgcacac tcaagtctcg attcagcaat tgcttaagct gccagcggaa   480
tgctttcatc ctaaaccaaa agtaaacagt gtcttaataa aacttacccg ccataccaca   540
gatgttccag ataatattg gaagctatat acgtactttg tttcaaaatg ggtcaatcga   600
```

| gaatatcgtc aactgtttac taaaaatcag tttcatcaag caatgaaaca cgccaaagta | 660 |
| aacaatttaa gtaccgttac ttatgagcaa gtattgtcta tttttaatag ttatctatta | 720 |
| tttaacggga ggaaataa | 738 |

<210> SEQ ID NO 132
<211> LENGTH: 3792
<212> TYPE: DNA
<213> ORGANISM: Artificial Sequence
<220> FEATURE:
<223> OTHER INFORMATION: Optimized Mad7 CDS for B. subtilis

<400> SEQUENCE: 132

| atgaacaacg gcacaaataa ttttcagaac tttattggca tttcatcatt gcagaaaacg | 60 |
| ttaagaaatg ctttaattcc gacggaaaca acgcaacagt ttattgttaa aaacggaatt | 120 |
| attaagaag atgaattaag aggcgaaaac agacagattt aaaagatat tatggatgac | 180 |
| tactacagag gatttatttc tgaaacatta tcatctattg atgacattga ttggacaagc | 240 |
| ttatttgaaa aaatggaaat tcagttaaaa aatggtgata taaagatac attaattaaa | 300 |
| gaacagacag aatatagaaa agcaattcat aaaaaatttg cgaacgacga tagatttaaa | 360 |
| aacatgttta gcgccaaatt aatttcgac attttacctg aatttgttat tcataacaat | 420 |
| aattattcag catcagaaaa agaagaaaaa acacaggtga ttaaattgtt ttcaagattt | 480 |
| gcgacaagct ttaagatta cttttaaaaac agagcaaatt gcttttcagc ggacgatatt | 540 |
| tcatcaagca gctgccatag aattgttaac gacaatgcag aattttttt ttcaaatgcg | 600 |
| ttagtttaca gaagaattgt aaaatcatta gcaatgacg atattaacaa atttcaggc | 660 |
| gatatgaaag attcattaaa agaaatgtca ttagaagaaa tttattctta cgaaaaatat | 720 |
| ggcgaattta ttacacagga aggcattagc ttttataatg atatttgtgg caaagtgaat | 780 |
| tcttttatga acttatattg tcagaaaaat aaagaaaaca aaatttata caaacttcag | 840 |
| aaacttcata acagattct gtgcattgcg gacacaagct atgaagttcc gtataaattt | 900 |
| gaatcagacg aagaagtgta ccaatcagtt aacggctttc ttgataacat tagcagcaaa | 960 |
| catattgttg aaagattaag aaaaattggc gataactata cggctacaa cttagataaa | 1020 |
| atttatattg tgtccaaatt ttacgaaagc gttagccaaa aaacatacag agactgggaa | 1080 |
| acaattaata cagccttaga aattcattac aataatattt tgccgggtaa cggtaaatca | 1140 |
| aaagccgaca agtaaaaaa agcggttaaa aatgatttac agaaatccat tacagaaatt | 1200 |
| aatgaactgg tgtcaaacta taattatgc tcagacgaca cattaaagc ggaaacatat | 1260 |
| attcatgaaa ttagccatat tttgaataac tttgaagcac aggaattgaa atacaatccg | 1320 |
| gaaattcatc tggttgaatc cgaattaaaa gcgtcagaac ttaaaacgt gttagacgtg | 1380 |
| attatgaatg cgtttcattg gtgttcagtt tttatgacag aagaacttgt tgataaagac | 1440 |
| aacaattttt atgcggaatt agaagaaatt tacgatgaaa tttatccggt aatttcatta | 1500 |
| tacaacttag ttagaaacta cgttacacag aaaccgtaca gcacgaaaaa aattaaattg | 1560 |
| aactttggaa ttccgacgtt agcagacggt tggtcaaaat ccaagaata ttctaataac | 1620 |
| gctattattt taatgagaga caattttatat tatttaggca tttttaatgc gaaaaataaa | 1680 |
| ccggacaaaa aaattattga aggtaatacg tcagaaaata aaggtgacta caaaaaatg | 1740 |
| atttataatt tgttaccggg tccgaacaaa atgattccga agttttttt gagcagcaaa | 1800 |
| acgggcgtgg aaacgtataa accgagcgcc tatattctgg aaggctataa acagaataaa | 1860 |
| catattaaat cttcaaaaga ctttgatatt acattttgtc atgatttaat tgactacttt | 1920 |

```
aaaaactgta ttgcaattca tccggaatgg aaaaactttg gttttgattt tagcgacaca    1980
tcaacatatg aagacatttc cggcttttat agagaagtag aattacaagg ttacaaaatt    2040
gattggacat acattagcga aaaagacatt gatttattac aggaaaaagg tcaattatat    2100
ttatttcaga tttataacaa agattttca aaaaaatcaa caggcaatga caaccttcat    2160
acaatgtact taaaaatct ttttcagaa gaaatctta aagatattgt tttaaaactt    2220
aacggcgaag cggaaatttt ttttagaaaa agcagcatta aaaacccgat tattcataaa    2280
aaaggctcaa ttttagttaa cagaacatac gaagcagaag aaaaagacca gtttggcaac    2340
attcaaattg tgagaaaaaa tattccggaa aacatttatc aggaattata caaatacttt    2400
aacgataaaa gcgacaaaga attatctgat gaagcagcca aattaaaaaa tgtagtggga    2460
catcatgaag cagcgacgaa tattgttaaa gactatagat acacgtatga taaatacttt    2520
cttcatatgc ctattacgat taattttaaa gccaataaaa cgggttttat taatgataga    2580
attttacagt atattgctaa agaaaaagac ttacatgtga ttggcattga tagaggcgaa    2640
agaaacttaa tttacgtgtc cgtgattgat acatgtggta atattgttga acagaaaagc    2700
tttaacattg taaacggcta cgactatcag attaaattaa acaacagga aggcgctaga    2760 cagattgcga gaaagaatg gaaagaaatt ggtaaaatta agaaattaa agaaggctac    2820 ttaagcttag taattcatga aatttctaaa atggtaatta atacaatgc aattattgcg    2880 atggaagatt tgtcttatgg ttttaaaaaa ggcagattta agttgaaag acaagtttac    2940 cagaaatttg aaacaatgtt aattaataaa ttaaactatt tagtatttaa agatatttca    3000
attacagaaa atggcggttt attaaaaggt tatcagttaa catacattcc tgataaactt    3060
aaaaacgtgg gtcatcagtg cggctgcatt ttttatgtgc ctgctgcata cacgagcaaa    3120
attgatccga caacaggctt tgtgaatatt tttaaattta aagacttaac agtggacgca    3180
aaaagagaat ttattaaaaa atttgactca attagatatg actcagaaaa aaatttattt    3240
tgctttacat ttgactacaa taactttatt acgcaaaaca cggttatgag caaatcatca    3300
tggtcagtgt atacatacgg cgtgagaatt aaaagaagat tgtgaacgg cagattttca    3360 aacgaatcag atacaattga cattacaaaa gatatggaaa aaacgttgga atgacggac    3420 attaactgga gagatggcca tgatcttaga caagacatta ttgattatga aattgttcag    3480
catatttttg aaatttttag attaacagtg caaatgagaa actccttgtc tgaattagaa    3540
gacagagatt acgatagatt aatttcacct gtattaaacg aaaataacat ttttatgac    3600 agcgcgaaag cgggcgatgc acttcctaaa gatgccgatg caaatggtgc gtattgtatt    3660
gcattaaaag gcttatatga aattaaacaa attacagaaa attggaaaga agatggtaaa    3720
ttttcaagag ataaattaaa aattagcaat aaagattggt ttgactttat tcagaataaa    3780
agatatttat aa                                                       3792
```

<210> SEQ ID NO 133
<211> LENGTH: 10469
<212> TYPE: DNA
<213> ORGANISM: Artificial Sequence
<220> FEATURE:
<223> OTHER INFORMATION: pCas9cond

<400> SEQUENCE: 133

```
catggataaa aagtacagta ttggtctaga cataggaact aactctgttg ggtgggctgt      60
tataacagat gaatataaag ttccatcaaa aaaatttaaa gtattaggaa acactgatag     120
```

-continued

```
acattcaata aaaaaaaact tgataggtgc tttattattc gattcaggag agactgctga    180
agctacacgt ttaaaaagaa cagctagacg tagatataca agaagaaaaa ataggatatg    240
ttatcttcaa gaaatttta gtaatgaaat ggcaaaagtt gatgattcat tctttcacag     300
actagaagaa agtttcttag ttgaagaaga taagaagcat gaaagacacc ctattttttgg   360 taatatcgta gatgaagtag catatcatga aagtatcca actatctatc atttaagaaa     420
gaaattagtt gattctacag ataaagctga tctgagatta atatatttag ctttagctca    480
tatgattaaa tttagaggac atttttttaat agaaggtgat ttaaacccag acaacagcga   540
tgtagataaa ttatttatcc aattagttca aacttataat caattattcg aagagaatcc    600
aattaatgca agtggtgtag acgctaaggc tatattatca gctagattat caaaatctag    660
aagattagaa aatctaatag ctcaacttcc tggagaaaag aaaaatggac tttttgggaa    720
cctaatagct ctctcactcg gactaacacc aaatttttaaa agcaattttg atcttgctga   780
agacgcaaag ttacaactat caaaggatac atacgatgat gatttagata atttgttagc    840
tcaaataggt gatcaatatg ctgatttgtt tcttgcagca aaaaacttaa gtgatgcaat    900
tttactatca gatatactta gagtaaatac agaaataaca aaggctcctt tatcagcaag    960
tatgattaaa cgatatgatg agcatcatca agatttaaca ttattaaagg cacttgtaag   1020
acaacaatta ccagaaaaat ataaagaaat tttctttgat caatctaaaa atggatatgc   1080
tggatatata gacggtggag caagtcaaga agagttttat aaatttataa agcctatttt   1140
agaaaaaatg gatggaactg aagaattact tgttaaactt aacagagaag atttacttag   1200
aaaacaaaga acttttgata atggttcaat tcctcaccaa attcatttag gagaattaca   1260
tgctatacta agaagacaag aagatttttta tccatttctt aaagataata gagaaaaaat   1320
tgaaaaaatt ttaacttta gaataccata ttatgtagga ccacttgcaa ggggaaattc   1380
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaagaag attacttcaa aaaaattgaa tgctttgata gtgttgaaat   1740
atcaggagtt gaagatagat ttaatgcttc acttggtaca tatcacgatc tcttaaaaat   1800
tataaaagat aaggatttt tagataatga agaaaatgaa gatattcttg aagatatagt   1860
attaacattg acacttttttg aagatagaga aatgatagaa gaaagattaa aaacatatgc   1920 acatctttttt gatgataagg ttatgaagca acttaaaaga agaagatata caggttgggg   1980
acgtttgtca agaaagctaa ttaatggtat tagagataaa caatcaggaa agactattct   2040 cgatttttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa aagaacatcc   2400
agttgaaaat actcaattgc aaaatgaaaa gttatatttg tattacttac aaaatggaag   2460
agatatgtat gttgatcaag aactcgatat taatagatta agtgactatg atgttgatca   2520
```

```
tattgttcct caatcatttt taaaagatga ttcaatcgat aacaaagtat taactagatc   2580
agataaaaat agaggaaagt cagataatgt accatctgaa gaagttgtta aaaaaatgaa   2640
gaactattgg agacaacttt taaatgcaaa gctaattaca caaagaaaat ttgacaattt   2700
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaaggattt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaaatatt tcttttatag   3120
taatataatg aattttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
aaaagaactt cttggtatca caattatgga aagatcttca tttgaaaaaa atccaattga   3540 cttttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
tgatttaagt caactaggcg gagattaagt cgacaaagta ttgttaaaaa taactctgta   4140
gaattataaa ttagttctac agagttattt tttgacccgg gtaccgagct cgaattcgta   4200
atcatggtca tagctgtttc ctgtgtgaaa ttgttatccg ctcacaattc cacacaacat   4260
acgagccgga agcataaagt gtaaagcctg gggtgcctaa tgagtgagct aactcacatt   4320
aattgcgttg cgctcactgc ccgctttcca gtcgggaaac ctgtcgtgcc agctgcatta   4380
atgaatcggc caacgcgcgg ggagaggcgg tttgcgtatt gggcgctctt ccgcttcctc   4440
gctcactgac tcgctgcgct cggtcgttcg gctgcggcga gcggtatcag ctcactcaaa   4500
ggcggtaata cggttatcca cagaatcagg ggataacgca ggaaagaaca tgtgagcaaa   4560
aggccagcaa aaggccagga accgtaaaaa ggccgcgttg ctggcgtttt tccataggct   4620
ccgcccccct gacgagcatc acaaaaatcg acgctcaagt cagaggtggc gaaacccgac   4680
aggactataa agataccagg cgtttccccc tggaagctcc ctcgtgcgct ctcctgttcc   4740
gaccctgccg cttaccggat acctgtccgc ctttctccct tcgggaagcg tggcgctttc   4800
tcatagctca cgctgtaggt atctcagttc ggtgtaggtc gttcgctcca agctgggctg   4860
```

```
tgtgcacgaa ccccccgttc agcccgaccg ctgcgcctta tccggtaact atcgtcttga    4920
gtccaacccg gtaagacacg acttatcgcc actggcagca gccactggta acaggattag    4980
cagagcgagg tatgtaggcg gtgctacaga gttcttgaag tggtggccta actacggcta    5040
cactagaagg acagtatttg gtatctgcgc tctgctgaag ccagttacct tcggaaaaag    5100
agttggtagc tcttgatccg gcaaacaaac caccgctggt agcggtggtt ttttttgtttg    5160 caagcagcag attacgcgca gaaaaaaagg atctcaagaa gatcctttga tcttttctac    5220
ggggtctgac gctcagtgga acgaaaactc acgttaaggg attttggtca tgagattatc    5280
aaaaaggatc ttcacctaga tccttttaaa ttaaaaatga agttttaaat caatctaaag    5340
tatatatgag taaacttggt ctgacagtta ccaatgctta atcagtgagg cacctatctc    5400
agcgatctgt ctatttcgtt catccatagt tgcctgactc cccgtcgtgt agataactac    5460
gatacgggag ggcttaccat ctggccccag tgctgcaatg ataccgcgag acccacgctc    5520
accggctcca gatttatcag caataaacca gccagccgga agggccgagc gcagaagtgg    5580
tcctgcaact ttatccgcct ccatccagtc tattaattgt tgccgggaag ctagagtaag    5640
tagttcgcca gttaatagtt tgcgcaacgt tgttgccatt gctacaggca tcgtggtgtc    5700
acgctcgtcg tttggtatgg cttcattcag ctccggttcc caacgatcaa ggcgagttac    5760
atgatccccc atgttgtgca aaaaagcggt tagctccttc ggtcctccga tcgttgtcag    5820
aagtaagttg gccgcagtgt tatcactcat ggttatggca gcactgcata attctcttac    5880
tgtcatgcca tccgtaagat gcttttctgt gactggtgag tactcaacca agtcattctg    5940
agaatagtgt atgcggcgac cgagttgctc ttgcccggcg tcaatacggg ataataccgc    6000
gccacatagc agaactttaa aagtgctcat cattggaaaa cgttcttcgg ggcgaaaact    6060
ctcaaggatc ttaccgctgt tgagatccag ttcgatgtaa cccactcgtg cacccaactg    6120
atcttcagca tcttttactt tcaccagcgt ttctgggtga gcaaaaacag gaaggcaaaa    6180
tgccgcaaaa aagggaataa gggcgacacg gaaatgttga atactcatac tcttcctttt    6240
tcaatattat tgaagcattt atcagggtta ttgtctcatg agcggataca tatttgaatg    6300
tatttagaaa aataaacaaa tagggggttcc gcgcacattt ccccgaaaag tgccacctga    6360
ctgccgggcc tcttgcggga tcaaaagaaa acgaaatga tacaccaatc agtgcaaaaa    6420 aagatatat gggagataag acggttcgtg ttcgtgctga cttgcaccat atcataaaaa    6480
tcgaaacagc aaagaatggc ggaaacgtaa aagaagttat ggaaataaga cttagaagca    6540
aacttaagag tgtgttgata gtgcagtatc ttaaaatttt gtataatagg aattgaagtt    6600
aaattagatg ctaaaaattt gtaattaaga aggagtgatt acatgaacaa aaatataaaa    6660
tattctcaaa acttttttaac gagtgaaaaa gtactcaacc aaataataaa acaattgaat    6720
ttaaaagaaa ccgataccgt ttacgaaatt ggaacaggta aagggcattt aacgacgaaa    6780
ctggctaaaa taagtaaaca ggtaacgtct attgaattag acagtcatct attcaactta    6840
tcgtcagaaa aattaaaact gaatactcgt gtcactttaa ttcaccaaga tattctacag    6900
tttcaattcc ctaacaaaca gaggtataaa attgttggga gtattcctta ccatttaagc    6960
acacaaatta ttaaaaagt ggttttttgaa agccatgcgt ctgacatcta tctgattgtt    7020
gaagaaggat tctacaagcg taccttggat attcaccgaa cactagggtt gctcttgcac    7080
actcaagtct cgattcagca attgcttaag ctgccagcgg aatgctttca tcctaaacca    7140
aaagtaaaca gtgtcttaat aaaacttacc cgccatacca cagatgttcc agataaatat    7200
tggaagctat atacgtactt tgtttcaaaa tgggtcaatc gagaatatcg tcaactgttt    7260
```

```
actaaaaatc agtttcatca agcaatgaaa cacgccaaag taaacaattt aagtaccgtt    7320
acttatgagc aagtattgtc tattttttaat agttatctat tatttaacgg gaggaaataa    7380
ttctatgagt ccctaggccc aactaactca acgctagtag tggatttaat cccaaatgag    7440
ccaacagaac cagaaccaga aacagaatca gaacaagtaa cattggattt agaaatggaa    7500
gaagaaaaaa gcaatgactt cgtgtgaata atgcacgaaa tcgttgctta ttttttttta    7560
aaagcggtat actagatata acgaaacaac gaactgaata gaaacgaaaa aagagccatg    7620
acacatttat aaaatgtttg acgacatttt ataaatgcat agcccgataa gattgccaaa    7680
ccaacgctta tcagttagtc agatgaactc ttccctcgta agaagttatt taattaactt    7740
tgtttgaaga cggtatataa ccgtactatc attatatagg gaaatcagag agttttcaag    7800
tatctaagct actgaattta agaattgtta agcaatcaat cggaaatcgt ttgattgctt    7860
tttttgtatt catttataga aggtggagtt tgtatgaatc atgatgaatg taaaacttat    7920
ataaaaaata gttattgga gataagaaaa ttagcaaata tctatacact agaaacgttt    7980
aagaaagagt tagaaaagag aaatatctac ttagaaacaa aatcagataa gtattttct    8040
tcggaggggg aagattatat atataagtta atagaaaata acaaaataat ttattcgatt    8100
agtggaaaaa aattgactta taaaggaaaa aaatcttttt caaaacatgc aatattgaaa    8160
cagttgaatg aaaaagcaaa ccaagttaat taaacaacct attttatagg atttatagga    8220
aaggagaaca gctgaatgaa tatcccttt gttgtagaaa ctgtgcttca tgacggcttg    8280
ttaaagtaca aatttaaaaa tagtaaaatt cgctcaatca ctaccaagcc aggtaaaagc    8340
aaagggcta ttttgcgta tcgctcaaaa tcaagcatga ttggcggtcg tggtgttgtt    8400
ctgacttccg aggaagcgat tcaagaaaat caagatacat ttacacattg acacccaac    8460
gtttatcgtt atggaacgta tgcagacgaa aaccgttcat acacgaaagg acattctgaa    8520
aacaatttaa gacaaatcaa taccttcttt attgattttg atattcacac ggcaaaagaa    8580
actatttcag caagcgatat tttaacaacc gctattgatt taggttttat gcctactatg    8640
attatcaaat ctgataaagg ttatcaagca tattttgttt tagaaacgcc agtctatgtg    8700
acttcaaaat cagaatttaa atctgtcaaa gcagccaaaa taatttcgca aaatatccga    8760
gaatattttg gaaagtcttt gccagttgat ctaacgtgta atcatttgg tattgctcgc    8820
ataccaagaa cggacaatgt agaattttt gatcctaatt accgttattc tttcaaagaa    8880
tggcaagatt ggtctttcaa acaaacagat aataagggct ttactcgttc aagtctaacg    8940
gttttaagcg gtacagaagg caaaaaacaa gtagatgaac cctggtttaa tctcttattg    9000
cacgaaacga aattttcagg agaaaagggt ttaatagggc gtaataacgt catgtttacc    9060
ctctcttag cctactttag ttcaggctat tcaatcgaaa cgtgcgaata taatatgttt    9120
gagtttaata atcgattaga tcaaccctta gaagaaaaag aagtaatcaa aattgttaga    9180
agtgcctatt cagaaaacta tcaagggct aataggaat acattaccat tctttgcaaa    9240
gcttgggtat caagtgattt aaccagtaaa gattatttg tccgtcaagg gtggtttaaa    9300
ttcaagaaaa aaagaagcga acgtcaacgt gttcatttgt cagaatggaa agaagattta    9360
atggcttata ttagcgaaaa aagcgatgta tacaagcctt atttagtgac gaccaaaaaa    9420
gagattagag aagtgctagg cattcctgaa cggacattag ataaattgct gaaggtactg    9480
aaggcgaatc aggaaatttt ctttaagatt aaaccaggaa gaaatggtgg cattcaactt    9540
gctagtgtta aatcattgtt gctatcgatc attaaagtaa aaaaagaaga aaaagaaagc    9600
```

| | |
|---|---|
| tatataaagg cgctgacaaa ttcttttgac ttagagcata cattcattca agagacttta | 9660 |
| aacaagctag cagaacgccc taaaacggac acacaactcg atttgtttag ctatgataca | 9720 |
| ggctgaaaat aaaacccgca ctatgccatt acatttatat ctatgatacg tgtttgtttt | 9780 |
| ttctttgctg tttagcgaat gattagcaga aatatacaga gtaagatttt aattaattat | 9840 |
| taggggagag aggagagagt agcccgaaaa cttttagttg gcttggactg aacgaagtga | 9900 |
| gggaaaggct actaaaacgt cgaggggcag tgagagcgaa gcgaacactt gatttttaa | 9960 |
| ttttctatct tttataggtc attagagtat acttatttgt cctataaact atttagcagc | 10020 |
| ataatagatt tattgaatag gtcatttaag ttgagcatat tagaggagga aaatcttgga | 10080 |
| gaaatatttg aagaacccga ttacatggat tggattagtt cttgtggtta cgtggttttt | 10140 |
| aactaaaagt agtgaatttt tgattttgg tgtgtgtgtc ttgttgttag tatttgctag | 10200 |
| tcaaagtgat taaatagaat tctagcgcca ttcgccattc aggctgcgca actgttggga | 10260 |
| agggcgatcg gtgcgggcct cttcgctatt acgccagctg gcgaaagggg gatgtgctgc | 10320 |
| aaggcgatta agttgggtaa cgccaggggtt ttcccagtca cgacgttgta aaacgacggc | 10380 |
| cagtgccaag cttgcatgcc tgcaggcctc gagtatattg ataaaaataa taatagtggg | 10440 |
| tataattaag ttgttaggag gttagttac | 10469 |

<210> SEQ ID NO 134
<211> LENGTH: 8559
<212> TYPE: DNA
<213> ORGANISM: Artificial Sequence
<220> FEATURE:
<223> OTHER INFORMATION: pMAD7

<400> SEQUENCE: 134

| | |
|---|---|
| tcgagtccct atcagtgata gattgaaact ctatcattga tagagtataa tatctttgtt | 60 |
| cattagagcg ataaacttga atttgagagg gaacttagat gaacaacggc acaaataatt | 120 |
| ttcagaactt catagggata tcaagtttgc agaaaacgtt aagaaatgct ttaatacccca | 180 |
| cggaaaccac gcaacagttc atagttaaga acggaataat taagaagat gagttaagag | 240 |
| gcgaaacag acagatttta aaagatataa tggatgacta ctacagagga ttcatatctg | 300 |
| agactttaag ttctattgat gacatagatt ggactagctt attcgaaaaa atggaaattc | 360 |
| agttaaaaaa tggtgataat aaagatacct taattaagga acagacagag tatagaaaag | 420 |
| caatacataa aaaatttgcg aacgacgata gatttaagaa catgtttagc gccaaattaa | 480 |
| ttagtgacat attacctgaa tttgttatac acaacaataa ttattcggca tcagagaaag | 540 |
| aggaaaaaac ccaggtgata aaattgtttt cgagatttgc gactagcttt aaagattact | 600 |
| tcaagaacag agcaaattgc ttttcagcgg acgatatttc atcaagcagc tgccatagaa | 660 |
| tagttaacga caatgcagag atattctttt caaatgcgtt agtttacaga agaatagtaa | 720 |
| aatcgttaag caatgacgat ataaacaaaa tttcgggcga tatgaaagat tcattaaaag | 780 |
| aaatgagttt agaagaaata tattcttacg agaagtatgg ggaatttatt acccaggaag | 840 |
| gcattagctt ctataatgat atatgtggga agtgaattc ttttatgaac ttatattgtc | 900 |
| agaaaaataa agaaaacaaa aatttataca aacttcagaa acttcacaaa cagattctat | 960 |
| gcattgcgga cactagctat gaggttccgt ataaatttga agtgacgag gaagtgtacc | 1020 |
| aatcagttaa cggcttcctt gataacatta gcagcaaaca tatagttgaa agattaagaa | 1080 |
| aaataggcga taactataac ggctacaact tagataaaat ttatatagtg tccaaatttt | 1140 |
| acgagagcgt tagccaaaaa acctacagag actgggaaac aattaatacc gccttagaaa | 1200 |

```
ttcattacaa taatatattg ccgggtaacg gtaaaagtaa agccgacaaa gtaaaaaaag    1260
cggttaagaa tgatttacag aaatccataa ccgaaataaa tgaactagtg tcaaactata    1320
agttatgcag tgacgacaac ataaaagcgg agacttatat acatgagatt agccatatat    1380
tgaataactt tgaagcacag gaattgaaat acaatccgga aattcaccta gttgaatccg    1440
agttaaaagc gagtgagctt aaaaacgtgt tagacgtgat aatgaatgcg tttcattggt    1500
gttcggtttt tatgactgag gaacttgttg ataaagacaa caatttttat gcggaattag    1560
aggagattta cgatgaaatt tatccagtaa ttagtttata caacttagtt agaaactacg    1620
ttacccagaa accgtacagc acgaaaaaga ttaaattgaa ctttggaata ccgacgttag    1680
cagacggttg gtcaaagtcc aaagagtatt ctaataacgc tataatatta atgagagaca    1740
atttatatta tttaggcata tttaatgcga agaataaacc ggacaagaag attatagagg    1800
gtaatacgtc agaaaataag ggtgactaca aaagatgat ttataatttg ttaccgggtc    1860
ccaacaaaat gataccgaaa gttttcttga gcagcaagac gggggtggaa acgtataaac    1920
cgagcgccta tatactagag gggtataaac agaataaaca tataaagtct tcaaaagact    1980
ttgatataac tttctgtcat gatttaatag actacttcaa aaactgtatt gcaattcatc    2040
ccgagtggaa aaacttcggt tttgatttta gcgacaccag tacttatgaa gacatttccg    2100
ggttttatag agaggtagag ttacaaggtt acaagattga ttggacatac attagcgaaa    2160
aagacattga tttattacag gaaaaaggtc aattatattt attccagata tataacaaag    2220
atttttcgaa aaaatcaacc gggaatgaca accttcacac catgtactta aaaaatcttt    2280
tctcagaaga aaatcttaag gatatagttt taaaacttaa cggcgaagcg gaaatattct    2340
tcaggaagag cagcataaag aacccaataa ttcataaaaa aggctcgatt ttagttaaca    2400
gaacctacga agcagaagaa aaagaccagt ttggcaacat tcaaattgtg agaaaaaata    2460
ttccggaaaa catttatcag gagttataca aatacttcaa cgataaaagc gacaaagagt    2520
tatctgatga agcagccaaa ttaaagaatg tagtgggaca ccacgaggca gcgacgaata    2580
tagttaagga ctatagatac acgtatgata aatacttcct tcatatgcct attacgataa    2640
atttcaaagc caataaaacg ggttttatta atgataggat attacagtat atagctaaag    2700
aaaaagactt acatgtgata ggcattgata gaggcgagag aaacttaata tacgtgtccg    2760
tgattgatac ttgtggtaat atagttgaac agaaaagctt taacattgta aacggctacg    2820
actatcagat aaaattaaaa caacaggagg gcgctagaca gattgcgaga aaagaatgga    2880
aagaaattgg taaattaaaa gagataaaag agggctactt aagcttagta atacacgaga    2940
tatctaaaat ggtaataaaa tacaatgcaa ttatagcgat ggaggatttg tcttatggtt    3000
ttaaaaaagg gagatttaag gttgaaagac aagtttacca gaaatttgaa accatgttaa    3060
taaataaatt aaactattta gtatttaaag atatttcgat taccgagaat ggcggtttat    3120
taaaggttta tcagttaaca tacattcctg ataaacttaa aaacgtgggt catcagtgcg    3180
gctgcatttt ttatgtgcct gctgcataca cgagcaaaat tgatccgacc accggctttg    3240
tgaatatatt taaatttaaa gacttaacag tggacgcaaa aagagaattc attaaaaaat    3300
ttgactcaat tagatatgac agtgaaaaaa atttattctg ctttcatttt gactacaata    3360
actttattac gcaaaacacg gttatgagca atcatcgtg gagtgtgtat acatacggcg    3420
tgagaataaa aagaagattt gtgaacggca gattctcaaa cgaaagtgat accattgaca    3480
taaccaaaga tatggagaaa acgttggaaa tgacggacat taactggaga gatggccacg    3540
```

```
atcttagaca agacattata gattatgaaa ttgttcagca catattcgaa attttcagat   3600
taacagtgca aatgagaaac tccttgtctg aattagagga cagagattac gatagattaa   3660
tttcacctgt attaaacgaa aataacattt tttatgacag cgcgaaagcg ggggatgcac   3720
ttcctaagga tgccgatgca aatggtgcgt attgtattgc attaaaaggg ttatatgaaa   3780
ttaaacaaat taccgaaaat tggaaagaag atggtaaatt ttcgagagat aaattaaaaa   3840
taagcaataa agattggttc gactttatac agaataagag atatttataa gtcgacaaag   3900
tattgttaaa aataactctg tagaattata aattagttct acagagttat ttttgaccc    3960
gggtatattg ataaaaataa taatagtggg tataattaag ttgttaggag gttagttaga   4020
atgatgtcaa gattagataa aagtaaagtg attaacagcg cattagagct gcttaatgag   4080
gtcggaatcg aaggtttaac aacccgtaaa ctcgcccaga agctaggtgt agagcagcct   4140
acattgtatt ggcatgtaaa aaataagcgg gctttgctcg acgccttagc cattgagatg   4200
ttagataggc accatactca cttttgccct ttagaagggg aaagctggca agatttttta   4260
cgtaataacg ctaaaagttt tagatgtgct ttactaagtc atcgcgatgg agcaaaagta   4320
catttaggta cacggcctac agaaaaacag tatgaaactc tcgaaaatca attagccttt   4380
ttatgccaac aaggttttc actagagaat gcattatatg cactcagcgc tgtgggggcat   4440
tttactttag gttgcgtatt ggaagatcaa gagcatcaag tcgctaaaga agaaagggaa   4500
acacctacta ctgatagtat gccgccatta ttacgacaag ctatcgaatt atttgatcac   4560
caaggtgcag agccagcctt cttattcggc cttgaattga tcatatgcgg attagaaaaa   4620
caacttaaat gtgaaagtgg gtcttaaaag cagcataacc ttttccgtg atggtaactt   4680
cacggtaacc aagatgtcga gttgagctcg aattcgtaat catggtcata gctgtttcct   4740
gtgtgaaatt gttatccgct cacaattcca cacaacatac gagccggaag cataaagtgt   4800
aaagcctggg gtgcctaatg agtgagctaa ctcacattaa ttgcgttgcg ctcactgccc   4860
gctttccagt cgggaaacct gtcgtgccag ctgcattaat gaatcggcca acgcgcgggg   4920
agaggcggtt tgcgtattgg gcgctcttcc gcttcctcgc tcactgactc gctgcgctcg   4980
gtcgttcggc tgcggcgagc ggtatcagct cactcaaagg cggtaatacg ttatccaca    5040
gaatcagggg ataacgcagg aaagaacatg tgagcaaaag gccagcaaaa ggccaggaac   5100
cgtaaaaagg ccgcgttgct ggcgtttttc cataggctcc gcccccctga cgagcatcac   5160
aaaaatcgac gctcaagtca gaggtggcga aacccgacag gactataaag ataccaggcg   5220
tttccccctg gaagctccct cgtgcgctct cctgttccga ccctgccgct taccggatac   5280
ctgtccgcct ttctcccttc gggaagcgtg gcgctttctc atagctcacg ctgtaggtat   5340
ctcagttcgg tgtaggtcgt tcgctccaag ctgggctgtg tgcacgaacc ccccgttcag   5400
cccgaccgct gcgccttatc cggtaactat cgtcttgagt ccaacccggt aagacacgac   5460
ttatcgccac tggcagcagc cactggtaac aggattagca gagcgaggta tgtaggcggt   5520
gctacagagt tcttgaagtg gtggcctaac tacggctaca ctagaaggac agtatttggt   5580
atctgcgctc tgctgaagcc agttaccttc ggaaaaagag ttggtagctc ttgatccggc   5640
aaacaaacca ccgctggtag cggtggtttt tttgtttgca agcagcagat tacgcgcaga   5700
aaaaaaggat ctcaagaaga tcctttgatc ttttctacgg ggtctgacgc tcagtggaac   5760
gaaaactcac gttaagggat tttggtcatg agattatcaa aaaggatctt cacctagatc   5820
cttttaaatt aaaaatgaag ttttaaatca atctaaagta tatatgagta aacttggtct   5880
gacagttacc aggtccactg ccgggcctct tgcgggatca aagaaaaac gaaatgatac    5940
```

```
accaatcagt gcaaaaaaag atataatggg agataagacg gttcgtgttc gtgctgactt    6000
gcaccatatc ataaaaatcg aaacagcaaa gaatggcgga aacgtaaaag aagttatgga    6060
aataagactt agaagcaaac ttaagagtgt gttgatagtg cagtatctta aaattttgta    6120
taataggaat tgaagttaaa ttagatgcta aaaatttgta attaagaagg agtgattaca    6180
tgaacaaaaa tataaaatat tctcaaaact ttttaacgag tgaaaaagta ctcaaccaaa    6240
taataaaaca attgaattta aaagaaaccg ataccgttta cgaaattgga acaggtaaag    6300
ggcatttaac gacgaaactg gctaaaataa gtaaacaggt aacgtctatt gaattagaca    6360
gtcatctatt caacttatcg tcagaaaaat taaaactgaa tactcgtgtc actttaattc    6420
accaagatat tctacagttt caattcccta acaaacagag gtataaaatt gttgggagta    6480
ttccttacca tttaagcaca caaattatta aaaaagtggt ttttgaaagc catgcgtctg    6540
acatctatct gattgttgaa gaaggattct acaagcgtac cttggatatt caccgaacac    6600
tagggttgct cttgcacact caagtctcga ttcagcaatt gcttaagctg ccagcggaat    6660
gctttcatcc taaaccaaaa gtaaacagtg tcttaataaa acttacccgc cataccacag    6720
atgttccaga taatattgg aagctatata cgtactttgt ttcaaaatgg gtcaatcgag    6780
aatatcgtca actgtttact aaaaatcagt ttcatcaagc aatgaaacac gccaaagtaa    6840
acaatttaag taccgttact tatgagcaag tattgtctat ttttaatagt tatctattat    6900
ttaacgggag gaaataattc tatgagtccc taggcaggcc tccgccatta tttttttgaa    6960
caattgacaa ttcatttctt atttttatt aagtgatagt caaaaggcat aacagtgctg    7020
aatagaaaga aatttacaga aaagaaaatt atagaattta gtatgattaa ttatactcat    7080
ttatgaatgt ttaattgaat acaaaaaaaa atacttgtta tgtattcaat tacgggttaa    7140
aatatagaca agttgaaaaa tttaataaaa aaataagtcc tcagctctta tatattaagc    7200
taccaactta gtatataagc caaaacttaa atgtgctacc aacacatcaa gccgttagag    7260
aactctatct atagcaatat ttcaaatgta ccgacataca agagaaacat taactatata    7320
tattcaattt atgagattat cttaacagat ataaatgtaa attgcaataa gtaagattta    7380
gaagtttata gcctttgtgt attggaagca gtacgcaaag gctttttat ttgataaaaa    7440
ttagaagtat atttatttt tcataattaa tttatgaaaa tgaaaggggg tgagcaaagt    7500
gacagaggaa agcagtatct tatcaaataa caaggtatta gcaatatcat tattgacttt    7560
agcagtaaac attatgactt ttatagtgct tgtagctaag tagtacgaaa ggggagctt    7620
taaaaagctc cttggaatac atagaattca taaattaatt tatgaaaaga agggcgtata    7680
tgaaaacttg taaaaattgc aaagagttta ttaaagatac tgaaatatgc aaaatacatt    7740
cgttgatgat tcatgataaa acagtagcaa cctattgcag taaatacaat gagtcaagat    7800
gtttacataa agggaaagtc caatgtatta attgttcaaa gatgaaccga tatggatggt    7860
gtgccataaa aatgagatgt tttacagagg aagaacagaa aaaagaacgt acatgcatta    7920
aatattatgc aaggagcttt aaaaaagctc atgtaaagaa gagtaaaaag aaaaaataat    7980
ttatttatta atttaatatt gagagtgccg acacagtatg cactaaaaaa tatatctgtg    8040
gtgtagtgag ccgatacaaa aggatagtca ctcgcatttt cataatacat cttatgttat    8100
gattatgtgt cggtgggact tcacgacgaa aacccacaat aaaaaaagag ttcggggtag    8160
ggttaagcat agttgaggca actaaacaat caagctagga tatgcagtag cagaccgtaa    8220
ggtcgttgtt taggtgtgtt gtaatacata cgctattaag atgtaaaaat acggatacca    8280
```

```
atgaagggaa aagtataatt tttggatgta gtttgtttgt tcatctatgg gcaaactacg    8340
tccaaagccg tttccaaatc tgctaaaaag tatatccttt ctaaaatcaa agtcaagtat    8400
gaaatcataa ataaagttta attttgaagt tattatgata ttatgttttt ctattaaaat    8460
aaattaagta tatagaatag tttaataata gtatatactt aatgtgataa gtgtctgaca    8520
gtgtcacaga aaggatgatt gttatggatt ataagcggc                           8559
```

OPTIMIZED GENETIC TOOL FOR MODIFYING *CLOSTRIDIUM* BACTERIA

The Sequence Listing for this application is labeled "Seq-List.txt" which was created on May 14, 2019 and is 358 KB. The entire content of the sequence listing is incorporated herein by reference in its entirety.

The present invention concerns a genetic tool comprising at least two distinct nucleic acids optimized to facilitate the transformation and modification by homologous recombination of a bacterium of the genus *Clostridium*, typically of a solventogenic bacterium of the genus *Clostridium*.

TECHNOLOGICAL BACKGROUND

Bacteria belonging to the genus *Clostridium*, phylum Firmicutes, are Gram-positive, obligate anaerobic, endospore-forming bacilli. This genus contains many species studied because of their pathogenicity or their industrial and medical interest. For example, *Clostridium tetani*, *Clostridium botulinum*, *Clostridium perfringens* and *Clostridium difficile* are the agents responsible for tetanus, botulism, gas gangrene and pseudomembranous colitis, respectively. *Clostridium novyi* and *Clostridium sporogenes* have been used in studies to develop cancer therapies. At the same time, other species such as *Clostridium acetobutylicum*, *Clostridium butyricum* and *Clostridium beijerinckii*, which are not pathogenic to humans, are used in fermentation.

*Clostridium* species of so-called industrial interest are capable of producing compounds of interest such as acids and solvents from a wide variety of sugars and substrates ranging from glucose to cellulose. The growth of solvent-producing *Clostridium* bacteria ("solventogenic bacteria") is called biphasic. Acids (acetic and butyric) are produced during the exponential growth phase. Then, when cell growth stops and the bacteria enter the stationary phase, they produce solvents.

Most solventogenic strains of *Clostridium* produce acetone, butanol and ethanol as final products. These strains are called "ABE strains". This is the case, for example, for strains *C. acetobutylicum* DSM 792 (also known as ATCC 824 or LMG 5710) and *C. beijerinckii* NCIMB 8052. Other strains are also capable of reducing all or part of acetone to isopropanol, and are called "IBE strains". This is the case, for example, of strain *C. beijerinckii* DSM 6423 (also known as NRRL B-593, LMG 7814, LMG 7815) which has in its genome an adh gene encoding a primary/secondary alcohol dehydrogenase that reduces acetone to isopropanol.

Although used in industry for more than a century, knowledge of bacteria belonging to the genus *Clostridium* has long been limited by the difficulties encountered in genetically modifying them. Various genetic tools have been developed in recent years to optimize strains of this genus, the latest generation being based on the use of CRISPR (Clustered Regularly Interspaced Short Palindromic Repeats)/Cas (CRISPR-associated protein) technology. This method is based on the use of an enzyme called nuclease (typically a Cas nuclease such as the Cas9 protein of *Streptococcus pyogenes*), which will, guided by an RNA molecule, make a double-stranded cut within a DNA molecule (target sequence of interest). The guide RNA (gRNA) sequence will determine the nuclease cleavage site, giving it a very high specificity (FIG. 1).

Since a double-stranded cut in an essential DNA molecule is lethal to an organism, its survival will depend on its ability to repair it (see for example Cui & Bikard, 2016). In bacteria of the genus *Clostridium*, the repair of a double-stranded cut depends on a homologous recombination mechanism requiring an intact copy of the cleaved sequence. By providing the bacterium with a DNA fragment that allows it to perform this repair while modifying the original sequence, it is possible to force the microorganism to integrate the desired changes within its genome. The modification performed must no longer allow the targeting of genomic DNA by the Cas9-gRNA ribonucleoprotein complex, via the modification of the target sequence or the PAM site (FIG. 2).

Different approaches have been described to try to make this genetic tool functional in *Clostridium* bacteria. These microorganisms are known to be difficult to genetically modify because of their low transformation and homologous recombination frequencies. Several approaches are based on the use of Cas9, expressed constitutively in *C. beijerinckii* and *C. ljungdahlii* (Wang et al., 2015; Huang et al., 2016) or under the control of an inducible promoter in *C. beijerinckii*, *C. saccharoperbutylacetonicum* and *C. authoethanogenum* (Wang et al., 2016; Nagaraju et al., 2016; Wang et al., 2017). Other authors have described the use of a modified version of the nuclease, Cas9n, which makes single-stranded, rather than double-stranded, cuts within the genome (Xu et al., 2015; Li et al., 2016). This choice is due to observations that the toxicity of Cas9 is too high for its use in *Clostridium* bacteria under the experimental conditions tested. All the tools described above are based on the use of a single plasmid. Finally, it is also possible to use endogenous CRISPR/Cas systems when they have been identified within the microorganism's genome, as for example in *C. pasteurianum* (Pyne et al., 2016).

Unless they use (as in the last case described above) the endogenous machinery of the strain to be modified, tools based on CRISPR technology have the major disadvantage of significantly limiting the size of the nucleic acid of interest (and therefore the number of coding sequences or genes) that can be inserted into the bacterial genome (about 1.8 kb at best according to Xu et al., 2015).

The inventors have recently developed and described a more efficient genetic tool for modifying bacteria, adapted to *Clostridium* bacteria, based on the use of two distinct nucleic acids, typically two plasmids (WO2017064439, Wasels et al., 2017 and FIG. 3), which solves this problem. In a particular embodiment, the first nucleic acid of this tool allows the expression of cas9 and a second nucleic acid, specific to the modification to be made, contains one or more gRNA expression cassettes as well as a repair template allowing the replacement of a portion of the bacterial DNA targeted by Cas9 by a sequence of interest. The toxicity of the system is limited by placing cas9 and/or the gRNA expression cassette(s) under the control of inducible promoters.

The inventors have also very recently succeeded in genetically modifying bacteria with, in the wild-type state, a gene giving the bacteria resistance to one or more antibiotics in order to make them sensitive to said antibiotic(s), which has made it possible to facilitate the use of their genetic tool based on the use of at least two nucleic acids. They were thus able to genetically modify strain *C. beijerinckii* DSM 6423, a natural producer of isopropanol. In particular, they have succeeded in removing from this strain a natural plasmid not essential for the strain, identified in the present description as "pNF2" (see FR18/73492). The inventors have also discovered and reveal here that the removal of this plasmid pNF2 makes it possible, in the context of the present invention, to obtain a *C. beijerinckii* DSM 6423 bacterium for which the genetic material introduction efficiency (i.e.

the transformation efficiency) is increased by a factor comprised between about $10^1$ and $5 \times 10^3$.

The inventors describe in the present text an improved genetic tool for modifying bacteria of the genus *Clostridium* that makes it possible to very significantly increase the transformation efficiency of said bacteria and thus to obtain, in number and useful quantity (particularly in the context of selecting robust strains for industrial-scale production), mutant (genetically modified) bacteria of interest obtained. As explained below, the inventors have succeeded in improving the genetic tool according to the invention, in particular by using part of plasmid pNF2 to design specific nucleic acids carrying a sequence for modifying the genetic material of a bacterium and/or for expressing within a bacterium a DNA sequence absent from the genetic material present in the wild-type version of said bacterium. These nucleic acids and new tools dramatically improve the transformation efficiency of bacteria, in particular the transformation efficiency of bacteria that have first been cleaned of the natural plasmid(s) they contain in the wild-type state.

The invention thus very advantageously facilitates the transformation efficiency and the use of these bacteria, particularly on an industrial scale.

SUMMARY OF THE INVENTION

The inventors describe, in the context of the present invention and for the first time, a genetic tool allowing the optimized transformation, and the genetic modification by homologous recombination, of a bacterium of the genus *Clostridium* and/or the expression within said bacterium of a DNA sequence partially or totally absent from the genetic material of said bacterium in the wild-type state. This tool is typically characterized i) in that it comprises:
- a "first" nucleic acid encoding at least one DNA endonuclease, for example the Cas9 enzyme, wherein the sequence encoding the DNA endonuclease is placed under the control of a promoter, and
- at least a "second" nucleic acid containing a repair template allowing, by a homologous recombination mechanism, the replacement of a portion of the bacterial DNA targeted by the endonuclease by a sequence of interest, in that ii) at least one of said nucleic acids further encodes one or more guide RNAs (gRNAs) or in that the genetic tool further comprises one or more guide RNAs, each guide RNA comprising a DNA-endonuclease-binding RNA structure and a sequence complementary to the targeted portion of the bacterial DNA, and iii) that at least one of said nucleic acids further comprises a sequence encoding an anti-CRISPR protein placed under the control of an inducible promoter, or in that the genetic tool further comprises a "third" nucleic acid encoding an anti-CRISPR protein placed under the control of an inducible promoter.

In this improved tool, at least one nucleic acid comprises a sequence encoding an anti-CRISPR protein ("acr"), placed under the control of an inducible promoter. This anti-CRISPR protein suppresses the activity of the DNA endonuclease/guide RNA complex. The expression of the protein is regulated to allow its expression only during the step of transformation of the bacterium.

Compared to the tools of the prior art, this tool has the advantage of considerably facilitating the transformation of *Clostridium* bacteria and therefore the production, in number and useful quantity, on an industrial scale, of genetically modified bacteria of interest.

The inventors also describe, in the context of the present invention and for the first time, a nucleic acid (also identified in the present text as "OPT" nucleic acid) that facilitates the transformation of bacteria (by improving the maintenance within said bacteria of all genetic material introduced). The OPT nucleic acid comprises i) all or part of sequence SEQ ID NO: 126 and ii) a sequence allowing the modification of the genetic material of a bacterium and/or the expression within said bacterium of a DNA sequence partially or totally absent from the genetic material present within the wild-type version of said bacterium. SEQ ID NO: 126 is also identified in the present text as "OREP" nucleic acid.

The inventors have succeeded in improving the transformation frequencies of a nucleic acid within the bacterium *C. beijerinckii* DSM 6423, in particular by deleting the OREP sequence within said bacterium and by advantageously using all or part of this OREP sequence to construct nucleic acids and/or genetic tools allowing the modification of the genetic material of a bacterium and/or the expression within said bacterium of a DNA sequence partially or totally absent from the genetic material present within the wild-type version of said bacterium.

The OREP sequence comprises a nucleotide sequence (SEQ ID NO: 127) encoding a protein involved in replication of an OPT nucleic acid of interest. This protein involved in replication is also identified in the present text as "REP" protein (SEQ ID NO: 128—"TESEELKEQSQLLL-DKCTKKKKKNPKFS SYIEPLVSKKLSERIKECGD-FLQMLSDLN LENSKLHRASFCGNRFCPMCSWRI-ACKDSLEISILMEHLRKEESKEFIFLTLTTPNVKGADL-DN SIKAYNKAFKKLMERKEVK-SIVKGYIRKLEVTYNLDKSSKSYNTYHPHFHVV-LAVNRSYFKK QNLY-INHHRWLSLWQESTGDYSITQVDVRKAKINDYKEV-YELAKYSAKDSDYLINREVFTVF YKSLKGKQVLVFSGLFKDAHKMYKNGELD-LYKKLDTIEYAYMVSYNWLKKKYDTSNIRELT EEEKQKFNKNLIEDVDIE"). The REP protein has a conserved domain in Firmicutes, called "COG 5655" (Plasmid rolling-circle replication initiator protein REP), of sequence SEQ ID NO: 129.

In particular, the present invention thus describes a genetic tool comprising at least:
- a "first" nucleic acid encoding at least one DNA endonuclease, wherein the sequence encoding the DNA endonuclease is placed under the control of a promoter, and
- an "other" nucleic acid comprising, or consisting of, an "OREP nucleic acid sequence", i.e. comprising, or consisting of, i) all or part of sequence SEQ ID NO: 126 and ii) a sequence allowing the modification of the genetic material of a bacterium and/or the expression within said bacterium of a DNA sequence partially or totally absent from the genetic material present within the wild-type version of said bacterium.

In a particular embodiment, the "second nucleic acid containing a repair template" as described above comprises this "other nucleic acid".

A process for transforming, and typically for genetically modifying for example by homologous recombination, a bacterium of the genus *Clostridium*, typically a solventogenic bacterium of the genus *Clostridium*, is also described, as well as the bacterium or bacteria obtained (transformed and typically genetically modified) by such a process. This process comprises the following steps:
a) introducing into the bacterium a genetic tool according to the invention in the presence of an inducer of expression of the anti-CRISPR protein, and b) culturing the transformed bacterium obtained at the end of step a) on a medium not containing the inducer of expression of the anti-CRISPR protein and typically allowing the expression of the DNA endonuclease/gRNA ribonucleoprotein complex.

An example of such a process advantageously comprises a step of transforming the bacterium by introducing into said bacterium all or part of a genetic tool as described in the present text, in particular a nucleic acid ("OPT nucleic acid") comprising, or consisting of, i) all or part of sequence SEQ ID NO: 126 and ii) a sequence allowing the modification of the genetic material of a bacterium and/or the expression within said bacterium of a DNA sequence partially or totally absent from the genetic material present in the wild-type version of said bacterium.

The inventors also describe a kit for transforming, and preferably genetically modifying, a bacterium of the genus *Clostridium*, or for producing at least one solvent, for example a mixture of solvents, using a bacterium of the genus *Clostridium*. This kit includes a nucleic acid as described in the present text or the elements of the genetic tool as described in the present text, and at least one inducer adapted to the inducible promoter of expression of the selected anti-CRISPR protein used within the tool. In a particular embodiment, the kit includes all or some of the elements of a genetic tool as described in the present text.

Also described is the use of a nucleic acid or a genetic tool, first disclosed in the present text, to transform and optionally genetically modify a bacterium of the genus *Clostridium*, for example a bacterium of the genus *Clostridium* having in the wild-type state both a bacterial chromosome and at least one DNA molecule distinct from chromosomal DNA (typically a natural plasmid).

Also described is the use of a nucleic acid or of a genetic tool, of the process for transforming and preferably genetically modifying, typically by homologous recombination, a bacterium of the genus *Clostridium*, of the bacterium obtained by said process, and/or of a kit, disclosed for the first time in the present text, to enable the production, preferably on an industrial scale, of a solvent or of a mixture of solvents, preferably acetone, butanol, ethanol, isopropanol or a mixture thereof, typically an isopropanol/butanol, butanol/ethanol or isopropanol/ethanol mixture.

DETAILED DESCRIPTION OF THE INVENTION

Although used in industry for more than a century, knowledge of solventogenic bacteria, particularly those belonging to the genus *Clostridium*, is limited by the difficulties encountered in genetically modifying them. For example, bacteria of the genus *Clostridium* naturally producing isopropanol, typically having in their genome an adh gene encoding a primary/secondary alcohol dehydrogenase that reduces acetone to isopropanol, are both genetically and functionally distinct from bacteria capable in the natural state of ABE fermentation.

The genetic tool described in the present text has the advantage of considerably facilitating the transformation of a bacterium of the genus *Clostridium* by a sequence of interest in order to improve its properties.

This tool is typically characterized i) in that it comprises:
a "first" nucleic acid encoding at least one DNA endonuclease, for example the Cas9 enzyme, wherein the sequence encoding the DNA endonuclease is placed under the control of a promoter, and at least a "second" nucleic acid containing a repair template allowing, by a homologous recombination mechanism, the replacement of a portion of the bacterial DNA targeted by the endonuclease by a sequence of interest, in that ii) at least one of said nucleic acids further encodes one or more guide RNAs (gRNAs) or in that the genetic tool further comprises one or more guide RNAs, each guide RNA comprising a DNA-endonuclease-binding RNA structure and a sequence complementary to the targeted portion of the bacterial DNA, and iii) in that at least one of said nucleic acids further comprises a sequence encoding an anti-CRISPR protein placed under the control of an inducible promoter, or in that the genetic tool further comprises a "third" nucleic acid encoding an anti-CRISPR protein placed under the control of an inducible promoter.

This tool allows the insertion of large fragments of nucleic acid sequences.

The tool described by the inventors can be used to transform and/or genetically modify a bacterium of interest, typically a bacterium as described in the present text belonging to the genus *Clostridium*, preferably a bacterium of the genus *Clostridium* naturally capable (i.e. capable in the wild-type state) of producing isopropanol, in particular naturally capable of IBE fermentation, preferably a bacterium naturally resistant to one or more antibiotics, such as *C. beijerinckii*. A preferred bacterium has in the wild-type state both a bacterial chromosome and at least one DNA molecule distinct from chromosomal DNA.

The expression "bacteria of the genus *Clostridium*" refers in particular to the *Clostridium* species of so-called industrial interest, typically solventogenic or acetogenic bacteria of the genus *Clostridium*. The expression "bacteria of the genus *Clostridium*" comprises wild-type bacteria as well as strains derived therefrom genetically modified to improve their performance (for example overexpressing ctfA, ctfB and adc genes) without having been exposed to the CRISPR system.

The expression "*Clostridium* species of industrial interest" refers to those species capable of producing, by fermentation, solvents and acids such as butyric acid or acetic acid, from sugars or monosaccharides, typically from 5-carbon sugars such as xylose, arabinose or fructose, 6-carbon sugars such as glucose or mannose, polysaccharides such as cellulose or hemicelluloses and/or any other carbon source that can be assimilated and used by bacteria of the genus *Clostridium* ($CO$, $CO_2$ and methanol, for example). Examples of solventogenic bacteria of interest are the bacteria of the genus *Clostridium* that produce acetone, butanol, ethanol and/or isopropanol, such as the strains identified in the literature as "ABE strain" [strains that produce acetone, butanol and ethanol via fermentation] and "IBE strain" [strains that produce isopropanol (by reducing acetone), butanol and ethanol via fermentation]. Solventogenic bacteria of the genus *Clostridium* can be selected from *C. acetobutylicum*, *C. cellulolyticum*, *C. phytofermentans*, *C. beijerinckii*, *C. saccharobutylicum*, *C. saccharoperbutylacetonicum*, *C. sporogenes*, *C. butyricum*, *C. aurantibutyricum* and *C. tyrobutyricum*, preferably from *C. acetobutylicum*, *C. beijerinckii*, *C. butyricum*, *C. tyrobutyricum* and *C. cellulolyticum*, and even more preferably from *C. acetobutylicum* and *C. beijerinckii*.

A bacterium capable of producing isopropanol in the wild-type state, in particular capable of IBE fermentation in the wild-type state, can for example be a bacterium selected from *C. beijerinckii*, *C. diolis*, *C. puniceum*, *C. butyricum*,

*C. saccharoperbutylacetonicum, C. botulinum, C. drakei, C. scatologenes, C. perfringens*, and *C. tunisiense*, preferably a bacterium selected from *C. beijerinckii, C. diolis, C. puniceum* and *C. saccharoperbutylacetonicum*. A bacterium naturally capable of producing isopropanol, in particular capable of IBE fermentation in the wild-type state, particularly preferred is *C. beijerinckii*.

Acetogenic bacteria of interest are bacteria that produce acids and/or solvents from $CO_2$ and $H_2$. Acetogenic bacteria of the genus *Clostridium* can be selected for example from *C. aceticum, C. thermoaceticum, C. ljungdahlii, C. autoethanogenum, C. difficile, C. scatologenes* and *C. carboxydivorans*.

In a particular embodiment, the bacterium of the genus *Clostridium* concerned is an "ABE strain", preferably strain *C. acetobutylicum* DSM 792 (also known as ATCC 824 or LMG 5710) or strain *C. beijerinckii* NCIMB 8052.

In another particular embodiment, the bacterium of the genus *Clostridium* concerned is an "IBE strain", preferably a subclade of *C. beijerinckii* selected from DSM 6423, LMG 7814, LMG 7815, NRRL B-593, NCCB 27006, or *C. aurantibutyricum* DSZM 793 (Georges et al., 1983), and a subclade of such a *C. beijerinckii* or *C. aurantibutyricum* bacterium having at least 90%, 95%, 96%, 97%, 98% or 99% identity with strain DSM 6423. A particularly preferred *C. beijerinckii* bacterium, or a subclade of *C. beijerinckii* bacterium, is devoid of plasmid pNF2.

The respective genomes of subclades LMG 7814, LMG 7815, NRRL B-593 and NCCB 27006 on the one hand, and DSZM 793 on the other hand, have sequence identity percentages of at least 97% with the genome of subclade DSM 6423.

The inventors carried out fermentation tests confirming that *C. beijerinckii* bacteria of subclade DSM 6423, LMG 7815 and NCCB 27006 are capable of producing isopropanol in the wild-type state (see Table 1).

(Jinek et al., Science 2012). The gRNA combines in a single transcript the targeting specificity of the crRNA corresponding to the "spacer sequences" that guide Cas proteins and the conformational properties of the tracrRNA. When the gRNA and the Cas protein are expressed simultaneously in the cell, the target genomic sequence can be permanently modified using a provided repair template.

In recent experiments, the inventors have been successful in transforming and in genetically modifying a bacterium of the genus *Clostridium* naturally producing isopropanol, the bacterium *C. beijerinckii* DSM 6423, as well as the reference strain *C. acetobutylicum* DSM 792.

Some of the work described in the experimental section was carried out within a strain capable of IBE fermentation, i.e. strain *C. beijerinckii* DSM 6423, the genome and transcriptomic analysis of which have recently been described by the inventors (Mate de Gerando et al., 2018).

During the assembly of the genome of this strain, the inventors discovered, in addition to the chromosome, the presence of mobile genetic elements (accession number PRJEB11626—see Worldwide Website: ebi.ac.uk/ena/data/view/PRJEB11626): two natural plasmids (pNF1 and pNF2) and a linear bacteriophage (Φ6423).

The strain *C. beijerinckii* DSM 6423 is naturally erythromycin-sensitive but thiamphenicol-resistant. Patent application no. FR18/73492 describes a particular strain, strain *C. beijerinckii* DSM 6423 ΔcatB, made thiamphenicol-sensitive. In a particular embodiment of the invention, the inventors succeeded in removing from strain *C. beijerinckii* DSM 6423 its natural pNF2 plasmid and obtained a strain *C. beijerinckii* DSM6423 ΔcatB ΔpNF2. This strain was registered on Feb. 20, 2019 under deposit number LMG P-31277 with the BCCM-LMG collection. The description also concerns any derived bacteria, clones, mutants or genetically modified versions thereof. It also concerns more

TABLE 1

| | | | Concentration (g/L) | | | | | Glucose consumed (g/L) | Yield |
|---|---|---|---|---|---|---|---|---|---|
| | Glucose | Acetic acid | Butyric acid | Ethanol | Acetone | isopropanol | Butanol | solvents | | |
| Control | 56.19 | 2.1406 | 0 | — | — | — | — | 0.00 | | |
| DSM 6423_A | 31.70 | 0 | 0 | 0.16 | 0.24 | 3.72 | 6.16 | 10.11 | 24.50 | 0.41 |
| DSM 6423_B | 29.08 | 0 | 0 | 0.18 | 0.23 | 4.33 | 6.94 | 11.50 | 27.12 | 0.42 |
| LMG_7815_A | 27.65 | 0.93 | 0.73 | 0.16 | 0.35 | 3.93 | 7.28 | 11.56 | 28.55 | 0.40 |
| LMG_7815_B | 27.50 | 0.63 | 0.73 | 0.18 | 0.29 | 4.30 | 7.63 | 12.22 | 28.70 | 0.43 |
| NCCB 27006_A | 36.28 | 0.98 | 2.59 | 0.13 | 0.15 | 2.83 | 5.22 | 8.19 | 19.91 | 0.41 |
| NCCB 27006_B | 36.10 | 1.08 | 2.27 | 0.13 | 0.15 | 2.70 | 5.17 | 8.02 | 20.10 | 0.40 |

Summary of glucose fermentation tests using the naturally isopropanol-producing strains *C. beijerinckii* DSM 6423, LMG 7815 and NCCB 27006. In a particularly preferred embodiment of the invention, the *C. beijerinckii* bacterium is the bacterium of subclade DSM 6423.

In still another preferred embodiment of the invention, the *C. beijerinckii* bacterium is a strain *C. beijerinckii* IFP963 ΔcatB ΔpNF2 (registered on Feb. 20, 2019 under deposit number LMG P-31277 in the BCCM-LMG collection).

The CRISPR/DNA endonuclease system contains two distinct essential components, i.e. i) an endonuclease, in the present case the nuclease associated with the CRISPR system (Cas or "CRISPR-associated protein"), typically Cas9, and ii) a guide RNA. Guide RNA is a chimeric RNA consisting of a combination of a bacterial CRISPR RNA (crRNA) and a tracrRNA (trans-activating CRISPR RNA)

generally any bacterium having in the wild-type state both a bacterial chromosome and at least one DNA molecule distinct from chromosomal DNA (identified in the present text as "non-chromosomal (bacterial) DNA" or "natural (bacterial) plasmid"), genetically modified using a nucleic acid and/or genetic tool described in the present text in such a way as to no longer include at least one of its non-chromosomal DNA molecules, typically several of its non-chromosomal DNA molecules (for example two, three or four non-chromosomal DNA molecules), preferably all its non-chromosomal DNA molecules.

The inventors observed that the removal of the natural pNF2 plasmid has a significant advantage for the introduction and maintenance of additional natural or synthetic genetic elements (for example expression cassette(s) or expression plasmid vector(s)). Strain DSM 6423 ΔcatB ΔpNF2 can thus be transformed with an efficiency 10 to 5×10³ times higher than its wild-type counterpart or than strain DSM 6423 ΔcatB.

The inventors thus describe, in the present application, a bacterium of the genus *Clostridium* naturally capable (i.e. capable in the wild-type state) of producing isopropanol, in particular naturally capable of IBE fermentation, which has been genetically modified and has, as a result of this genetic modification, in particular lost at least one natural plasmid (i.e. a plasmid naturally present in the wild-type version of said bacterium), preferably all its natural plasmids, as well as the tools, in particular the genetic tools, used to obtain it.

These tools have the advantage of considerably facilitating the transformation and genetic modification of bacteria. The experiments carried out by the inventors have demonstrated the possible use of the tools and, more generally, of the technology described in the present text to genetically modify a bacterium of the genus *Clostridium*, in particular bacteria of the genus *Clostridium* capable, in the wild-type state, of producing isopropanol, in particular to carry out IBE fermentation, in particular those carrying a gene encoding an enzyme responsible for resistance to an antibiotic, in particular a gene encoding an amphenicol-O-acetyltransferase, for example a chloramphenicol-O-acetyltransferase or a thiamphenicol-O-acetyltransferase.

In a particular embodiment, the inventors have thus succeeded in making sensitive to an antibiotic of the class of amphenicols, a bacterium naturally carrying (carrying in the wild-type state) a gene encoding an enzyme responsible for resistance to these antibiotics.

Other preferred bacteria contain, in the wild-type state, both a bacterial chromosome and at least one DNA molecule distinct from chromosomal DNA.

Also preferred bacteria contain, in the wild-type state, both a bacterial chromosome and at least one DNA molecule distinct from chromosomal DNA, as well as a gene conferring resistance to an antibiotic. In a particular embodiment, this gene encodes an amphenicol-O-acetyltransferase, for example a chloramphenicol-O-acetyltransferase or a thiamphenicol-O-acetyltransferase.

A particular bacterium intended to be transformed, and preferably genetically modified, is preferably a bacterium that has been exposed to a first step of transformation and to a first step of genetic modification using a nucleic acid or genetic tool according to the invention that has made it possible to remove at least one extrachromosomal DNA molecule (typically at least one plasmid) naturally present within said bacterium in the wild-type state.

An object described by the inventors concerns a nucleic acid (identified in the present text as "OPT" nucleic acid), which can be advantageously used to facilitate the transformation of bacteria by improving the maintenance within said bacteria of all the introduced genetic material. This OPT nucleic acid comprises i) all or part of sequence SEQ ID NO: 126 ("OREP" sequence) or a functional variant thereof and ii) a sequence (also identified in the present text as "sequence of interest") allowing the modification of the genetic material of a bacterium and/or the expression within said bacterium of a DNA sequence partially or totally absent from the genetic material present within the wild-type version of said bacterium.

The OREP sequence (SEQ ID NO: 126) comprises a nucleotide sequence of sequence SEQ ID NO: 127. Sequence SEQ ID NO: 127 preferably comprises a sequence encoding a protein involved in replication of the OPT nucleic acid. A protein considered to be involved in replication is also identified in the present text as "REP" protein (SEQ ID NO: 128). The REP protein has a conserved domain in Firmicutes, called "COG 5655", of sequence SEQ ID NO: 129.

In a particular embodiment, the OPT nucleic acid comprises a part of the OREP sequence (SEQ ID NO: 126), typically one or more fragments of the OREP sequence, preferably at least the sequence encoding the REP protein (SEQ ID NO: 128) or a functional variant or fragment thereof (i.e. the fragment involved in replication), typically sequence SEQ ID NO: 127 or a variant or fragment thereof encoding the fragment involved, within the REP protein, in the replication of an OPT nucleic acid. The functional fragment of the OREP sequence encoding the fragment, present within the REP protein, involved in replication of an OPT nucleic acid, comprises the domain of sequence SEQ ID NO: 129. Examples of such nucleic acid fragments encoding a functional fragment of the REP protein, and variants thereof, can be easily prepared by the skilled person. A typical example of a variant has a sequence homology with sequence SEQ ID NO: 127 comprised between 70% and 100%, preferably between 85 and 99%, more preferably between 95 and 99%, for example of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In a preferred embodiment, the functional variant or fragment of the OREP sequence encodes a protein involved in replication of the OPT nucleic acid.

In a preferred embodiment of the invention, the functional variant or fragment of the OREP sequence comprises, in addition to the sequence encoding a protein (for example REP protein) involved in replication of the OPT nucleic acid (for example a plasmid-like genetic construct) or a functional variant or fragment thereof, a site of 1 to 150 bases, preferably of 1 to 15 bases, for example a sequence rich in A and T bases (Rajewska et al.), preferably a site present within pNF2 plasmid of sequence SEQ ID NO: 118, allowing the binding of a protein allowing the replication of the OPT nucleic acid.

The sequence of interest allowing the modification of the genetic material of the bacterium is typically a modification template allowing, for example by a homologous recombination mechanism, the replacement of a portion of the genetic material of the bacterium by a sequence of interest. The sequence of interest allowing the modification of the genetic material of the bacterium may also be a recognition sequence (binding at least in part), and preferably targeting, i.e. recognizing and allowing the cleavage, in the genome of a bacterium of interest, of at least one strand i) of a target sequence, ii) of a sequence controlling the transcription of a target sequence, or iii) of a sequence flanking a target sequence.

The sequence of interest allowing the expression within said bacterium of a DNA sequence partially or totally absent from the genetic material present in the wild-type version of said bacterium typically allows the bacterium to express one or more proteins that it is unable to express, or to express in sufficient quantity, in the wild-type state.

According to a particular aspect, the "OPT nucleic acid" further comprises iii) a sequence encoding a DNA endonuclease, for example Cas9, and/or iv) one or more guide RNAs (gRNAs), each gRNA comprising a DNA-endonuclease-binding RNA structure and a sequence complementary to the targeted portion of the bacterial genetic material.

According to another particular aspect, the "OPT nucleic acid" does not have methylation at the motifs recognized by Dam and Dcm methyltransferases.

Preferably, the "OPT nucleic acid" is selected from an expression cassette and a vector, and is preferably a plasmid, for example a plasmid having a sequence selected from SEQ ID NO: 119, SEQ ID NO: 123, SEQ ID NO: 124 and SEQ ID NO: 125.

Thus described in particular is a genetic tool comprising at least:
a first nucleic acid encoding at least one DNA endonuclease, wherein the sequence encoding the DNA endonuclease is placed under the control of a promoter, and another nucleic acid (or an "nth nucleic acid") comprising or consisting of, an "OPT" nucleic acid sequence, i.e. a sequence comprising i) all or part of sequence SEQ ID NO: 126 ("OREP") and ii) a sequence allowing the modification of the genetic material of a bacterium and/or the expression within said bacterium of a DNA sequence partially or totally absent from the genetic material present in the wild-type version of said bacterium, at least one of said nucleic acids of this particular genetic tool preferably further comprising a sequence encoding an anti-CRISPR protein placed under the control of an inducible promoter, or said particular genetic tool further comprising preferably a third nucleic acid encoding an anti-CRISPR protein placed under the control of an inducible promoter.

In a particular embodiment the "second" or "nth nucleic acid containing a repair template" as described above comprises, or consists of, this "other nucleic acid".

In another particular embodiment, the "first nucleic acid" also encodes one or more guide RNAs (gRNAs).

In the sense of the invention, the term "nucleic acid" means any natural, synthetic, semi-synthetic or recombinant DNA or RNA molecule, optionally chemically modified (i.e. comprising non-natural bases, modified nucleotides having, for example, a modified bond, modified bases and/or modified sugars), or optimized so that the codons of transcripts synthesized from the coding sequences are the codons most frequently found in a bacterium of the genus *Clostridium* for use therein. In the case of the genus *Clostridium*, the optimized codons are typically codons rich in adenine ("A") and thymine ("T") bases.

The genetic tool according to the invention comprises a first nucleic acid encoding at least one endonuclease, typically a Cas nuclease, for example Cas9 or MAD7. "Cas9" refers to a Cas9 (also called CRISPR-associated protein 9, Csn1 or Csx12) protein or a functional protein, peptide or polypeptide fragment thereof, i.e. capable of interacting with the guide RNA(s) and carrying out the enzymatic (nuclease) activity that allows it to make the double-stranded cut in the DNA of the target genome. "Cas9" can thus refer to a modified protein, for example truncated to remove protein domains not essential to the predefined functions of the protein, in particular domains not necessary for interaction with the gRNA(s).

MAD7 nuclease (the amino acid sequence of which corresponds to sequence SEQ ID NO: 72), also identified as "Cas12" or "Cpf1", can otherwise be advantageously used in the context of the present invention by combining it with one or more gRNAs known to the skilled person capable of binding to such a nuclease (see Garcia-Doval et al., 2017 and Stella S. et al., 2017).

According to a particular aspect, the sequence encoding MAD7 nuclease is a sequence optimized to be easily expressed in *Clostridium* strains, preferably sequence SEQ ID NO: 71.

The sequence encoding Cas9 (the whole protein or a fragment thereof) as used in the context of the invention can be obtained from any known Cas9 protein (Makarova et al., 2011). Examples of Cas9 proteins that can be used in the present invention include, but are not limited to, the Cas9 proteins from *S. pyogenes*, *Streptococcus thermophilus*, *Streptococcus mutans*, *Campylobacter jejuni*, *Pasteurella multocida*, *Francisella novicida*, *Neisseria meningitidis*, *Neisseria lactamica* and *Legionella pneumophila* (see Fonfara et al., 2013; Makarova et al., 2015).

In a particular embodiment, the Cas9 protein, or a functional protein, peptide or polypeptide fragment thereof, encoded by one of the nucleic acids of the genetic tool according to the invention comprises, or consists of, the amino acid sequence SEQ ID NO: 75, or any other amino acid sequence having at least 50%, preferably at least 60%, identity therewith, and containing at the least the two aspartic acids ("D") occupying positions 10 ("D10") and 840 ("D840") of the amino acid sequence SEQ ID NO: 75.

In a preferred embodiment, Cas9 comprises, or consists of, the Cas9 protein (NCBI accession number: WP_010922251.1, SEQ ID NO: 75), encoded by the cas9 gene from strain *S. pyogenes* M1 GAS (NCBI accession number: NC_002737.2 SPy_1046, SEQ ID NO: 76) or a version thereof having undergone optimization ("optimized version") resulting in a transcript containing the codons preferentially used by bacteria of the genus *Clostridium*, typically codons rich in adenine ("A") and thymine ("T") bases, allowing facilitated expression of the Cas9 protein within this bacterial genus. These optimized codons respect the codon usage bias, well-known to the skilled person, specific to each bacterial strain.

In the peptide sequences described in this document, amino acids are represented by their single-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine.

According to a particular embodiment, the Cas9 domain consists of a whole Cas9 protein, preferably the *S. pyogenes* Cas9 protein or an optimized version thereof.

The sequence encoding the DNA endonuclease, for example Cas9, present within one of the nucleic acids of the genetic tool according to the invention is placed under the control of a promoter. This promoter may be a constitutive promoter or an inducible promoter. In a preferred embodiment, the promoter controlling Cas9 expression is an inducible promoter.

Examples of constitutive promoters that can be used in the present invention may be selected from the promoter of the thl gene, of the ptb gene, of the adc gene, of the BCS operon, or a derivative thereof, preferably a functional but shorter (truncated) derivative such as the "miniPthl" derivative of the thl gene promoter from *C. acetobutylicum* (Dong et al., 2012), or any other promoter, well-known to the skilled person, allowing the expression of a protein within a bacterium of the genus *Clostridium*.

Examples of inducible promoters that can be used in context of the present invention can be selected, for example, from a promoter whose expression is controlled by the transcriptional repressor TetR, for example the promoter of the tetA gene (tetracycline resistance gene originally present on the *E. coli* transposon Tn10); a promoter whose expression is controlled by L-arabinose, for example the ptk gene promoter (Zhang et al., 2015), preferably in combination with the araR regulator expression cassette of *C. acetobutylicum* so as to construct an ARAi system (Zhang et al., 2015); a promoter whose expression is controlled by laminaribiose (β-1,3 glucose dimer), for example the celC gene promoter, preferably immediately followed by the repressor gene glyR3 and the gene of interest (Mearls et al., 2015) or the celC gene promoter (Newcomb et al., 2011); a promoter whose expression is controlled by lactose, for example the bgaL gene promoter (Banerjee et al., 2014); a promoter whose expression is controlled by xylose, for example the xylB gene promoter (Nariya et al., 2011); and a promoter whose expression is controlled by UV exposure, for example the bcn gene promoter (Dupuy et al., 2005).

A promoter derived from one of the promoters described above, preferably a functional but shorter (truncated) derivative, may also be used in the context of the invention.

Other inducible promoters that can be used in the context of the present invention are also described, for example, in the articles by Ransom et al. (2015), Currie et al. (2013) and Hartman et al. (2011).

A preferred inducible promoter is an anhydrotetracycline (aTc)-inducible promoter derived from tetA (aTc is less toxic than tetracycline and capable of releasing the inhibition of the transcriptional repressor TetR at lower concentration), selected from Pcm-2tetO1 and Pcm-2tetO2/1 (Dong et al., 2012).

Another preferred inducible promoter is a xylose-inducible promoter, for example the xylB promoter from *Clostridium difficile* 630 (Nariya et al., 2011).

Still another preferred inducible promoter is a lactose-inducible promoter, for example the promoter of the bgaL gene (Banerjee et al., 2014).

A particular nucleic acid of interest, typically an expression cassette or vector, comprises one or more expression cassettes, each cassette encoding a gRNA (guide RNA).

The term "guide RNA" or "gRNA" refers within the meaning of the invention to an RNA molecule capable of interacting with a DNA endonuclease such as Cas9 in order to guide it to a target region of the bacterial chromosome. The specificity of the cut is determined by the gRNA. As explained above, each gRNA comprises two regions:
 a first region (commonly called the "SDS" region), at the 5' end of the gRNA, which is complementary to the target chromosomal region and mimics the endogenous CRISPR system crRNA, and
 a second region (commonly called the "handle" region), at the 3' end of the gRNA, which mimics the base-pairing interactions between the tracrRNA (trans-activating crRNA) and the endogenous CRISPR system crRNA and has a double-stranded stem-loop structure ending in the 3' direction with an essentially single-stranded sequence. This second region is essential for the binding of the gRNA to the DNA endonucleasoendonuclease.

The first region of the gRNA ("SDS" region) varies according to the targeted chromosomal sequence.

The "SDS" region of the gRNA, which is complementary to the target chromosomal region, comprises at least 1 nucleotide, preferably at least 1, 2, 3, 4, 5, 10, 15, 20, 25, 30, 35 or 40 nucleotides, typically between 1 and 40 nucleotides. Preferably, this region has a length of 20, 21, 22, 23, 24, 25, 26, 27, 28, 29 or 30 nucleotides.

The second region of the gRNA ("handle" region) has a stem-loop (or hairpin) structure. The handle regions of the different gRNAs do not depend on the selected chromosomal target.

According to a particular embodiment, the "handle" region comprises, or consists of, a sequence of at least 1 nucleotide, preferably at least 1, 50, 100, 200, 500 and 1000 nucleotides, typically between 1 and 1000 nucleotides. Preferably, this region has a length of 40 to 120 nucleotides.

The overall length of a gRNA is generally from 50 to 1000 nucleotides, preferably from 80 to 200 nucleotides, and more particularly preferably from 90 to 120 nucleotides. According to a particular embodiment, a gRNA as used in the present invention has a length comprised between 95 and 110 nucleotides, for example a length of about 100 or about 110 nucleotides.

The skilled person can easily define, using well-known techniques, the sequence and structure of gRNAs according to the chromosomal region to be targeted (see for example the article by DiCarlo et al., 2013).

The targeted DNA region/portion/sequence within the bacterial chromosome can correspond to a portion of non-coding DNA or a portion of coding DNA.

In a particular embodiment consisting in modifying a given sequence, the targeted portion of bacterial DNA is essential for bacterial survival. It corresponds, for example, to any region of the bacterial chromosome or to any region located on non-chromosomal DNA, for example on a mobile genetic element essential for the survival of the microorganism under particular growth conditions, for example a plasmid containing an antibiotic resistance marker when the expected growth conditions require the bacterium to be grown in the presence of said antibiotic.

In another particular embodiment aimed at removing a genetic element that is not essential under the particular growth conditions associated with the culture of the microorganism, the targeted portion of the bacterial DNA may correspond to any region of said non-chromosomal bacterial DNA, for example of said mobile genetic element.

Particular examples of a targeted DNA portion within a bacterium of the genus *Clostridium* are the sequences used in example 1 of the experimental section. They are, for example, the sequences encoding the bdhA (SEQ ID NO: 77) and bdhB (SEQ ID NO: 78) genes. The targeted DNA region/portion/sequence is followed by a protospacer adjacent motif ("PAM") sequence that is involved in Cas9 binding.

The "SDS" region of a given gRNA is identical (100%) or at least 80% identical, preferably 85%, 90%, 95%, 96%, 97%, 98% or 99% identical at least to the targeted DNA region/portion/sequence within the bacterial chromosome and is capable of hybridizing with all or part of the complementary sequence of said region/portion/sequence, typically with a sequence comprising at least 1 nucleotide, preferably at least 1, 2, 3, 4, 5, 10, 15, 20, 25, 30, 35 or 40 nucleotides, typically between 1 and 40 nucleotides, preferably a sequence comprising 14, 15, 16, 17, 18, 19, 20, 21, 22, 23, 24, 25, 26, 27, 28, 29 or 30 nucleotides.

In the process according to the invention, one or more gRNAs targeting a sequence ("target sequence", "targeted sequence" or "recognized sequence") can be used simultaneously. These different gRNA can target chromosomal regions, or regions belonging to non-chromosomal bacterial DNA (for example mobile genetic elements) that may be present within the microorganism, which may be identical or different.

The gRNAs can be introduced into the bacterial cell as gRNA molecules (mature or precursor), as precursors or as one or more nucleic acids encoding said gRNAs. The gRNAs are preferably introduced into the bacterial cell as one or more nucleic acids encoding said gRNAs.

When the one or more gRNAs are introduced into the cell directly as RNA molecules, these gRNAs (mature or precursor) can contain modified nucleotides or chemical modifications allowing them, for example, to increase their resistance to nucleases and thus increase their lifespan in the cell. In particular, they can comprise at least one modified or unnatural nucleotide such as, for example, a nucleotide with a modified base, such as inosine, methyl-5-deoxycytidine, dimethylamino-5-deoxyuridine, deoxyuridine, diamino-2,6-purine, bromo-5-deoxyuridine or any other modified base allowing hybridization. The gRNA used according to the invention can also be modified at the level of the internucleotide bond, such as phosphorothioates, H-phosphonates or alkyl-phosphonates; or at the level of the backbone, such as alpha-oligonucleotides, 2'-O-alkyl ribose or peptide nucleic acids (PNA) (Egholm et al., 1992).

The gRNAs can be natural RNAs, synthetic RNAs, or RNAs produced by recombinant techniques. These gRNA can be prepared by any methods known to the skilled person, such as, for example, chemical synthesis, transcription in vivo or amplification techniques.

When the gRNAs are introduced into the bacterial cell as one or more nucleic acids, the sequence(s) encoding the gRNA(s) is/are placed under the control of an expression promoter. This promoter can be constitutive or inducible.

When several gRNAs are used, the expression of each gRNA can be controlled by a different promoter. Preferably, the promoter used is the same for all the gRNAs. The same promoter can in a particular embodiment be used to allow the expression of several, for example of only a few, or in other words all or part, of the gRNAs intended to be expressed.

In a preferred embodiment, the promoter(s) controlling the expression of the gRNAs is/are inducible promoters.

Examples of constitutive promoters that can be used in the context of the present invention can be selected from the promoter of the thl gene, of the ptb gene or of the BCS operon, or a derivative thereof, preferably miniPthl, or any other promoter, well-known to the skilled person, allowing the synthesis of an RNA (coding or non-coding) within *Clostridium*.

Examples of inducible promoters that can be used in the context of the present invention can be selected from the promoter of the tetA gene, of the xylA gene, of the lad gene, or of the bgaL gene, or a derivative thereof, preferably 2tetO1 or tetO2/1. A preferred inducible promoter is 2tetO1.

The promoters controlling the expression of the DNA endonuclease, for example Cas9, and of the gRNA(s) can be identical or different and constitutive or inducible. In a particular and preferred embodiment of the invention, the promoters controlling respectively the expression of the DNA endonuclease or of the gRNA(s) are different promoters but inducible by the same inducer.

The inducible promoters as described above make it possible to advantageously control the action of the DNA endonuclease/gRNA ribonucleoprotein complex and to facilitate the selection of transformants that have undergone the desired genetic modifications.

The genetic tool according to the invention advantageously comprises a sequence encoding at least one anti-CRISPR protein (also identified in the present text as "anti-CRISPR/DNA endonuclease protein" or "anti-CRISPR/Cas9 protein"), i.e. a protein capable of inhibiting or preventing/neutralizing the action of Cas, and/or a protein capable of inhibiting or preventing/neutralizing the action of a CRISPR/Cas system, for example a CRISPR/Cas type II system when the nuclease is a Cas9 nuclease. This sequence is typically placed under the control of an inducible promoter different from the promoters controlling the expression of the DNA endonuclease and/or of the gRNA(s), and is inducible by another inducer. In a preferred embodiment, the sequence encoding the anti-CRISPR protein is also typically located on one of the at least two nucleic acids present within the genetic tool. In a particular embodiment, the sequence encoding the anti-CRISPR protein is located on a nucleic acid distinct from the first two (typically a "third nucleic acid"). In still another particular embodiment, both the sequence encoding the anti-CRISPR protein and the sequence encoding the transcriptional repressor of said anti-CRISPR protein are integrated into the bacterial chromosome.

In a preferred embodiment, the sequence encoding an anti-CRISPR protein is placed, within the genetic tool, on the nucleic acid encoding the DNA endonuclease (also identified in the present text as "first nucleic acid"). In another embodiment, the sequence encoding an anti-CRISPR protein is placed, within the genetic tool, on a different nucleic acid than the one encoding the DNA endonuclease, for example on the nucleic acid identified in the present text as "second nucleic acid" or on an "nth" (typically a "third") nucleic acid optionally included in the genetic tool.

The anti-CRISPR protein is typically an "anti-Cas9" protein, i.e. a protein capable of inhibiting or preventing/neutralizing the action of Cas9, and/or a protein capable of inhibiting or preventing/neutralizing the action of a CRISPR/Cas9 type II system.

The anti-CRISPR protein is advantageously an "anti-Cas9" protein or an "anti-MAD7" protein, i.e. a protein capable of inhibiting or preventing/neutralizing the action of Cas9 or of CAST.

The anti-CRISPR protein is advantageously an "anti-Cas9" protein, for example selected from AcrIIA1, AcrIIA2, AcrIIA3, AcrIIA4, AcrIIA5, AcrIIC1, AcrIIC2 and AcrIIC3 (Pawluk et al., 2018). Preferably the "anti-Cas9" protein is AcrIIA2 or AcrIIA4. More preferably the "anti-Cas9" protein is AcrIIA4. Such a protein is typically able to significantly limit, ideally to prevent, the action of Cas9, for example by binding to the Cas9 enzyme (Dong et al., 2017; Rauch et al., 2017).

Another advantageously useful anti-CRISPR protein is an "anti-MAD7" protein, for example AcrVA1 (Marino et al., 2018).

In a preferred embodiment, the anti-CRISPR protein is capable of inhibiting, preferably neutralizing, the action of the DNA endonuclease, preferably during the phase of introducing nucleic acid sequences from the genetic tool into the bacterial strain of interest.

The promoter controlling the expression of the sequence encoding the anti-CRISPR protein is preferably an inducible promoter. The inducible promoter is associated with a constitutively expressed gene, typically responsible for the expression of a protein allowing transcriptional repression from said inducible promoter. This promoter can for example be selected from the promoter of the tetA gene, of the xylA gene, of the lad gene, or of the bgaL gene, or a derivative thereof.

An example of an inducible promoter that can be used in the context of the invention is the Pbgal promoter (lactose-inducible) present, within the genetic tool and on the same nucleic acid, alongside the constitutively expressed bgaR gene and whose expression product allows transcriptional repression from Pbgal. In the presence of the inducer, lactose, the transcriptional repression of the Pbgal promoter is released, allowing the transcription of the gene placed downstream thereof. Preferably, the gene placed downstream corresponds, in the context of the present invention, to the gene encoding the anti-CRISPR protein, for example acrIIA4.

The promoter controlling the expression of the anti-CRISPR protein makes it possible to advantageously control the action of the DNA endonuclease, for example of the Cas9 enzyme, and thus facilitate the transformation of bacteria of the genus *Clostridium* and the production of transformants having undergone the desired genetic modifications.

In the sense of the invention, the term "nucleic acid" means any natural, synthetic, semi-synthetic or recombinant DNA or RNA molecule, optionally chemically modified (i.e. comprising non-natural bases, modified nucleotides with, for example, a modified bond, modified bases and/or modified sugars), or optimized so that the codons of transcripts synthesized from the coding sequences are the codons most frequently found in a bacterium of the genus *Clostridium* on order to use it therein. As explained above, in the case of the genus *Clostridium*, the optimized codons are typically codons rich in adenine ("A") and thymine ("T") bases.

Each of the nucleic acids present within the genetic tool according to the invention, typically the "first" nucleic acid and the "second" or "nth" nucleic acid, consists of a distinct entity and corresponds, for example, i) to an expression cassette (or "construction") such as a nucleic acid comprising at least one transcriptional promoter operably linked (as understood by the skilled person) to one or more sequences (coding) of interest, typically to an operon comprising several coding sequences of interest whose expression products contribute to the performance of a function of interest within the bacterium, or such as a nucleic acid further comprising an activation sequence and/or a transcription terminator; or ii) to a circular or linear, single- or double-stranded vector, for example a plasmid, a phage, a cosmid, an artificial or synthetic chromosome, comprising one or more expression cassettes as defined above. Preferably, the vector is a plasmid.

The nucleic acids of interest, typically expression cassettes and vectors, can be constructed by conventional techniques well-known to the skilled person and can comprise one or more promoters, bacterial origins of replication (ORI sequences), termination sequences, selection genes, for example antibiotic-resistance genes, and sequences ("flanking regions") allowing targeted insertion of the cassette or vector. In addition, these cassettes and expression vectors can be integrated into the genome using techniques well-known to the skilled person.

ORI sequences of interest can be chosen from pIP404, pAMβ1, repH (origin of replication in *C. acetobutylicum*), ColE1 or rep (origin of replication in *E. coli*), or any other origin of replication allowing the vector, typically the plasmid, to be maintained within a *Clostridium* cell.

In the context of the present invention, a preferred ORI sequence is that present within the OREP sequence (SEQ ID NO: 126) of plasmid pNF2 (SEQ ID NO: 118).

Termination sequences of interest can be chosen from those of the adc or thl genes, of the bcs operon, or of any other terminator, well-known to the skilled person, allowing transcription to be stopped within *Clostridium*.

Selection genes (resistance genes) of interest can be chosen from ermB, catP, bla, tetA, tetM, and/or any other gene for resistance to ampicillin, to erythromycin, to chloramphenicol, to thiamphenicol, to spectinomycin, to tetracycline or to any other antibiotic that can be used to select bacteria of the genus *Clostridium* well-known to persons skilled in the art.

A particular vector comprises one or more expression cassettes, each cassette encoding a gRNA.

In a particular embodiment, the invention concerns a genetic tool comprising as "first" nucleic acid as identified in the claims a plasmid vector whose sequence is that of SEQ ID NO: 23.

In a particular embodiment, the invention concerns a genetic tool comprising as "second" or "nth" nucleic acid a plasmid vector whose sequence is selected from one of the sequences SEQ ID NO: 79, SEQ ID NO: 80, SEQ ID NO: 119, SEQ ID NO: 123, SEQ ID NO: 124 and SEQ ID NO: 125.

In still another particular embodiment, the invention concerns a genetic tool comprising a plasmid vector whose sequence is selected from one of the sequences SEQ ID NO: 119, SEQ ID NO: 123, SEQ ID NO: 124 and SEQ ID NO: 125 as "OPT nucleic acid". In another particular embodiment, the genetic tool comprises several (for example at least two or three) sequences among SEQ ID NO: 23, 79, 80, 119, 123, 124 and 125, said sequences being different from each other.

The sequence of interest is introduced into the bacterial genome via a homologous recombination mechanism guided by a selected repair template (according to CRISPR technology). The sequence of interest replaces the targeted portion within the bacterial genome. The recombination process thus allows the total or partial modification or deletion of the targeted portion within the bacterium's genome or allows the insertion of nucleic acid fragments (in a particular embodiment large fragments) into the bacterium's genome. The selected repair template can include all or part of the targeted sequence of the bacterial genome or a more or less modified version thereof according to the nature of the desired transformation. Like the targeted portion of DNA, the template itself can thus include one or more nucleic acid sequences or nucleic acid sequence portions corresponding to natural and/or synthetic, coding and/or non-coding sequences. The template can also include one or more "foreign" sequences, i.e. sequences naturally absent from the genome of bacteria belonging to the genus *Clostridium* or from the genome of particular species of said genus. The template can also include a combination of sequences as described above.

The genetic tool according to the invention allows the repair template to guide the incorporation into the bacterial genome of bacteria of the genus *Clostridium* of a nucleic acid of interest, typically a DNA sequence or sequence portion comprising at least 1 base pair (bp), preferably at least 1, 2, 3, 4, 5, 10, 15, 20, 50, 100, 1,000, 10,000, 100,000 or 1,000,000 bp, typically between 1 bp and 20 kb or between 1 bp and 10 kb, preferably between 10 bp and 10 kb or between 1 kb and 10 kb, for example between 1 bp and 5 kb, between 2 kb and 5 kb, or between 2.5 or 3 kb and 5 kb.

The inventors describe examples of nucleic acid of interest, typically DNA sequences of interest, that allow the expression within a bacterium of a DNA sequence that is partially or completely absent from the genetic material present in the wild-type version of said bacterium.

In a particular embodiment, expression of the DNA sequence of interest allows the bacterium of the genus *Clostridium* to ferment (typically simultaneously) several different sugars, for example at least two different sugars, typically at least two different sugars among 5-carbon sugars (such as glucose or mannose) and/or among 6-carbon sugars (such as xylose, arabinose or fructose), preferably at least three different sugars, selected for example from glucose, xylose and mannose; glucose, arabinose and mannose; and glucose, xylose and arabinose.

In another particular embodiment, the DNA sequence of interest encodes at least one product of interest, preferably a product promoting solvent production by the bacterium of the genus *Clostridium*, typically at least one protein of interest, for example an enzyme; a membrane protein such as a transporter; a maturation protein of other proteins (chaperone protein); a transcription factor; or a combination thereof.

In a preferred embodiment, the DNA sequence of interest promotes solvent production and is typically selected from a sequence encoding i) an enzyme, for example an enzyme involved in the conversion of aldehydes to alcohol, for example selected from a sequence encoding an alcohol dehydrogenase (for example a sequence selected from adh, adhE, adhE1, adhE2, bdhA, bdhB and bdhC), a sequence encoding a transferase (for example a sequence selected from ctfA, ctfB, atoA and atoB), a sequence encoding a decarboxylase (for example adc), a sequence encoding a hydrogenase (for example a sequence selected from etfA, etfB and hydA), and a combination thereof, ii) a membrane protein, for example a sequence encoding a phosphotransferase (for example a sequence selected from glcG, bglC, cbe4532, cbe4533, cbe4982, cbe4983, cbe0751), iii) a transcription factor (for example a sequence selected from sigE, sigF, sigG, sigH, sigK) and iv) a combination thereof.

The inventors also describe examples of nucleic acid of interest recognizing (binding at least in part), and preferably targeting, i.e. recognizing and allowing the cleavage, in the genome of a bacterium of interest, of at least one strand i) of a target sequence, ii) of a sequence controlling the transcription of a target sequence, or iii) of a sequence flanking a target sequence.

The recognized sequence is also identified in the present text as "target sequence" or "targeted sequence".

A genetic tool comprising, or consisting of, such a nucleic acid of interest is also described. In this case, the nucleic acid of interest is typically present within the "second" or "nth" nucleic acid of a genetic tool as described in the present text.

The nucleic acid of interest is typically used in the context of the present description to remove the recognized sequence from the bacterium's genome or to modify its expression, for example to modulate/regulate its expression, in particular to inhibit it, preferably to modify it so as to render said bacterium incapable of expressing a protein, in particular a functional protein, from said sequence.

When the target sequence is a sequence encoding an enzyme that allows the bacteria of interest to grow in a culture medium containing an antibiotic to which it confers resistance, a sequence that controls the transcription of such a sequence or a sequence flanking such a sequence, the antibiotic is typically an antibiotic belonging to the class of amphenicols. Examples of amphenicols of interest in the context of the present description are chloramphenicol, thiamphenicol, azidamfenicol and florfenicol (Schwarz S. et al., 2004), in particular chloramphenicol and thiamphenicol.

In a particular embodiment, the nucleic acid of interest comprises at least one region complementary to the target sequence that is 100% identical or at least 80% identical, preferably 85%, 90%, 95%, 96%, 97%, 98% or 99% at least to the targeted DNA region/portion/sequence within the bacterial genome and is capable of hybridizing to all or part of the complementary sequence of said region/portion/sequence, typically to a sequence comprising at least 1 nucleotide, preferably at least 1, 2, 3, 4, 5, 10, 14, 15, 20, 25, 30, 35 or 40 nucleotides, typically between 1, 10 or 20 and 1000 nucleotides, for example between 1, 10 or 20 and 900, 800, 700, 600, 500, 400, 300 or 200 nucleotides, between 1, 10 or 20 and 100 nucleotides, between 1, 10 or 20 and 50 nucleotides, or between 1, 10 or 20 and 40 nucleotides, for example between 10 and 40 nucleotides, between 10 and 30 nucleotides, between 10 and 20 nucleotides, between 20 and 30 nucleotides, between 15 and 40 nucleotides, between 15 and 30 nucleotides or between 15 and 20 nucleotides, preferably a sequence comprising 14, 15, 16, 17, 18, 19, 20, 21, 22, 23, 24, 25, 26, 27, 28, 29 or 30 nucleotides. The complementary region of the target sequence present within the nucleic acid of interest may correspond to the "SDS" region of a guide RNA (gRNA) used in a CRISPR tool as described in the present text.

In another particular embodiment described, the nucleic acid of interest comprises at least two complementary regions each of a target sequence, 100% identical or at least 80% identical, preferably 85%, 90%, 95%, 96%, 97%, 98% or 99% at least to said targeted DNA region/portion/sequence within the bacterial genome. These regions are capable of hybridizing to all or part of the complementary sequence of said region/portion/sequence, typically to a sequence as described above comprising at least 1 nucleotide, preferably at least 100 nucleotides, typically between 100 and 1000 nucleotides. Regions complementary to the target sequence present within the nucleic acid of interest may recognize, preferably target, the 5' and 3' flanking regions of the target sequence in a genetic modification tool as described in the present text.

According to a particular aspect, the target sequence is a sequence encoding an amphenicol-O-acetyltransferase, for example a chloramphenicol-O-acetyltransferase or a thiamphenicol-O-acetyltransferase, controlling the transcription of such a sequence or flanking such a sequence, within the genome of a bacterium of interest, for example of the genus *Clostridium*, capable of growing in a culture medium containing one or more antibiotics belonging to the class of amphenicols, for example chloramphenicol and/or thiamphenicol.

The recognized sequence is for example sequence SEQ ID NO: 18 corresponding to the catB gene (CIBE_3859) encoding a chloramphenicol-O-acetyltransferase from *C. beijerinckii* DSM 6423 or an amino acid sequence at least 70%, 75%, 80%, 85%, 90% or 95% identical to said chloramphenicol-O-acetyltransferase, or a sequence comprising all or at least 70%, 75%, 80%, 85%, 90%, 95%, 96%, 97%, 98% or 99% of sequence SEQ ID NO: 18. Otherwise formulated, the recognized sequence may be a sequence comprising at least 1 nucleotide, preferably at least 1, 2, 3, 4, 5, 10, 15, 20, 25, 30, 35 or 40 nucleotides, typically between 1 and 40 nucleotides, preferably a sequence comprising 14, 15, 16, 17, 18, 19, 20, 21, 22, 23, 24, 25, 26, 27, 28, 29 or 30 nucleotides of sequence SEQ ID NO: 18.

Examples of amino acid sequences at least 70% identical to the chloramphenicol-O-acetyltransferase encoded by sequence SEQ ID NO: 18 correspond to the sequences identified in the NCBI database under the following references: WP_077843937.1, SEQ ID NO: 44 (WP_063843219.1), SEQ ID NO: 45 (WP_078116092.1), SEQ ID NO: 46 (WP_077840383.1), SEQ ID NO: 47 (WP_077307770.1), SEQ ID NO: 48 (WP_103699368.1), SEQ ID NO: 49 (WP_087701812.1), SEQ ID NO: 50 (WP_017210112.1), SEQ ID NO: 51 (WP_077831818.1), SEQ ID NO: 52 (WP_012059398.1), SEQ ID NO: 53 (WP_077363893.1), SEQ ID NO: 54 (WP_015393553.1), SEQ ID NO: 55 (WP_023973814.1), SEQ ID NO: 56

(WP_026887895.1), SEQ ID NO 57 (AWK51568.1), SEQ ID NO: 58 (WP_003359882.1), SEQ ID NO: 59 (WP_091687918.1), SEQ ID NO: 60 (WP_055668544.1), SEQ ID NO: 61 (KGK90159.1), SEQ ID NO: 62 (WP_032079033.1), SEQ ID NO: 63 (WP_029163167.1), SEQ ID NO: 64 (WP_017414356.1), SEQ ID NO: 65 (WP_073285202.1), SEQ ID NO: 66 (WP_063843220.1), and SEQ ID NO: 67 (WP_021281995.1).

Examples of amino acid sequences at least 75% identical to chloramphenicol-O-acetyltransferase encoded by SEQ ID NO: 18 correspond to sequences WP_077843937.1, WP_063843219.1, WP_078116092.1, WP_077840383.1, WP_077307770.1, WP_103699368.1, WP_087701812.1, WP_017210112.1, WP_077831818.1, WP_012059398.1, WP_077363893.1, WP_015393553.1, WP_023973814.1, WP_026887895.1 AWK51568.1, WP_003359882.1, WP_091687918.1, WP_055668544.1 and KGK90159.1.

Examples of amino acid sequences at least 90% identical to chloramphenicol-O-acetyltransferase encoded by SEQ ID NO: 18 are WP_077843937.1, WP_063843219.1, WP_078116092.1, WP_077840383.1, WP_077307770.1, WP_103699368.1, WP_087701812.1, WP_017210112.1, WP_077831818.1, WP_012059398.1, WP_077363893.1, WP_015393553.1, WP_023973814.1, WP_026887895.1 and AWK51568.1

Examples of amino acid sequences at least 95% identical to the chloramphenicol-O-acetyltransferase encoded by SEQ ID NO: 18 correspond to sequences WP_077843937.1, WP_063843219.1, WP_078116092.1, WP_077840383.1, WP_077307770.1, WP_103699368.1, WP_087701812.1, WP_017210112.1, WP_077831818.1, WP_012059398.1, WP_077363893.1, WP_015393553.1, WP_023973814.1, and WP_02688787895.1.

Preferred amino acid sequences, at least 99% identical to the chloramphenicol-O-acetyltransferase encoded by SEQ ID NO: 18, are WP_077843937.1, SEQ ID NO: 44 (WP_063843219.1) and SEQ ID NO: 45 (WP_078116092.1).

A particular sequence identical to SEQ ID NO: 18 is the sequence identified in the NCBI database as WP_077843937.1.

According to a particular example, the target sequence is sequence SEQ ID NO: 68 corresponding to the catQ gene encoding a chloramphenicol-O-acetyltransferase from *C. perfringens* whose amino acid sequence corresponds to SEQ ID NO: 66 (WP_063843220.1), or a sequence at least 70%, 75%, 80%, 80%, 85%, 90% or 95% identical to said chloramphenicol-O-acetyltransferase, or a sequence comprising all or at least 70%, 75%, 80%, 85%, 90%, 95%, 96%, 97%, 98% or 99% of sequence SEQ ID NO: 68.

Otherwise formulated, the recognized sequence may be a sequence comprising at least 1 nucleotide, preferably at least 1, 2, 3, 4, 5, 10, 15, 20, 25, 30, 35 or 40 nucleotides, typically between 1 and 40 nucleotides, preferably a sequence comprising 14, 15, 16, 17, 18, 19, 20, 21, 22, 23, 24, 25, 26, 27, 28, 29 or 30 nucleotides of sequence SEQ ID NO: 68.

According to still another particular example, the recognized sequence is selected from a nucleic acid sequence catB (SEQ ID NO: 18), catQ (SEQ ID NO: 68), catD (SEQ ID NO: 69, Schwarz S. et al., 2004) or catP (SEQ ID NO: 70, Schwarz S. et al., 2004) known to the skilled person, naturally present within a bacterium or artificially introduced into a such a bacterium.

As indicated above, according to another particular example, the target sequence may also be a sequence controlling the transcription of a coding sequence as described above (encoding an enzyme allowing the bacterium of interest to grow in a culture medium containing an antibiotic to which it confers resistance), typically a promoter sequence, for example the promoter sequence (SEQ ID NO: 73) of the catB gene or that (SEQ ID NO: 74) of the catQ gene.

The nucleic acid of interest then recognizes, and is therefore typically able to bind to, a sequence controlling the transcription of a coding sequence as described above.

According to another particular example, the target sequence may be a sequence flanking a coding sequence as described above, for example a sequence flanking the catB gene of sequence SEQ ID NO: 18 or a sequence at least 70% identical thereto. Such a flanking sequence typically comprises 1, 10 or 20 and 1000 nucleotides, for example between 1, 10 or 20 and 900, 800, 700, 600, 500, 400, 300 or 200 nucleotides, between 1, 10 or 20 and 100 nucleotides, between 1, 10 or 20 and 50 nucleotides, or between 1, 10 or 20 and 40 nucleotides, for example between 10 and 40 nucleotides, between 10 and 30 nucleotides, between 10 and 20 nucleotides, between 20 and 30 nucleotides, between 15 and 40 nucleotides, between 15 and 30 nucleotides or between 15 and 20 nucleotides.

According to a particular aspect, the target sequence corresponds to the pair of sequences flanking such a coding sequence, each flanking sequence typically comprising at least 20 nucleotides, typically between 100 and 1000 nucleotides, preferably between 200 and 800 nucleotides.

In the context of the present description, a particular example of nucleic acid of interest, used to transform and/or genetically modify a bacterium of interest, is a DNA fragment i) recognizing a coding sequence, ii) controlling the transcription of a coding sequence, or iii) flanking a coding sequence, an enzyme of interest, preferably an amphenicol-O-acetyltransferase, for example a chloramphenicol-O-acetyltransferase or a thiamphenicol-O-acetyltransferase, within the genome of a bacterium, for example a bacterium of the genus *Clostridium* as described above.

An example of nucleic acid of interest according to the invention is capable of removing the recognized sequence ("target sequence") from the bacterium's genome or modifying its expression, for example, modulating it, in particular inhibiting it, preferably modifying it so as to render said bacterium incapable of expressing a protein, for example an amphenicol-O-acetyltransferase, in particular a functional protein, from said sequence.

In a particular embodiment where the recognized sequence encoding an enzyme is a sequence that confers on the bacterium resistance to chloramphenicol and/or to thiamphenicol, the selection gene used is not a chloramphenicol and/or thiamphenicol resistance gene, and is preferably none of the catB, catQ, catD or catP genes.

In a particular embodiment, the nucleic acid of interest comprises one or more guide RNAs (gRNAs) targeting a coding sequence, controlling the transcription of a coding sequence, or flanking a coding sequence, an enzyme of interest, in particular an amphenicol-O-acetyltransferase, and/or a modification template (also identified in the present text as "editing template"), for example a template for removing or modifying all or part of the target sequence, preferably for the purpose of inhibiting or suppressing the expression of the target sequence, typically a template comprising sequences homologous (corresponding) to the sequences located upstream and downstream of the target sequence as described above, typically sequences (homologous to said sequences located upstream and downstream of the target sequence) each comprising between 10 or 20 base pairs and 1000, 1500 or 2000 base pairs, for example between 100, 200, 300, 400 or 500 base pairs and 1000, 1200, 1300, 1400 or 1500 base pairs, preferably between 100 and 1500 or between 100 and 1000 base pairs, and even more preferably between 500 and 1000 base pairs or between 200 and 800 base pairs.

In a particular embodiment, the nucleic acid of interest used to transform and/or genetically modify a bacterium of interest is a nucleic acid that does not have methylation at the motifs recognized by Dam and Dcm methyltransferases (prepared from an *Escherichia coli* bacterium having the dam-dcm-genotype).

When the bacterium of interest to be transformed and/or genetically modified is a *C. beijerinckii* bacterium, in particular belonging to one of subclades DSM 6423, LMG 7814, LMG 7815, NRRL B-593 and NCCB 27006, the nucleic acid of interest used as genetic tool, for example the plasmid, is a nucleic acid that does not have methylation at the motifs recognized by Dam and Dcm methyltransferases, typically a nucleic acid in which the adenosine ("A") of the GATC motif and/or the second cytosine ("C") of the CCWGG motif (W may correspond to adenosine ("A") or thymine ("T")) are demethylated.

A nucleic acid that does not have methylation at the motifs recognized by Dam and Dcm methyltransferases can typically be prepared from an *Escherichia coli* bacterium with the dam$^-$ dcm$^-$ genotype (for example *Escherichia coli* INV 110, Invitrogen). The same nucleic acid may have other methylations, for example, by EcoKI methyltransferases, the latter targeting adenines ("A") of the motifs AAC(N6) GTGC and GCAC(N6)GTT (N may correspond to any base).

In a particular embodiment, the targeted sequence corresponds to a gene encoding an amphenicol-O-acetyltransferase, for example a chloramphenicol-O-acetyltransferase such as the catB gene, a sequence controlling the transcription of this gene, or a sequence flanking this gene.

A particular nucleic acid of interest described by the inventors is for example a vector, preferably a plasmid, for example plasmid pCas9ind-ΔcatB of sequence SEQ ID NO: 21 or plasmid pCas9ind-gRNA_catB of sequence SEQ ID NO: 38 described in the experimental section of the present description (see example 2), in particular a version of said sequence which does not have methylation at the motifs recognized by Dam and Dcm methyltransferases.

The present description also comprises the use of a nucleic acid of interest to transform and/or genetically modify a bacterium of interest as described in the present text.

The present invention also concerns a process for transforming, and typically genetically modifying by homologous recombination, a bacterium of the genus *Clostridium*, preferably a solventogenic bacterium of the genus *Clostridium*. This process advantageously comprises a step of transforming the bacterium by introducing into said bacterium a genetic tool according to the invention as described in the present application, preferably an "OPT nucleic acid" comprising, or consisting of, i) all or part of sequence SEQ ID NO: 126 (OREP) and ii) a sequence allowing the modification of the genetic material of a bacterium and/or the expression within said bacterium of a DNA sequence partially or totally absent from the genetic material present in the wild-type version of said bacterium. The process can further comprise a step of obtaining, recovering, selecting or isolating the transformed bacterium, i.e. the bacterium having the desired recombination(s)/modification(s)/optimization(s).

The present invention is typically advantageously implemented when the genetic modification tool selected to transform, and preferably to genetically modify, a bacterium of the genus *Clostridium*, is intended to be used on a bacterium, such as *C. beijerinckii*, a carrier in the wild-type state of a gene encoding an enzyme responsible for resistance to one or more antibiotics and/or a carrier in the wild-type state of at least one extra-chromosomal DNA sequence, and that the implementation of said genetic tool comprises a step of transforming said bacterium using a nucleic acid allowing the expression of a marker of resistance to an antibiotic to which said bacterium is resistant in the wild-type state and/or a step of selecting bacteria transformed and/or genetically modified using said antibiotic (to which the bacterium is resistant in the wild-type state), preferably selecting, among said bacteria, bacteria that have lost said extra-chromosomal DNA sequence.

A modification advantageously achievable with the present invention, typically using a CRISPR genetic modification tool, consists in removing an undesirable sequence, for example a sequence encoding an enzyme that gives the bacterium resistance to one or more antibiotics, or in rendering that undesirable sequence non-functional. Another modification advantageously achievable through the present invention consists in genetically modifying a bacterium in order to improve its performance, for example its performance in the production of a solvent or mixture of solvents of interest, said bacterium having already been previously modified through the invention to make it sensitive to an antibiotic to which it was resistant in the wild-type state, and/or to clean it of an extra-chromosome DNA sequence present in the wild-type form of said bacterium.

The process according to the invention is based on the use of (implements) the CRISPR (Clustered Regularly Interspaced Short Palindromic Repeats) genetic tool/technology, in particular the CRISPR/Cas (CRISPR-associated protein) genetic tool.

The present invention can be implemented using a conventional CRISPR/Cas genetic tool using a single plasmid comprising a nuclease, a gRNA and a repair template as described by Wang et al. (2015).

The sequence and structure of gRNAs can be easily defined by the skilled person according to the chromosomal region or mobile genetic element to be targeted using well-known techniques (see for example the article by DiCarlo et al., 2013).

The inventors have developed and described a genetic tool for modifying bacteria, adapted to bacteria of the genus *Clostridium*, which can also be used in the context of the present invention, based on the use of two plasmids (see WO2017/064439, Wasels et al., 2017, and FIG. 15 associated with the present description).

In a particular embodiment, the "first" plasmid of this tool allows the expression of the Cas nuclease and a "second" plasmid, specific to the modification to be performed, contains one or more gRNA expression cassettes (typically targeting different regions of bacterial DNA) as well as a repair template allowing, by a homologous recombination mechanism, the replacement of a portion of the bacterial DNA targeted by Cas with a sequence of interest. The cas gene and/or the gRNA expression cassette(s) are placed under the control of constitutive or inducible expression promoters, preferably inducible, known to the skilled person (for example described in application WO2017/064439 and incorporated by reference to the present description), and preferably different but inducible by the same inducer.

The gRNA that may be used correspond to the gRNA as described above in the present text.

A particular process according to the invention for transforming, and typically genetically modifying by homologous recombination, a solventogenic bacterium of the genus *Clostridium*, comprises, in order, the following steps:
a) introducing into the bacterium a nucleic acid or a genetic tool as described in the present application in the presence of an inducer of expression of the anti-CRISPR protein, and
b) culturing the transformed bacterium obtained at the end of step a) on a medium not containing (or under conditions not involving) the inducer of expression of the anti-CRISPR protein, typically allowing the expression of the DNA endonuclease/gRNA ribonucleoprotein complex, typically Cas/gRNA (in order to stop the production of said anti-CRISPR protein and to allow the action of the endonuclease).

The elements (nucleic acids or gRNA) of the genetic tool according to the invention are introduced into the bacterium by any method, direct or indirect, known to the skilled person, for example by transformation, conjugation, microinjection, transfection, electroporation, etc., preferably by electroporation (Mermelstein et al., 1993).

The inducer of expression of the anti-CRISPR protein is present in sufficient quantity to induce said expression. In the case of the Pbgal promoter, the inducer, lactose, releases the inhibition of expression (transcriptional repression) of the anti-CRISPR protein linked to the expression of the BgaR protein.

The inducer of expression of the anti-CRISPR protein is preferably used at a concentration comprised between about 1 mM and about 1 M, preferably between about 10 mM and about 100 mM, for example about 40 mM.

In a preferred embodiment, the anti-CRISPR protein is capable of inhibiting, preferably neutralizing, the action of the nuclease, preferably during the phase of introducing the nucleic acid sequences of the genetic tool into the bacterial strain of interest.

As demonstrated in the experimental section, the invention advantageously allows the transformation of bacteria of the genus *Clostridium* containing a Cas9 expression cassette and an expression cassette for an anti-CRISPR protein such as AcrIIA4 with any nucleic acid containing a gRNA expression cassette.

The transformed bacterium obtained at the end of step a) of the process described above is then grown on a medium not containing the inducer of expression of the anti-CRISPR protein (in order to stop the production of said anti-CRISPR protein and to allow the action of the nuclease).

In a particular embodiment, the process further comprises, during or after step b), a step of inducing the expression of the inducible promoter(s) controlling the expression of the nuclease and/or of the guide RNA(s) when such promoter(s) is/are present within the genetic tool, in order to allow the genetic modification of interest to the bacterium once said genetic tool is introduced into said bacterium. Induction is typically performed using a substance that releases the inhibition of expression related to the selected inducible promoter.

The induction step, when present, can be carried out by any culture method on a medium allowing the expression of the DNA endonuclease/gRNA ribonucleoprotein complex known to the skilled person after introducing into the target bacteria the genetic tool according to the invention. It is carried out, for example, by bringing the bacteria into contact with a suitable substance, present in sufficient amount, or by exposure to UV light. This substance releases the inhibition of expression associated with the selected inducible promoter. When the selected promoter is an anhydrotetracycline (aTc)-inducible promoter, chosen from Pcm-2tetO1 and Pcm-tetO2/1, aTc is preferably used at a concentration comprised between about 1 ng/mL and about 5000 ng/mL, preferably between about 10 ng/mL and 1000 ng/mL, 10 ng/mL and 800 ng/mL, 10 ng/mL and 500 ng/mL, 100 ng/mL or 200 ng/mL and about 800 ng/mL or 1000 ng/mL, or between about 100 ng/mL or 200 ng/mL and about 500 ng/mL, 600 ng/mL or 700 ng/mL, for example about 50 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL or 800 ng/mL. In a particular embodiment, aTc is preferably used at a concentration comprised between about 200 ng/mL and about 1000 ng/mL or between about 200 ng/mL and about 800 ng/mL, for example about 500 ng/mL.

In a particular embodiment, the process comprises an additional step c) of removing the nucleic acid containing the repair template (the bacterial cell being then considered as "cleaned" of said nucleic acid) and/or removing the guide RNA(s) or sequences encoding the guide RNA(s) introduced with the genetic tool during step a).

In another particular embodiment, the process comprises one or more additional steps, subsequent to step b) or to step c), of introducing an nth—for example a third, fourth, fifth, etc.—nucleic acid containing a repair template distinct from the one(s) already introduced and one or more guide RNA expression cassettes allowing the integration of the sequence of interest contained in said distinct repair template into a targeted area of the bacterium's genome, in the presence of an inducer of expression of the anti-CRISPR protein, each additional step being followed by a step of culturing the bacterium thus transformed on a medium not containing the inducer of expression of the anti-CRISPR protein, typically allowing the expression of the Cas/gRNA ribonucleoprotein complex, for example Cas9/gRNA.

In a particular embodiment of the process according to the invention, the bacterium is transformed using a nucleic acid or a genetic tool such as those described above, using (for example, encoding) an enzyme responsible for cleaving at least one strand of the target sequence of interest, wherein the enzyme is in a particular embodiment a nuclease, preferably a Cas nuclease, preferentially selected from a Cas9 enzyme and a MAD7 enzyme. In an exemplary embodiment, the target sequence of interest is a sequence, for example the catB gene, encoding an enzyme that confers on the bacterium resistance to one or more antibiotics, preferably one or more antibiotics belonging to the class of amphenicols, typically an amphenicol-O-acetyltransferase such as a chloramphenicol-O-acetyltransferase, a sequence controlling the transcription of the coding sequence or a sequence flanking said coding sequence.

When used, the anti-CRISPR protein is typically an "anti-Cas" protein as described above. The anti-CRISPR protein is advantageously an "anti-Cas9" protein or an "anti-MAD7" protein.

Like the targeted DNA portion ("recognized sequence"), the editing/repair template may itself include one or more nucleic acid sequences or portions of nucleic acid sequence corresponding to natural and/or synthetic, encoding and/or non-coding sequences. The template may also include one or more "foreign" sequences, i.e. naturally absent from the genome of bacteria belonging to the genus *Clostridium*, or from the genome of particular species of said genus. The template can also include a combination of sequences.

The genetic tool used in the present invention allows the repair template to guide the incorporation into the bacterial genome of a nucleic acid of interest, typically a DNA sequence or sequence portion comprising at least 1 base pair (bp), preferably at least 1, 2, 3, 4, 5, 10, 15, 20, 50, 100, 1000, 10,000, 100,000 or 1,000,000 bp, typically between 1 bp and 20 kb, for example 2, 3, 4, 5, 6, 7, 8, 9, 10, 11, 12 or 13 kb, or between 1 bp and 10 kb, preferably between 10 bp and 10 kb or between 1 kb and 10 kb, for example between 1 bp and 5 kb, between 2 kb and 5 kb, or between 2.5 or 3 kb and 5 kb.

In a particular embodiment, the expression of the DNA sequence of interest allows the bacterium belonging to the phylum Firmicutes, in particular of the genus *Clostridium*, the genus *Bacillus* or the genus *Lactobacillus*, to ferment (typically simultaneously) several different sugars, for example at least two different sugars, typically at least two different sugars among 5-carbon sugars (such as glucose or mannose) and/or among 6-carbon sugars (such as xylose, arabinose or fructose), preferably at least three different sugars, selected for example from glucose, xylose and mannose; glucose, arabinose and mannose; and glucose xylose and arabinose.

In another particular embodiment, the DNA sequence of interest encodes at least one product of interest, preferably a product promoting solvent production by the modified bacterium, typically at least one protein of interest, for example an enzyme; a membrane protein such as a transporter; a maturation protein of other proteins (chaperone protein); a transcription factor; or a combination thereof.

Particularly advantageously, the genetic tool according to the invention allows the introduction of both small and large sequences of interest, in one step, i.e. using a single nucleic acid (typically the "OPT nucleic acid", the "second" or the "nth" nucleic acid as described in the present text) or in several steps, i.e. using several nucleic acids (typically the "second" and the "nth" nucleic acids as described in the present text), preferably in one step.

In a particular embodiment of the invention, the nucleic acids such as this "nth" nucleic acid, and genetic tools described in the present text, allow the targeted portion of the bacterial DNA to be removed or to be replaced with a sequence that is shorter (for example by a sequence from which at least one base pair has been deleted) and/or non-functional. In a particular preferred embodiment of the invention, the "second" or "nth" nucleic acid advantageous introduces into the bacterium, for example into the bacterial genome, a nucleic acid of interest comprising at least one base pair, and up to 2, 3, 4, 5, 6, 7, 8, 9, 10, 11, 12, 13, 14 or 15 kb.

The nucleic acids of interest can be inserted into the bacterial chromosome in identical or different regions depending on the gRNAs used.

By virtue of the invention, typically by virtue of the genetic tool and the process according to the invention, it is now possible to systematically transform, and to modify effectively (high frequency of homologous recombination), substantially (possible incorporation into the bacterium's genome of a large nucleic acid of interest) and stably (no need to maintain the transformed bacteria in contact with antibiotics), bacteria of the genus *Clostridium* so as to obtain transformed bacteria of interest, for example improved mutants with a genotypic or phenotypic difference compared to the bacteria from which they are derived, typically industrially-useful bacteria, for example bacteria useful in the production of solvents or biofuels.

Another object of the invention concerns a bacterium of the genus *Clostridium*, typically a solventogenic bacterium of the genus *Clostridium*, obtained using the process and/or transformed and ideally genetically modified using the genetic tool according to the invention, as well as any derived bacteria, clone, mutant, or genetically modified version thereof, and uses thereof. Such a bacterium expresses the nucleic acid(s) of interest introduced into its genome by homologous recombination using the repair template. Such a bacterium may comprise all or part of the genetic tool according to the invention, typically a nuclease such as Cas9 or a nucleic acid encoding a nuclease such as Cas9.

An exemplary bacterium thus transformed and/or genetically modified by the invention is a bacterium that no longer expresses an enzyme that gives it resistance to one or more antibiotics, in particular a bacterium that no longer expresses an amphenicol-O-acetyltransferase, for example a bacterium that in the wild-type state expresses the catB gene, and is devoid of said catB gene or is unable to express said catB gene once transformed and/or genetically modified by the invention. The bacterium thus transformed and/or genetically modified through the invention is made sensitive to an amphenicol, for example to an amphenicol as described in the present text, in particular to chloramphenicol or to thiamphenicol.

A particular example of a preferred genetically modified bacterium according to the invention is the bacterium identified in the present description as *C. beijerinckii* IFP962 ΔcatB (also identified herein as *C. beijerinckii* DSM6423 ΔcatB) as registered under deposit number LMG P-31151 with the Belgian Co-ordinated Collections of Micro-organisms ("BCCM", K. L. Ledeganckstraat 35, B-9000 Gent—Belgium) on 6 Dec. 2018.

Another particular example of a preferred genetically modified bacterium according to the invention is the bacterium identified in the present description as *C. beijerinckii* is strain *C. beijerinckii* IFP963 ΔcatB ΔpNF2 as registered under deposit number LMG P-31277 with the BCCM-LMG collection on Feb. 20, 2019.

The description also concerns any derived bacteria, clone, mutant or genetically modified version of one of said bacteria, for example any derived bacteria, clone, mutant or genetically modified version remaining sensitive to an amphenicol such as thiamphenicol and/or chloramphenicol.

According to a particular embodiment, the bacteria transformed and/or genetically modified according to the invention, for example *C. beijerinckii* DSM 6423 ΔcatB or *C. beijerinckii* DSM6423 ΔcatB ΔpNF2, is still able to be transformed, and preferably genetically modified. It can be done with a nucleic acid, for example a plasmid as described in the present description, for example in the experimental section. An exemplary nucleic acid that could be advantageously used is plasmid pCas9$_{acr}$ of sequence SEQ ID NO: 23 (described in the experimental section of the present description) or a plasmid selected from pCas9$_{ind}$ (SEQ ID NO: 22), pCas9$_{cond}$ (SEQ ID NO: 133) and pMAD7 (SEQ ID NO: 134).

A particular aspect of the invention concerns the use of a genetically modified bacterium described in the present text, preferably the bacterium *C. beijerinckii* IFP962 ΔcatB deposited under number LMG P-31151, more preferably *C. beijerinckii* IFP963 ΔcatB ΔpNF2 registered under number LMG P-31277, or a genetically modified version of one of these, for example using one of the nucleic acids, genetic tools or processes described in the present text, to produce, thanks to the expression of the nucleic acid(s) of interest intentionally introduced into its genome, one or more solvents, preferably at least isopropanol, preferably on an industrial scale.

In a particular embodiment, the bacterium of the genus *Clostridium* according to the invention, obtained using the process and the genetic tool according to the invention, is able to produce one or more solvents only owing to the expression of the nucleic acid or acids of interest intentionally introduced into its genome.

The invention also concerns a kit for transforming, and typically genetically modifying, a bacterium of the genus *Clostridium* comprising all or part of the elements of the genetic tool as described in the present text, typically i) a first nucleic acid encoding one DNA endonuclease such as Cas9, in which the sequence encoding the endonuclease is placed under the control of a promoter, and ii) at least a second nucleic acid encoding a repair template allowing, by a homologous recombination mechanism, the replacement of a portion of the bacterial DNA targeted by the endonuclease by a sequence of interest, and at least one inducer adapted to the inducible promoter of expression of the selected anti-CRISPR protein used within the tool. The kit may also include one or more inducers adapted to the selected inducible promoter(s) optionally used within the tool to control the expression of the endonuclease and/or of one or more guide RNAs.

Also described is a kit is comprising (i) a nucleic acid as described in the present text, for example an "OPT nucleic acid" or a DNA fragment recognizing a target sequence in a bacterium as described in the present text, and (ii) at least one tool, preferably several tools, selected from the elements of a genetic modification tool as described in the present text to transform, and typically genetically modify, such a bacterium, in order to produce an improved variant of said bacterium; a nucleic acid as gRNA; a nucleic acid as repair matrix; an "OPT nucleic acid"; at least one pair of primers, for example a pair of primers as described in the context of the present invention; and an inducer for expressing a protein encoded by said tool, for example a Cas9 or MAD7 nuclease.

The genetic modification tool to transform, and typically genetically modify, a bacterium as described in the present text, may for example be selected from an "OPT nucleic acid", a CRISPR tool, a tool based on the use of type II introns and an allelic exchange tool, as explained above.

In a particular embodiment, the kit comprises all or some of the elements of a genetic tool as described in the present text.

A particular kit for transforming, and preferably genetically modifying, a bacterium belonging to phylum Firmicutes as described in the present text, or for producing at least one solvent, for example a mixture of solvents, using such a bacterium, comprises a nucleic acid comprising, or consisting of, i) all or part of sequence SEQ ID NO: 126 and ii) a sequence allowing the modification of the genetic material of a bacterium and/or the expression within said bacterium of a DNA sequence partially or totally absent from the genetic material present in the wild-type version of said bacterium; and at least one inducer adapted to the inducible promoter of expression of the selected anti-CRISPR protein used within a genetic tool described in the present text.

The kit may also include one or more inducers adapted to the selected inducible promoter(s) optionally used within the genetic tool to control the expression of the nuclease used and/or of one or more guide RNAs.

A particular kit according to the invention allows the expression of an endonuclease, for example a Cas9 or MAD7 protein comprising a tag.

The kits according to the invention can further comprise one or more consumables such as a culture medium, at least one competent bacterium of the genus *Clostridium* (i.e. packaged for transformation), at least one gRNA, a nuclease, for example a Cas9 or MAD7 protein, one or more selection molecules, or a set of instructions.

The invention typically concerns a kit for carrying out the process of transformation and ideally of genetic modification described in the present text, and/or for producing solvent(s) (at least one solvent) using a bacterium of the genus *Clostridium*.

The invention also concerns the potential uses of the nucleic acids, of the genetic tool, of the process, or of the kit according to the invention to transform, and typically genetically modify, a bacterium of the genus *Clostridium*, typically a solventogenic bacterium of the genus *Clostridium*, for example to generate improved variants of a bacterium of the genus *Clostridium*.

The description concerns in particular the use of a kit according to the invention, or of one or more of the elements of this kit, to implement a process described in the present text of transformation, and ideally of genetic modification, of a bacterium as described in the present text, typically a bacterium of the genus *Clostridium* (for example, *C. beijerinckii* IFP962 ΔcatB deposited under the number LMG P-31151), preferably a bacterium having in the wild-type state both a bacterial chromosome and at least one DNA molecule distinct from chromosomal DNA (typically a natural plasmid), most preferably the bacterium *C. beijerinckii* IFP963 ΔcatB ΔpNF2 bacteria deposited under number LMG P-31277.

Finally, the invention concerns the potential uses of the nucleic acids, of the genetic tool, of the process, of the kit or of the bacterium of the genus *Clostridium* transformed according to the invention, in particular to enable the production of solvent(s) or biofuel(s), or mixtures thereof, typically on an industrial scale. Solvents that can be produced are typically acetone, butanol, ethanol, isopropanol or a mixture thereof, typically an ethanol/isopropanol, butanol/isopropanol, or ethanol/butanol mixture, preferably an isopropanol/butanol mixture.

In a particular embodiment, the ratio of the ethanol/isopropanol mixture is at least equal to 1/4. This ratio is preferably comprised between 1/3 and 1, and is more preferably equal to 1.

In a particular embodiment, the ratio of the ethanol/butanol mixture is at least equal to 1/4. This ratio is preferably comprised between 1/3 and 1, and is more preferably equal to 1.

In a particular embodiment, the ratio of the isopropanol/butanol mixture is at least equal to 1/4. This ratio is preferably comprised between 1/3 and 1, and is more preferably equal to 1.

The use of transformed bacteria according to the invention typically allows the annual industrial production on an industrial scale of at least 100 tons of acetone, at least 100 tons of ethanol, at least 1000 tons of isopropanol, at least 1800 tons of butanol, or at least 40,000 tons of a mixture thereof.

The following examples and figures are intended to illustrate the invention more fully without limiting its scope.

gRNA, guide RNA; PAM, protospacer adjacent motif. Figure modified from Jinek et al., 2012.

Figure 1:
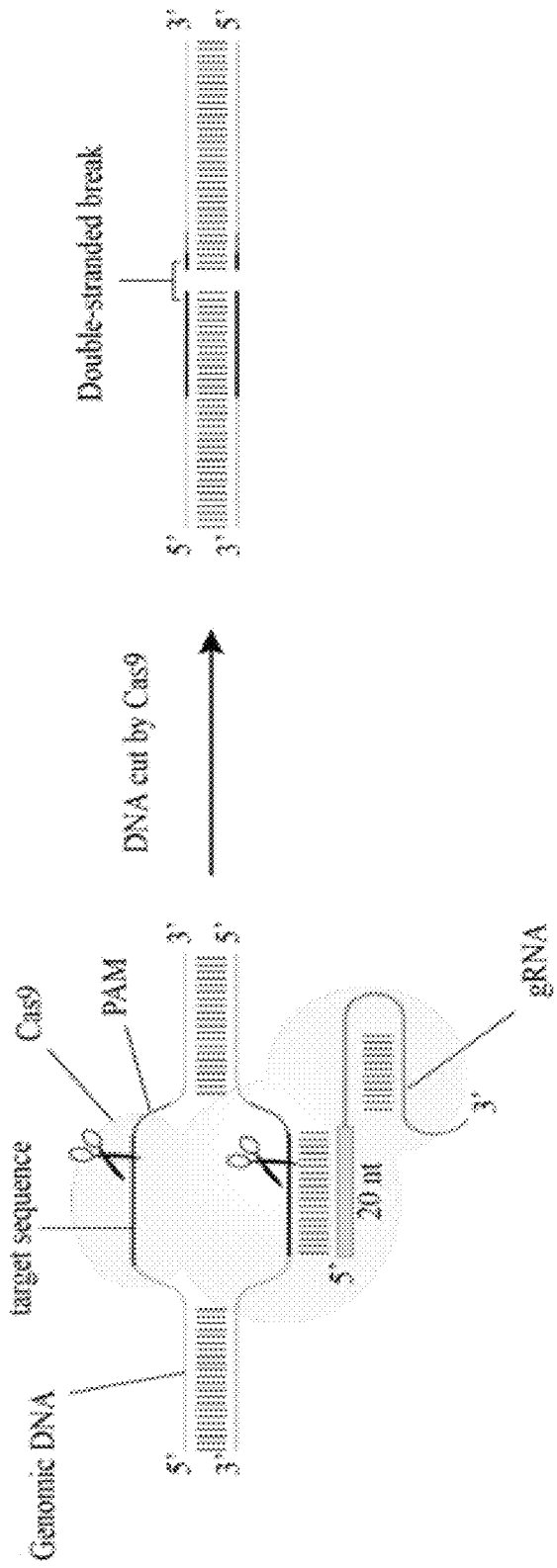
FIG. 1: CRISPR/Cas9 system used for genome editing as a genetic tool to create, using Cas9 nuclease, one or more double-stranded cuts in genomic DNA directed by gRNA.
Figure 2:
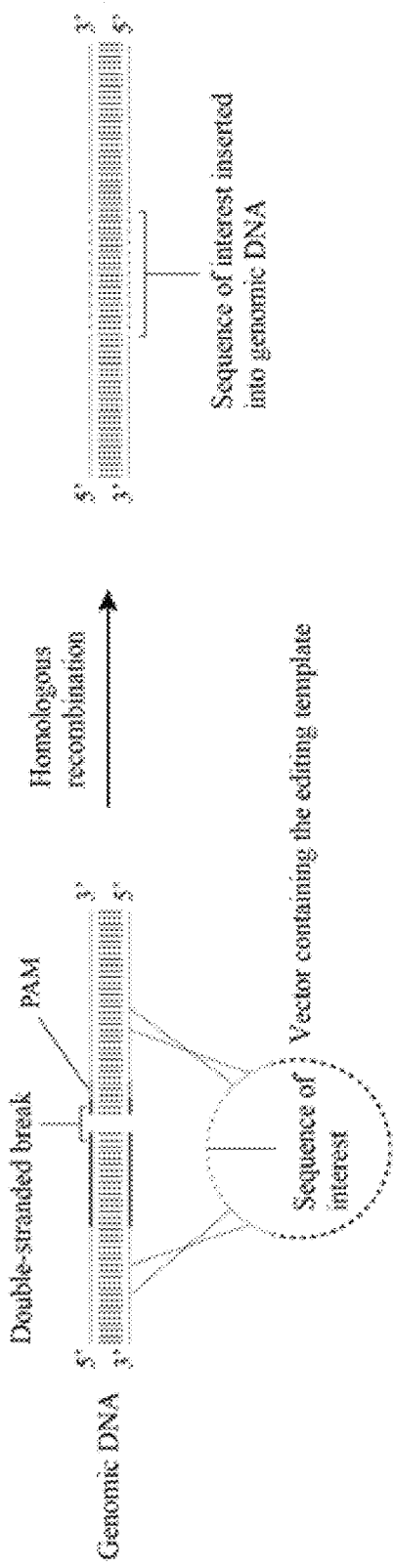

FIG. 2: Repair by homologous recombination of a Cas9-induced double-stranded cut. PAM, protospacer adjacent motif.

Figure 3:
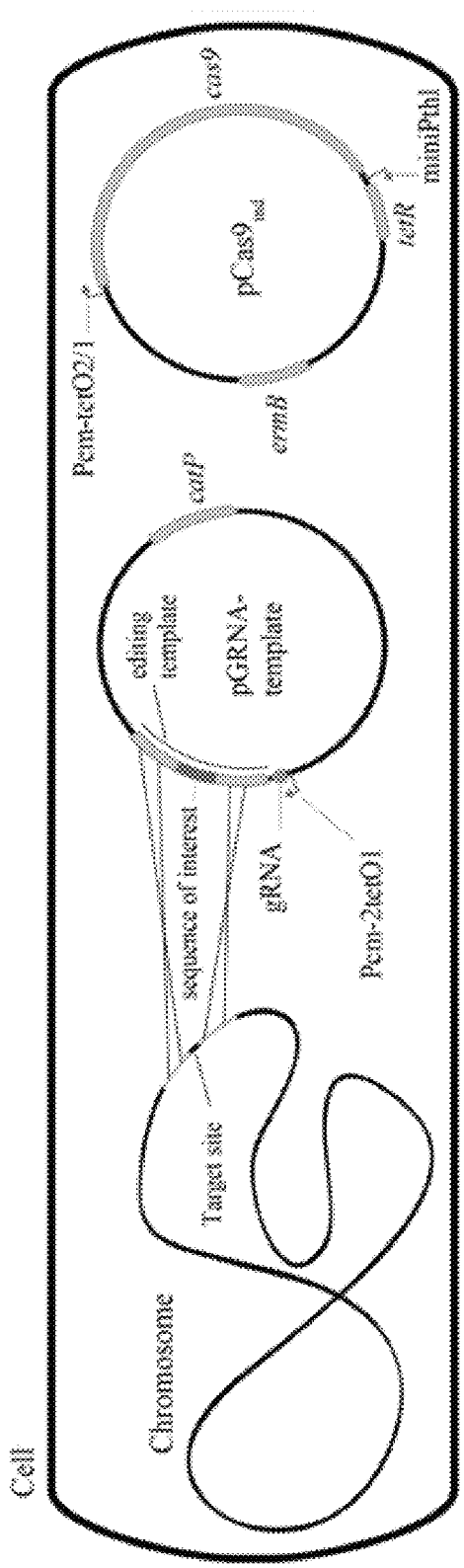

FIG. 3: Use of CRISPR/Cas9 in *Clostridium*.

ermB, erythromycin resistance gene; catP (SEQ ID NO: 70), thiamphenicol/chloramphenicol resistance gene; tetR, gene whose expression product represses transcription from Pcm-tetO2/1; Pcm-2tetO1 and Pcm-tetO2/1, anhydrotetracycline (aTc)-inducible promoters (Dong et al., 2012); miniPthl, constitutive promoter (Dong et al., 2012).

Figure 4:
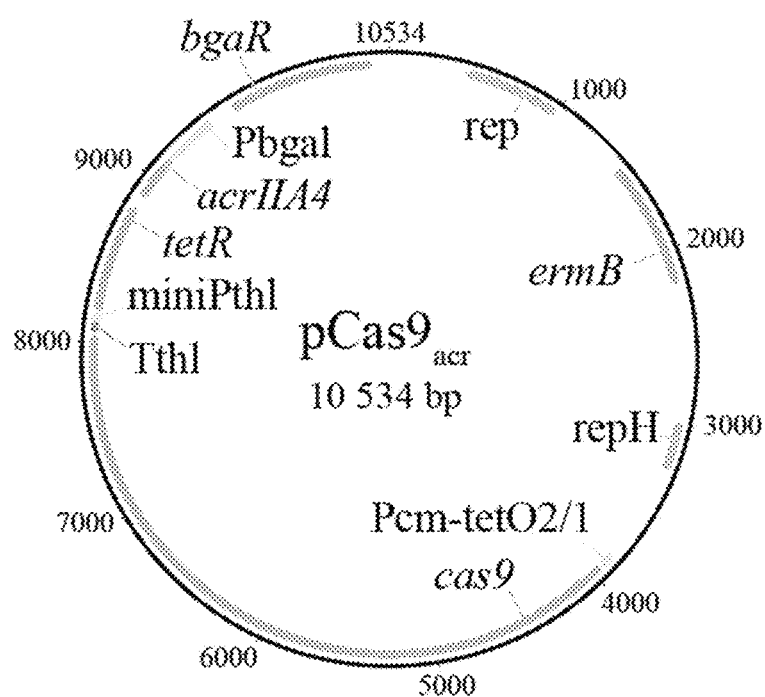

FIG. 4: pCas9$_{acr}$ plasmid map (SEQ ID NO: 23).

ermB, erythromycin resistance gene; rep, origin of replication in *E. coli*; repH, origin of replication in *C. acetobutylicum*; Tthl, thiolase terminator; miniPthl, constitutive promoter (Dong et al., 2012); Pcm-tetO2/1, promoter repressed by the product of tetR and inducible by anhydrotetracycline (aTc) (Dong et al., 2012); Pbgal, a promoter repressed by the product of lacR and inducible by lactose (Hartman et al., 2011); acrIIA4, gene encoding the anti-CRISPR protein AcrII14; bgaR, gene whose expression product represses transcription from Pbgal.

Figure 5:
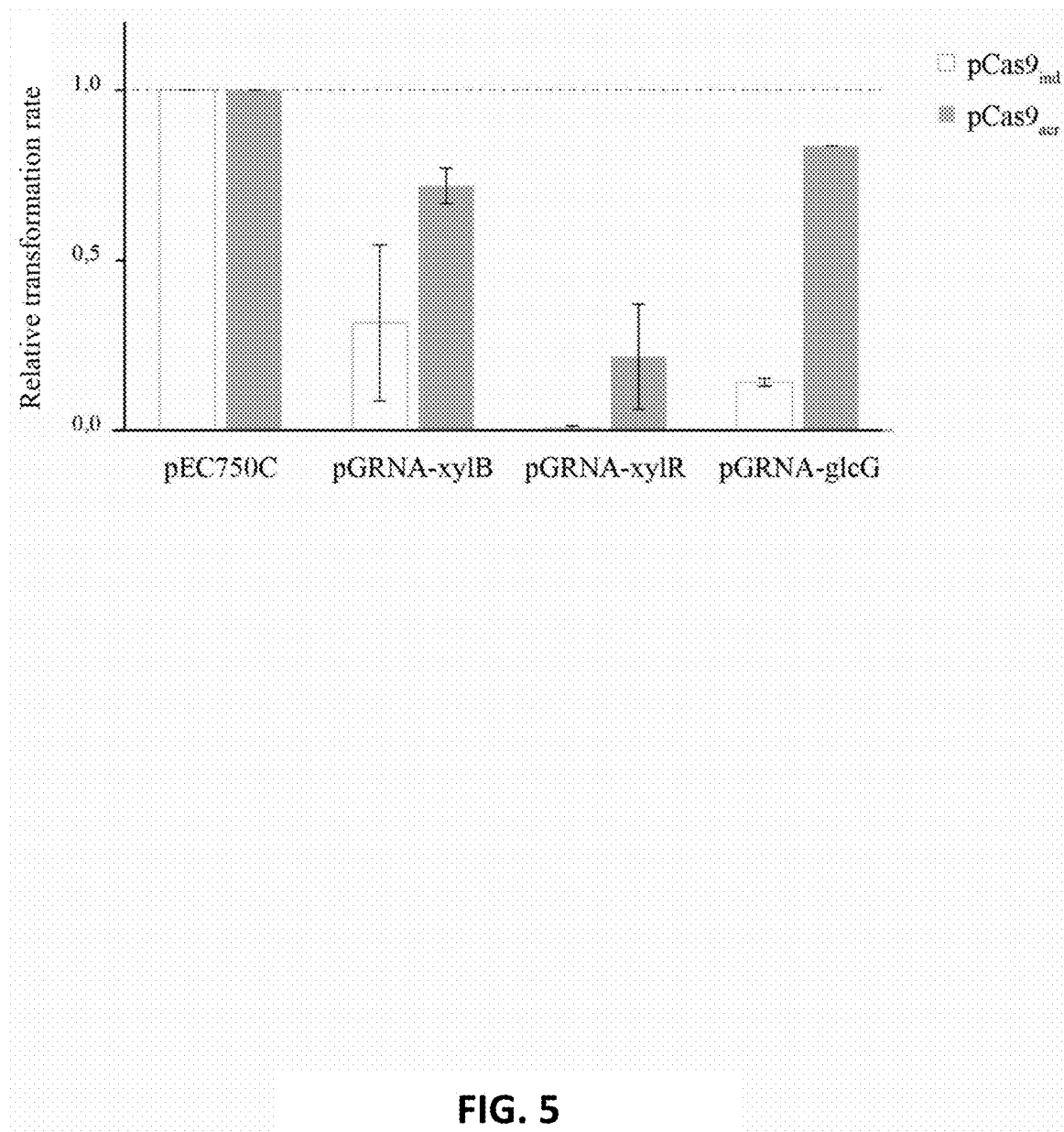

FIG. 5: Relative transformation rates of *C. acetobutylicum* DSM 792 containing pCas9$_{ind}$ (SEQ ID NO: 22) or pCas9$_{acr}$ (SEQ ID NO: 23). Frequencies are expressed as the number of transformants obtained per μg of DNA used in the transformation, in relation to the transformation frequencies of pEC750C (SEQ ID NO: 106), and represent the means of at least two independent experiments.

Figure 6:
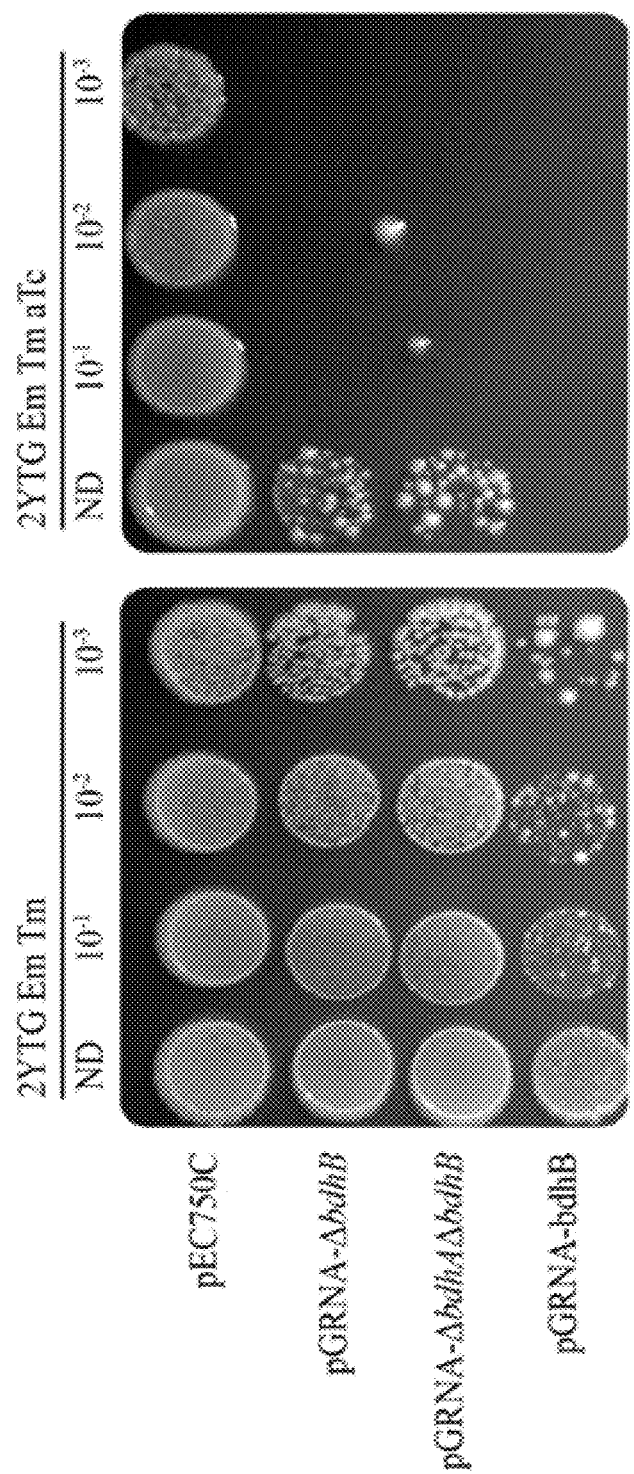

FIG. 6: Induction of the CRISPR/Cas9 system in strain DSM 792 transformants containing pCas9$_{acr}$ and an expression plasmid for the gRNA targeting bdhB, with (SEQ ID NO: 79 and SEQ ID NO: 80) or without (SEQ ID NO: 105) repair template. Em, erythromycin; Tm, thiamphenicol; aTc, anhydrotetracycline; ND, not diluted.

Figure 7:
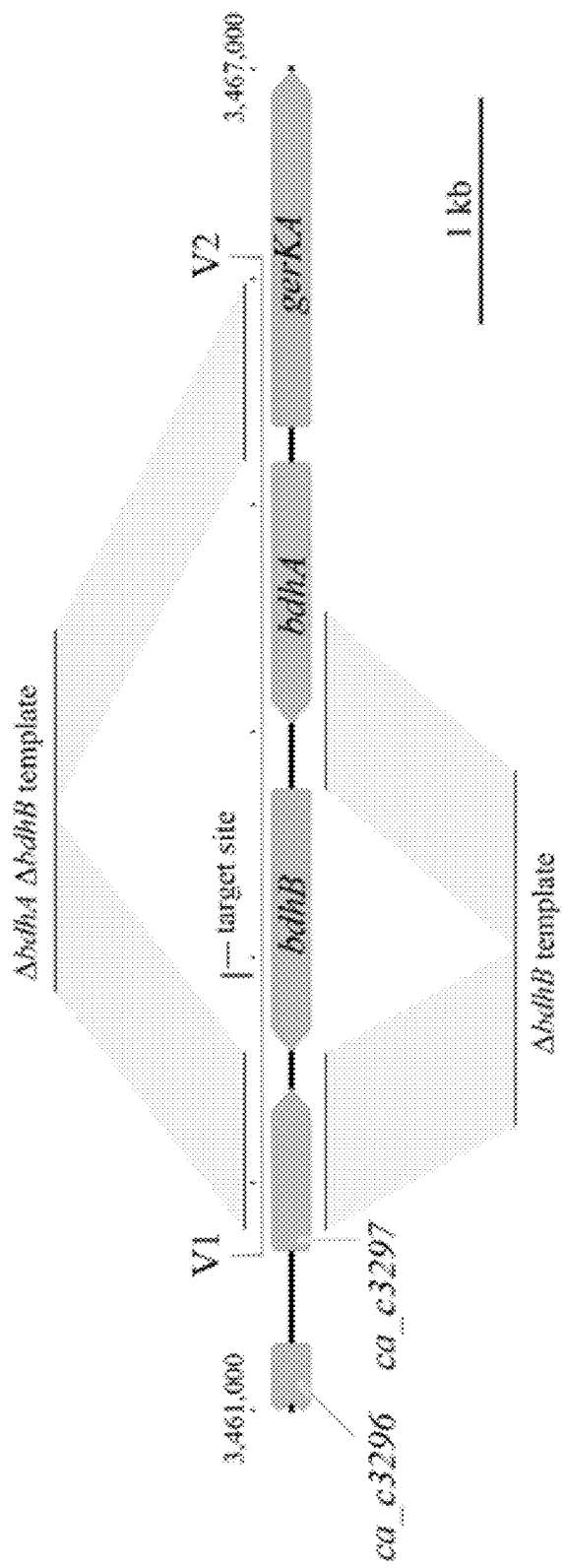
Figure 7:
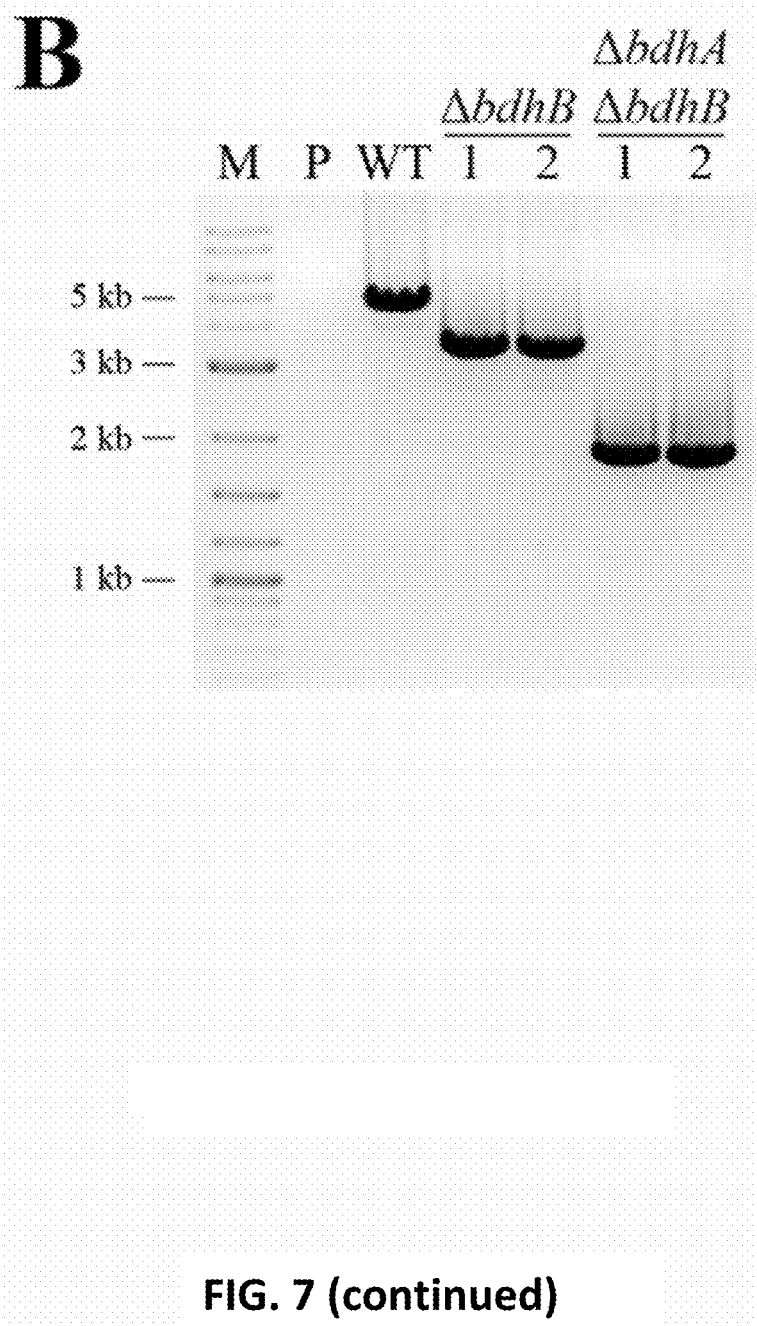

FIG. 7: Modification of the bdh locus of *C. acetobutylicum* DSM792 via the CRISPR/DNA endonuclease system.

A, genetic organization of the bdh locus. Homologies between repair template and genomic DNA are indicated with light gray parallelograms. The hybridization sites of primers V1 and V2 are also shown.

B, amplification of the bdh locus using primers V1 and V2. M, 2-log size marker (NEB); P, pGRNA-ΔbdhAΔbdhB plasmid; WT, wild-type strain.

Figure 8:
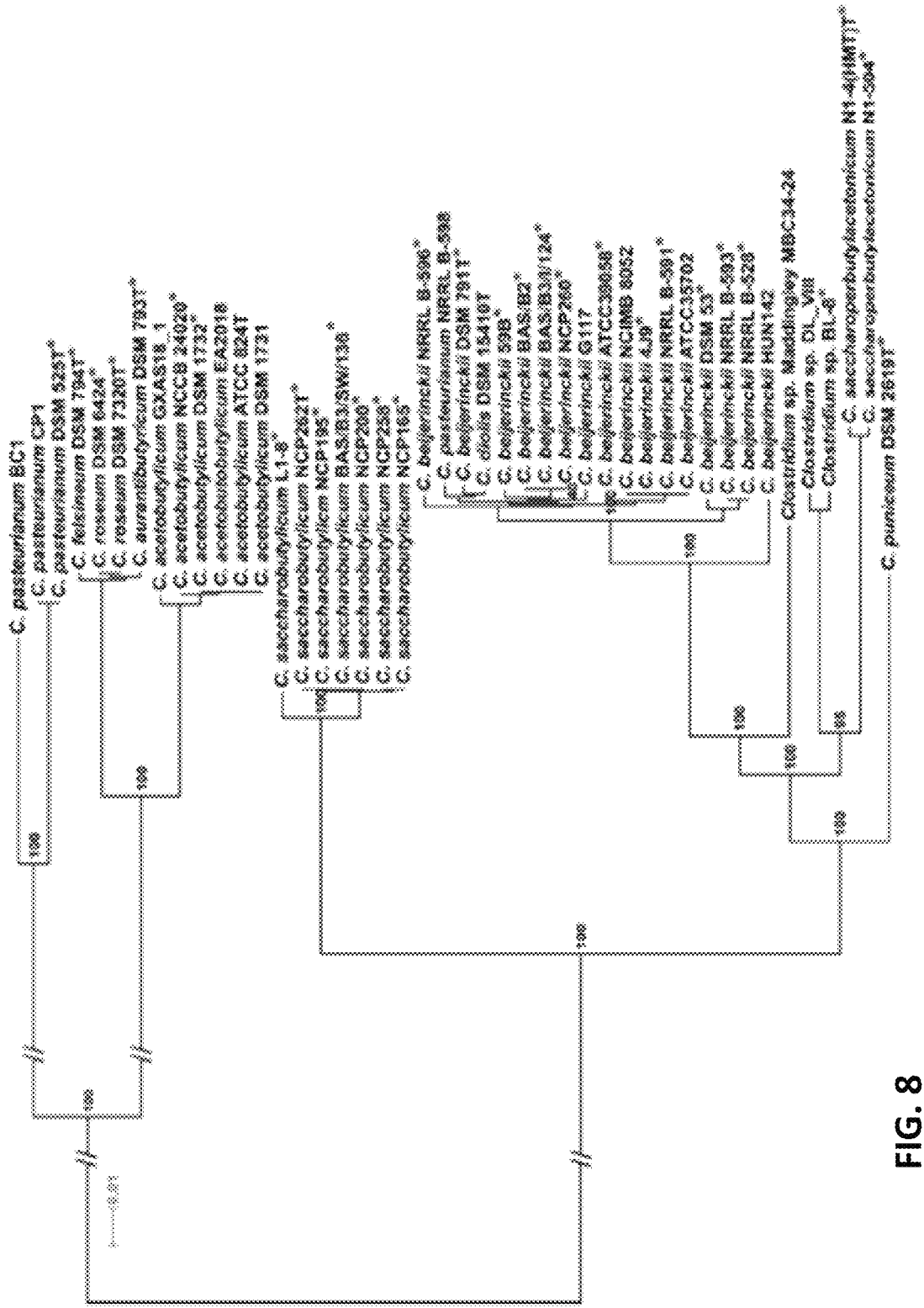

FIG. 8: Classification of 30 solventogenic *Clostridium* strains, according to Poehlein et al., 2017. Note that sub-clade *C. beijerinckii* NRRL B-593 is also identified in the literature as *C. beijerinckii* DSM 6423.

Figure 9:
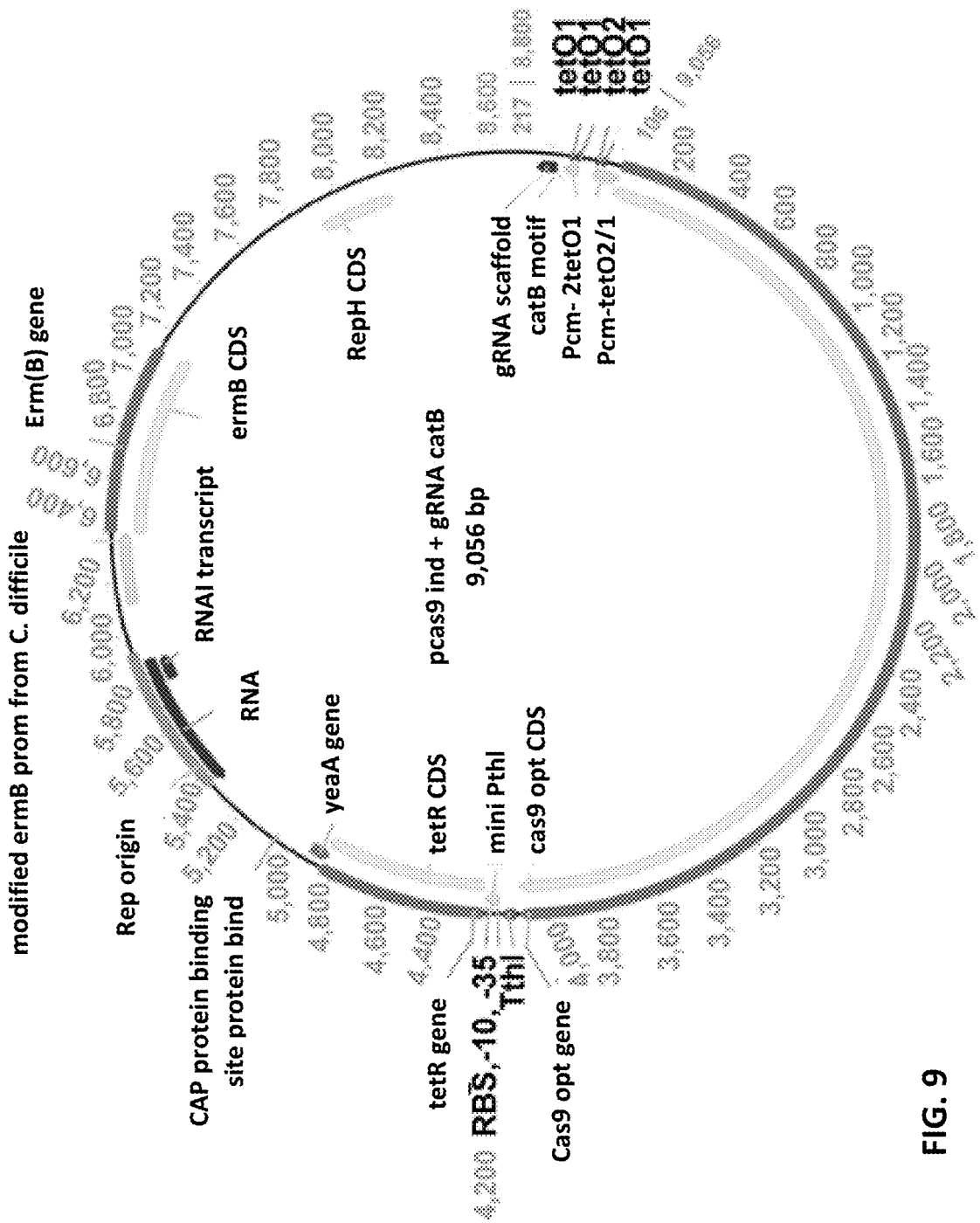

FIG. 9: pCas9ind-ΔcatB plasmid map.

Figure 10:
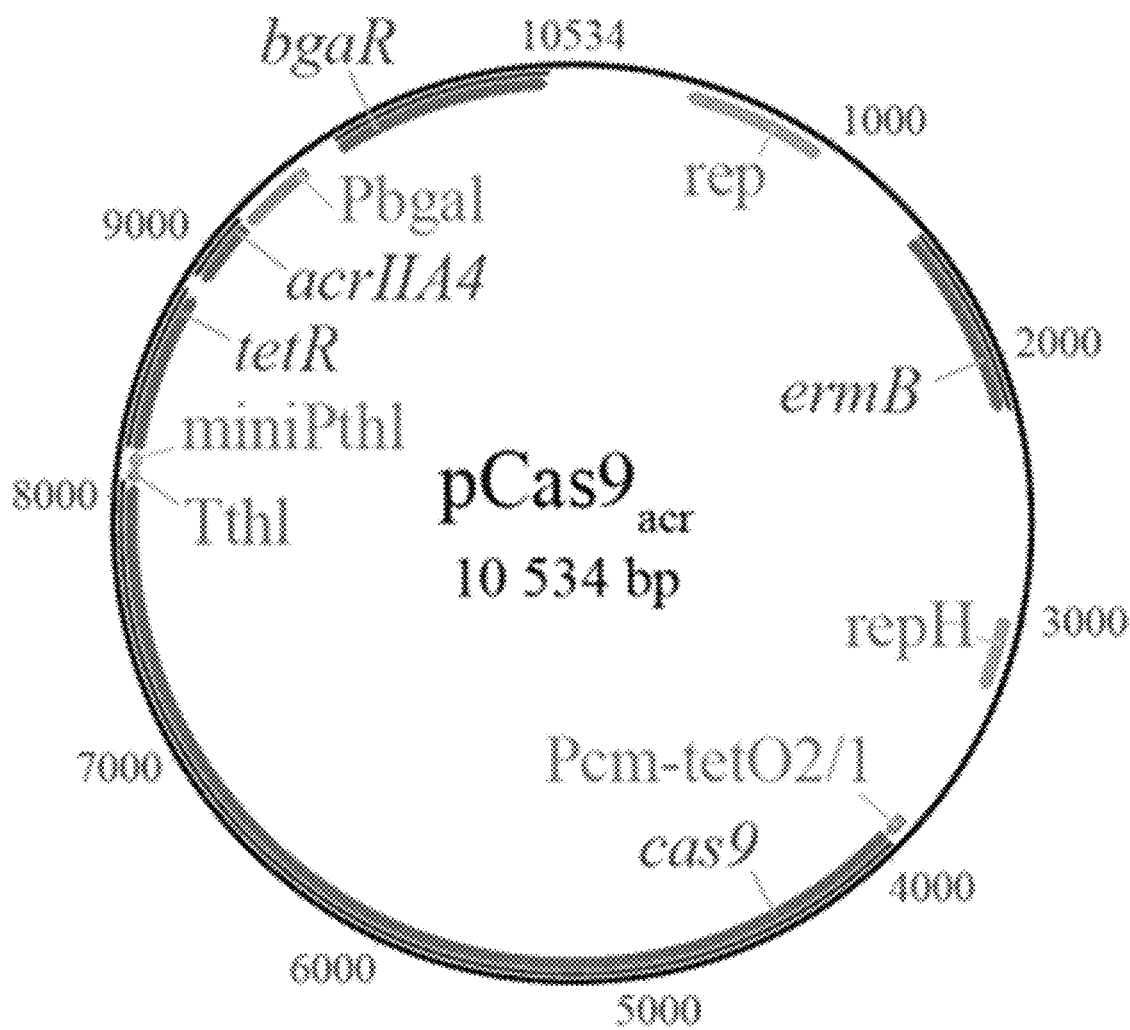

FIG. 10: pCas9acr plasmid map.

Figure 11:
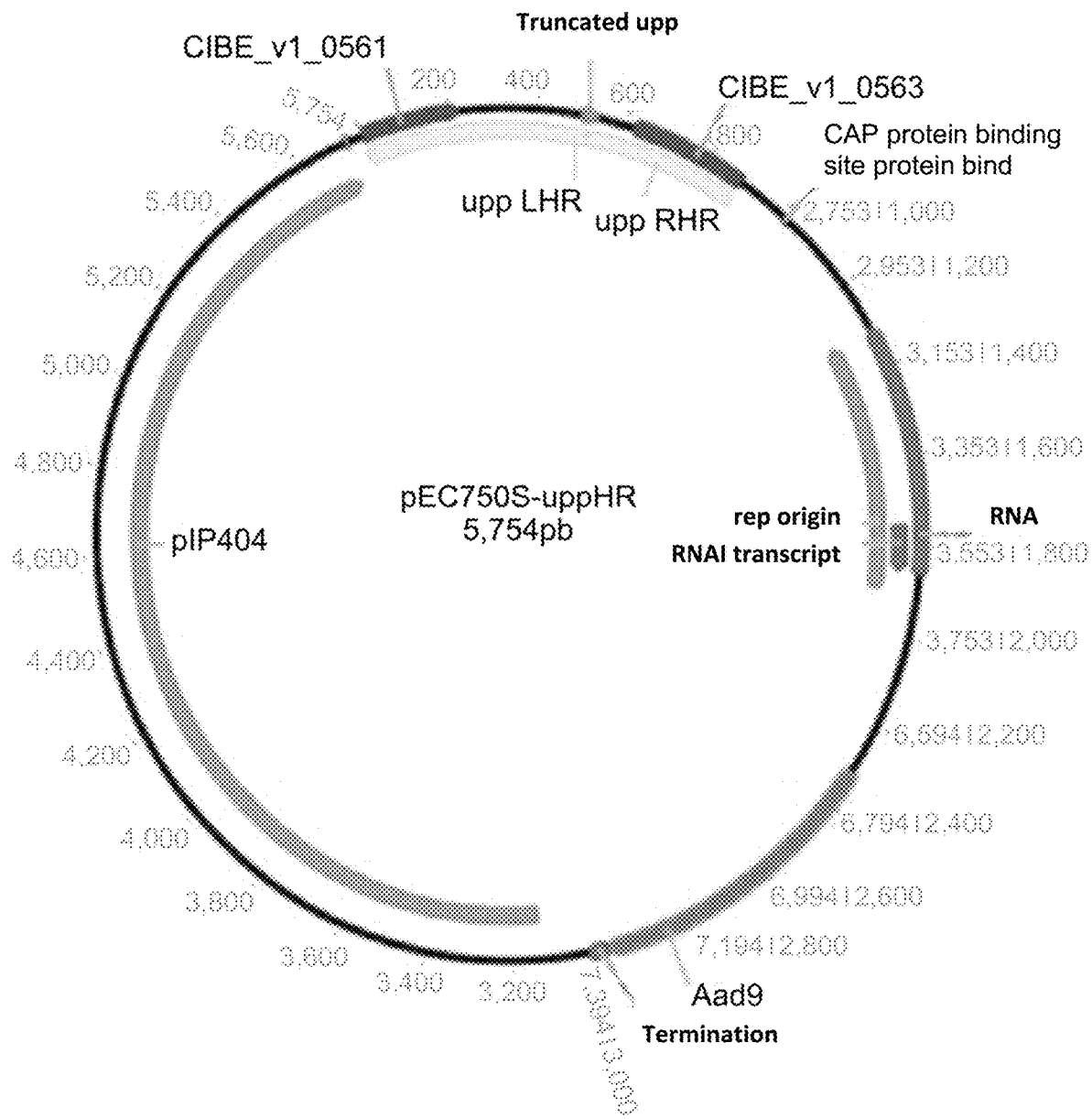

FIG. 11: pEC750S-uppHR plasmid map.

Figure 12:
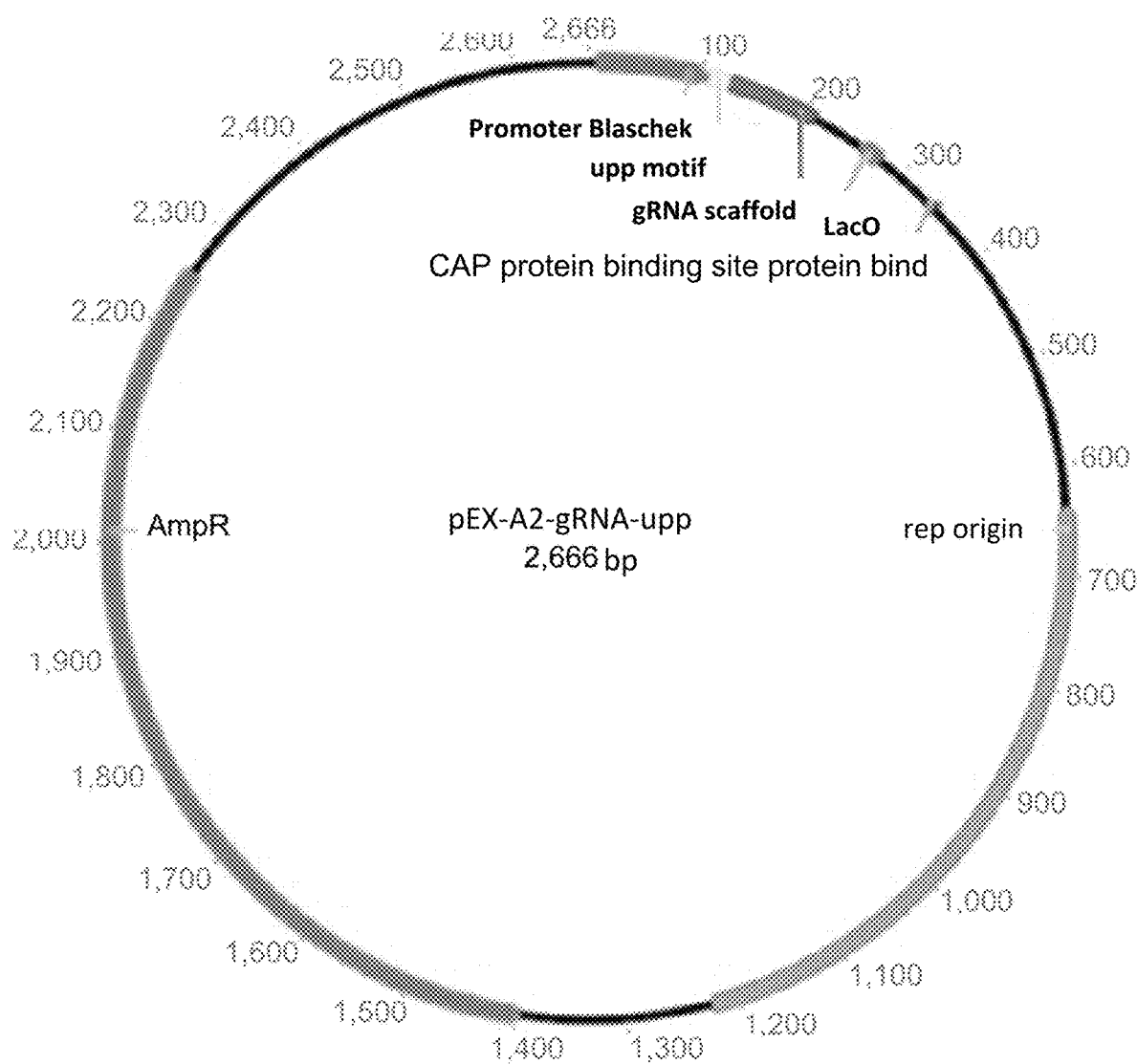

FIG. 12: pEX-A2-gRNA-upp plasmid map.

Figure 13:
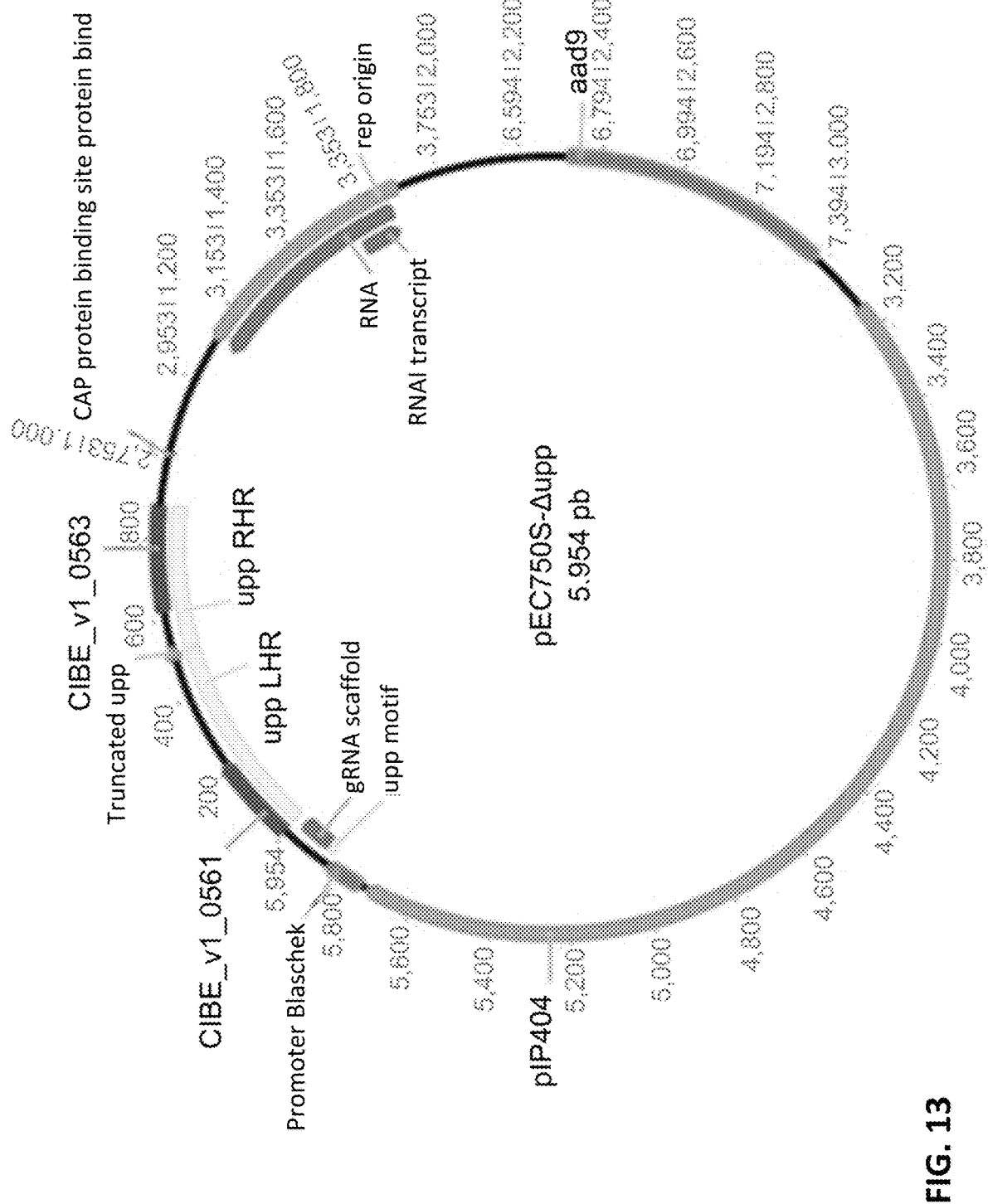

FIG. 13: pEC750S-Δupp plasmid map.

Figure 14:
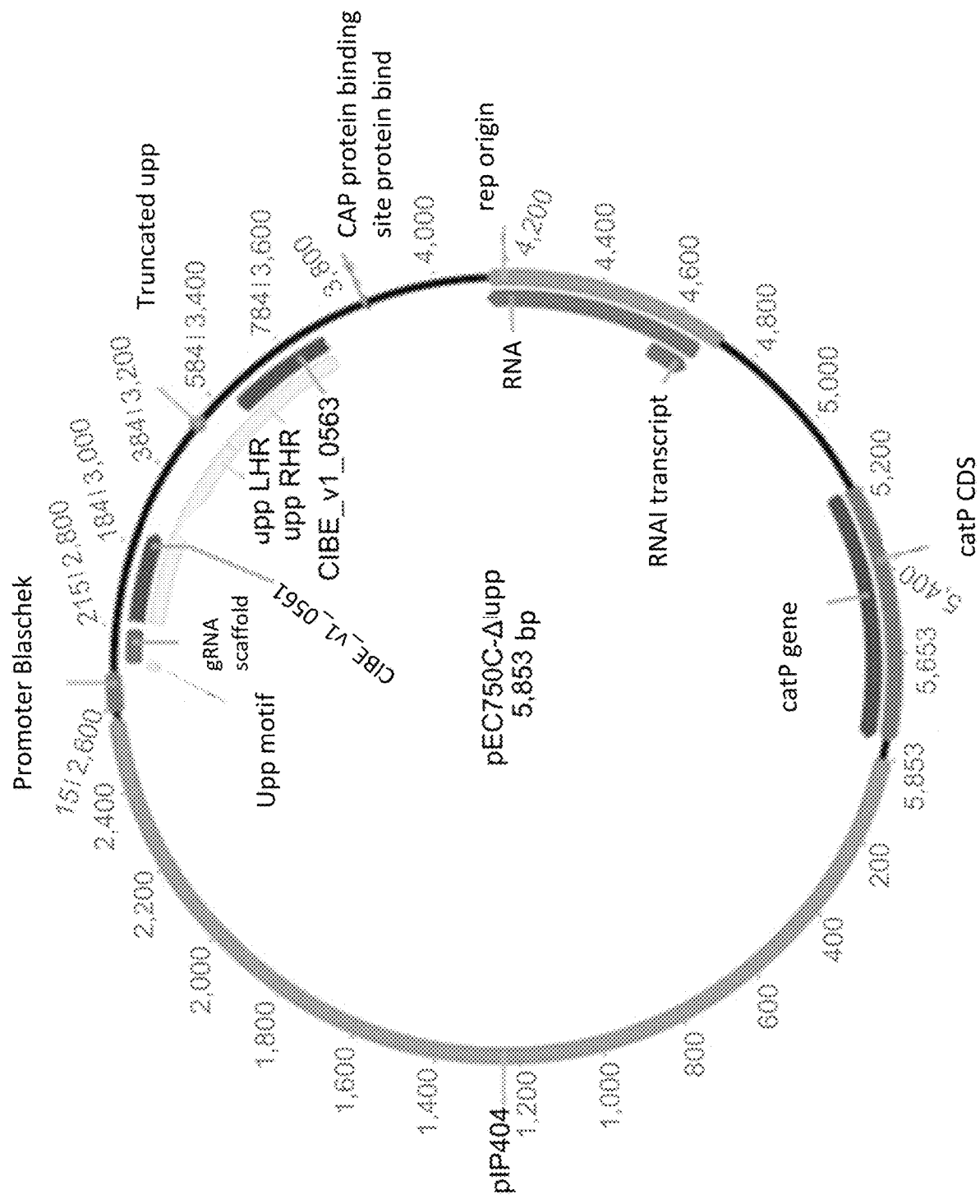

FIG. 14: pEC750C-Δupp plasmid map.

Figure 15:
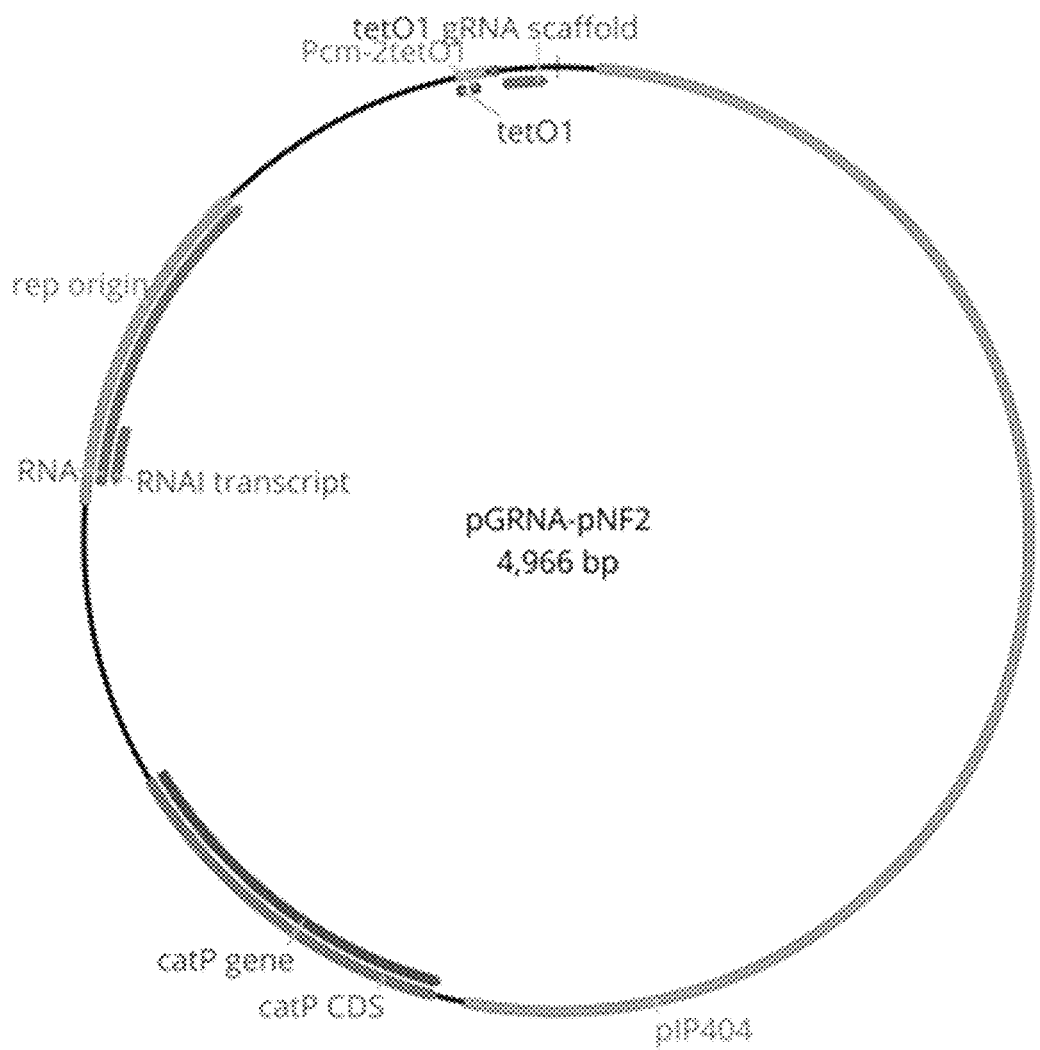

FIG. 15: pGRNA-pNF2 map.

Figure 16:
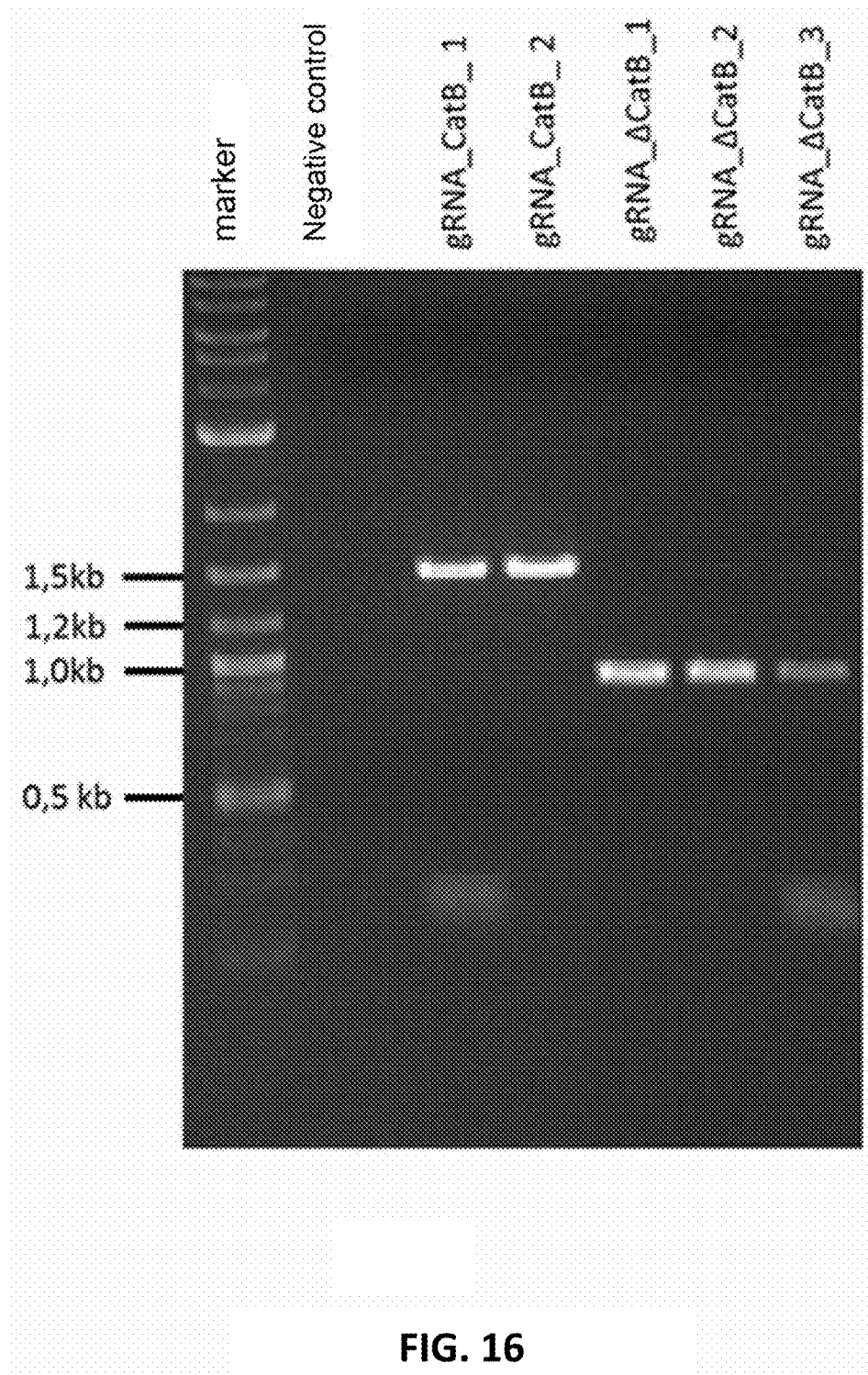

FIG. 16: PCR amplification of the catB gene in clones derived from the bacterial transformation of strain *C. beijerinckii* DSM 6423.

Amplification of about 1.5 kb if the strain still has the catB gene, or about 900 bp if this gene is deleted.

Figure 17:
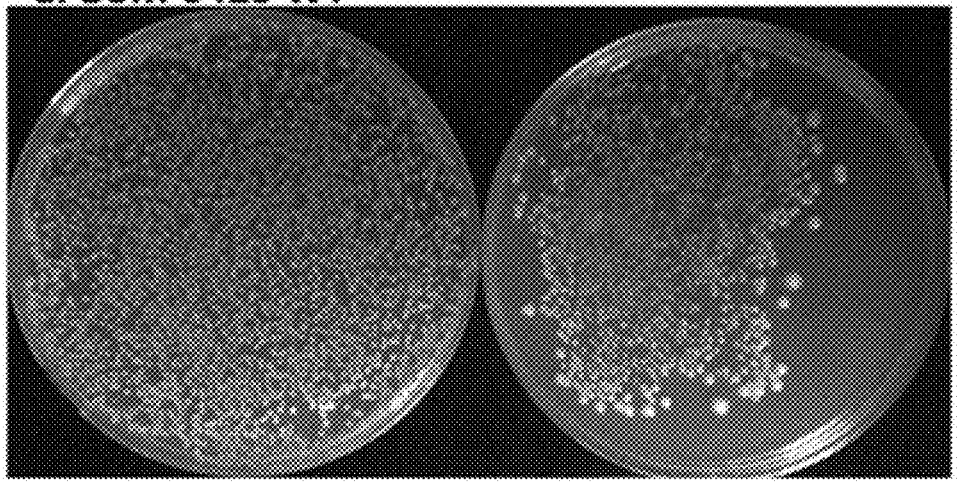
Figure 17:
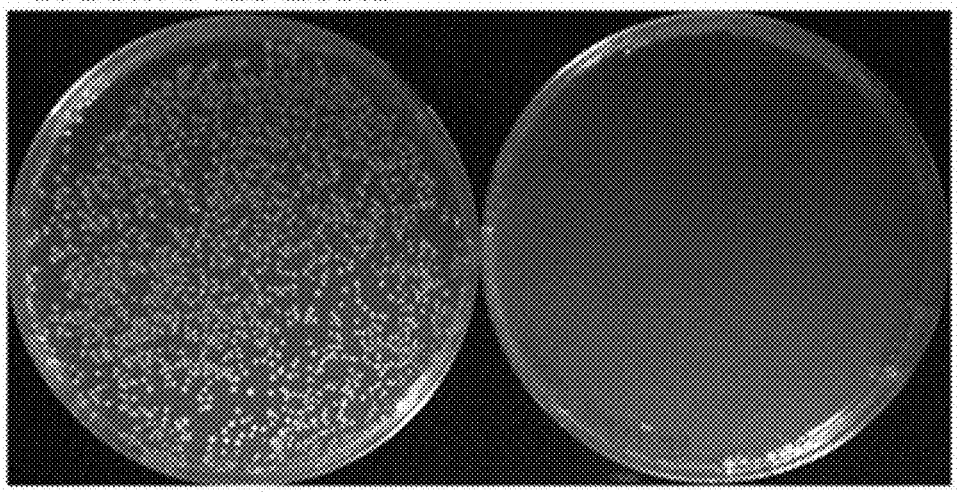

FIG. 17: Growth of strains *C. beijerinckii* DSM 6423 WT and ΔcatB on 2YTG medium and 2YTG thiamphenicol selective medium.

Figure 18:
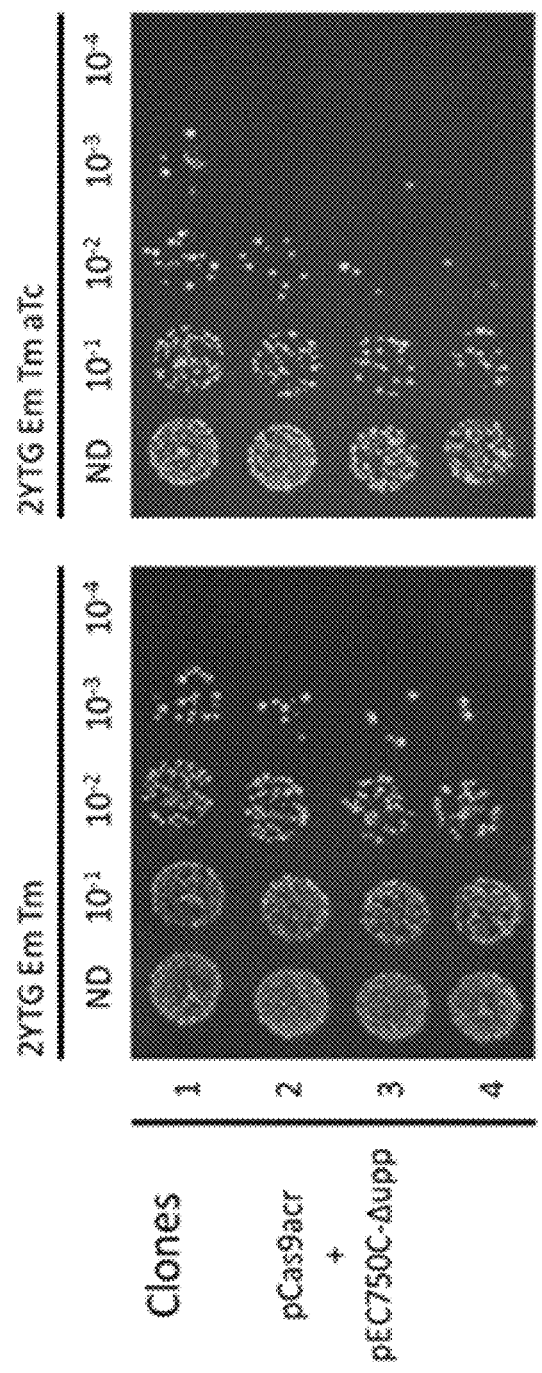

FIG. 18: Induction of the CRISPR/Cas9acr system in transformants of strain *C. beijerinckii* DSM 6423 containing pCas9$_{acr}$ and an expression plasmid for the gRNA targeting upp, with or without repair matrix. Legend: Em, erythromycin; Tm, thiamphenicol; aTc, anhydrotetracycline; ND, not diluted.

Figure 19:
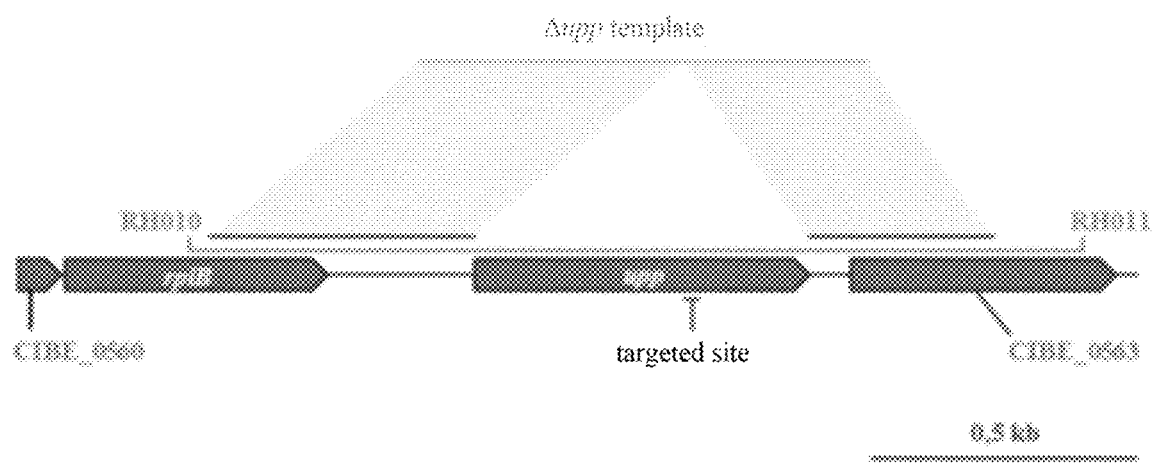
Figure 19:
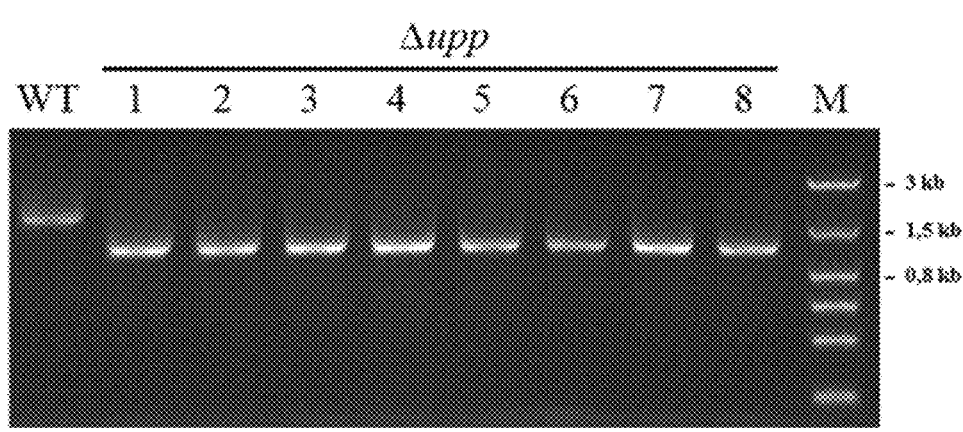

FIG. 19: FIG. 19A shows the modification of the upp locus of *C. beijerinckii* DSM 6423 via the CRISPR/Cas9 system. FIG. 19A shows the genetic organization of the upp locus: genes, gRNA target site and repair matrices, associated with the corresponding regions of homology on genomic DNA. The hybridization sites of the primers for PCR verification (RH010 and RH011) are also indicated.

FIG. 19B shows the modification of the upp locus of *C. beijerinckii* DSM 6423 via the CRISPR/Cas9 system. FIG. 19B shows the amplification of the upp locus using primers RH010 and RH011. An amplification of 1680 bp is expected in the case of a wild-type gene, compared to 1090 bp for a modified upp gene. M, 100 bp-3 kb size marker (Lonza); WT, wild-type strain.

Figure 20:
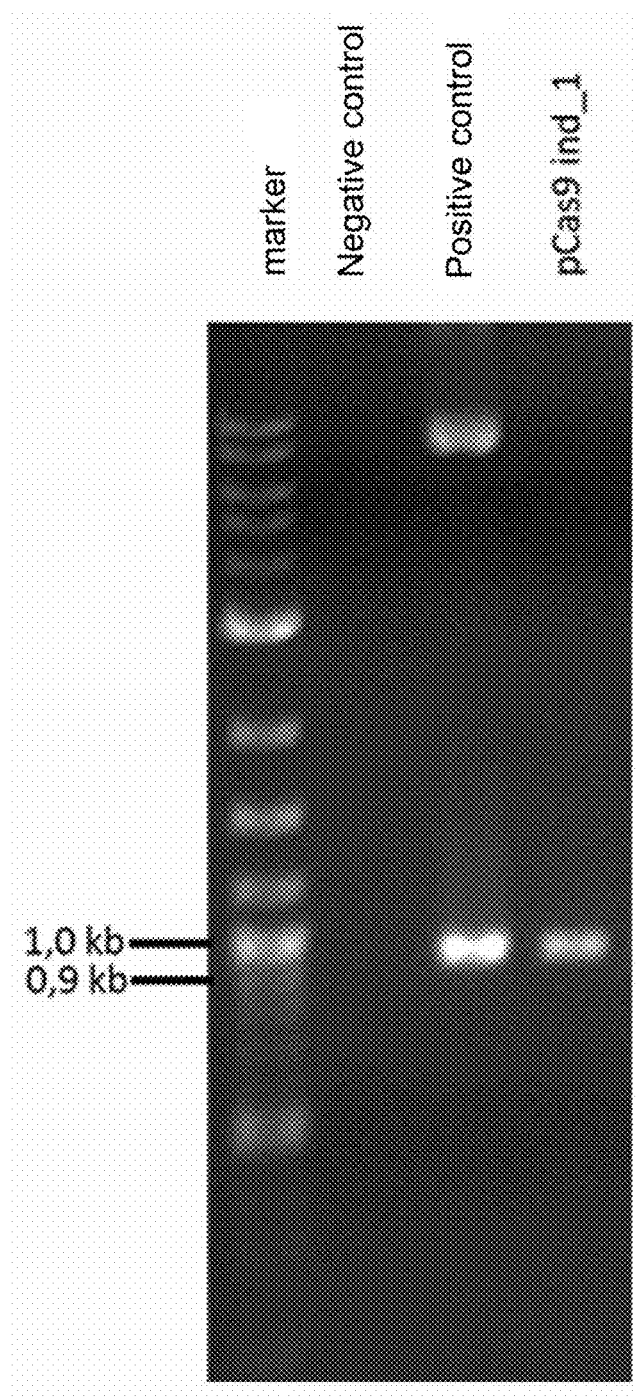

FIG. 20: PCR amplification verifying the presence of plasmid pCas9$_{ind}$ in strain *C. beijerinckii* 6423 ΔcatB.

Figure 21:
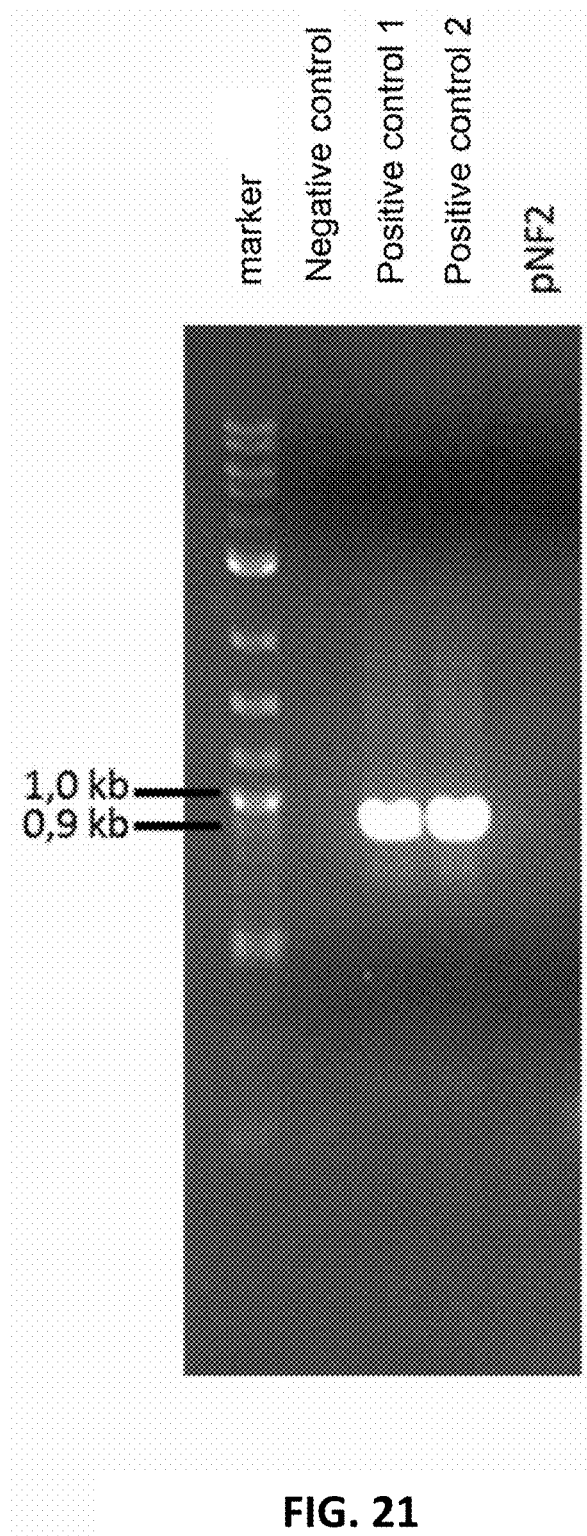

FIG. 21: PCR amplification (≈900 bp) verifying the presence or absence of the natural pNF2 plasmid before induction (positive control 1 and 2) then after induction on medium containing aTc from the CRISPR-Cas9 system.

Figure 22:
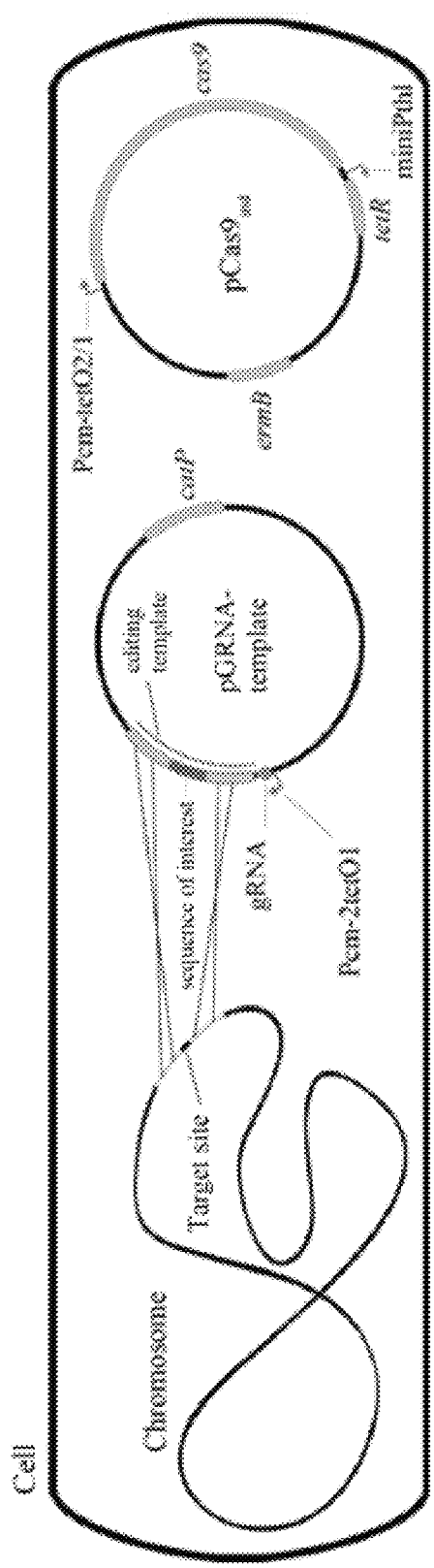

FIG. 22: Genetic tool for modifying bacteria, adapted to bacteria of the genus *Clostridium*, based on the use of two plasmids (cf. WO2017/064439, Wasels et al., 2017).

Figure 23:
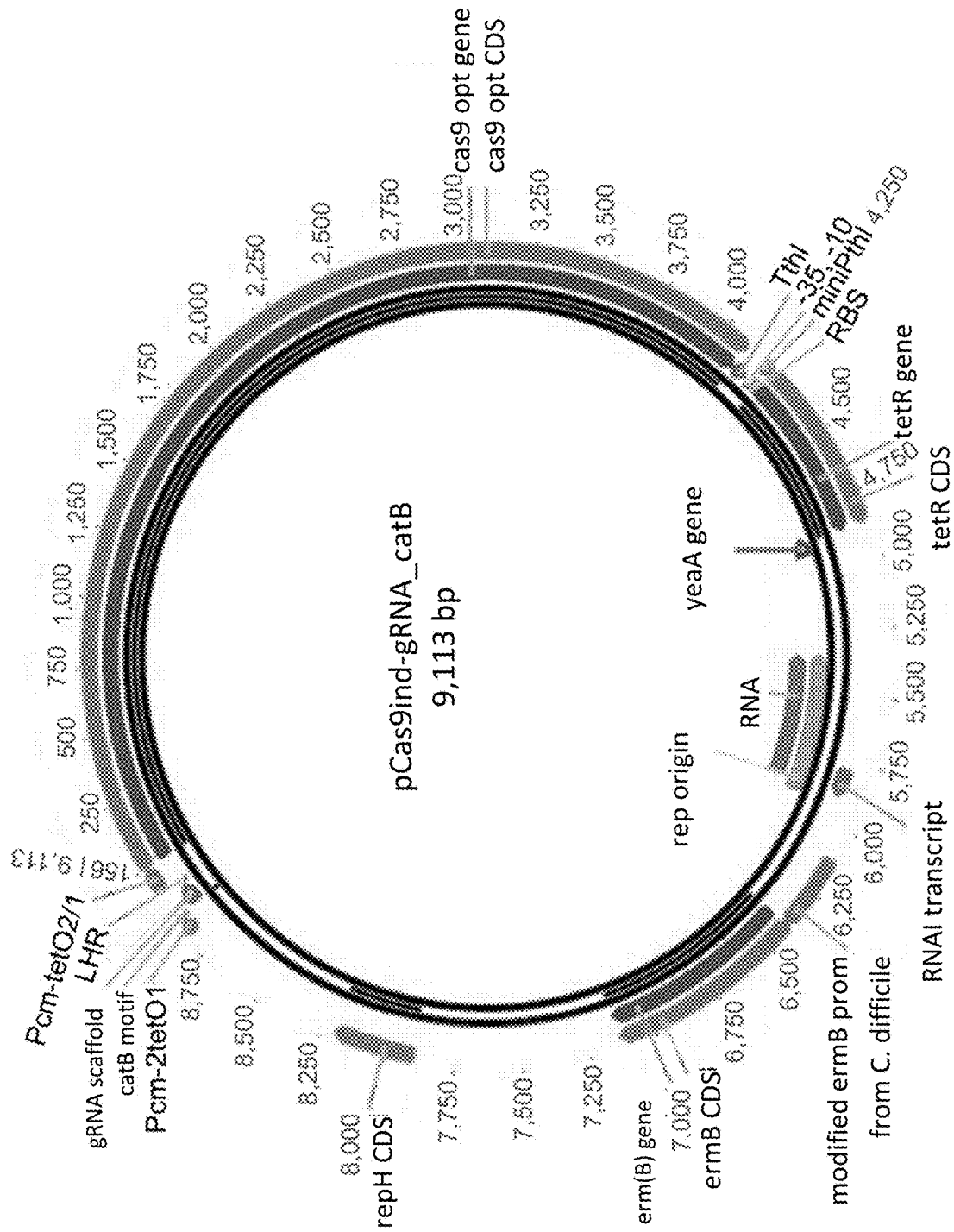

FIG. 23: pCas9ind-gRNA_catB plasmid map.

Figure 24:
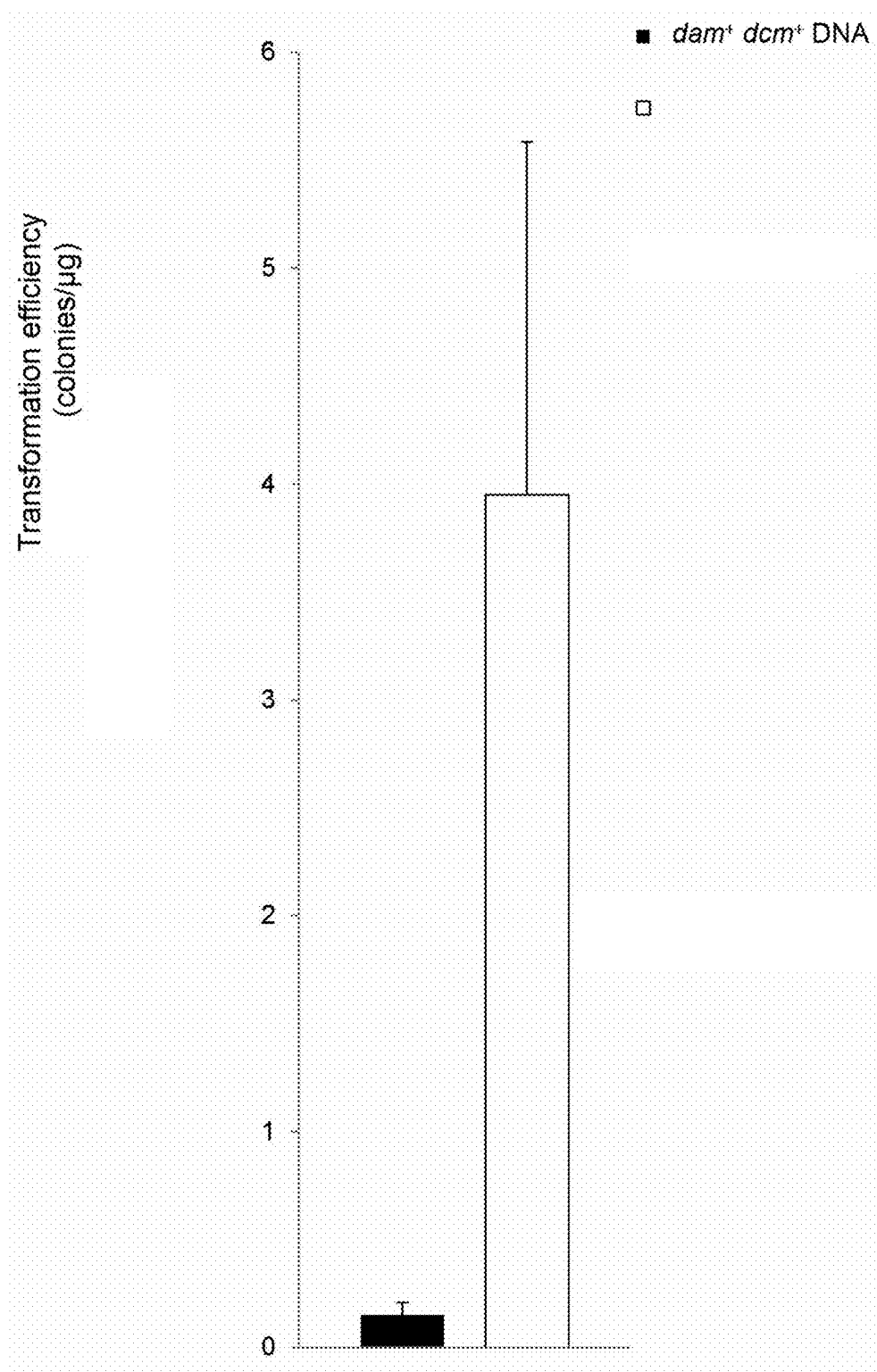

FIG. 24: Transformation efficiency (in colonies observed per μg of transformed DNA) for 20 μg of pCas9$_{ind}$ plasmid in strain *C. beijerinckii* DSM6423. The error bars represent the standard error of the mean for a biological triplicate.

Figure 25:
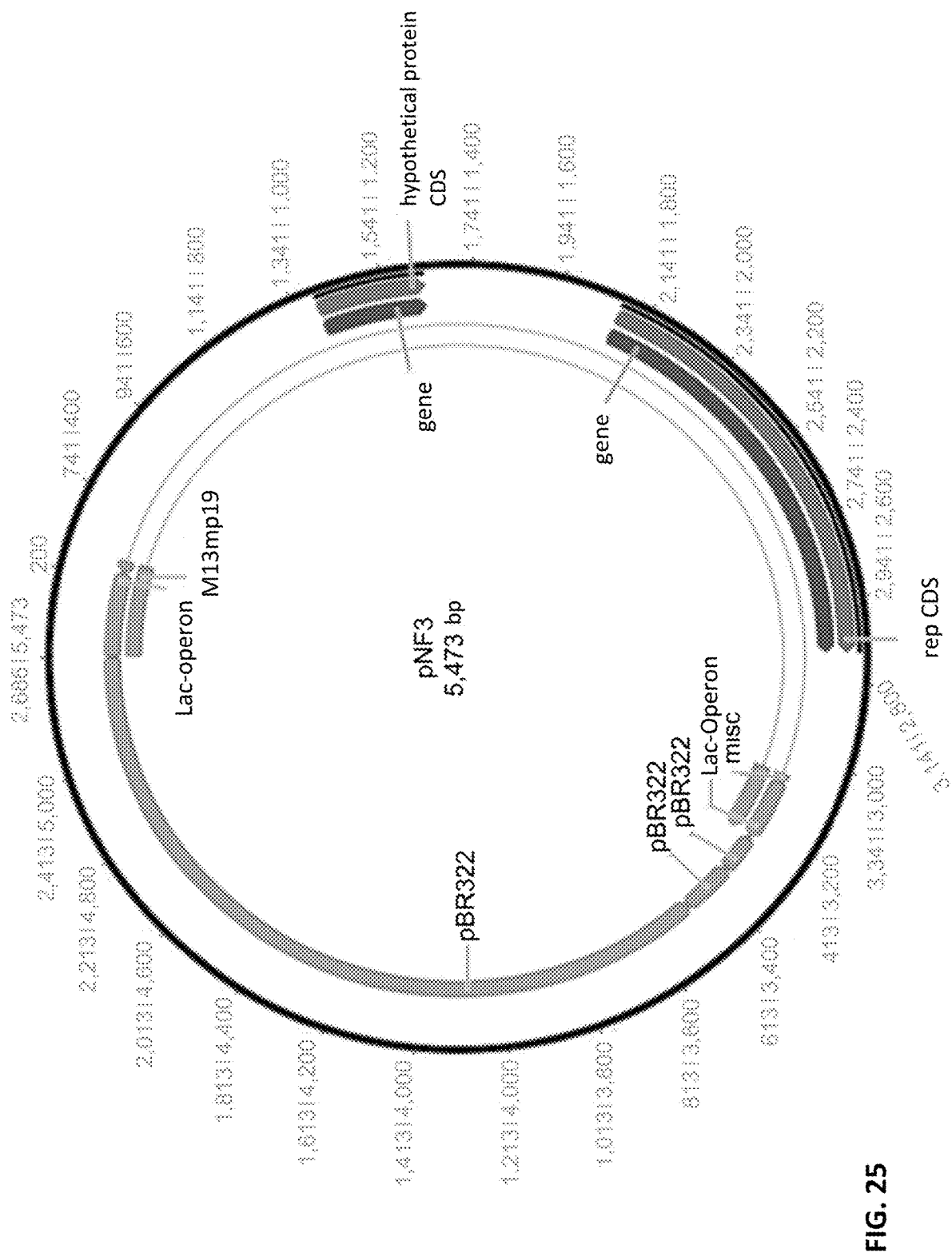

FIG. 25: pNF3 plasmid map.

Figure 26:
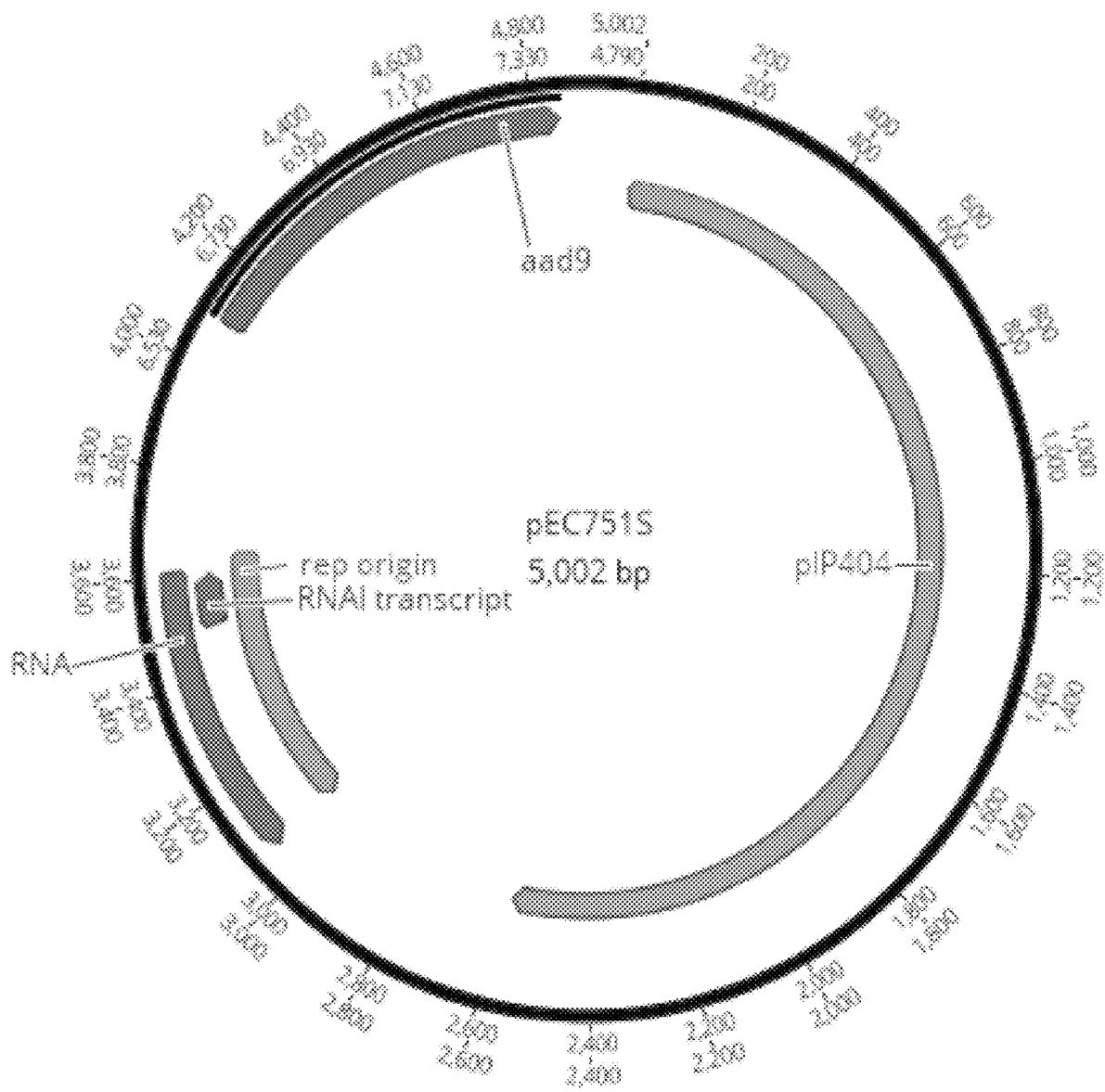

FIG. 26: pEC751S plasmid map.

Figure 27:
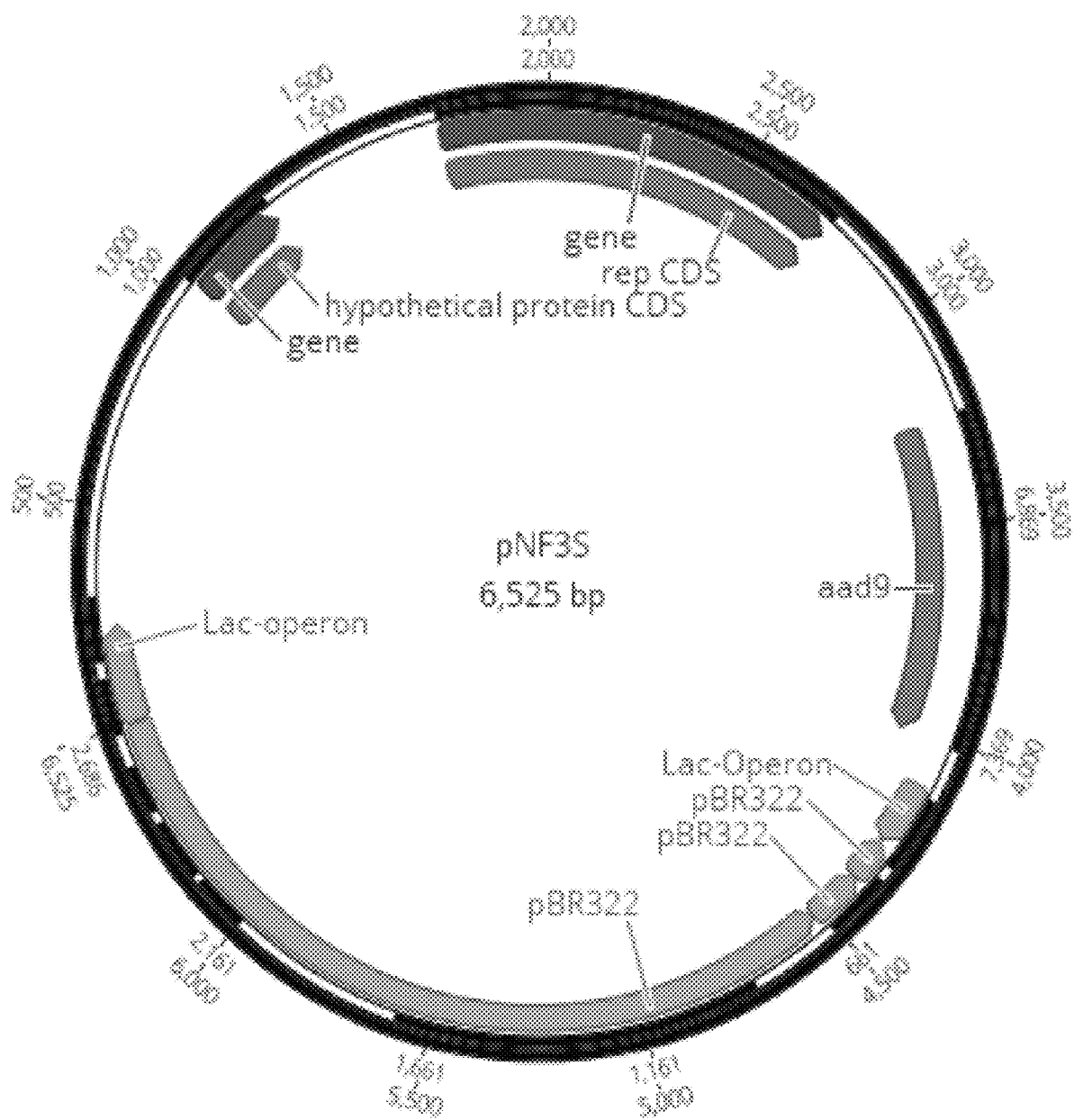

FIG. 27: pNF3S plasmid map.

Figure 28:
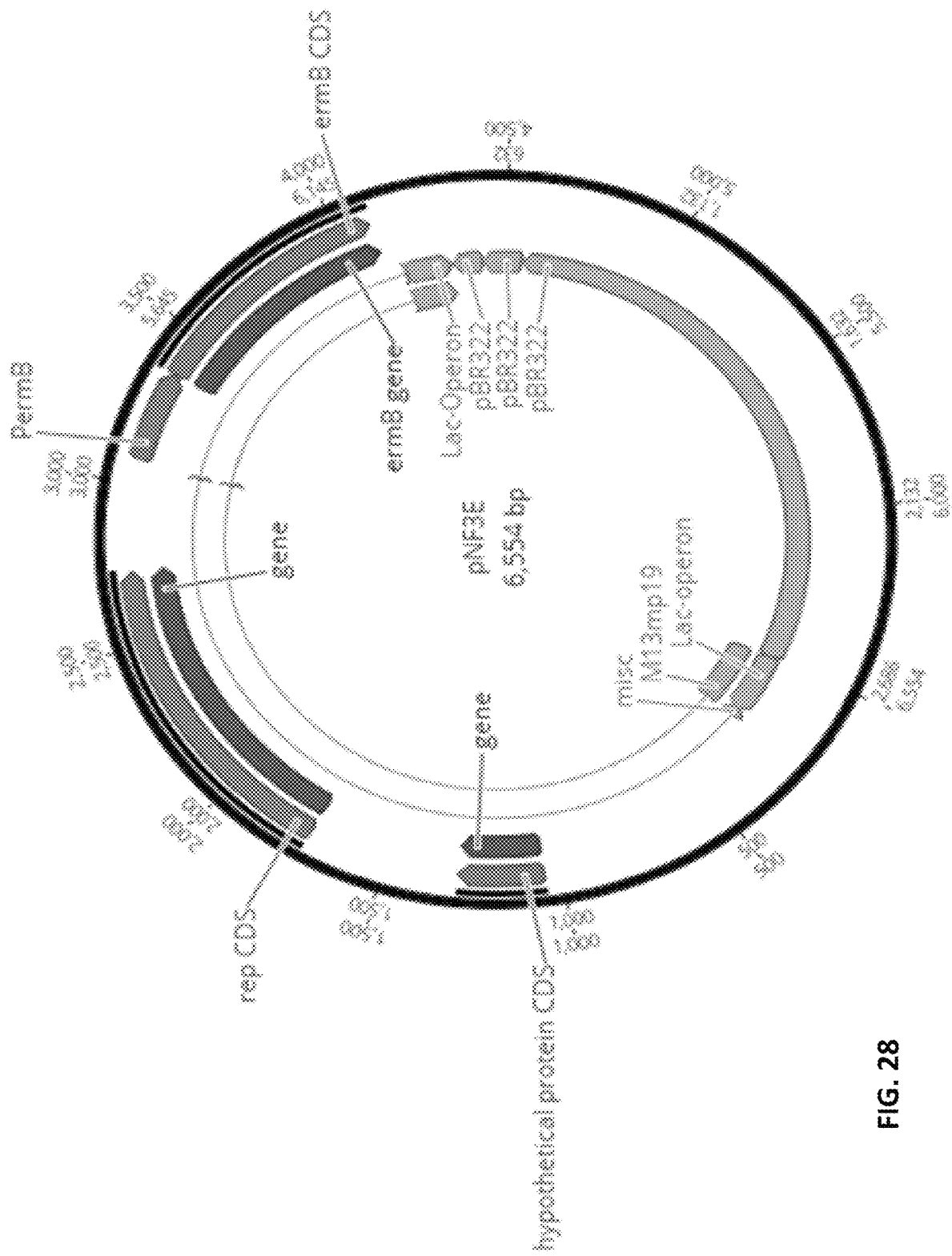

FIG. 28: pNF3E plasmid map.

Figure 29:
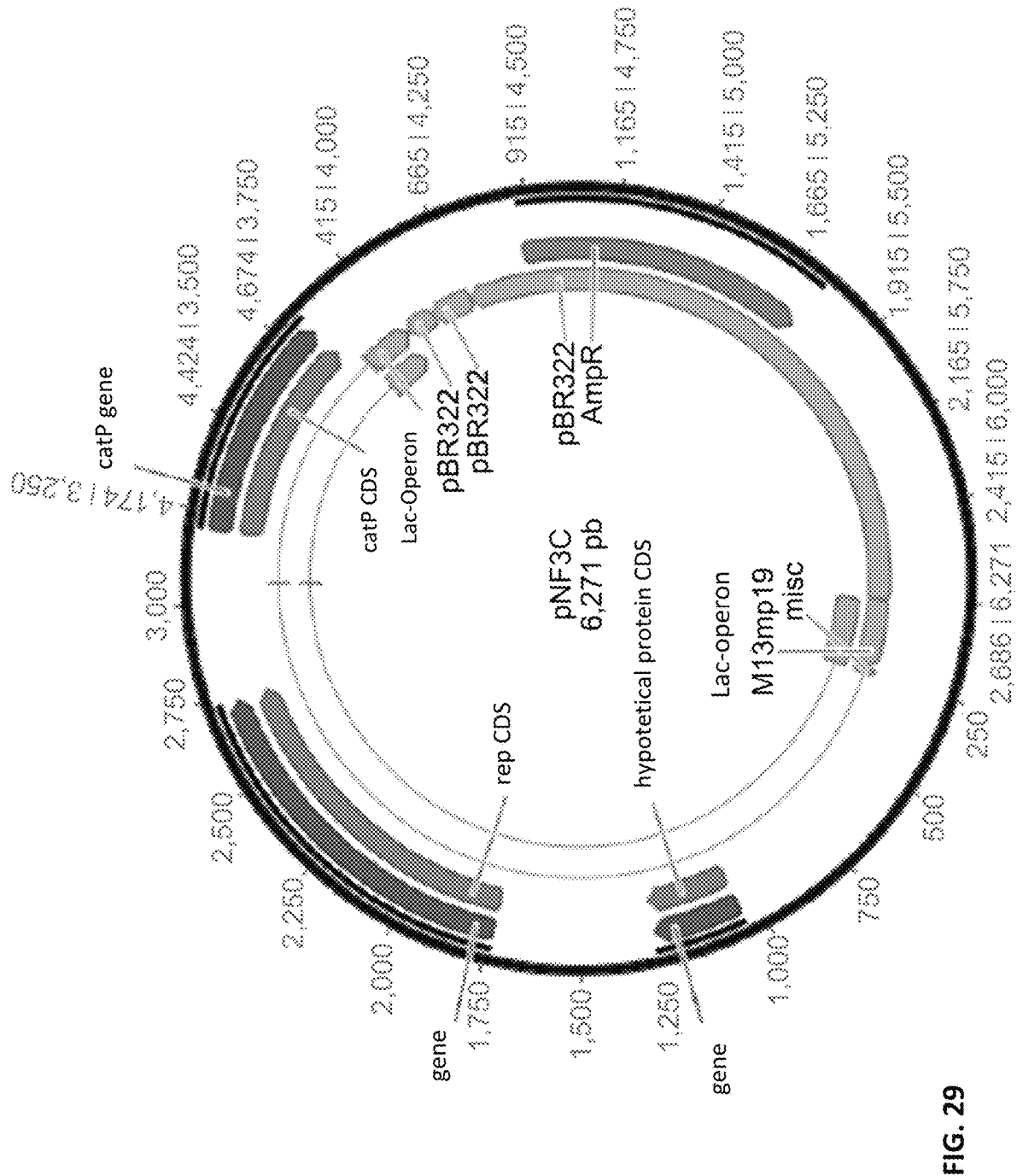

FIG. 29: pNF3C plasmid map.

Figure 30:
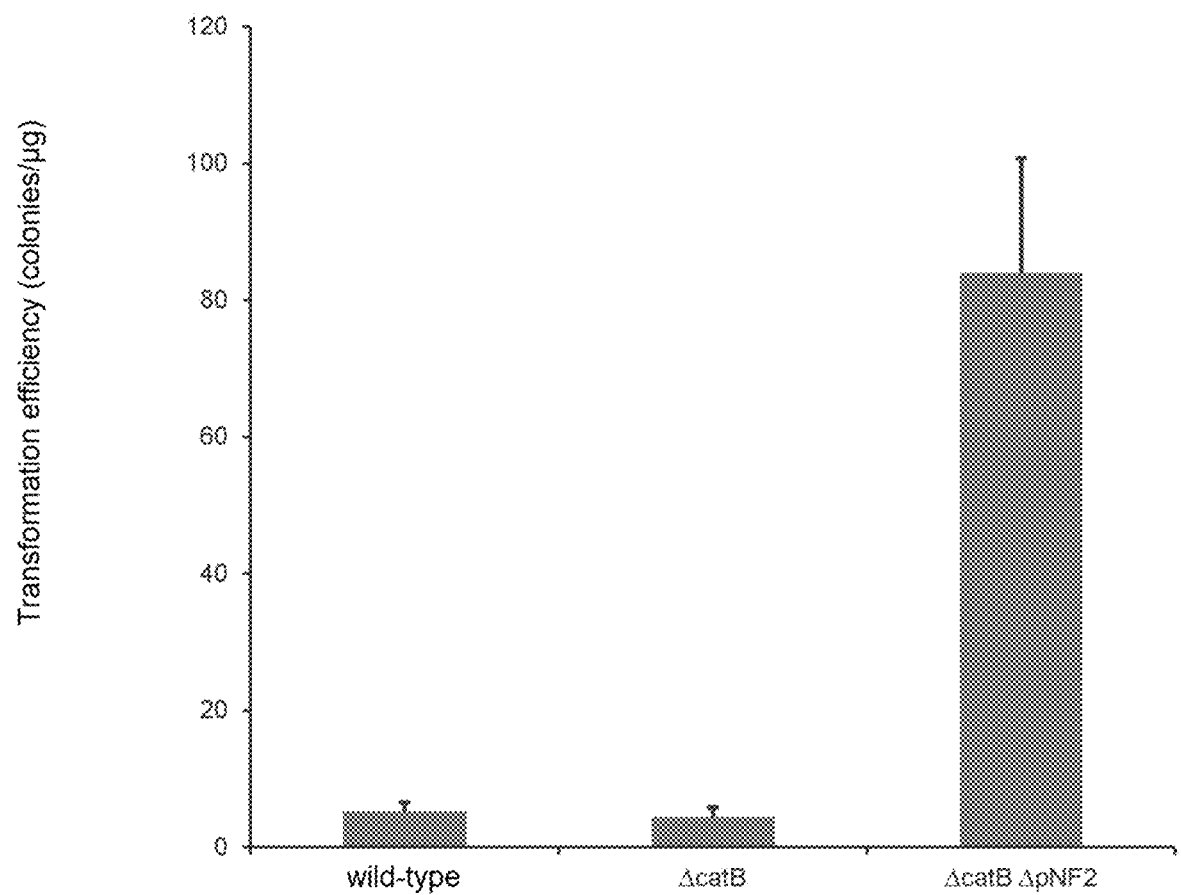

FIG. 30: Transformation efficiency (in colonies observed per μg of transformed DNA) of plasmid pCas9$_{ind}$ in three strains of *C. beijerinckii* DSM 6423. The error bars correspond to the standard deviation of the mean for a biological replicate.

Figure 31:
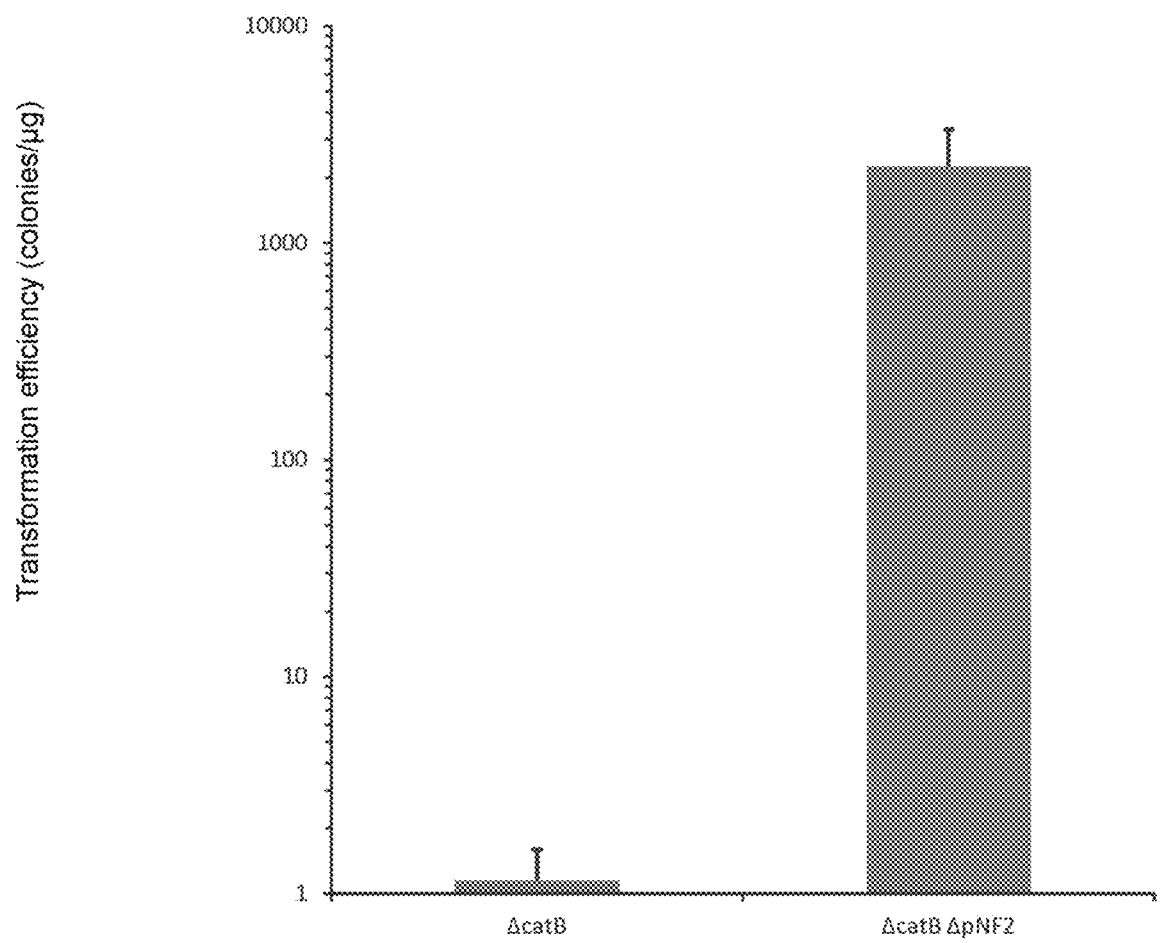

FIG. 31: Transformation efficiency (in colonies observed per μg of transformed DNA) of plasmid pEC750C in two strains derived from *C. beijerinckii* DSM 6423. The error bars correspond to the standard deviation of the mean for a biological replicate.

Figure 32:
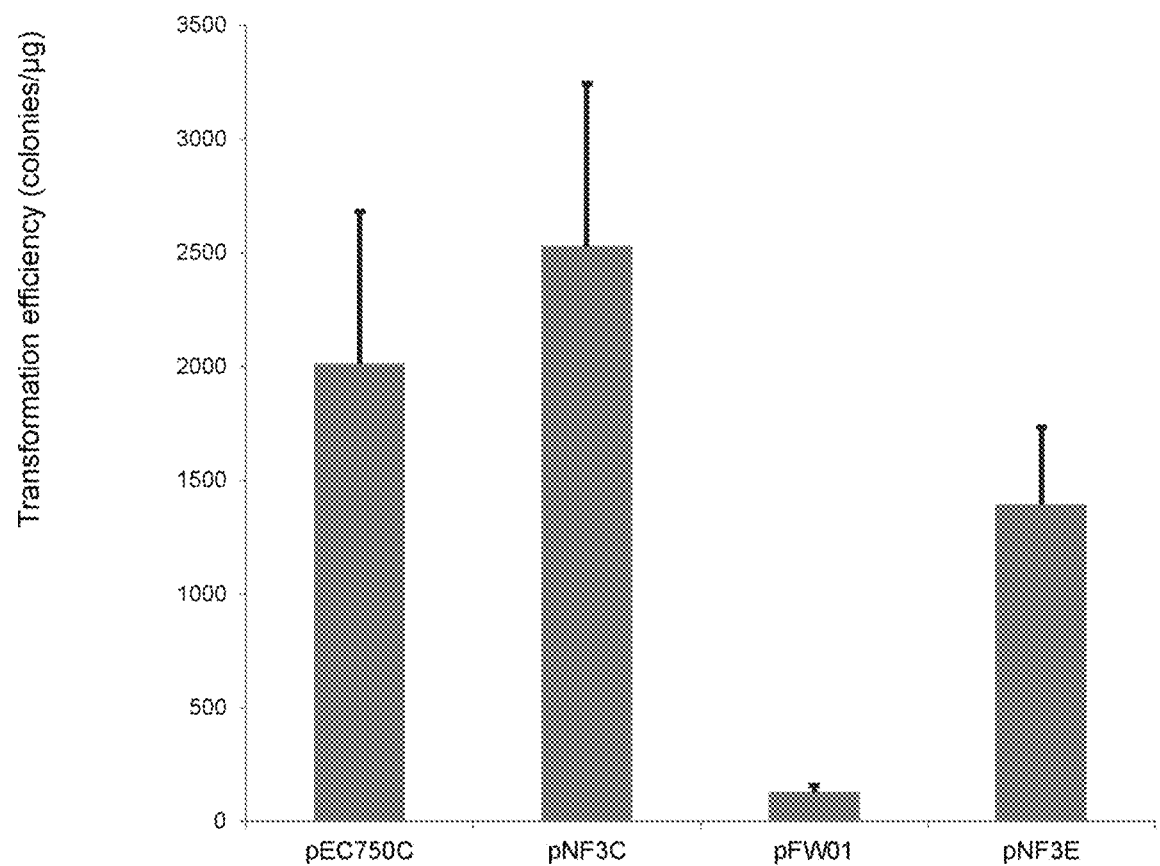

FIG. 32: Transformation efficiency (in colonies observed per μg of transformed DNA) of plasmids pEC750C, pNF3C, pFW01 and pNF3E in strain *C. beijerinckii* DSM 6423ΔcatB ΔpNF2. The error bars correspond to the standard deviation of the mean for a biological triplicate.

Figure 33:
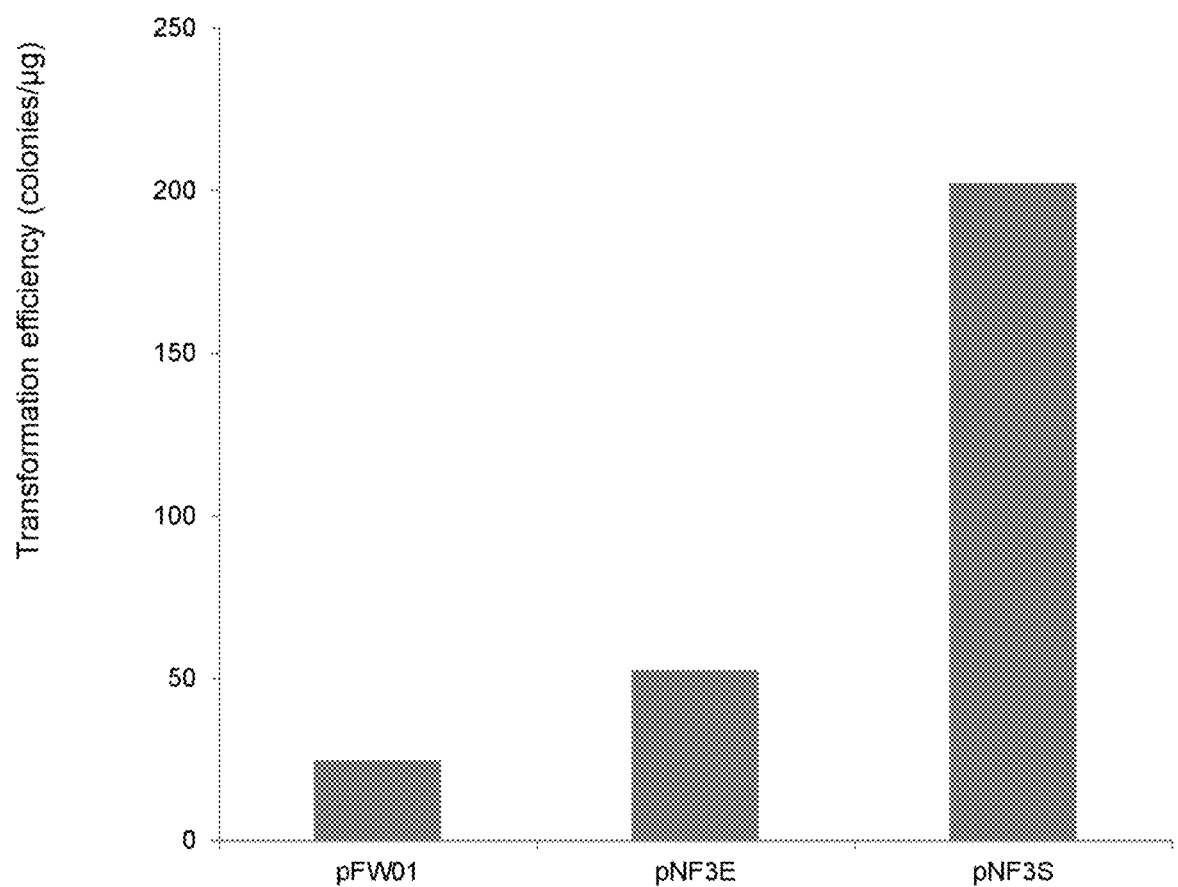

FIG. 33: Transformation efficiency (in colonies observed per μg of transformed DNA) of plasmids pFW01, pNF3E and pNF3S in strain *C. beijerinckii* NCIMB 8052.

EXAMPLES

Example 1

Materials and Methods
Growing Conditions

*C. acetobutylicum* DSM 792 was grown in 2YTG medium (16 g/l tryptone, 10 g/l yeast extract, 5 g/l glucose, 4 g/l NaCl). *E. coli* NEB10B was grown in LB medium (10 g/l tryptone, 5 g/l yeast extract, 5 g/l NaCl). The solid media were made by adding 15 g/l agarose to the liquid media. Erythromycin (at concentrations of 40 or 500 mg/l respectively in 2YTG or LB medium), chloramphenicol (25 or 12.5 mg/l respectively in solid or liquid LB) and thiamphenicol (15 mg/l in 2YTG medium) were used when necessary.

Use of Nucleic Acids

All enzymes and kits used were done so according to the suppliers' recommendations.

Plasmid Construction

The pCas9$_{acr}$ plasmid (SEQ ID NO: 23), shown in FIG. 4, was constructed by cloning the fragment (SEQ ID NO: 1) containing bgaR and acrIIA4 under the control of the Pbgal promoter synthesized by Eurofins Genomics at the SacI site of the pCas9$_{ind}$ vector (Wasels et al., 2017).

The pGRNA$_{ind}$ plasmid (SEQ ID NO: 82) was constructed by cloning an expression cassette (SEQ ID NO: 83) for a gRNA under the control of promoter Pcm-2tetO1 (Dong et al., 2012) synthesized by Eurofins Genomics at the SacI site of the pEC750C vector (SEQ ID NO: 106) (Wasels et al., 2017).

The pGRNA-xylB (SEQ ID NO: 102), pGRNA-xylR (SEQ ID NO: 103), pGRNA-glcG (SEQ ID NO: 104) and pGRNA-bdhB (SEQ ID NO: 105) plasmids were constructed by cloning the respective primer pairs 5'-TCAT-GATTTCTCCATATTAGCTAG-3' (SEQ ID NO: 84) and 5'-AAACCTAGCTAATATGGAGAAATC-3' (SEQ ID NO: 85), 5'-TCATGTTACACTTGGAACAGGCGT-3' (SEQ ID NO: 86) and 5'-AAACACGCCTGTTCCAAGTGTAAC-3' (SEQ ID NO: 87), 5'-TCATTTCCGGCAGTAG-GATCCCCA-3' (SEQ ID NO: 88) and 5'-AAACTGGG-GATCCTACTGCCGGAA-3' (SEQ ID NO: 89), 5'-TCATGCTTATTACGACATAACACA-3' (SEQ ID NO: 90) and 5'-AAACTGTGTTATGTCGTAATAAGC-3' (SEQ ID NO: 91) within the pGRNA$_{ind}$ plasmid (SEQ ID NO: 82) digested by BsaI.

The pGRNA-ΔbdhB plasmid (SEQ ID NO: 79) was constructed by cloning the DNA fragment obtained by overlapping PCR assembly of the PCR products obtained with the primers 5'-ATGCATGGATCCAAACGAACC-CAAAAAGAAAGTTTC-3' (SEQ ID NO: 92) and 5'-GGTTGATTTCAAATCTGTGTAAACCTACCG-3' (SEQ ID NO: 93) on the one hand, 5'-ACACAGATTT-GAAATCAACCACTTTAACCC-3' (SEQ ID NO: 94) and 5'-ATGCATGTCGACTCTTAAGAA-CATGTATAAAGTATGG-3' (SEQ ID NO: 95) on the other hand, in the pGRNA-bdhB vector digested by BamHI and SacI.

The pGRNA-ΔbdhAΔbdhB plasmid (SEQ ID NO: 80) was constructed by cloning the DNA fragment obtained by overlapping PCR assembly of the PCR products obtained with the primers 5'-ATGCATGGATCCAAACGAACC-CAAAAAGAAAGTTTC-3' (SEQ ID NO: 96) and 5'-GCTAAGTTTTAAATCTGTGTAAACCTACCG-3' (SEQ ID NO: 97) on the one hand, 5'-ACACAGATT-TAAAACTTAGCATACTTCTTACC-3' (SEQ ID NO: 98) and 5'-ATGCATGTCGACCTTCTAATCTCCTCTACTAT-TTTAG-3' (SEQ ID NO: 99) on the other hand, in the pGRNA-bdhB vector digested by BamHI and SacI.

Transformation

C. acetobutylicum DSM 792 was transformed according to the protocol described by Mermelstein et al., 1993. The selection of C. acetobutylicum DSM 792 transformants already containing a Cas9 expression plasmid (pCas9$_{ind}$ or pCas9$_{acr}$) transformed with a plasmid containing a gRNA expression cassette was performed on solid 2YTG medium containing erythromycin (40 mg/l), thiamphenicol (15 mg/l) and lactose (40 nM).

Induction of Cas9 Expression

The induction of cas9 expression was achieved through the growth of transformants obtained on a solid 2YTG medium containing erythromycin (40 mg/l), thiamphenicol (15 mg/l) and the inducer of expression of cas9 and of the gRNA, aTc (1 mg/l).

Amplification of the Bdh Locus

Verification of the editing of the C. acetobutylicum DSM 792 genome at the bdhA and bdhB gene locus was performed by PCR using the Q5® High-Fidelity DNA Polymerase (NEB) enzyme with primers V1 (5'-ACACATT-GAAGGGAGCTTTT-3', SEQ ID NO: 100) and V2 (5'-GGCAACAACATCAGGCCTTT-3', SEQ ID NO: 101).

Results

Transformation Efficiency

In order to evaluate the impact of the insertion of the acrIIA4 gene on the transformation frequency of the cas9 expression plasmid, different gRNA expression plasmids were transformed in strain DSM 792 containing pCas9$_{ind}$ (SEQ ID NO: 22) or pCas9$_{acr}$(SEQ ID NO: 23), and the transformants were selected on a medium supplemented with lactose. The transformation frequencies obtained are presented in FIG. 5.

Generation of ΔbdhB and ΔbdhAΔbdhB Mutants

The targeting plasmid containing the expression cassette for the gRNA targeting bdhB (pGRNA-bdhB-SEQ ID NO: 105) as well as two derived plasmids containing repair matrices allowing the deletion of the bdhB gene alone (pGRNA-AbdhB-SEQ ID NO: 79) or bdhA and bdhB genes (pGRNA-AbdhAAbdhB-SEQ ID NO: 80) were transformed in strain DSM 792 containing pCas9$_{ind}$ (SEQ ID NO: 22) or pCas9$_{acr}$ (SEQ ID NO: 23). The resulting transformation frequencies are presented in Table 2:

TABLE 2

Transformation frequencies of strain DSM 792 containing pCas9$_{ind}$ or pCas9$_{acr}$ with plasmids targeting bdhB. Frequencies are expressed as the number of transformants obtained per μg of DNA used in the transformation, and represent the means of at least two independent experiments.

| | DSM 792 | |
|---|---|---|
| | pCas9$_{ind}$ | pCas9$_{acr}$ |
| pEC750C | 32.6 ± 27.1 cfu/μg | 24.9 ± 27.8 cfu/μg |
| pGRNA-bdhB | 0 cfu/μg | 17.0 ± 10.7 cfu/μg |
| pGRNA-ΔbdhB | 0 cfu/μg | 13.3 ± 4.8 cfu/μg |
| pGRNA-ΔbdhAΔbdhB | 0 cfu/μg | 33.1 ± 13.4 cfu/μg |

The transformants obtained underwent a phase of induction of the expression of the CRISPR/Cas9 system via a passage on medium supplemented with anhydrotetracycline (aTc) (FIG. 6).

The desired modifications were confirmed by PCR on the genomic DNA of two aTc-resistant colonies (FIG. 7).

Conclusions

The CRISPR/Cas9-based genetic tool described in Wasels et al. (2017) uses two plasmids:

the first plasmid, pCas9$_{ind}$, contains cas9 under the control of an aTc-inducible promoter, and the second plasmid, derived from pEC750C, contains the expression cassette for a gRNA (placed under the control of a second aTc-inducible promoter) as well as an editing template for repairing the double-stranded break induced by the system.

However, the inventors observed that some gRNAs still appeared to be too toxic, despite the control of their expression as well as that of Cas9 using aTc-inducible promoters, thus limiting the efficiency of bacterial transformation by the genetic tool and thus the modification of the chromosome.

In order to improve this genetic tool, the cas9 expression plasmid was modified, via the insertion of an anti-CRISPR gene, acrIIA4, under the control of a lactose-inducible promoter. The transformation efficiencies of different gRNA expression plasmids have thus been significantly improved, allowing transformants to be obtained for all plasmids tested.

It was also possible to edit the bdhB locus within the *C. acetobutylicum* DSM 792 genome using plasmids that could not be introduced into strain DSM 792 containing pCas9$_{ind}$. The modification frequencies observed are the same as those observed previously (Wasels et al., 2017), with 100% of the colonies tested modified.

In conclusion, the modification of the cas9 expression plasmid allows better control of the Cas9-gRNA ribonucleoprotein complex, advantageously facilitating the production of transformants in which the action of Cas9 can be triggered in order to obtain mutants of interest.

Example 2

Materials and Methods
Growing Conditions

*C. beijerinckii* DSM 6423 was grown in 2YTG medium (16 g/l tryptone, 10 g/l yeast extract, 5 g/l glucose, 4 g/l NaCl). *E. coli* NEB 10-beta and INV110 were grown in LB medium (10 g/l tryptone, 5 g/l yeast extract, 5 g/l NaCl). The solid media were prepared by adding 15 g/l agarose to the liquid media. Erythromycin (at concentrations of 20 or 500 mg/l respectively in 2YTG or LB medium), chloramphenicol (25 or 12.5 mg/l respectively in solid or liquid LB), thiamphenicol (15 mg/l in 2YTG medium) or spectinomycin (at concentrations of 100 or 650 mg/l respectively in LB or 2YTG medium) were used if necessary.

Nucleic Acids and Plasmid Vectors

All enzymes and kits used were used according to the suppliers' recommendations.

The colony PCR tests followed the following protocol:

An isolated *C. beijerinckii* DSM 6423 colony was resuspended in 100 μL of 10 mM Tris, pH 7.5, 5 mM EDTA. This solution is heated to 98° C. for 10 min without agitation. 0.5 μL of this bacterial lysate can then be used as a PCR matrix in 10 μL reactions with Phire (Thermo Scientific), Phusion (Thermo Scientific), Q5 (NEB) or KAPA2G Robust (Sigma-Aldrich) polymerase.

The list of primers used for all constructions (name/DNA sequence) is detailed below:

ΔcatB_fwd:
(SEQ ID NO: 1)
TGTTATGGATTATAAGCGGCTCGAGGACGTCAAACCATGTTAATCATTGC

ΔcatB_rev:
(SEQ ID NO: 2)
AATCTATCACTGATAGGGACTCGAGCAATTTCACCAAAGAATTCGCTAGC

ΔcatB_gRNA_rev:
(SEQ ID NO: 41)
AATCTATCACTGATAGGGACTCGAGGGGCAAAAGTGTAAAGACAAGCTTC

RH076:
(SEQ ID NO: 3)
CATATAATAAAAGGAAACCTCTTGATCG

RH077:
(SEQ ID NO: 4)
ATTGCCAGCCTAACACTTGG

RH001:
(SEQ ID NO: 5)
ATCTCCATGGACGCGTGACGTCGACATAAGGTACCAGGAATTAGAGCAGC

RH002:
(SEQ ID NO: 6)
TCTATCTCCAGCTCTAGACCATTATTATTCCTCCAAGTTTGCT

RH003:
(SEQ ID NO: 7)
ATAATGGTCTAGAGCTGGAGATAGATTATTTGGTACTAAG

RH004:
(SEQ ID NO: 8)
TATGACCATGATTACGAATTCGAGCTCGAAGCGCTTATTATTGCATTAGC pEX-fwd:
(SEQ ID NO: 9)
CAGATTGTACTGAGAGTGCACC pEX-rev:
(SEQ ID NO: 10)
GTGAGCGGATAACAATTTCACAC pEC750C-fwd:
(SEQ ID NO: 11)
CAATATTCCACAATATTATATTATAAGCTAGC M13-rev:
(SEQ ID NO: 12)
CAGGAAACAGCTATGAC

RH010:
(SEQ ID NO: 13)
CGGATATTGCATTACCAGTAGC

RH011:
(SEQ ID NO: 14)
TTATCAATCTCTTACACATGGAGC

RH025:
(SEQ ID NO: 15)
TAGTATGCCGCCATTATTACGACA

RH134:
(SEQ ID NO: 16)
GTCGACGTGGAATTGTGAGC pNF2_fwd:
(SEQ ID NO: 39)
GGGCGCACTTATACACCACC pNF2_rev:
(SEQ ID NO: 40)
TGCTACGCACCCCCTAAAGG

RH021:
(SEQ ID NO: 107)
ACTTGGGTCGACCACGATAAAACAAGGTTTTAAGG

RH022:
(SEQ ID NO: 108)
TACCAGGGATCCGTATTAATGTAACTATGATATCAATTCTTG aad9-fwd2:
(SEQ ID NO: 109)
ATGCATGGTCCCAATGAATAGGTTTACACTTACTTTAGTTTTATGG aad9-rev:
(SEQ ID NO: 110)
ATGCGAGTTAACAACTTCTAAAATCTGATTACCAATTAG

RH031:
(SEQ ID NO: 111)
ATGCATGGATCCCAATGAATAGGTTTACACTTACTTTAGTTTTATGG

-continued

RH032:
(SEQ ID NO: 112)
ATGCGAGAGCTCAACTTCTAAAATCTGATTACCAATTAG

RH138:
(SEQ ID NO: 113)
ATGCATGGATCCGTCTGACAGTTACCAGGTCC

RH139:
(SEQ ID NO: 114)
ATGCGAGAGCTCCAATTGTTCAAAAAAATAATGGCGGAG

RH140:
(SEQ ID NO: 115)
ATGCATGGATCCCGGCAGTTTTTCTTTTTCGG

RH141:
(SEQ ID NO: 116)
ATGCGAGAGCTCGGTTAAATACTAGTTTTTAGTTACAGAC

The following plasmid vectors were prepared:

Plasmid No. 1: pEX-A258-ΔcatB (SEQ ID NO: 17)

It contains the ΔcatB fragment of synthesized DNA cloned into plasmid pEX-A258. This ΔcatB fragment comprises i) an expression cassette for a guide RNA targeting the catB gene (chloramphenicol resistance gene encoding a chloramphenicol-O-acetyltransferase-SEQ ID NO: 18) from *C. beijerinckii* DSM6423 under the control of an anhydrotetracycline-inducible promoter (expression cassette: SEQ ID NO: 19), and ii) an editing matrix (SEQ ID NO: 20) comprising 400 homologous bp located upstream and downstream of the catB gene.

Plasmid No. 2: pCas9ind-ΔcatB (see FIG. 9 and SEQ ID NO: 21)

It contains the ΔcatB fragment amplified by PCR (primers ΔcatB_fwd and ΔcatB_rev) and cloned into pCas9ind (described in patent application WO2017/064439-SEQ ID NO: 22) after digestion of the different DNA by the restriction enzyme XhoI.

Plasmid No. 3: pCas9acr (see FIG. 10 and SEQ ID NO: 23)

Plasmid No. 4: pEC750S-uppHR (see FIG. 11 and SEQ ID NO: 24)

It contains a repair matrix (SEQ ID NO: 25) used for the deletion of the upp gene and consisting of two homologous DNA fragments upstream and downstream of the upp gene (respective sizes: 500 (SEQ ID NO: 26) and 377 (SEQ ID NO: 27) base pairs). The assembly was obtained using the Gibson cloning system (New England Biolabs, Gibson assembly Master Mix 2X). To that end, the upstream and downstream parts were amplified by PCR from the genomic DNA of strain DSM 6423 (see Matéde Gerando et al., 2018 and accession number PRJEB11626 (see Worldwide Website: ebi.ac.uk/ena/data/view/PRJEB11626)) using the respective primers RH001/RH002 and RH003/RH004. These two fragments were then assembled in the previously linearized pEC750S by enzymatic restriction (SalI and SacI restriction enzymes).

Plasmid No. 5: pEX-A2-gRNA-upp (see FIG. 12 and SEQ ID NO: 28)

This plasmid comprises the gRNA-upp DNA fragment corresponding to an expression cassette (SEQ ID NO: 29) for a guide RNA targeting the upp gene (protospacer targeting upp (SEQ ID NO: 31)) under the control of a constitutive promoter (non-coding RNA of sequence SEQ ID NO: 30), inserted into a replication plasmid named pEX-A2.

Plasmid No. 6: pEC750S-Δupp (see FIG. 13 and SEQ ID NO: 32)

It is based on plasmid pEC750S-uppHR (SEQ ID NO: 24) and additionally contains the DNA fragment containing an expression cassette for a guide RNA targeting the upp gene under the control of a constitutive promoter.

This fragment was inserted into a pEX-A2, called pEX-A2-gRNA-upp. The insert was then amplified by PCR with primers pEX-fwd and pEX-rev, then digested with restriction enzymes XhoI and NcoI. Finally, this fragment was cloned by ligation into the pEC750S-uppHR first digested by the same restriction enzymes to obtain pEC750S-Δupp.

Plasmid No. 7: pEC750C-Δupp (see FIG. 14 and SEQ ID NO: 33)

The cassette with the guide RNA and the repair matrix were then amplified with primers pEC750C-fwd and M13-rev. The amplicon was digested by enzymatic restriction with the enzymes XhoI and SacI, then cloned by enzymatic ligation into pEC750C to obtain pEC750C-Δupp.

Plasmid No. 8: pGRNA-pNF2 (see FIG. 15 and SEQ ID NO: 34)

This plasmid is based on pEC750C and contains an expression cassette for a guide RNA targeting plasmid pNF2 (SEQ ID NO: 118).

Plasmid No. 9: pCas9ind-gRNA_catB (see FIG. 23 and SEQ ID NO: 38)

It contains the sequence encoding the guide RNA targeting the catB locus amplified by PCR (primers ΔcatB_fwd and ΔcatBgRNA_rev) and cloned into pCas9ind (described in patent application WO2017/064439) after digestion of the different DNA by the restriction enzyme XhoI and ligation.

Plasmid No. 10: pNF3 (see FIG. 25 and SEQ ID NO: 119)

It contains a part of pNF2, including the origin of replication and a gene encoding a plasmid replication protein (CIBE_p20001), amplified with primers RH021 and RH022. This PCR product was then cloned at the SalI and BamHI restriction sites in plasmid pUC19 (SEQ ID NO: 117).

Plasmid No. 11: pEC751S (see FIG. 26 and SEQ ID NO: 121)

It contains all the elements of pEC750C (SEQ ID NO: 106), except the chloramphenicol resistance gene catP (SEQ ID NO: 70). The latter was replaced by the aad9 gene of *Enterococcus faecalis* (SEQ ID NO: 130), which confers resistance to spectinomycin. This element was amplified with primers aad9-fwd2 and aad9-rev from plasmid pMTL007S-E1 (SEQ ID NO: 120) and cloned into the AvaII and HpaI sites of pEC750C, instead of the catP gene (SEQ ID NO: 70).

Plasmid No. 12: pNF3S (see FIG. 27 and SEQ ID NO: 123)

It contains all the elements of pNF3, with an insertion of the aad9 gene (amplified with primers RH031 and RH032 from pEC751S) between the BamHI and SacI sites.

Plasmid No. 13: pNF3E (see FIG. 28 and SEQ ID NO: 124)

It contains all the elements of pNF3, with an insertion of the ermB gene of *Clostridium difficile* (SEQ ID NO: 131) under the control of the miniPthl promoter. This element was amplified from pFW01 with primers RH138 and RH139 and cloned between the BamHI and SacI sites of pNF3E.

Plasmid No. 14: pNF3C (see FIG. 29 and SEQ ID NO: 125)

It contains all the elements of pNF3, with an insertion of the catP gene of *Clostridium perfringens* (SEQ ID NO: 70). This element was amplified from pEC750C with primers RH140 and RH141 and cloned between the BamHI and SacI sites of pNF3E.

Results No. 1
Processing of Strain C. beijerinckii DSM 6423

The plasmids were introduced and replicated in an E. coli dam⁻ dcm⁻ strain (INV110, Invitrogen). This allows the removal of Dam and Dcm methylations on the pCas9ind-ΔcatB plasmid before introducing it by transformation into strain DSM 6423 according to the protocol described by Mermelstein et al. (1993), with the following modifications: the strain is transformed with a larger amount of plasmid (20 µg), with an $OD_{600}$ of 0.8, and using the following electroporation parameters: 100 Ω, 25 µF, 1400 V. Streaking on Petri dishes containing erythromycin (20 µg/mL) produced C. beijerinckii DSM 6423 transformants containing the pCas9ind-ΔcatB plasmid.

Induction of Cas9 Expression and Production of Strain C. beijerinckii DSM 6423 ΔcatB Several erythromycin-resistant colonies were then taken up in 100 µL of culture medium (2YTG) and diluted in series up to a dilution factor of $10^4$ in culture medium. For each colony, 8 µL of each dilution was deposited on a Petri dish containing erythromycin and anhydrotetracycline (200 ng/mL) to induce expression of the gene encoding the Cas9 nuclease.

After extraction of genomic DNA, the deletion of the catB gene in the clones grown on this dish was verified by PCR, using primers RH076 and RH077 (see FIG. 16).

Verification of the Sensitivity to Thiamphenicol of Strain C. beijerinckii DSM 6423 ΔcatB To ensure that the deletion of the catB gene indeed confers a new sensitivity to thiamphenicol, comparative analyses on agar medium were carried out. Precultures of C. beijerinckii DSM 6423 and C. beijerinckii DSM 6423 ΔcatB were prepared on 2YTG medium and then 100 µL of these precultures was spread on 2YTG agar media optionally supplemented with thiamphenicol at a concentration of 15 mg/L. FIG. 17 shows that only the initial C. beijerinckii DSM 6423 strain is capable of growing on a thiamphenicol supplemented medium.

Deletion of the Upp Gene by the CRISPR-Cas9 Tool in Strain C. beijerinckii DSM 6423 ΔcatB A clone of strain C. beijerinckii DSM 6423 ΔcatB was first transformed with the pCas9$_{acr}$ vector not having methylation at the motifs recognized by dam and dcm methyltransferases (prepared from an Escherichia coli bacterium with the dam⁻ dcm⁻ genotype). The verification of the presence of plasmid pCas9$_{acr}$ maintained in strain C. beijerinckii DSM 6423 was verified by colony PCR with primers RH025 and RH134.

An erythromycin-resistant clone was then transformed with pEC750C-Δupp demethylated beforehand. The colonies thus obtained were selected on medium containing erythromycin (20 µg/mL), thiamphenicol (15 µg/mL) and lactose (40 mM).

Several of these clones were then resuspended in 100 µL of culture medium (2YTG) and diluted in series in culture medium (to a dilution factor of $10^4$). Five microliters of each dilution was placed on a Petri dish containing erythromycin, thiamphenicol and anhydrotetracycline (200 ng/mL) (see FIG. 18).

For each clone, two aTc-resistant colonies were tested by colony PCR with primers to amplify the upp locus (see FIG. 19).

Deletion of the Natural pNF2 Plasmid by the CRISPR-Cas9 Tool in Strain C. beijerinckii DSM 6423 ΔcatB A clone of strain C. beijerinckii DSM 6423 ΔcatB was first transformed with vector pCas9$_{ind}$ not having methylation at the motifs recognized by Dam and Dcm methyltransferases (prepared from an Escherichia coli bacterium having the dam⁻ dcm⁻ genotype). The presence of plasmid pCas9$_{ind}$ in strain C. beijerinckii DSM6423 was verified by PCR with primers pCas9$_{ind}$_fwd (SEQ ID NO: 42) and pCas9$_{ind}$_rev (SEQ ID NO: 43) (see FIG. 20).

An erythromycin-resistant clone was then used to transform pGRNA-pNF2, prepared from an Escherichia coli bacterium having the dam⁻ dcm⁻ genotype.

Several colonies obtained on media containing erythromycin (20 µg/mL) and thiamphenicol (15 µg/mL) were resuspended in culture media and diluted in series to a dilution factor of $10^4$. Eight microliters of each dilution were placed on a Petri dish containing erythromycin, thiamphenicol and anhydrotetracycline (200 ng/mL) in order to induce expression of the CRISPR/Cas9 system.

The absence of the natural pNF2 plasmid was verified by PCR with primers pNF2_fwd (SEQ ID NO: 39) and pNF2_rev (SEQ ID NO: 40) (see FIG. 21).

Conclusions

During this work, the inventors succeeded in introducing and maintaining different plasmids within strain Clostridium beijerinckii DSM 6423. They were able to remove the catB gene using a CRISPR-Cas9 tool based on the use of a single plasmid. The sensitivity to thiamphenicol of the recombinant strains obtained was confirmed by tests on agar media.

This deletion allowed them to use more effectively the CRISPR-Cas9 tool requiring two plasmids described in patent application FR1854835. Two examples were carried out to demonstrate the interest of the present application: the deletion of the upp gene and the removal of a natural plasmid not essential for strain Clostridium beijerinckii DSM 6423.

Results No. 2
Transformation of C. beijerinckii Strains

The plasmids prepared in strain E. coli NEB 10-beta are also used to transform strain C. beijerinckii NCIMB 8052. In contrast, for C. beijerinckii DSM 6423, the plasmids are first introduced and replicated in an E. coli dam⁻ dcm⁻ strain (INV110, Invitrogen). This allows the removal of Dam and Dcm methylations on the plasmids of interest before their introduction by transformation into strain DSM 6423.

Transformation is otherwise carried out similarly for each strain, i.e. according to the protocol described by Mermelstein et al. 1992, with the following modifications: the strain is transformed with a larger amount of plasmid (5-20 µg), with an $OD_{600}$ of 0.6-0.8, and the electroporation parameters are 100 Ω, 25 µF, 1400 V. After 3 hours of regeneration in 2YTG, the bacteria are streaked on a Petri dish (2YTG agar) containing the desired antibiotic (erythromycin: 20-40 µg/mL; thiamphenicol: 15 µg/mL; spectinomycin: 650 µg/mL).

Comparison of Transformation Efficiencies of C. beijerinckii DSM 6423 Strains

Transformations were carried out in biological replicates in the following C. beijerinckii strains: DSM 6423 wild-type, DSM 6423 ΔcatB and DSM 6423 ΔcatB ΔpNF2 (FIG. 30). To that end, the pCas9$_{ind}$ vector, which is notably difficult to use to modify a bacterium because it does not allow good transformation efficiencies, was used. It also contains a gene that gives the strain resistance to erythromycin, an antibiotic to which all three strains are sensitive.

The results indicate an increase in transformation efficiency by a factor of about 15-20 due to the loss of the natural pNF2 plasmid.

Transformation efficiency was also tested for plasmid pEC750C, which confers thiamphenicol resistance, only in strains DSM 6423 ΔcatB and DSM 6423 ΔcatB ΔpNF2, since the wild-type strain is resistant to this antibiotic (FIG. 31). For this plasmid, the gain in transformation efficiency is even more obvious (improvement by a factor of about 2000).

Comparison of the Transformation Efficiencies of pNF3 Plasmids with Other Plasmids In order to determine the transformation efficiency of plasmids containing the origin of replication of the natural pNF2 plasmid, plasmids pNF3E and pNF3C were introduced into strain C. beijerinckii DSM 6423 ΔcatB ΔpNF2. The use of vectors containing erythromycin or chloramphenicol resistance genes allows the transformation efficiency of the vector to be compared according to the nature of the resistance gene. Plasmids pFW01 and pEC750C were also transformed. These two plasmids contain resistance genes to different antibiotics (erythromycin and thiamphenicol respectively) and are commonly used to transform C. beijerinckii and C. acetobutylicum.

As shown in FIG. 32, vectors based on pNF3 have excellent transformation efficiency, and are particularly suitable for use in C. beijerinckii DSM 6423 ΔcatB ΔpNF2. In particular, pNF3E (which contains an erythromycin resistance gene) shows a significantly higher transformation efficiency than pFW01, which has the same resistance gene. This same plasmid could not be introduced into the wild-type C. beijerinckii DSM 6423 strain (0 colonies obtained with 5 μg of plasmids transformed into biological replicates), which demonstrates the impact of the presence of the natural pNF2 plasmid.

Verification of the Transformability of pNF3 Plasmids in Other Strains/Species

To illustrate the possibility of using this new plasmid in other solventogenic Clostridium strains, the inventors performed a comparative analysis of the transformation efficiencies of plasmids pFW01, pNF3E and pNF3S in the ABE strain C. beijerinckii NCIMB 8052 (FIG. 33). As strain NCIMB 8052 is naturally resistant to thiamphenicol, pNF3S, conferring resistance to spectinomycin, was used in place of pNF3C.

The results show that strain NCIMB 8052 is transformable with plasmids based on pNF3, which proves that these vectors are applicable to the species C. beijerinckii in the broad sense.

The applicability of the suite of synthetic vectors based on pNF3 was also tested in the reference strain C. acetobutylicum DSM 792. A transformation test thus showed the possibility of transforming this strain with plasmid pNF3C (transformation efficiency of 3 colonies observed per μg of transformed DNA compared to 120 colonies/μg for plasmid pEC750C).

Verification of the Compatibility of pNF3 Plasmids with the Genetic Tool Described in Application FR18/73492

Patent application FR18/73492 describes the ΔcatB strain and the use of a two-plasmid CRISPR/Cas9 system requiring the use of an erythromycin resistance gene and a thiamphenicol resistance gene. To demonstrate the interest of the new suite of pNF3 plasmids, vector pNF3C was transformed in strain ΔcatB already containing the pCas9$_{acr}$ plasmid. The transformation, performed in duplicate, showed a transformation efficiency of 0.625±0.125 colonies/μg DNA (mean±standard error), which proves that a vector based on pNF3C can be used in combination with pCas9$_{acr}$ in the ΔcatB strain.

In parallel with these results, part of plasmid pNF2 comprising its origin of replication (SEQ ID NO: 118) could be successfully reused to create a new suite of shuttle vectors (SEQ ID NO: 119, 123, 124 and 125), modifiable as desired, allowing in particular their replication in an E. coli strain as well as their reintroduction into C. beijerinckii DSM 6423. These new vectors have advantageous transformation efficiencies for genetic editing, for example in C. beijerinckii DSM 6423 and its derivatives, in particular using the CRISPR/Cas9 tool comprising two different nucleic acids.

These new vectors have also been successfully tested in another C. beijerinckii strain (NCIMB 8052), and Clostridium species (in particular C. acetobutylicum), demonstrating their applicability in other organisms of the phylum Firmicutes. A test is also performed on Bacillus.

Conclusions

These results show that suppression of the natural pNF2 plasmid significantly increases the transformation frequencies of the bacteria that contained it (by a factor of about 15 for pFW01 and a factor of about 2000 for pEC750C). This result is particularly interesting in the case of bacteria of the genus Clostridium, known to be difficult to transform, and in particular for strain C. beijerinckii DSM 6423 which naturally suffers from a low transformation efficiency (less than 5 colonies/μg plasmid).

REFERENCES

Banerjee, A., Leang, C., Ueki, T., Nevin, K. P., & Lovley, D. R. (2014). Lactose-inducible system for metabolic engineering of Clostridium ljungdahlii. Applied and environmental microbiology, 80(8), 2410-2416.

Chen J.-S., Hiu S. F. (1986) Acetone-butanol-isopropanol production by Clostridium beijerinckii (synonym, Clostridium butylicum). Biotechnol. Lett. 8:371-376.

Cui, L., & Bikard, D. (2016). Consequences of Cas9 cleavage in the chromosome of Escherichia coli. Nucleic acids research, 44(9), 4243-4251.

Currie, D. H., Herring, C. D., Guss, A. M., Olson, D. G., Hogsett, D. A., & Lynd, L. R. (2013). Functional heterologous expression of an engineered full length CipA from Clostridium thermocellum in Thermoanaerobacterium saccharolyticum. Biotechnology for biofuels, 6(1), 32.

DiCarlo, J. E., Norville, J. E., Mali, P., Rios, X., Aach, J., & Church, G. M. (2013). Genome engineering in Saccharomyces cerevisiae using CRISPR-Cas systems. Nucleic acids research, 41(7), 4336-4343.

Dong, H., Tao, W., Zhang, Y., & Li, Y. (2012). Development of an anhydrotetracycline-inducible gene expression system for solvent-producing Clostridium acetobutylicum: A useful tool for strain engineering. Metabolic engineering, 14(1), 59-67.

Dong, D., Guo, M., Wang, S., Zhu, Y., Wang, S., Xiong, Z., & Huang, Z. (2017). Structural basis of CRISPR-SpyCas9 inhibition by an anti-CRISPR protein. Nature, 546(7658), 436.

Dupuy, B., Mani, N., Katayama, S., & Sonenshein, A. L. (2005). Transcription activation of a UV-inducible Clostridium perfringens bacteriocin gene by a novel a factor. Molecular microbiology, 55(4), 1196-1206.

Egholm, M., Buchardt, O., Nielsen, P. E., & Berg, R. H. (1992). Peptide nucleic acids (PNA). Oligonucleotide analogs with an achiral peptide backbone. Journal of the American Chemical Society, 114(5), 1895-1897.

Fonfara, I., Le Rhun, A., Chylinski, K., Makarova, K. S., Lecrivain, A. L., Bzdrenga, J., & Charpentier, E. (2013). Phylogeny of Cas9 determines functional exchangeability of dual-RNA and Cas9 among orthologous type II CRISPR-Cas systems. Nucleic acids research, 42(4), 2577-2590.

Garcia-Doval C, Jinek M. Molecular architectures and mechanisms of Class 2 CRISPR-associated nucleases. Curr Opin Struct Biol. 2017 December; 47:157-166. doi: 10.1016/j.sbi.2017.10.015 Ajouter au projet Citavi par DOI. Epub 2017 Nov. 3. Review.

George H. A., Johnson J. L., Moore W. E. C., Holdeman, L. V., Chen J. S. (1983) Acetone, Isopropanol, and Butanol Production by *Clostridium beijerinckii* (syn. *Clostridium butylicum*) and *Clostridium aurantibutyricum*. Appl. Env. Microbiol. 45:1160-1163.

Gonzales y Tucker R D, Frazee B. View from the front lines: an emergency medicine perspective on clostridial infections in injection drug users. Anaerobe. 2014 December; 30:108-15.

Hartman, A. H., Liu, H., & Melville, S. B. (2011). Construction and characterization of a lactose-inducible promoter system for controlled gene expression in *Clostridium perfringens*. Applied and environmental microbiology, 77(2), 471-478.

Heap, J. T., Ehsaan, M., Cooksley, C. M., Ng, Y. K., Cartman, S. T., Winzer, K., & Minton, N. P. (2012). Integration of DNA into bacterial chromosomes from plasmids without a counter-selection marker. *Nucleic acids research,* 40(8), e59-e59.

Heap, J. T., Kuehne, S. A., Ehsaan, M., Cartman, S. T., Cooksley, C. M., Scott, J. C., & Minton, N. P. (2010). The ClosTron: mutagenesis in *Clostridium* refined and streamlined. *Journal of microbiological methods,* 80(1), 49-55.

Heap, J. T., Pennington, O. J., Cartman, S. T., Carter, G. P., & Minton, N. P. (2007). The ClosTron: a universal gene knock-out system for the genus *Clostridium. Journal of microbiological methods,* 70(3), 452-464.

Heap, J. T., Pennington, O. J., Cartman, S. T., & Minton, N. P. (2009). A modular system for *Clostridium* shuttle plasmids. *Journal of microbiological methods,* 78(1), 79-85.

Hidalgo-Cantabrana, C., O'Flaherty, S., & Barrangou, R. (2017). *CRISPR-based engineering of next-generation lactic acid bacteria*. Current opinion in microbiology, 37, 79-87.

Hiu S. F., Zhu C.-X., Yan R.-T., Chen J.-S. (1987) Butanol-ethanol dehydrogenase and butanol-ethanol-isopropanol dehydrogenase: different alcohol dehydrogenases in two strains of *Clostridium beijerinckii* (*Clostridium butylicum*). Appl. Env. Microbiol. 53:697-703.

Huang, H., Chai, C., Li, N., Rowe, P., Minton, N. P., Yang, S., & Gu, Y. (2016). CRISPR/Cas9-based efficient genome editing in *Clostridium ljungdahlii*, an autotrophic gas-fermenting bacterium. *ACS synthetic biology,* 5(12), 1355-1361.

Huggins, A. S., Bannam, T. L. and Rood, J. I. (1992) Comparative sequence analysis of the catB gene from *Clostridium butyricum*. Antimicrob. Agents Chemother. 36, 2548-2551.

Ismaiel A. A., Zhu C. X., Colby G. D., Chen, J. S. (1993). Purification and characterization of a primary-secondary alcohol dehydrogenase from two strains of *Clostridium beijerinckii*. J. Bacteriol. 175:5097-5105.

Jinek, M., Chylinski, K., Fonfara, I., Hauer, M., Doudna, J. A., & Charpentier, E. (2012). A programmable dual-RNA-guided DNA endonuclease in adaptive bacterial immunity. *Science,* 337(6096), 816-821.

Jones D. T., Woods D. R. (1986) Acetone-butanol fermentation revisited. Microbiological Reviews 50:484-524.

Kolek J., Sedlar K., Provaznik I., Patakova P. (2016). Dam and Dcm methylations prevent gene transfer into *Clostridium pasteurianum* NRRL B-598: development of methods for electrotransformation, conjugation, and sonoporation. Biotechnol Biofuels. 9:14.

Li, Q., Chen, J., Minton, N. P., Zhang, Y., Wen, Z., Liu, J., & Gu, Y. (2016). CRISPR-based genome editing and expression control systems in *Clostridium acetobutylicum* and *Clostridium beijerinckii. Biotechnology journal,* 11(7), 961-972.

Makarova, K. S., Haft, D. H., Barrangou, R., Brouns, S. J., Charpentier, E., Horvath, P., & Van Der Oost, J. (2011). Evolution and classification of the CRISPR-Cas systems. *Nature Reviews Microbiology,* 9(6), 467.

Makarova, K. S., Wolf, Y. I., Alkhnbashi, O. S., Costa, F., Shah, S. A., Saunders, S. J., & Horvath, P. (2015). An updated evolutionary classification of CRISPR-Cas systems. *Nature Reviews Microbiology,* 13(11), 722.

Marino, N. D., Zhang, J. Y., Borges, A. L., Sousa, A. A., Leon, L. M., Rauch, B. J., & Bondy-Denomy, J. (2018). Discovery of widespread type I and type V CRISPR-Cas inhibitors. *Science,* 362(6411), 240-242.

Máté de Gérando, H., Wasels, F., Bisson, A., Clement, B., Bidard, F., Jourdier E., Lopez-Contreras A., Lopes Ferreira N. (2018). Genome and transcriptome of the natural isopropanol producer *Clostridium beijerinckii* DSM 6423. BMC genomics. 19:242.

Mearls, E. B., Olson, D. G., Herring, C. D., & Lynd, L. R. (2015). Development of a regulatable plasmid-based gene expression system for *Clostridium thermocellum. Applied microbiology and biotechnology,* 99(18), 7589-7599.

Mermelstein, L. D., & Papoutsakis, E. T. (1993). In vivo methylation in *Escherichia coli* by the *Bacillus subtilis* phage phi 3T I methyltransferase to protect plasmids from restriction upon transformation of *Clostridium acetobutylicum* ATCC 824. *Applied and environmental microbiology,* 59(4), 1077-1081.

Mermelstein L. D., Welker N. E., Bennett G. N., Papoutsakis E. T. (1992). Expression of cloned homologous fermentative genes in *Clostridium acetobutylicum* ATCC 824 10:190-195.

Mermelstein L. D., Welker N. E., Bennett G. N., Papoutsakis E. T. (1993). Expression of cloned homologous fermentative genes in *Clostridium acetobutylicum* ATCC 824 10:190-195.

Moon H G, Jang Y S, Cho C, Lee J, Binkley R, Lee S Y. One hundred years of clostridial butanol fermentation. FEMS Microbiol Lett. 2016 February; 363(3).

Nagaraju, S., Davies, N. K., Walker, D. J. F., Köpke, M., & Simpson, S. D. (2016). Genome editing of *Clostridium autoethanogenum* using CRISPR/Cas9. *Biotechnology for biofuels,* 9(1), 219.

Nariya, H., Miyata, S., Kuwahara, T., & Okabe, A. (2011). Development and characterization of a xylose-inducible gene expression system for *Clostridium perfringens. Applied and environmental microbiology,* 77(23), 8439-8441.

Newcomb, M., Millen, J., Chen, C. Y., & Wu, J. D. (2011). Co-transcription of the celC gene cluster in *Clostridium thermocellum. Applied microbiology and biotechnology,* 90(2), 625-634.

Pawluk, A., Davidson, A. R., & Maxwell, K. L. (2018). Anti-CRISPR: Discovery, mechanism and function. *Nature Reviews Microbiology,* 16(1), 12.

Poehlein A., Solano J. D. M., Flitsch S. K., Krabben P., Winzer K., Reid S. J., Jones D. T., Green E., Minton N. P., Daniel R., Dürre P. (2017). Microbial solvent formation revisited by comparative genome analysis. Biotechnol Biofuels. 10:58.

Pyne, M. E., Bruder, M. R., Moo-Young, M., Chung, D. A., & Chou, C. P. (2016). Harnessing heterologous and endogenous CRISPR-Cas machineries for efficient markerless genome editing in *Clostridium. Scientific reports,* 6.

Rauch, B. J., Silvis, M. R., Hultquist, J. F., Waters, C. S., McGregor, M. J., Krogan, N. J., & Bondy-Denomy, J. (2017). Inhibition of CRISPR-Cas9 with bacteriophage proteins. *Cell,* 168(1-2), 150-158.

Rajewska M., Wegrzyn K, Konieczny I., FEMS Microbiol Rev. 2012 March; 36(2). *AT-rich region and repeated sequences—the essential elements of replication origins of bacterial replicons:*408-34.

Ransom, E. M., Ellermeier, C. D., & Weiss, D. S. (2015). Use of mCherry red fluorescent protein for studies of protein localization and gene expression in *Clostridium difficile. Applied and environmental microbiology,* 81(5), 1652-1660.

Rogers P., Chen J.-S., Zidwick M. (2006) in The prokaryotes. 3rd edition, Vol. 1, edited by Dworkin M (Springer, New York, USA, 2006). 3rd edition, Vol. 1, pp. 672-755.

Schwarz S, Kehrenberg C, Doublet B, Cloeckaert A. Molecular basis of bacterial resistance to chloramphenicol and florfenicol. FEMS Microbiol Rev. 2004 November; 28(5):519-42.

Stella S, Alcón P, Montoya G. Class 2 CRISPR-Cas RNA-guided endonucleases: Swiss Army knives of genome editing. Nat Struct Mol Biol. 2017 November; 24(11): 882-892. doi: 10.1038/nsmb.3486.

Wang, S., Dong, S., Wang, P., Tao, Y., & Wang, Y. (2017). Genome Editing in *Clostridium saccharoperbutylacetonicum* N1-4 with the CRISPR-Cas9 System. *Applied and Environmental Microbiology,* 83(10), e00233-17.

Wang Y, Li X, Milne C B, et al. Development of a gene knockout system using mobile group II introns (Targetron) and genetic disruption of acid production pathways in *Clostridium beijerinckii. Appl Environ Microbiol.* 2013; 79(19): 5853-63.

Wang, Y., Zhang, Z. T., Seo, S. O., Choi, K., Lu, T., Jin, Y. S., & Blaschek, H. P. (2015). Markerless chromosomal gene deletion in *Clostridium beijerinckii* using CRISPR/Cas9 system. *Journal of biotechnology,* 200, 1-5.

Wang, Y., Zhang, Z. T., Seo, S. O., Lynn, P., Lu, T., Jin, Y. S., & Blaschek, H. P. (2016). Bacterial genome editing with CRISPR-Cas9: deletion, Integration, single nucleotide modification, and desirable "clean" mutant selection in *Clostridium beijerinckii* as an example. *ACS synthetic biology,* 5(7), 721-732.

Wasels, F., Jean-Marie, J., Collas, F., López-Contreras, A. M., & Ferreira, N. L. (2017 September). A two-plasmid inducible CRISPR/Cas9 genome editing tool for *Clostridium acetobutylicum. Journal of microbiological methods,* 140, 5-11.

Xu, T., Li, Y., Shi, Z., Hemme, C. L., Li, Y., Zhu, Y., & Zhou, J. (2015). Efficient genome editing in *Clostridium cellulolyticum* via CRISPR-Cas9 nickase. *Applied and environmental microbiology,* 81(13), 4423-4431.

Yadav, R., Kumar, V., Baweja, M., & Shukla, P. (2018). *Gene editing and genetic engineering approaches for advanced probiotics: A Review. Critical reviews in food science and nutrition,* 58(10), 1735-1746.

Yue Chen, Bruce A. McClane, Derek J. Fisher, Julian I. Rood, Phalguni Gupta; Construction of an Alpha Toxin Gene Knockout Mutant of *Clostridium perfringens* Type A by Use of a Mobile Group II Intron; Appl. Environ. Microbiol. November 2005, 71 (11) 7542-7547; DOI: 10.1128/AEM.71.11.7542-7547.2005.

Zhang, J., Liu, Y. J., Cui, G. Z., & Cui, Q. (2015). A novel arabinose-inducible genetic operation system developed for *Clostridium cellulolyticum. Biotechnology for biofuels,* 8(1), 36.

Zhang C., Tinggang L. Jianzhong H. (2018) Characterization and genome analysis of a butanol-isopropanol-producing *Clostridium beijerinckii* strain BGS1. Biotechnol Biofuels (2018) 11:280.

Zhong, J., Karberg, M., & Lambowitz, A. M. (2003). Targeted and random bacterial gene disruption using a group II intron (targetron) vector containing a retrotransposition-activated selectable marker. *Nucleic acids research,* 31(6), 1656-1664.

---

We claim:

1. A genetic tool for improving efficiency of transformation over a gene editing tool that does not include anti-CRISPR proteins, and genetic modification by homologous recombination, of a bacterium of the genus *Clostridium*, characterized:
   i) in that the genetic tool comprises:
      a first nucleic acid encoding at least Cas9, wherein the nucleic acid encoding Cas9 is placed under the control of an inducible promoter, and
      at least a second nucleic acid allowing the expression of a repair template comprising a sequence of interest allowing, by a homologous recombination mechanism, replacement of a portion of bacterial DNA targeted by Cas9 by the sequence of interest,
   ii) in that at least one of said nucleic acids further encodes one or more guide RNAs (gRNAs) or in that the genetic tool further comprises one or more guide RNAs, each guide RNA comprising a Cas9-enzyme-binding RNA structure and a sequence complementary to the targeted portion of the bacterial DNA, and
   iii) in that the first nucleic acid further comprises a sequence encoding an anti-CRISPR protein placed under the control of an inducible promoter, said genetic tool improving efficiency of transformation over a gene editing tool that does not include anti-CRISPR proteins.

2. The genetic tool according to claim 1, characterized in that the bacterium of the genus *Clostridium* is a solventogenic bacterium selected from *C. acetobutylicum*, *C. cellulolyticum*, *C. phytofermentans*, *C. beijerinckii*, *C. saccharobutylicum*, *C. saccharoperbutylacetonicum*, *C. sporogenes*, *C. butyricum*, *C. aurantibutyricum*, or *C. tyrobutyricum*.

3. The genetic tool according to claim 2, characterized in that when the bacterium is *C. acetobutylicum*, said *C. acetobutylicum* bacterium is strain DSM 792 (ATCC 824 or LMG 5710), and when the solventogenic bacterium is *C. beijerinckii*, said *C. beijerinckii* bacterium is strain NCIMB 8052 or strain DSM 6423 (NRRL B-593, LMG 7814 or LMG 7815).

4. The genetic tool according to claim 1, characterized in that the anti-CRISPR protein is the protein AcrIIA2 or the protein AcrIIA4.

5. The genetic tool according to claim 1, characterized in that the expression of the DNA sequence of interest allows the bacterium of the genus *Clostridium* to ferment at least two different sugars among 6-carbon sugars and/or among 5-carbon sugars.

6. The genetic tool according to claim 1, characterized in that the sequence of interest encodes at least one product promoting solvent production by the bacterium of the genus *Clostridium*.

7. The genetic tool according to claim 1, characterized in that each of the first and at least second nucleic acids present within the tool is located in a distinct expression cassette or a distinct vector.

8. A kit for transforming a bacterium of the genus *Clostridium* or for producing at least one solvent using a bacterium of the genus *Clostridium*, wherein the kit comprises the genetic tool according to claim 1 and at least one inducer adapted to the inducible promoter of expression of the selected anti-CRISPR protein used within the tool.

9. A process for genetically modifying by homologous recombination, a bacterium of the genus *Clostridium*, characterized in that the process comprises a step of transforming the bacterium by introducing into said bacterium a genetic tool, the genetic tool comprising:
   a first nucleic acid encoding at least Cas9, wherein the sequence encoding Cas9 is placed under the control of an inducible promoter, and
   at least a second nucleic acid allowing the expression of a repair template comprising a sequence of interest allowing, by a homologous recombination mechanism, replacement of a portion of bacterial DNA targeted by Cas9 by the sequence of interest,
   in that at least one of said nucleic acids further encodes one or more guide RNAs (gRNAs) or in that the genetic tool further comprises one or more guide RNAs, each guide RNA comprising a Cas9-enzyme-binding RNA structure and a sequence complementary to the targeted portion of the bacterial DNA, and in that the first nucleic acid further comprises a sequence encoding an anti-CRISPR protein placed under the control of an inducible promoter.

10. The process according to claim 9, characterized in that the process further comprises (b) a step of culturing the transformed bacterium on a medium not containing an inducer of expression of the anti-CRISPR protein.

11. The process according to claim 10 further comprising (c) a step of removing the nucleic acid containing the repair template and/or the guide RNA(s) or sequences encoding the guide RNA(s) introduced with the genetic tool.

12. The process according to claim 11, characterized in that the process further comprises one or more additional steps (d), subsequent to step (b) or to step (c), comprising
   (i) introducing an nth nucleic acid containing a repair template distinct from that already introduced and one or more expression cassettes for guide RNAs allowing the integration of an nth sequence of interest contained in said distinct repair template into a targeted region of the bacterium's genome, in the presence of the inducer of expression of the anti-CRISPR protein,
   (ii) culturing the bacterium thus transformed on a medium not containing the inducer of expression of the anti-CRISPR protein, and (iii) allowing expression of a Cas9/gRNA ribonucleoprotein complex.

\* \* \* \* \*

UNITED STATES PATENT AND TRADEMARK OFFICE
CERTIFICATE OF CORRECTION

PATENT NO. : 11,946,067 B2
APPLICATION NO. : 16/421572
DATED : April 2, 2024
INVENTOR(S) : Nicolas Lopes Ferreira, François Wasels and Gwladys Chartier It is certified that error appears in the above-identified patent and that said Letters Patent is hereby corrected as shown below:

In the Specification

Column 15,
Line 41, "the lad gene," should read --the *lacI* gene,--.

Column 16,
Line 32, "of CAST." should read --of CAS7.--.

Signed and Sealed this
Twelfth Day of November, 2024

Katherine Kelly Vidal
*Director of the United States Patent and Trademark Office*